(12) United States Patent
Dadala et al.

(10) Patent No.: US 7,144,740 B2
(45) Date of Patent: Dec. 5, 2006

(54) METHOD FOR CHROMATOGRAPHIC FINGER PRINTING AND STANDARDIZATION OF SINGLE MEDICINES AND FORMULATIONS

(75) Inventors: Vijaya Kumar Dadala, Andhra Pradesh (IN); Kondapuram Vijaya Raghavan, Andhra Pradesh (IN)

(73) Assignee: Council of Scientific and Industrial Research, New Delhi, IN (US)

( * ) Notice: Subject to any disclaimer, the term of this patent is extended or adjusted under 35 U.S.C. 154(b) by 399 days.

(21) Appl. No.: 09/779,377

(22) Filed: Feb. 8, 2001

(65) Prior Publication Data

US 2003/0068828 A1    Apr. 10, 2003

(51) Int. Cl.
    G01N 30/02    (2006.01)
    G01N 21/76    (2006.01)
(52) U.S. Cl. .................. 436/161; 436/166; 436/172
(58) Field of Classification Search ........... 436/161, 436/172
    See application file for complete search history.

(56) References Cited

U.S. PATENT DOCUMENTS 6,002,986 A * 12/1999 Mito .................. 702/32
6,466,923 B1 * 10/2002 Young ................ 706/13
2002/0062683 A1 * 5/2002 Ishii et al. ........... 73/61.52

FOREIGN PATENT DOCUMENTS

JP    02253156 A  * 10/1990
JP    04355366 A  * 12/1992

OTHER PUBLICATIONS

Pozzan et al. "Pharmacophoric 3D mill hashed fingerprints: add another dimension to your similarity searching", Abstract of Papers, ACS Meeting, Apr. 2002.*

* cited by examiner

*Primary Examiner*—Yelena G. Gakh
(74) *Attorney, Agent, or Firm*—Butzel Long

(57) ABSTRACT

The present invention provides a method for the chromatographic fingerprinting, chemical and therapeutic standardization, bar-coding of the fingerprints and preparation of a data base for Enterprise Resource Planning (ERP) and Customer Relationship Management (CRM) machines and applications of medicines in general and traditional medicines in particular; this invention includes a software based instrumental method and a novel method of fingerprinting and standardization is proposed for the above purpose and the said method for the chromatographic finger printing which facilitates to correlate the traditional therapeutic standardization methods with the chemical properties of the medicines and humors and provides a rational basis to understand the methods used for the said purpose.

16 Claims, 219 Drawing Sheets

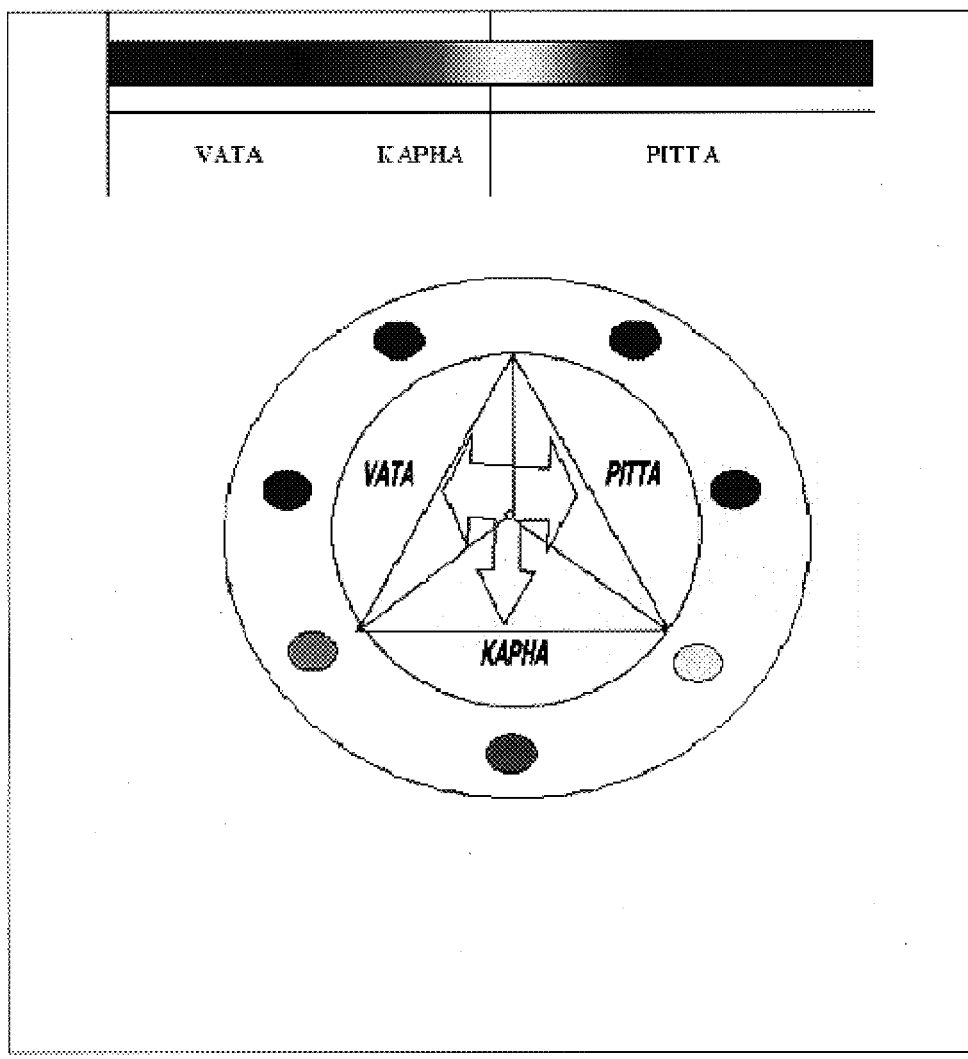

SHILAJIT

GOOD BY EFFICACY

SHILAJIT
POOR BY EFFICACY

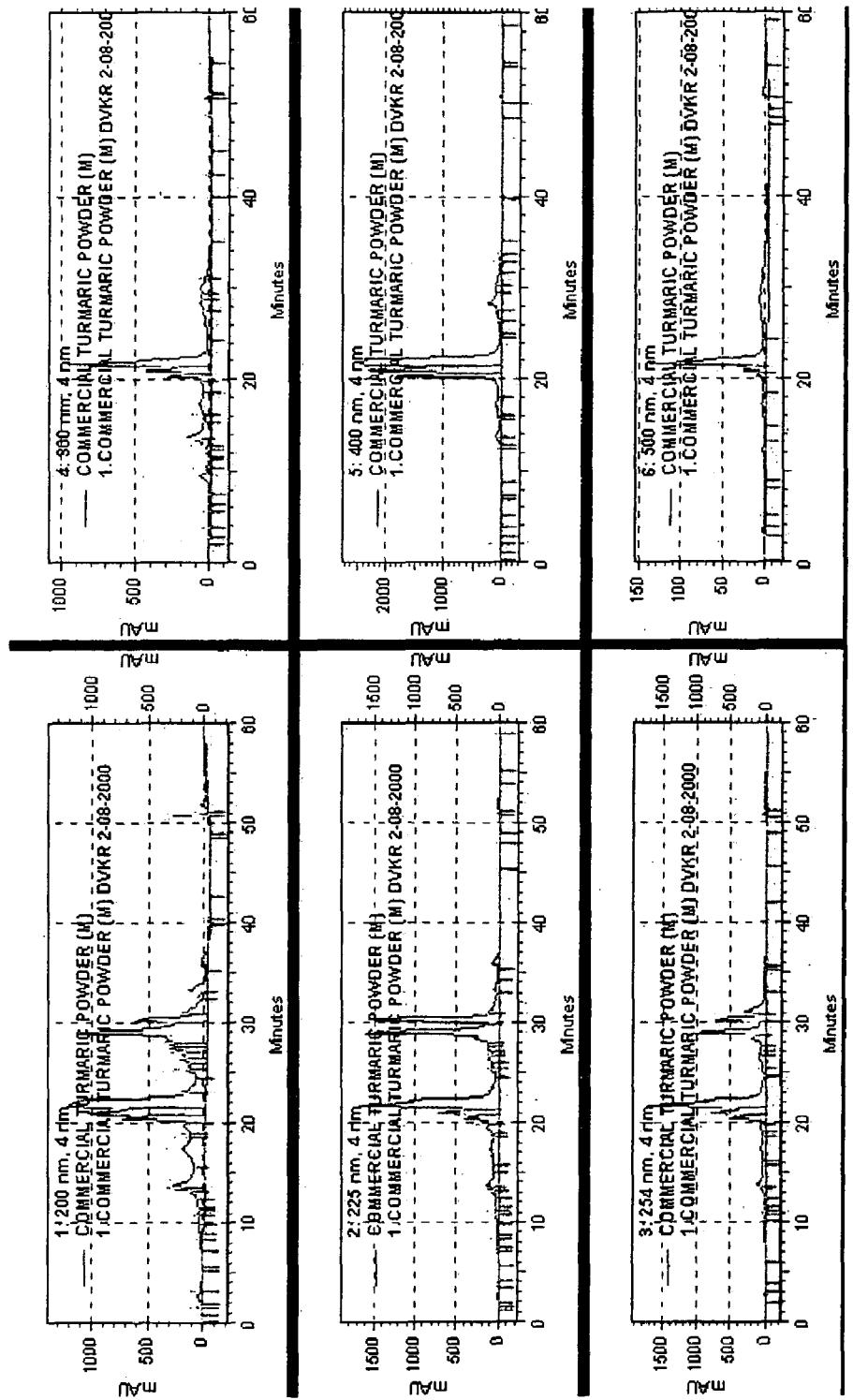
Figure 5 - Prior Art

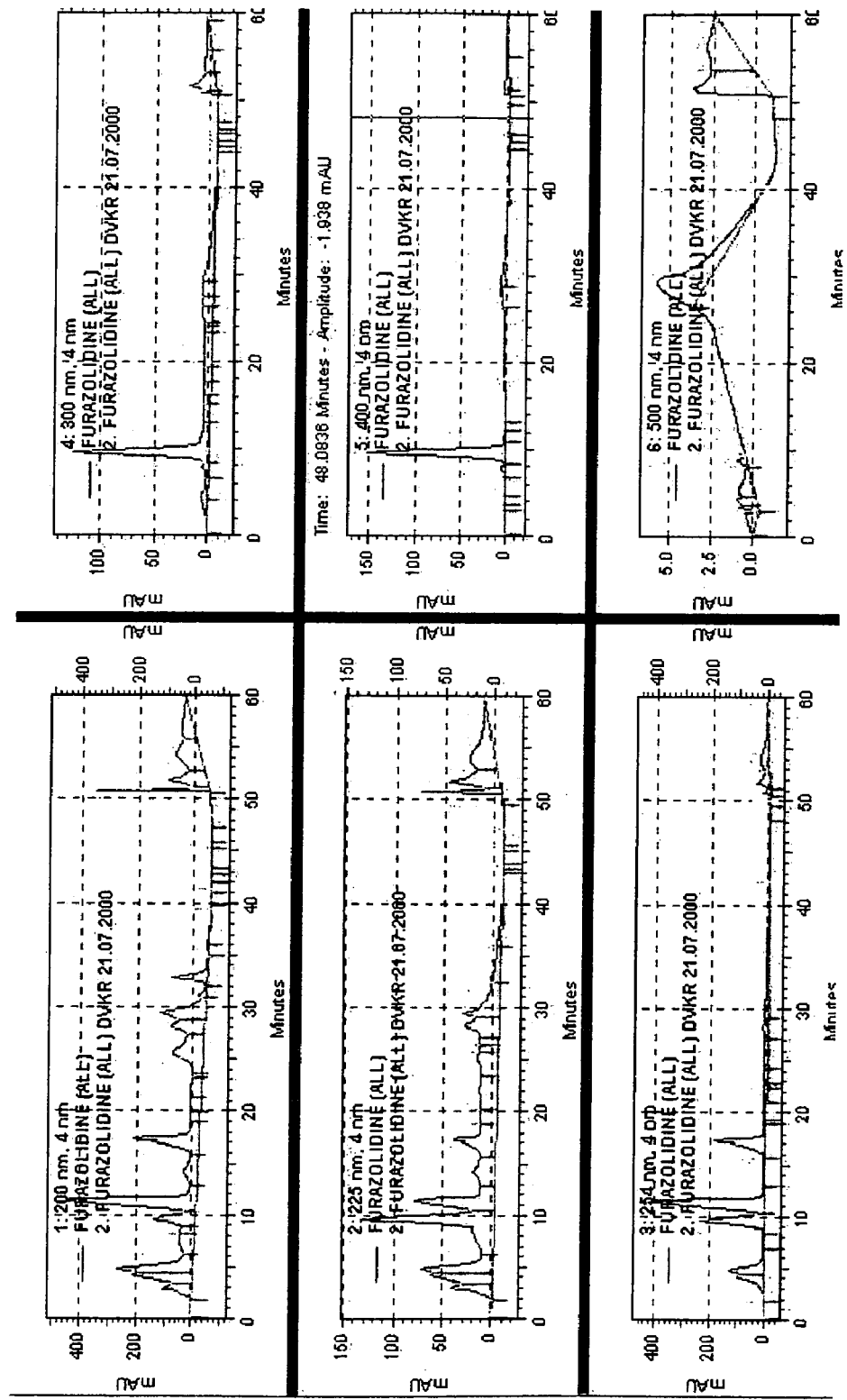
Figure 6 – Prior Art

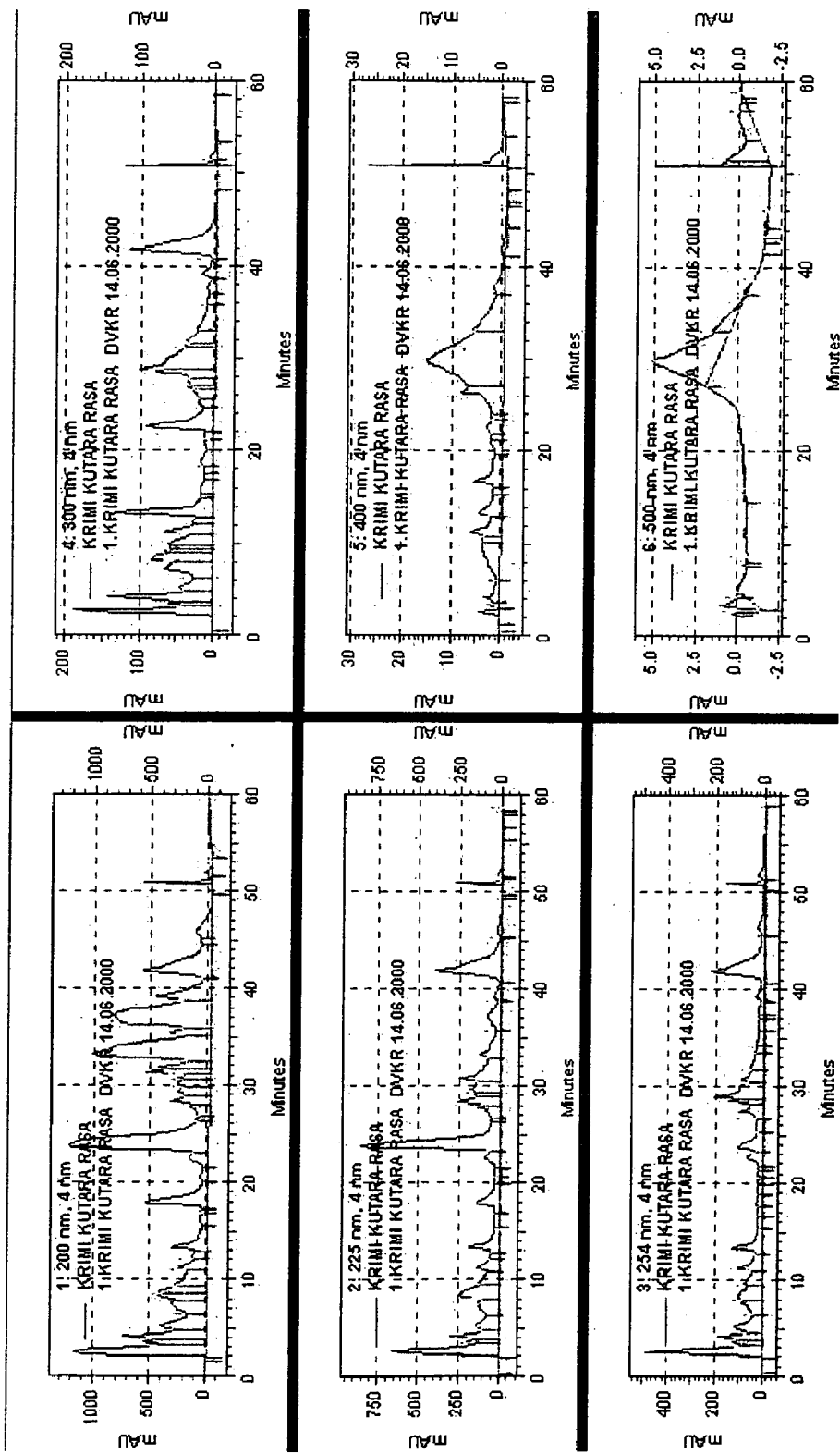
Figure 7 – Prior Art

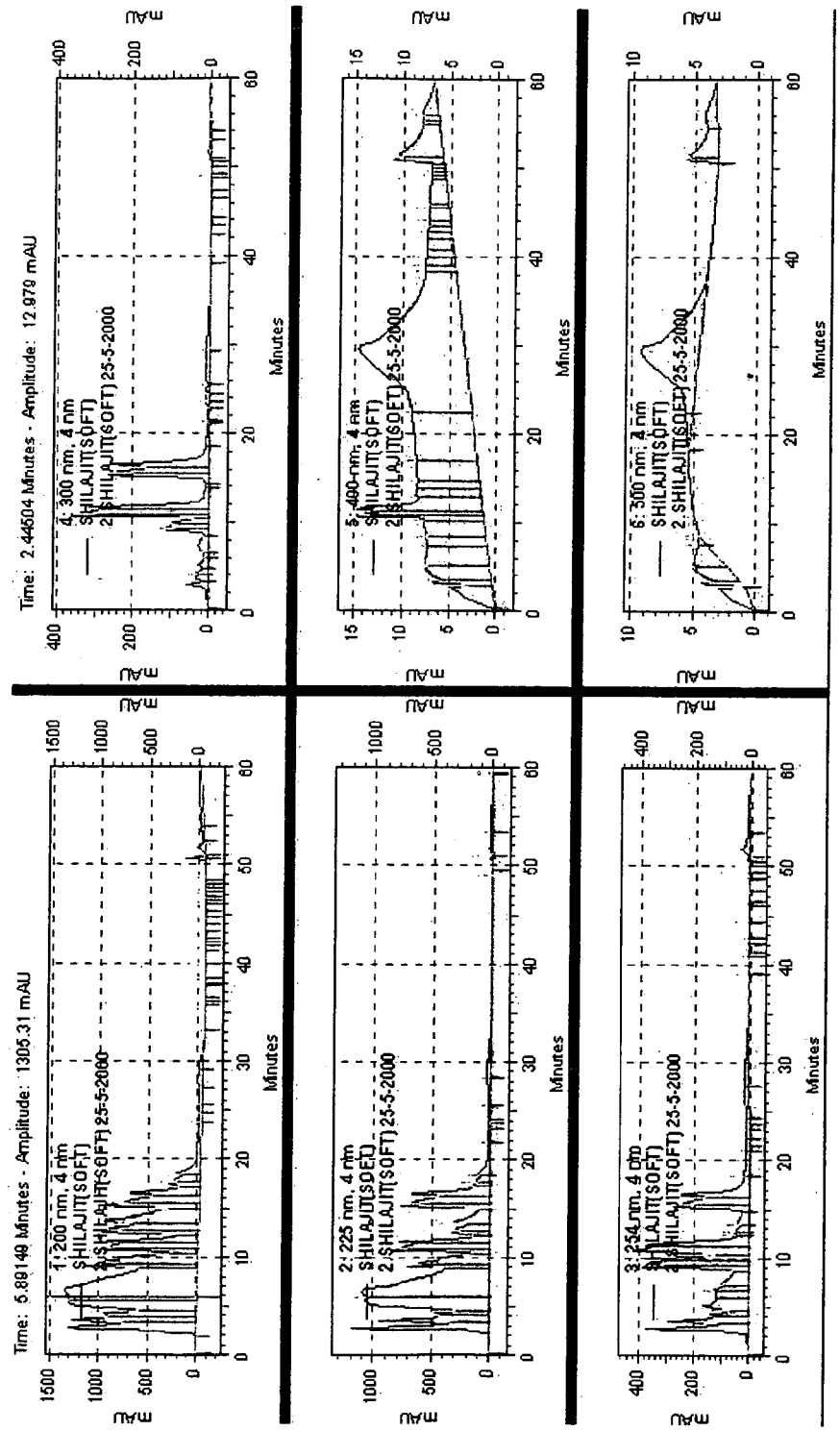
Figure 8 – Prior Art

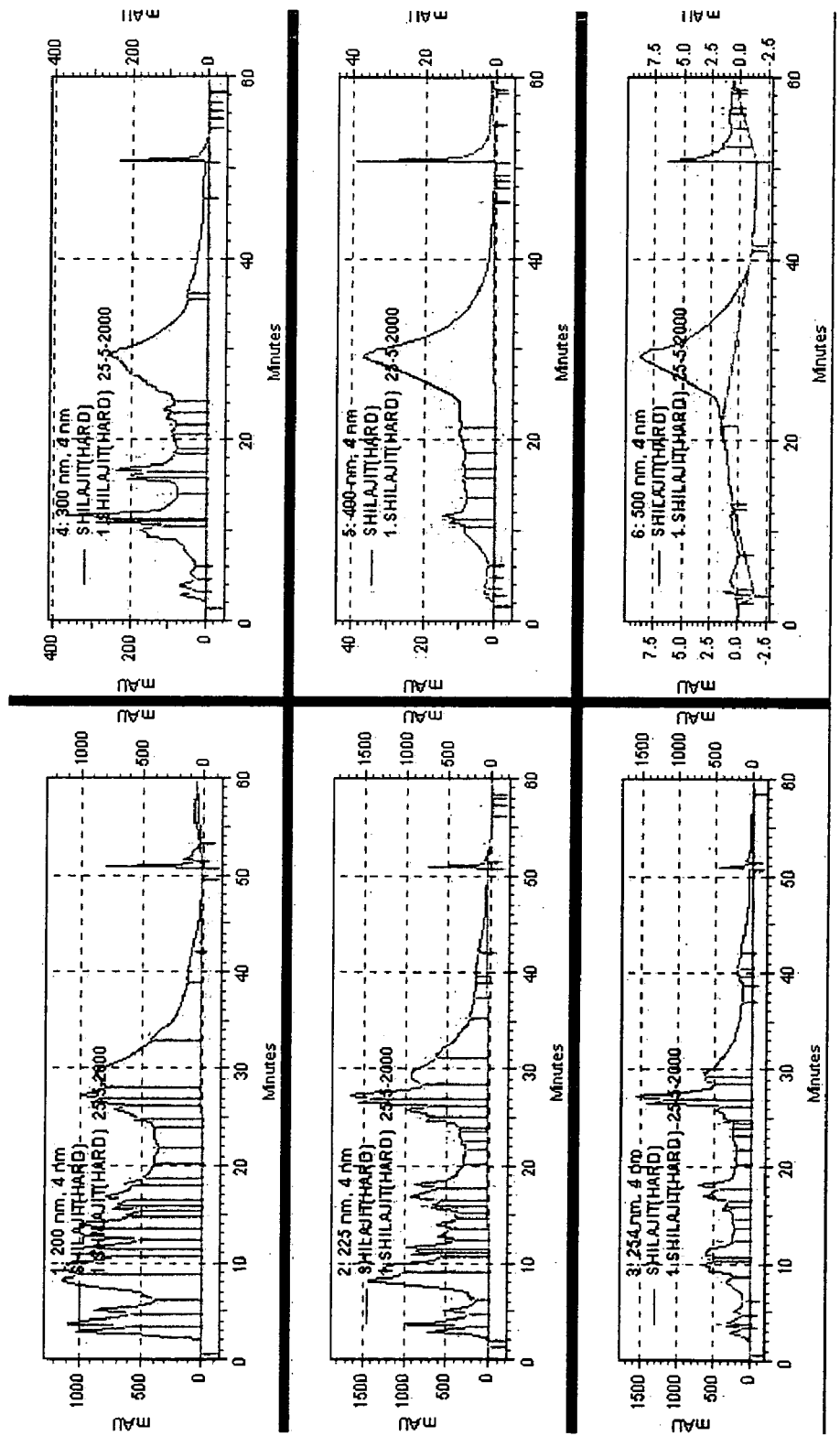
Figure 9 – Prior Art

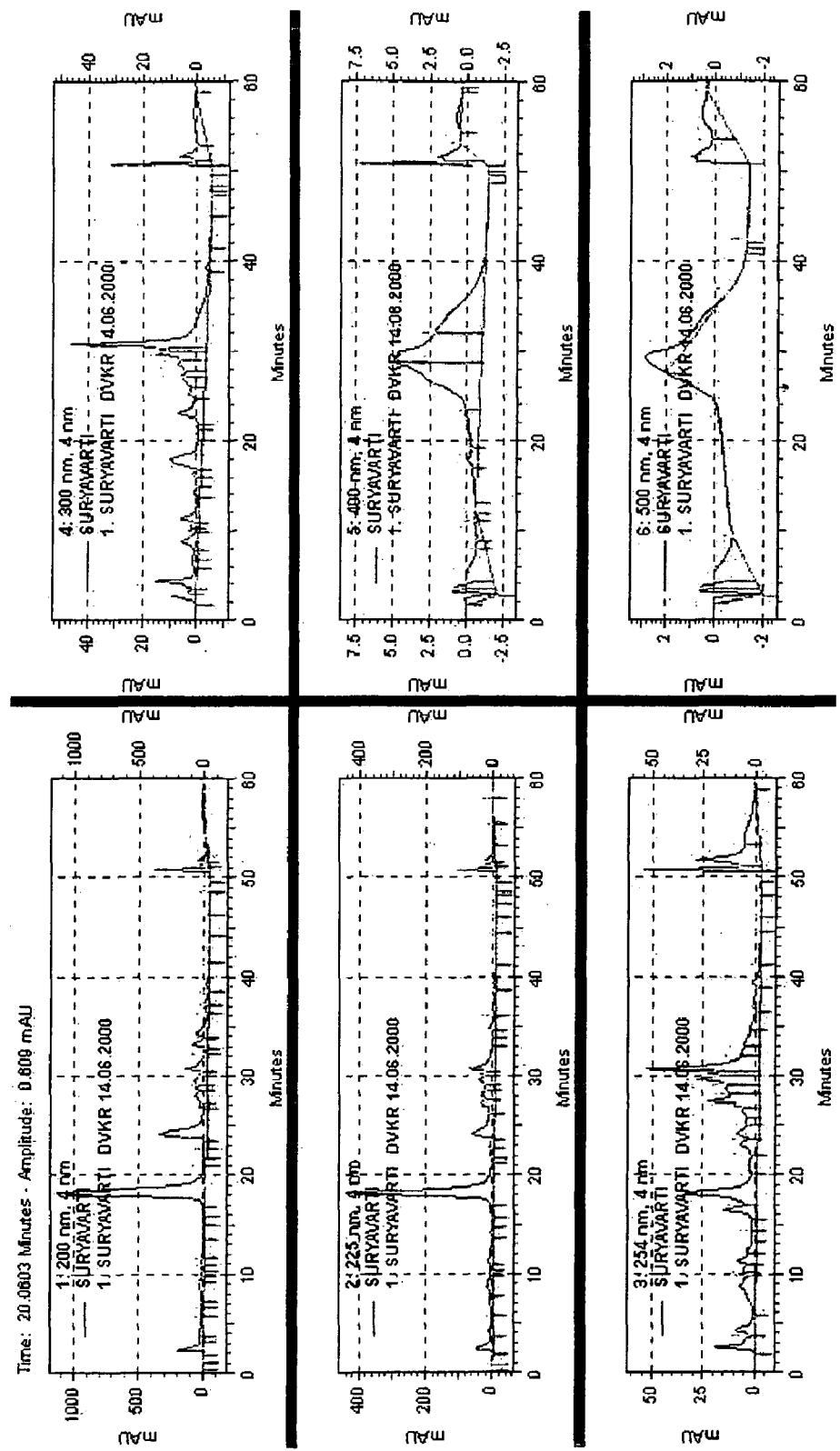
Figure 10 – Prior Art

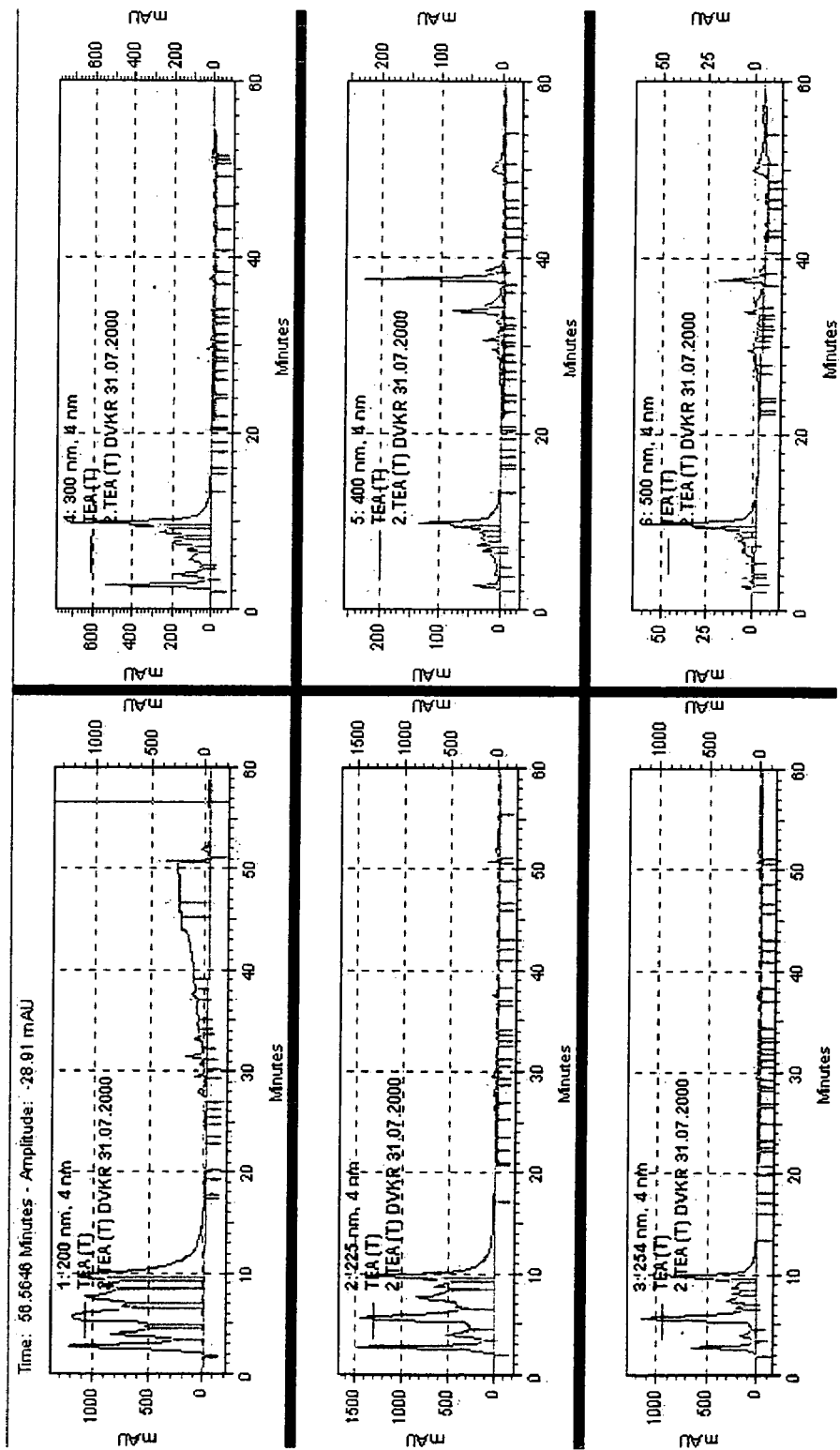
Figure 11 – Prior Art

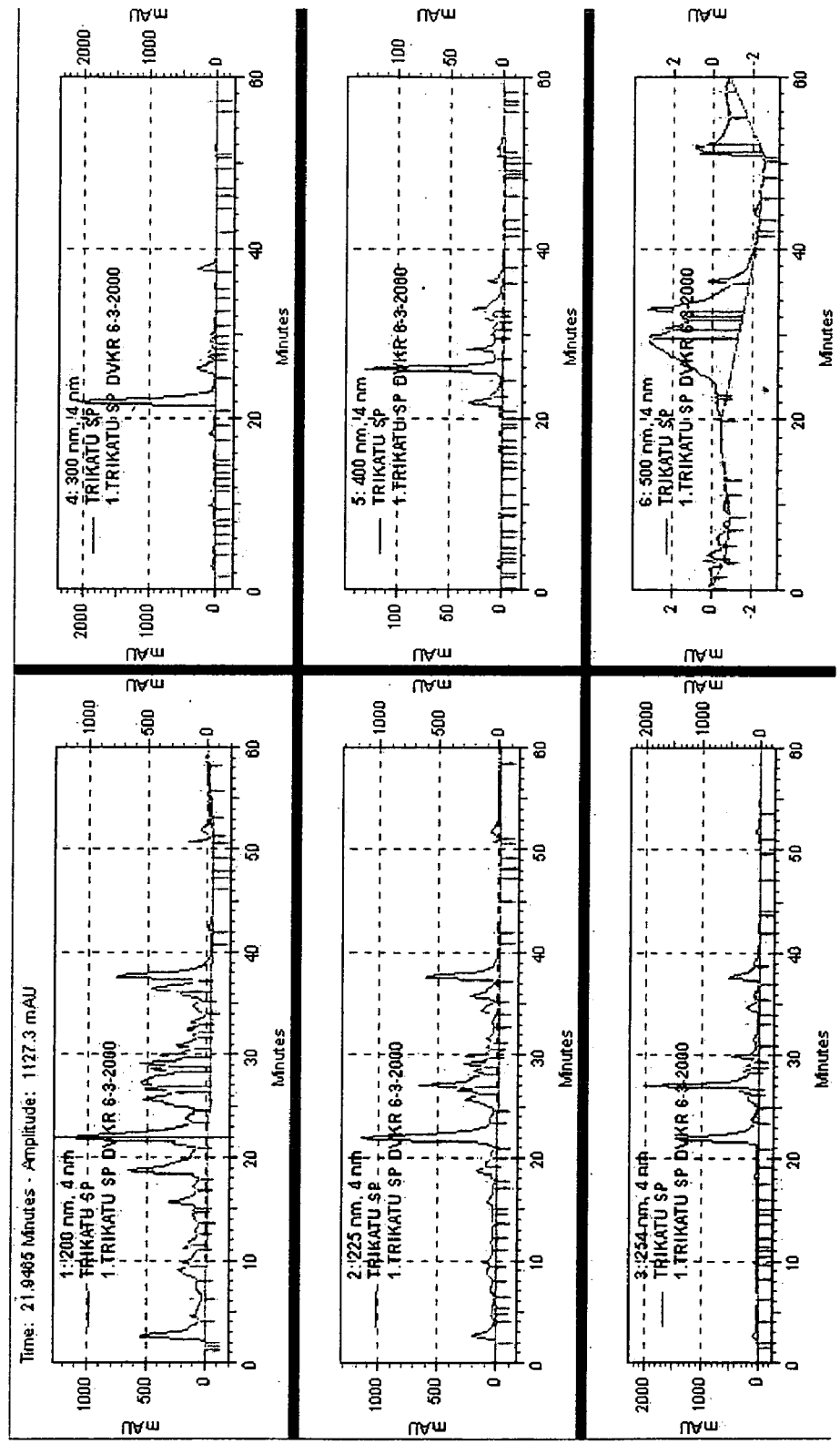
Figure 12 – Prior Art

PITTA HARA

PITTA HARA

PITTA HARA

PITTA HARA

PITTA HARA

PITTA HARA

KAPHA HARA

KAPHA NANA

KAPHA HARA

KAPHA HARA

KAPHA HARA

KAPHA HARA

VATA HARA

VATA HARA

Figure 16C
VATA HARA

VATA HARA

VATA HARA

VATA HARA

PITTA KAPHA HARA

PITTA KAPHA HARA

PITTA KAPHA HARA

PITTA KAPHA RARA

PITTA KAPHA HARA

PITTA KAPHA HARA

KAPHA VATA HARA

KAPHA VATA HARA

KAPHA VATA HARA

KAPHA VATA HARA

KAPHA VATA HARA

KAPHA VATA HARA

PITTA VATA HARA

PITTA VATA HARA

PITTA VATA HARA

PITTA VATA HARA

TRI DOSHA HARA

TRI DOSHA HARA

TRI DOSHA HARA

TRI DOSHA HARA

FINGER PRINTS OF CURCULIGO ORCHIOIDIS (KALIMUSALI)

FINGER PRINTS OF CURCULIGO ORCHIOIBIS (KALIMUSALI)

FINGER PRINTS OF ASPARAGUS ABESCENDENS (SAFED MUSALI)

FINGER PRINTS OF ASPARAGUS ABESCENDENS (SAFED MUSALI)

Figure 25
Figure : Indian Eco-regions
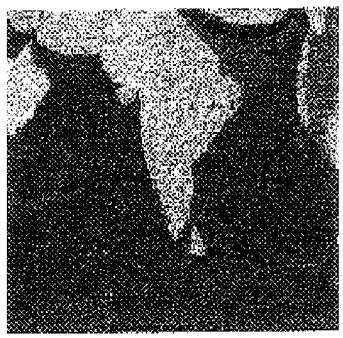
India-Eco-regions
India-Precipitations-January
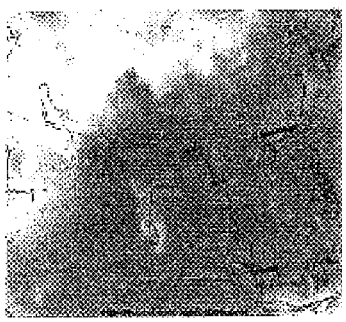
India-Precipitation-July
India-India precipitation -Annual
India-Temparature-January
India-Climate map Figure 69
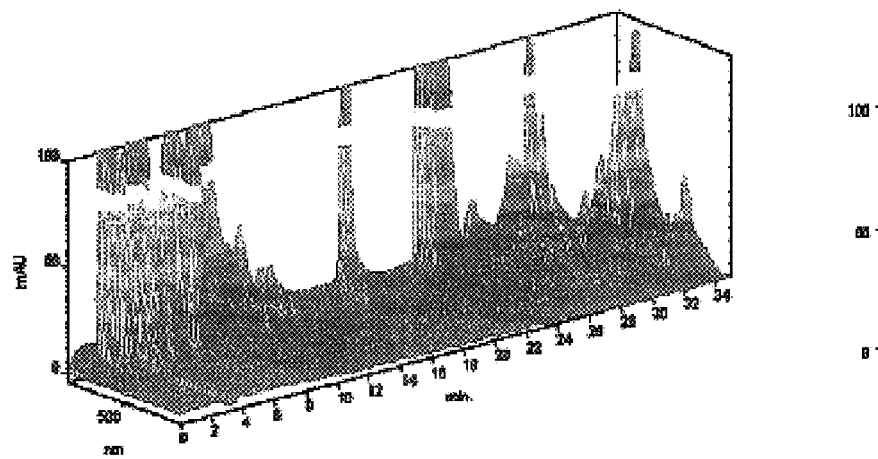
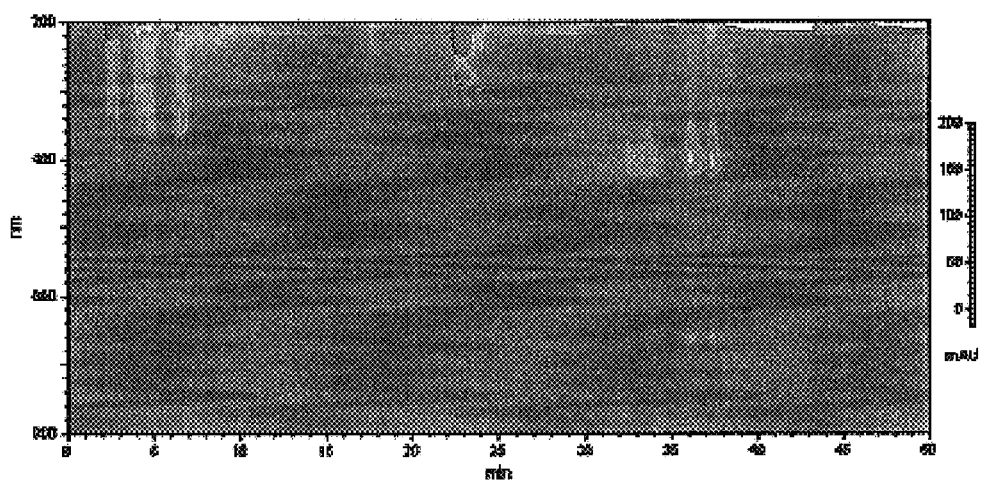

Figure 70
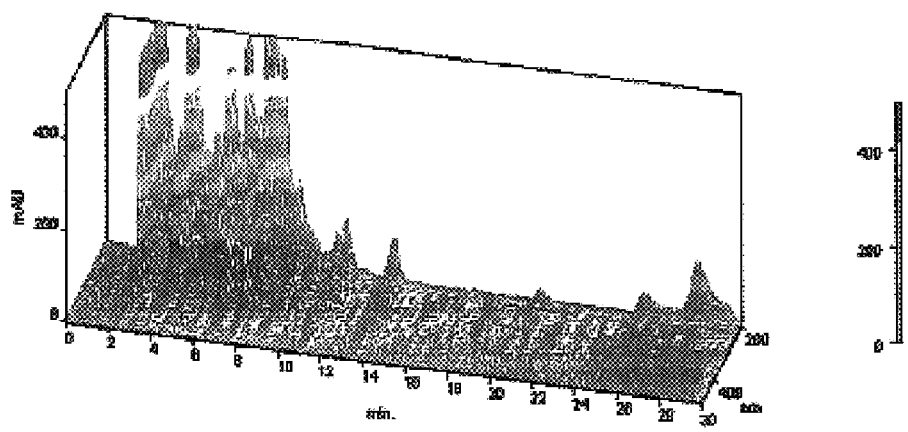
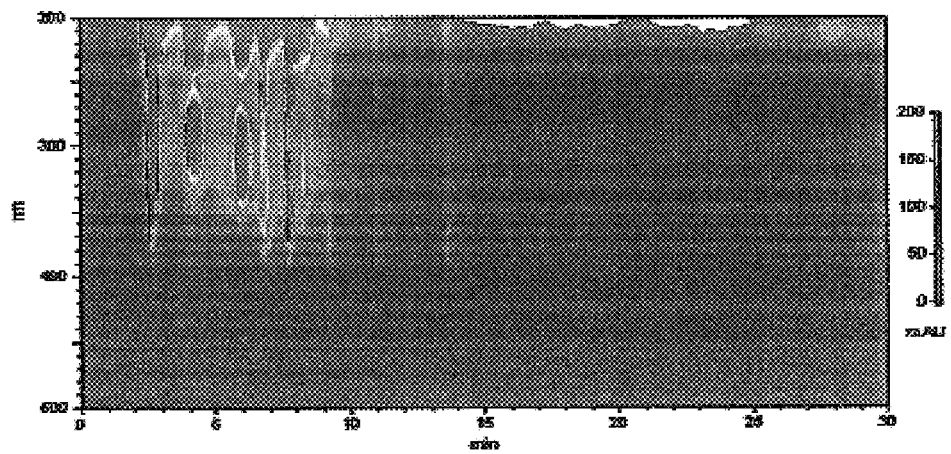

Figure 71
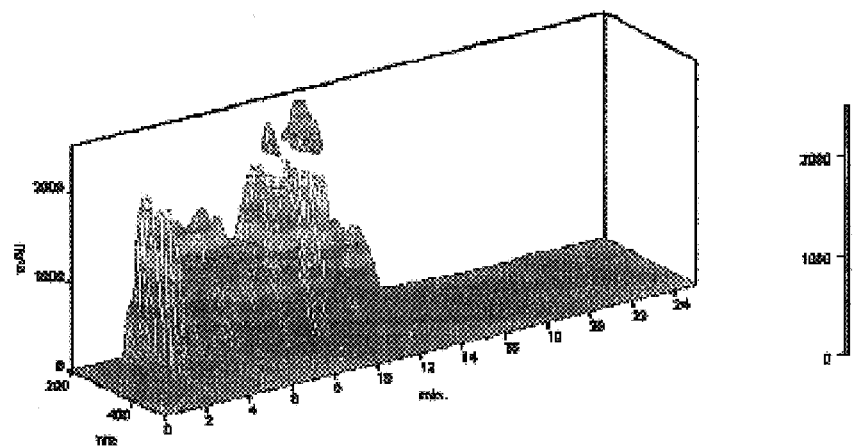
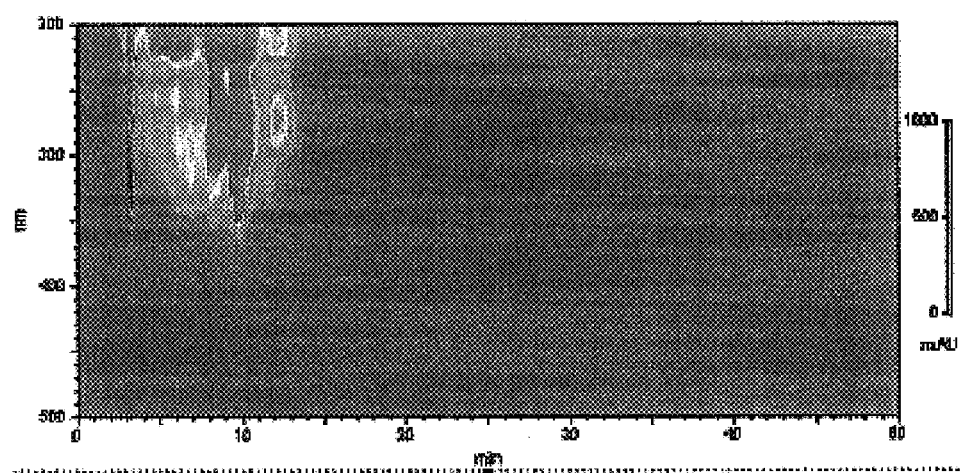

Figure 72
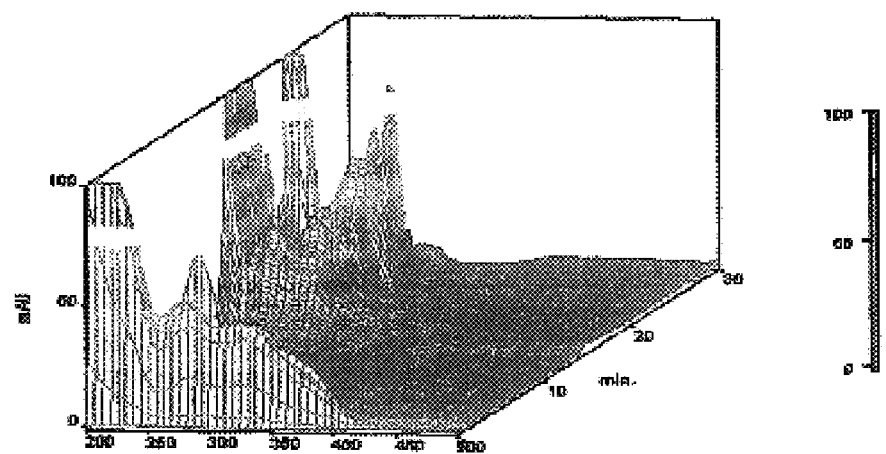
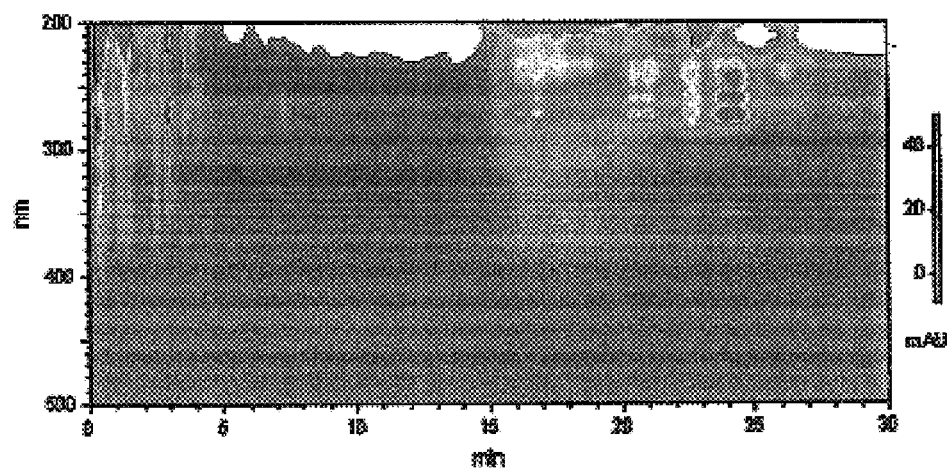

Figure 73
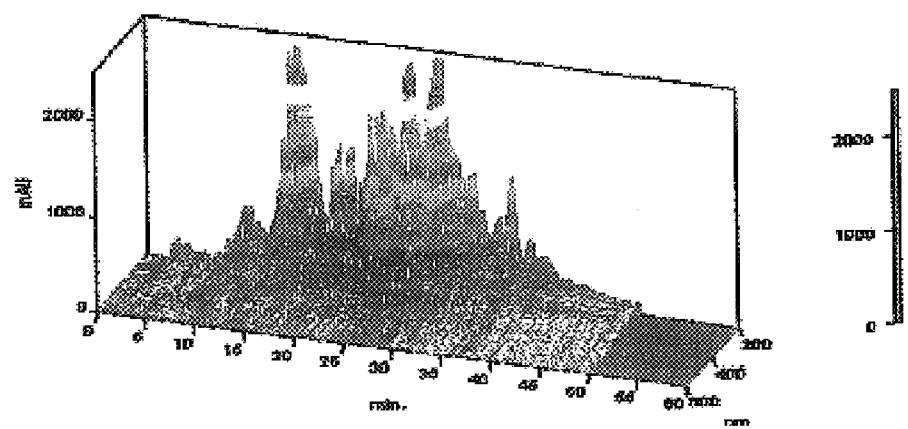
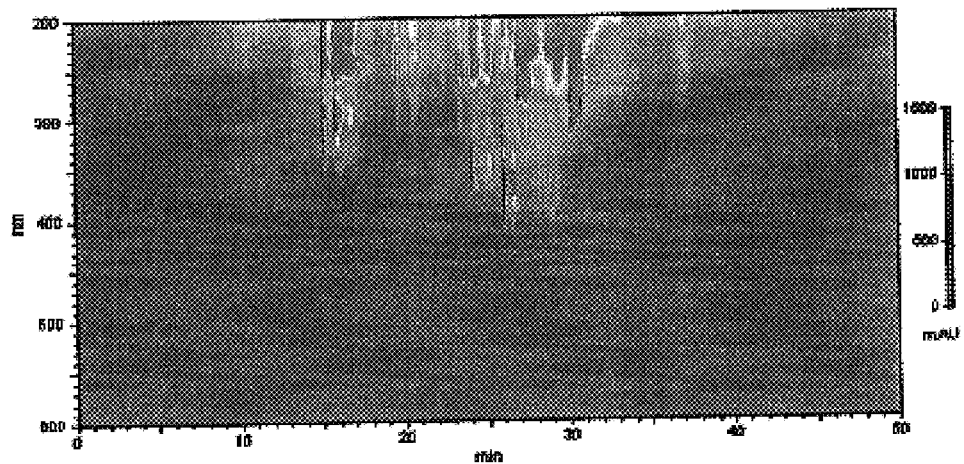

Figure 74
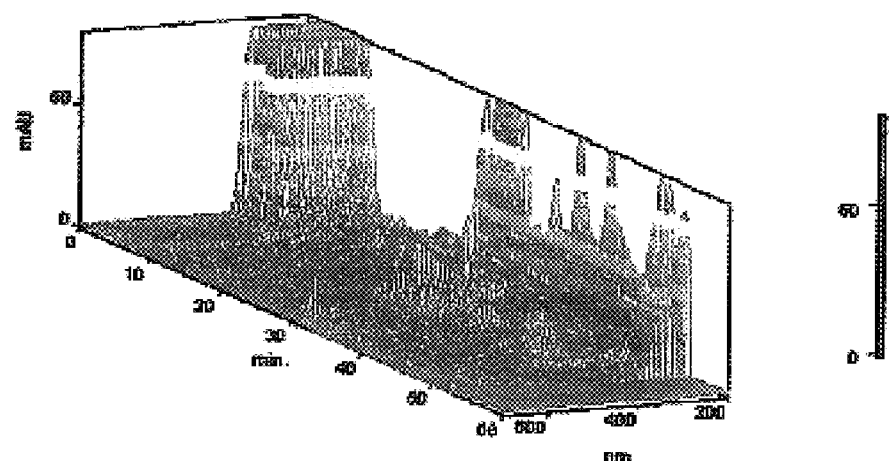
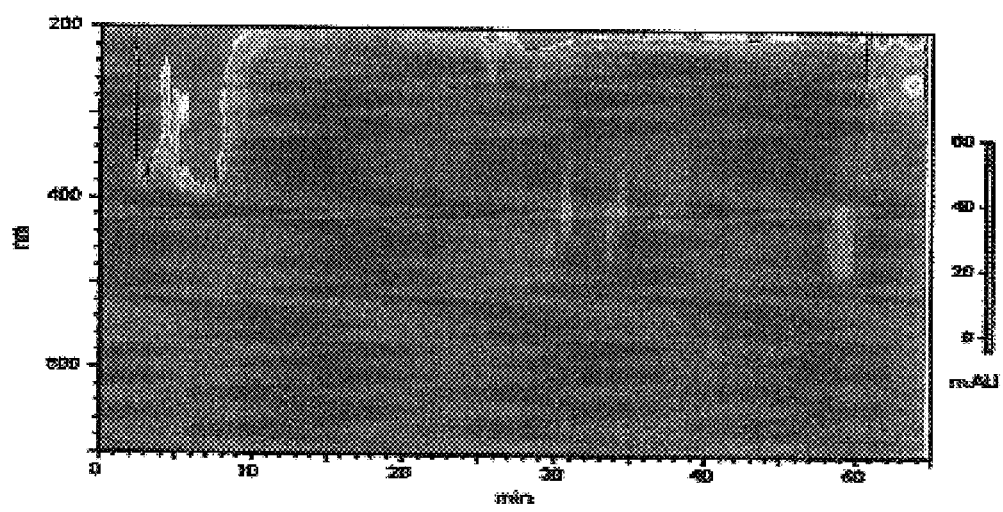

Figure 75
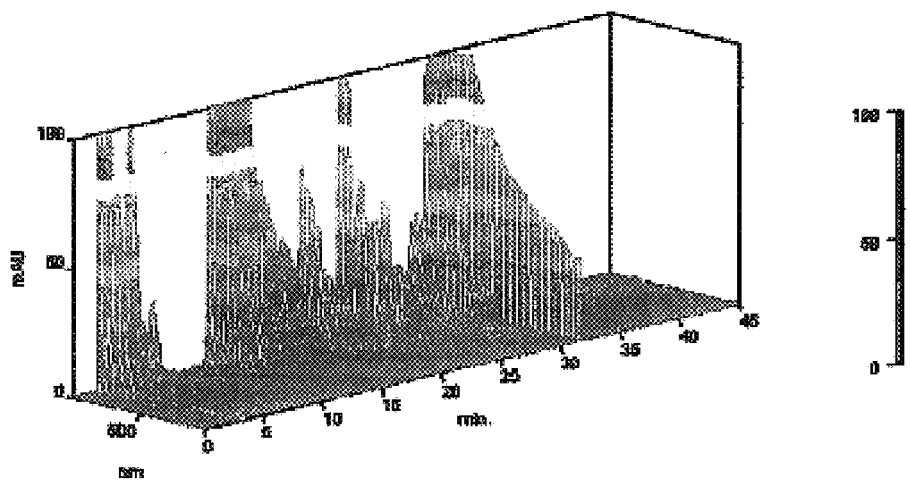
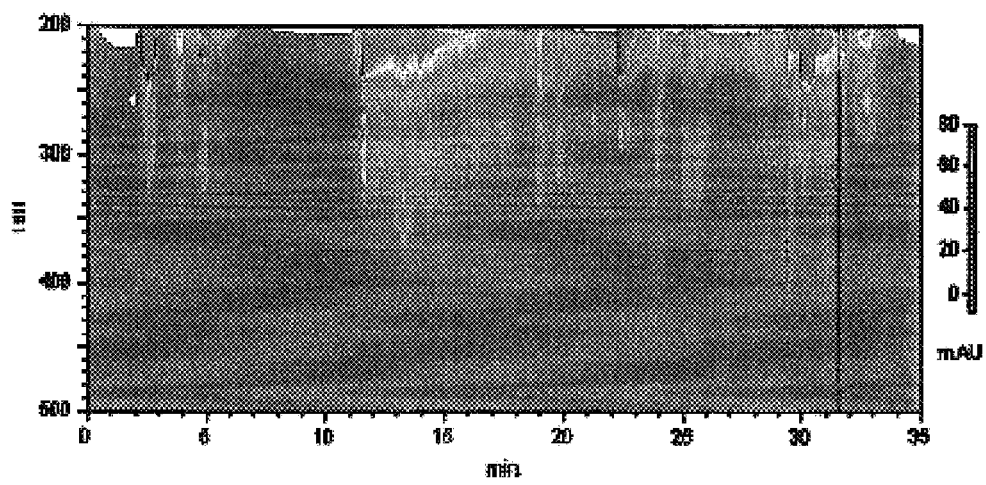

Figure 98
Name of the product: Krimikutara Ras
Owner: Industry
Finger prints:
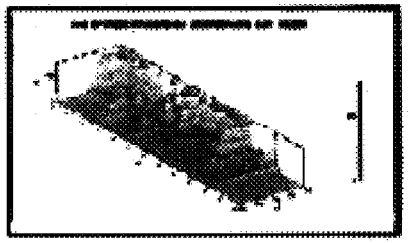
Mfg. Date:
Date of expiry:
Individual constituents:
Batch number:
Lot number:
M.R.P:
Dosage:
Precautions:
For Children:
For pregnant woman:
Barcode:

| | |
|---|---|
| Pitta | 2 |
| Pitta-Kaph | 1 |
| Kapha | 1 |
| Kapha-Vat | 1 |
| Vata | 3 |
| Vata-Pitta | 1 |

METHOD FOR CHROMATOGRAPHIC FINGER PRINTING AND STANDARDIZATION OF SINGLE MEDICINES AND FORMULATIONS

TECHNICAL FIELD

The present invention relates to a novel method of chromatographic finger printing useful for chemical and therapeutic standardization. More particularly, the present invention relates to chromatographic fingerprinting of organic and organo-metallic molecules which have UV-Visible radiation absorptive property present in a plant, animal or any other source capable of being used as a single or formulated medicine. The invention facilitates bar coding of one or many constituents present in the finger print images. It also facilitate commercial utilization of the fingerprint database having all the information about the medicines, development and using ERP (Enterprise Resource Planning) and CRM (Customer Relationship Management) net work applications like vending machines etc.

The present invention employs a novel method of the utilization of the Contour and 3D chromatograms of an herbal medicine and formulation developed under standardized experimental (chemical and instrumental) conditions proposed as a chromatographic finger print of the medicines.

In addition, the present invention relates to a computer-based method for the analysis of such chromatograms. This novel method is very much used for an authentic identification of the chemical constituents of the single medicines and formulations.

BACKGROUND ART

History of Traditional Medicines in the World

The ancient man after many years of evolution started thinking about him and tried to understand the nature. He started living under a cover, the caves and in-groups. The process of thought has encouraged him to understand the nature and its inter action with the living beings. He started using the naturally available flora and fauna for his daily needs, in which he used the plant and animal material for his dietary and health needs.

Under this process, he explored the properties of various components in the world, like geological, astral and medicinal properties of various biological and plant materials. This started happening from the Stone Age on words. He went on discovering, standardizing and using naturally available materials for his day-to-day living.

This took place in many places of the earth parallel in different parts of the world and it developed more in places where civilization has developed more based on the intellectuality. Therefore, the history of medicine has a direct relation with the history of civilization.

The evidences of an well-organized system of medicine in India were traced in Harappa and Mohanzadaro (History of Medicine in India, Dr Priya Vrit Sharma, Indian National Science Academy, New Delhi). In the Indus valley civilization, a system of medicine has prevailed, in which drugs of vegetable, animal and mineral origin were used. The Osadhisukta of the Rigveda is the oldest document of the knowledge about plants and herbal medicines. Medicine in India owes much to the traditional knowledge of Atharvaveda of which Ayurveda is said as an Upaveda. A large number of disease-syndrome relationships were defined and described by Charaka and Susruta in their medical treatises 'The Samhitas'. The treatment was also prescribed in a systematic manner and on rational basis.

On the other hand, it was realized that the biological phenomena could not be universally explained by mechanical means as each individual varies in his basic constitution i.e., Prakruthi that must be kept in mind while prescribing diet or drug to the patient. The binary concept like Prakriti-Purusha, Yin-Yang, Normal-Abnormal was seen in almost all philosophies.

Diseases are manifestations of humoral imbalance, which have to be tackled comprehensively on the psychosomatic basis. Health accordingly is equilibrium maintained on physical, mental and spiritual levels. Thus, the Tri-dimensional definition of health as propounded by Susrtuta is the ideal one, which has been reflected in the definition, adopted by WHO in modern times.

After going through the ancient literature it was found that, the medicines were standardized using their physico-chemical properties of the materials. The color, texture, odor and taste were used as a measure of the efficacy of any medicine. Even the shape of the medicines was used to understand the medicinal properties of the medicines. A summary of different philosophies and various factors used in the therapy is given in Tables 1–6 which are appearing in the later part of the description. FIG. 1 accompanying the specification gives a detailed information on the individual philosophies and concepts of Indian Ayurveda and Chinese Traditional medicines (Medicine in China by H. M. Sais and A hand book of Chinese Healing Herbs by Daniel Reid, Simon & Schuster) in particular and other philosophies in general. The therapeutic efficacy of a medicine ultimately depends on the chemical constituents present in the medicines under use and it is the chemical properties of the constituents that are going to bring a required change in the chemical constitution of the living animal.

Many Ayurvedic (one kind of Indian system of medicine) scholars have defined and classified the medicines based on color and their therapeutic efficacy. A brief summary is given in Table 7, which appears in the later part of the description. Thus, the physico-chemical properties of the materials and man is taken in to consideration to understand the properties of them and use for the therapy to achieve required therapeutic results. Tables 8–9 which are appearing in the later part of the description gives the information about how the physical properties (color) and chemical properties (taste) are used for understanding the therapeutic efficacy of medicines and their influence on the physiology of the human body. One part of the present work also uses the same methodology, but with instruments.

In general, the constituent molecules present in the drugs and foods can be broadly classified in to three categories as polar, medium polar and the non-polar molecules. The total polarity of the molecule depends on the total Electrophlic and Nucleophilic moieties attached to the molecule along with the unsaturation of the molecules by their conjugation. The living human body, animal body and plants will also contain the same type of molecules wherein different polar molecules will carry out different functions. Diseases were cured using the medicines of same polarity as that of the disease causing chemical constituents, i.e. the medicines which can create the disorder can cure the same disorder, as said by Dr Hanemann.

WHO Definition of Herbal Medicine:

WHO has defined herbal medicine as a "Finished, labeled medicinal products that contain as active ingredients aerial or underground parts of plants, or other plant material, or combinations thereof whether in the crude state or as plant preparations. Plant material includes juices, gums, fatty oils, essential oils, and any other substances of this nature. Herbal medicines may contain excipients in addition to the active ingredients. Medicines containing plant material combined with chemically defined active substances, including chemically defined, isolated constituents of plants, is not considered to be herbal medicines. Exceptionally, in some countries herbal medicines may also contain, by tradition, natural organic or inorganic active ingredients which are not of plant origin".

The objective of these guidelines, therefore, is "to define basic criteria for the evaluation of quality, safety, and efficacy of herbal medicines and thereby to assist national regulatory authorities, scientific organizations, and manufacturers to undertake an assessment of the documentation/submission/dossiers in respect of such products". As a general rule in this assessment, traditional experience means that long-term use as well as the medical, historical and ethnological background of those products shall be taken into account. The definition of long-term use may vary according to the country but should be at least several decades. Therefore, the assessment should take into account a description in the medical/pharmaceutical literature or similar sources, or a documentation of knowledge on the application of an herbal medicine without a clearly defined time limitation. Marketing authorizations of similar products should also be taken into account. As per the report, the assessment of quality should be done for the following parameters.

WHO guidelines were given for the finished product for which, the assessment of efficacy, activity, evidence required to support indications and combination products. Many herbal remedies consist of a combination of several active ingredients, and as experience of the use of traditional remedies is often based on combination products, assessment should differentiate between old and new combination products. Identical requirements for the assessment of old and new combinations would result in inappropriate assessment of certain traditional medicines. In the case of traditionally used combination products, the documentation of traditional uses (such as classical texts of Ayurveda, Traditional Chinese medicine, Unani and Siddha) and experience may serve as evidence of efficacy.

An explanation of new combination of well known substances including effective dose ranges and compatibility should be required in addition to the documentation of traditional knowledge of each single ingredient. Each active ingredient must contribute to the efficacy of the medicine. Clinical studies may be required to justify the efficacy of a new ingredient and its positive effect on the total combination.

In the report, it was also mentioned that the manufacturing procedure and formula, including the amount of excipients, should be described in detail. A finished product specification should be defined. A method of identification and where possible, quantification of the plant material in the finished product should also be defined If the identification of an active principle is not possible, it should be sufficient to identify a characteristic substance or mixture of substances (e.g., "chromatographic fingerprint") to ensure consistent quality of the product. The finished product should comply with general requirements for particular dosage forms. For imported finished products, confirmation of the regulatory status in the country of origin should be provided. The WHO Certification Scheme on the quality of pharmaceutical products moving in international commerce should be applied.

More details about stability, assessment of safety and utilization were given in the said WHO report.

The effective regulation of the quality of herbal medicines moving in international commerce also requires close liaison between national institutions that are able to keep under regular review all aspects of production and use of herbal medicines. Also, to conduct or sponsor evaluative studies of their efficacy, toxicity, safety, acceptability, cost and relative value are compared with other drugs used in modern medicine.

Hence, as mentioned above, there is a need for an authentic method of quality control as proposed in this work. It is clearly mentioned that there is a need of a method for all the above purposes. The proposed analytical will give answers for almost all of the needs described above.

Existing Methods of Standardization:

Before explaining the method of the invention of standardization, the existing methods of standardization (chemical and therapeutic) and chromatographic finger printing are discussed below.

A. Prior Art on Chemical Standardization:

I) Traditional:

The great sage Charaka explained in his Charaka Samhita that "The understanding of the totality of an entity does not arise from a fragmentary knowledge of it" (Charaka Samhita VI. 4.5). This makes it clear that standardization and therapeutic efficacy of any medicine for which all the constituents are not taken into consideration is futile.

The qualitative and quantitative profile of a herbal medicine will vary due to many geological, ecological factors, time of collection, place of collection, age of collection and weather conditions at the time of collection and so on.

Traditional herbalists used to select a medicine based on the organoleptic methods available at that time like color, texture, smell and taste by which they used to assess the chemical and therapeutic efficacy of a medicine.

These methods involve intrinsic knowledge and understanding of the inter and intra therapeutic interactions of the medicines and body constituents to cure diseases. This knowledge varies from individual to individual and depends on the individual skill and ability. Practically, it will be difficult to provide a rational justification for any mechanism to explain, using this method. Hence, modem science uses instruments for various purposes, which eliminates the individual factors and facilitates reproducibility in data and information.

ii) Modern:

The therapeutic property of any food or drug will depend on its chemical and physical status. Thus, understanding the chemical constituents using their physico-chemical properties will help to understand the therapeutic efficacy of the medicine.

The physico chemical properties of the medicines play a major role on the therapeutic activity of the medicine. These properties of molecules can be studied using two parameters, the polarity and conjugative properties. Polarity is a resultant electrochemical property due to different electron donating (nucleophilic) and electron accepting (electrophilic) moieties attached to the molecules along with the unsaturated double and triple bonds present in it. They will influence the rate of activity or reactivity of a molecule in chemical and biochemical reactions. A thorough estimation of the total polarity of the molecule will give the efficacy of a single or group of molecules as to how active they are chemically and therapeutically. Hence, any standardization, which assesses the above properties, will be useful to know their activity.

Along with the polarity, which relates mostly to the Electro-chemical property of the molecules the physical structure of the molecule also play an important role in the reactivity of the molecules. The more the number of active sites attached to the molecules, the more reactive they will be. The more the molecule is conjugated (having alternative double bond and triple bonds) the more it will be reactive chemically and so therapeutically.

The second parameter that influences the activity of the molecule is the spatial arrangement of atoms in the same molecule, which differs structurally. Due to this reason, the isomeric (geometric and chiral) molecules play an important role in the biological activity. This stereo-selective nature makes the molecules highly selective in their activity in the body where in a large number of biochemical pathways will be working parallel without cross interactions and interference's. Hence, the chemistry of chiral drugs has become very important. In other terms, no key (chiral molecule) will open a different lock (receptor).

Plants usually prepare a plurality/combinatorial library of molecules having the same basic mother structures and varying in the functional groups attached to it. For example, flavones, aurones and chalcones of flavoniods as they exist in nature and a single plant having such set of molecules will act like a multi drug.

Usually molecules having unsaturation and more conjugation absorbs the electromagnetic radiation in the UV-Visible radiation (200–800 nm). When the compounds interact with radiation they absorb at a specific wavelength (absorbance maxima) based on their chemical, conjugative and structural properties. It is called the characteristic wavelength. A molecule can have more than one-absorbance maxima based on its structural and functional properties. When a compound absorbs a particular color from the wholesome of the white light it will express the resultant color of the other colors unabsorbed. Thus, the materials will express different colors based on their chemical constituents absorbing various colors from white light and showing that their color is due to the various functional groups attached to it. (Table No 10, which appears later part of the description, explains the same). The same is taken as a measure of the chemical and physical properties of the molecules in spectrophotometry.

For example, the red colored medicines absorbs at 500–600 nm range. Thus, all the red colored medicines will have a peak in this wavelength range having specific structure and activity. Hence, the color of the medicines is being used as a measure of its therapeutic and chemical efficacy of the medicines. In ancient times, medicines were classified therapeutically based on the color. The present method proves the same. The FIG. 2 which accompanying the specification depicts relation of colors with humors shows the effect of different colors on different diseases.

FIG. 3, which accompany the specification, the fingerprints of two Shilajit samples prepared by the method of the invention, shows the difference in the chemical profile of both samples. Shilajit is a carbonaceous material that forms due to storage of vegetable and animal matter inside the earth for many years. Mostly due to lava floated over a forest destroying flora and fauna. This after undergoing many geological changes becomes carbonaceous material called Shilajit. It is abundantly available in Russia. It is the most widely used as medicine in the world. It is observed that although the general pattern of the molecules is found to be similar in Shilajit samples of different sources, the variation in the conjugative properties of the molecules is found different. This makes these medicines vary in their therapeutic efficacy hence, this type of fingerprinting is useful.

In the modern chemical analysis methods, determination of the percentage of active principles viz., alkaloids, flavonoids, enzymes, vitamins, essential oils, fats, carbohydrates, proteins, ash, acid-insoluble ash, and crude fiber is done by various analytical instruments. Some examples shown below explain how standardization is done in modern science.

It is reported (WWW//Shilajit, Fulvic acid etc,. html) that, one of the very important medicines used in Indian System of medicine Shilajit, is reported to have many compounds along with fulvic acids, and is claimed to be active principle. As this medicine from bituminous source is collected from earth stored for many years, it can be seen that the more it is in stored in the earth, the more it will be therapeutically active. Nevertheless, in the entire globe, the geological variations may not produce same molecules in all samples collected from different parts of the world. Another factor that influences the chemistry of these drugs is the purification process, which also needs to be standardized.

It is reported (WWW//Herbology. html) that, mostly standardization is done for the individual key components, which have been empirically, and scientifically proven to be most advantageous for the human system. So usually, standardization is done for certain molecules out of all present, which are found to have activity. However, the synergistic effect of other compounds present in the medicine making the total profile of the medicine should be taken into consideration for its efficacy.

It is reported (WWW//Tribulus Terrestrius puncture vine. html) that, the alcoholic extract of the fruits of Tribulus Terrestrius shows antiurolithiatic activity. In addition to this, the extract also shows a significant diuretic activity. The alkaloid Harman has been reported from the herb and Harmine from the seeds. The plant contains saponins, which on hydrolysis yield steriodal sapogenins. Many molecules of flavonoid in nature are reported in which the active principle is found saponins. The analytical report is given for the heavy metal analysis and total saponins content (20% w/w)

It is reported (WWW//Charak_com.—Quality control page—html) that, Human life is a synergy of Mental, Physical and Spiritual components, which are related to the Indian Philosophy of Ayurveda where Pitta, Kapha and Vata are considered as the basis for the total health of human beings. More details of standardization are given in the description of traditional methods of therapeutic standardization.

It is reported (WWW//Standardized Herbal Extracts\ A herbalists Perspective's, Dr.Micheal Tierra L. Ac.O.M.D html) that, due to European Guaranteed Potency Law, it becomes compulsory to standardize herbal medicines. The meaning of herbal standardization is defined as quantification of an active constituent or marker extract, where in the activity is attributed to be the most.

It is explained (Frank R Stermitz et al, PAINS/Feb15, 200/Vol 97, No 4, pp 1433–1437) that, in the plant *Berberis Aristata* the antimicrobial property of the extract is due to the presence of 5-Hydroxy Hydnocarpin, the berberin acting as anti microbial, and without which it will not. Hence, the synergistic effect of the entire constituents should be taken into consideration while dealing with an herbal medicine but not only an active constituent.

WHO in its Regional Publication (Dr Ranjit Roy Choudary, Hrebal Medicine for Human Health, Searo no 20)

clearly mentioned what standardization is and what the member countries should do for the better use of its medicines by the people.

The role of acidity and alkalinity can be understood by carefully understanding the extraction process of constituents from the medicines at different pH values of the extraction solvents. This helps to understand the drug release mechanism in the intestine from the medicine consumed by the persons having different intestinal pH. The role of acidity and alkalinity was studied and understood carefully in understanding the therapeutic efficacy of a medicines. Acidity and alkalinity of organic and inorganic molecules are studied thoroughly to know their properties as shown in Table 11 which appear later part of the specification. Of acidity and alkalinity shows the role of acidity and alkalinity on health (Health in Hands by Devendra Vora, Navaneet publications (India) Ltd).

It is reported (WWW//Chewing. Html) that, in a study it was observed that people with acidic systems absorb more pollution than people who had established proper blood alkalinity. Acid/alkaline (pH) balance is important for normal cell function. More details were given in the article. Hence, the study of the acidity or alkalinity (organic or inorganic) in terms of 'polarity' will give the information of the therapeutic efficacy of the medicines. Hence, the present method, which can do this job, will be of much use to know the therapeutic efficacy of the medicines. Using this proposed method, the acidity and alkalinity can be established for the therapeutic standardization of medicines.

References made above will explain the conventional and reported methods of standardization, wherein the individual constituents are isolated at a preparative scale and compared qualitatively and quantitatively with the same compound present in the sample medicine under study.

In one of the reports (Pharmaceutical grade Saw Palmetto, Khwaja, et al U.S. Pat. No. 6,039,950) it was reported that the different individual fractions of ethanolic extract of Saw Palmetto were studied for their bioactivity by measuring the determination of IC 50 in an androgen receptor binding inhibition assay. Measurement of total fatty acid assay of whole extract and individual fractions were discussed. The fractions containing linolic acid ethyl ester and lauric acid ethyl ester were identified. The activity was calculated for each of the fraction for which androgen receptor binding inhibition has been assayed compared to the total bioactivitty of the sample. The molecular weight and amount of the individual fatty acids were identified and incorporated in to the calculation of bioactivity. The total bioactivity of the extract was calculated comparing to the total percent activity of linolic and lauric acid ethyl ester fractions.

In the traditional medicine standardization, the total profile should be taken into consideration for the therapeutic efficacy of the herbal medicine. Hence, in the present computer-based instrumental method, the total properties of all the constituents are taken into consideration as suggested in traditional concepts world over. The fingerprints of the medicines were proposed as a visual tool and proof for many purposes of dealing with medicines particularly traditional. Before discussing the method of the invention, the existing method of analytical method is given below.

Existing Analytical Methods of Chemical Standardization:

Improvement and use of modern analytical methods and instrumentation have definitely led to excellence in quality control methods of medicines. Improvement in analysis has led to more precise harvesting of many herbs as explained above and helped to prepare standardized extracts.

Although there are traditional methods of identification of medicinal plants like organoleptic, microscopic and physical, none of them gives an authentic identification, as given by a fingerprint of the plant material, as far as the chemical profile is concerned.

Hence, it is proposed that the Chromatographic Fingerprint is much useful for quality control of medicinal plants instead of other organoleptic and microscopic studies. Since, ultimately it is the chemical constituents that are largely going to participate in the therapeutic efficacy of the medicine, along with other properties of the herbal medicines; the analytical data of the chemical constituents should be able to provide the authentic efficacy of the medicine. It is like fingerprint of an individual gives the identity of him.

Till now Thin Layer Chromatography (TLC), High Performance Thin Layer Chromatography (HPTLC).and High Pressure (Performance) Liquid Chromatography are the methods commonly used for the analysis of any organic or organometallic compounds and finger printing. But, all the methods have some merits and demerits for an authentic analysis of medicines. The enclosed Table 12 appearing later part of the description compare various commonly existing methods of analysis, provide a general idea of the merits and demerits of them.

The commercial use of a "Chromatographic fingerprint" on the label of a commercial product is known such as the "Daily Health Capsules" distributed by the Himalaya Drug Co. of Bangalore, India. Except for setting forth the assay of the constituents no more information is given on the product label as to the finger print.

After observing the above Table, it is found that the most suitable technique available for the analysis of a mixture of compounds is "Chromatography", which gives the profile of the mixture after the separation and identification with a suitable detector.

Out of the different types of chromatographic techniques available, the best suitable is 'High pressure liquid chromatography' (HPLC). Although thin layer chromatography was used till recent times, advancements brought out in the equipment and separation columns of HPLC has revolutionized the analytical field of chromatography.

Most of the pharmaceutical analysis was reported in the form of a chromatogram with the peaks due to molecules eluted by a mobile phase mostly reported in the official methods and pharmacopoeias. The constituents are analyzed after eluting on a HPLC separation column detected by using any suitable detectors for analysis.

Usually the chromatographic analysis is done using a reference standard (internal or external). Without a standard reference material, the analysis has no meaning because the peak of the chromatogram does not provide any kind of chemical properties of the compound eluted. Hence, the confirmation of the qualitative and quantitative properties (spectral or chemical) of the components are unclear.

In the qualitative and quantitative analysis of medicines/drugs (Single or Formulation), the emphasis is given mainly on the spectral and chemical properties of the components eluted after analyzing the sample. The analysis is done based on the influence of Electro magnetic radiation on the analytes (say the UV-Visible radiation) and their response to it. In the existing method of chromatography, the analytical report i.e., the chromatogram is not giving any of the chemical properties like polarity and UV-Visible absorptive properties of the constituents. The chromatogram is not able to show the presence of the molecules which does not absorb at that wave length or have a different "Absorbance maxima" other than the set wavelength (say 225 or 254 nm).

If the sample is 100% pure and if it is a known molecule then the analysis at a fixed wavelength is acceptable, but it is highly impractical in the case of medicines where in more than one active molecule are present. Some examples shown at single wavelength are given in FIGS. 5–12 where in the respective chromatograms at various wavelengths are given. None of the single chromatogram is able to provide complete information about the chemical properties of the constituents present in the medicine particularly in traditional medicines where more than one active principle may be existing. When the chromatograms and the fingerprints are compared, the utility of the fingerprints can be under stood.

Hence, any chromatogram presented at a specific wavelength is not able to provide the complete chemical profile of the ingredients present in a single medicine and a formulation. So, the chromatogram is partial in its report, and is not acceptable. Any analytical method, which is not giving complete information of the analysis, is not scientifically acceptable.

In the analysis of herbal medicines, where different types of molecules are present having different spectral properties (The absorbance maxima) the chromatogram at a fixed single wavelength will not be a meaningful analytical report or the chromatogram.

In the use of herbal medicines, the medicine as a whole is used with some standard therapeutic conditions prescribed in the ancient literature and scripts. Hence, the concept of searching for an active ingredient is said to be incomplete, because it is the total profile that is responsible for the medicinal property of the medicine. So, any analytical method, which does not speak about the complete chemical properties of all of the constituents present in the medicine under study, will not be useful.

Also the qualitative and quantitative profile of an herbal medicine vary due to many ecological factors like time of collection, place of collection, age of collection and monsoon conditions at the part of collection and soon.

It is already mentioned (Frank R Stermirtz et al,) that the synergy of the other constituents present along with the major constituent is equally important because the first will not be able to do its function without the other constituents present in the extract as explained in the beginning.

B. Prior Art on Therapeutic Standardization:

I) Traditional Method:

The great Indian Medical sages have understood and defined the concept of Indian medicine by clearly defining the properties, constituents and humors of the living beings. They also understood the inter and intra relations amongst them. In almost all the traditional philosophies, the basic concepts include the nature and its role on the humors of the human beings. It is said that the human body is made of seven types of constituents (Saptadhatus). The normal disorders (Tridosha) are of three types. The materialistic properties of any material in the universe are due to five elements (Pancha bhutas). The interactions of different permutation and combination of these elements will influence the health. Hence, the understanding of these properties will help to understand their physical and chemical properties and so, there by their therapeutic efficacy. The philosophers in different parts of world have also developed such concepts suitable for their tradition and society.

In ancient times (pre Samhitic and pre Susrutic period in India), the physicians used Nadisastra (Science of reading pulse) to know the status of the Tridosha (Vata, Kapha and Pitta) at the time of diagnosis to know the health status of the patient. The specific type of pulse (not the heart pulse) is studied to explain the type of disorder pre-dominant in the patient (History of Medicine in India by Dr Priya Vrat Sharma, Indian National Science Academy).

It is used to understand the type of dosha(s) predominant in the patient at the time of diagnosis and the respective dosha(s) to be vitiated to cure the disorder. But this art of reading Nadi (Pulse) was confined to some people of high caliber, personal skill and ability with lot of discipline. Hence, every traditional practitioner was not able to practice it.

To over come this, the art of understanding the physico-chemical properties of the medicines and the humors of the human being had been developed and standardized. The inter and intra relations of these properties with nature which influences health had been studied and standardized thus the art of pharmacology and pharmaco-therapeutics was developed by the physicians.

The therapeutic efficacy of a drug is defined with use of a substance that is capable of bringing about an (pharmacological) action in the human body (Kriyagunavat) and due to the collective functioning of many factors, (samavayikaranam), just as a piece of cloth results because from its many component threads acting together.

In the world, there are two main types of living things, the plants and animals. It is also said that this world is made of five great elements i.e. Earth, Water, Air, Fire and Space (as said Panchabhutas in Ayurveda). The basic properties of these materials are of two types, namely Strong (Powerful) and Mild (Soft). If we accede to this highly tenable logic, we can say that in this world, all actions are due to different permutation and combination series of the above properties, giving a wide range of properties and materials varying in their intensity.

In the philosophy of most of the traditional medicine world over, the co-inherence of the nature of the five constituents is taken into consideration by which the body is made. They will help in understanding the disease or disorder of the patient. This coherence is called Purusha in Ayurveda, Yin and Yang in Chinese medicine. Table 6 appearing later part of the description gives how the Chinese system has used the above two factors, how they were classified and defined to standardize the therapy and diseases.

Chinese medicine classifies the status of the human body as Yin and Yang representing sorrow and happiness as mentioned above. These factors are attributed for various properties of the medicines and living beings. The maintenance of these factors is done holistically by taking the role of chemical, physiological and social factors in to consideration. Most of the time the Chinese medicine has a direct or indirect relation with various bio energy centers located in the body. The art of acupuncture uses the same. The other factors that reported in other philosophies have resemblance with Chinese medicine. After the panchabhautic concept, the concept of Tridosha (Pitta, Kapha and Vata) plays a major role in the Indian traditional medicine and the seven constituents (Saptadhatus) by which the body is made up of. Ayurveda believes in the holistic philosophy of life and emphasis is given for the prevention of diseases rather than curing of diseases.

The holistic approach of ayurveda advocates that the soul, mind and the body are the three integral parts of life and when these are in dynamic equilibrium and harmony, the state is called good health (Arogya). When they are in inequilibrium and disharmony, the state is called disease. (Vaishamya).

According to Ayurveda, Tridosha maintains the physiological features of various systems in dynamic equilibrium status. In other words, harmony of tridoshas bestows good health, disharmony results to disease. Hence, most of the time the tridoshas are dealt with, in curing any disease. The selection of drug is made for the disease that should be dealt with.

A disease is defined as "Any thing that brings a sadness and grief to this person (Purusha) is a disease. They are of four types 1. The accidental (agantavaha) 2. The body born (Sarirah) 3. The Mind born (Manasah) and 4. The natural (Swabhavikah). It is for this reason, most of the traditional concepts deal with both psychosomatic factors to cure the disease along with a disciplined and standardized method of life.

The diseases were classified into three classes generally. 1. The curable (Sadhya) 2. The Mitigateable or manageable (Yapya) and 3. The incurable (Asadhya). As said above, it is mostly considered as those bodily diseases having their source arise by the incompatibilities of the thridoshas viz., Vata, Kapha and Pitta and blood individually or in combination with one another. But, the diseases that arise not due to the above reason like psychological are dealt in a different way. That is why any traditional concept is used to take all the psychosomatic factors in to consideration to deal with a disease. The individual properties of the doshas are explained as given below.

Broadly it is outlined that the Vata or vayu dosha deals with endocrinological, neuromuscular and nervous activities all those that cause the major or the gross dynamics of the life, the foods that cause gas formation can be classified in this category. Pitta dosha refers to digestion and chemical functions or rasa kriya in general and Kapha dosha includes factors providing form, stability, and cohesion and lubrication factors. As the first dosha, 'Vata' is considered to influence the other two it is considered as the key factor for any disease. An elaborate description of these humors is given in elsewhere in the body of the text.

The decrease of vata leads to general dullness in activity. Hence, the drugs, which decrease this dullness, will be of Vata Hara. The decrease of digestive capacity is called as pitta dosha. A medicine, which increase the digestive capacity or activate bile mechanism, will be of Pitta Hara in nature. The decrease of liquidity or mucous will lead to roughness, an internal burning, an emptiness in stomach, a looseness in the joints, thirst, weakness and a continues insomnia. These are the basic symptoms of kapha disorder. Any medicine that vitiates this disorder will be of Kapha Hara in nature.

A detailed description of all the factors is given for various philosophies in order to under stand more generally about different traditional medicines world over. Table No 1 and Table No 2 (which are appearing in the later part of the description) gives an elaborate description of the Indian Ayurvedic philosophy and various components in it.

Hence, to understand the therapeutic efficacy of a medicine or food, one needs to understand their physical and chemical properties. In the ancient times people use to understand these properties using the organoleptic methods like the taste, the smell and the color of the materials. The basic properties classified were 1. Taste (Rasa), 2. Quality (Guna) 3. Potency (Virya) 4. Post assimilative status and effect of the constituents (Vipaka) and 5. Special action (prabhava, geometrical and optical isomer molecules)

It is these three factors namely, the Doshas (Disorders), the Dhatus (constituents). and the Malas (excreta) that are mainly to be dealt for curing a disease or a disorder. If the above-mentioned properties of the medicines tally with the dosha, it will be vitiated or neutralized, thus the disease is cured.

The classification and differentiation of drugs according to Ayurvedic pharmacodynamic and genetic principles vary from one situation to another according to doshic predominance of the patient. In other words there is a relation between the dravya gunas (medicinal properties) and doshas (disorders). Addition or deletion of one or more drugs may be necessitated to treat an identical disease with the patients with different individual doshas or combination of doshas. Hence, Ayurvedic pharmacotherapy is more individualistic according to dosha predominance of the patient and not generalized as in the case of modern medical pharmacotherapy. Identification of properties (Rasa, Guna, Veerya, Vipaka and Prabhava) compatible to doshas is unique and more reliable in Ayurvedic pharmacotherapy.

ii) Modern Method of Therapeutic Standardization:

The existing pharmacotherapy has not taken the above mentioned concepts into consideration. Phytochemists are interested only in isolation, purification and structural elucidation of the active principles isolated from the plants and they passed on them to pharmacologists to study their biological activity. The pharmacologists in turn screen the molecule(s) for pharmacological activity, establish its mechanism(s) of action and substantially rate its efficacy in comparison with the existing standard drugs used in modern medicine.

This concept is in no way going to help the traditional medical practitioners since the isolation of the active principle(s) drastically change the holistic character of the medicines and their therapeutic efficacy.

Instead of assaying the solvent extraction fractions, active principles etc., obtained from the individual plants, the analysis of total extract from a medicine using a solvent compatible to the human cells and cell membranes of the body will be of much use to evaluate the pharmacological activity of such medicines.

In the modern clinical trials conducted for the therapeutic standardization, they are done in three phases (four in the case of international utility), involving large number of people. The information regarding a new medicine to be submitted to Drug Controller generally consists of:

1. Chemical structure
2. Pharmacological class
3. Formulation details
4. Data on animals including data on toxicity studies
5. Data on clinical pharmacology including pharmacokinetics (Behavior of the drug in the human body)
6. Pharmacodynamics (Actions of the drug inside the body)
7. Special studies and status of the drug in the rest of the world.
8 Data on Bio-Equivalence studies The Phase one study is mainly concerned with assessing the drug's safety to know how the medicine is absorbed, metabolized in the human body and excreted, also it envisages to estimate the side effects and the dosage.

The phase two studies are dedicated to test the efficacy in a randomized way. One group of patients will be given the actual medicine and the second with placebo.

In the phase three study, a large scale testing will be taken up to study the effectiveness, benefits and the range of possible adverse reactions of the drug. After successful completion of this step, the industry will go for marketing the drug.

In late phase III and IV studies, pharmaceutical companies will have several objectives. Studies will help to know the efficacy of the new drug compared to an existing drug. The long-term effectiveness and impact on a patient's quality of life due to the new drug will be known. The cost effectiveness of the drug therapy relative to other traditional and new therapies will be known.

But all the above studies are costly and time consuming. They will not be taking into account of the role of the ecological factors, the genetical discipline (as practiced in the Indian family and marriage relations), the psychological, the social and other variable parameters of the patient in to consideration. This will make the effectiveness of the drug limited to a particular group or genetic type of people.

C. Prior Art of Barcoding and Enterprise Resource Planning (ERP) Customer Relationship Management Applications:

The modern method of making any commercial goods proprietary is Bar-coding. For all commercial transactions, the barcode is widely used in many ways. To make the medicines identified as proprietary goods, a novel method of bar coding is proposed in this invention.

It is reported (Peernet bar-code store (Java Active X servlet e-business)) that 1800 character and 2700 digits (Even 9,99,999 numbers) can be fed to a commercially available bar coding software to generate a barcode of any item. When a digital value and/or numerical number is given to the bar-coding software it generates a specific barcode pattern by the logic specified in the software proprietary for a user.

The barcode thus generated will present and display the attached 'display window" file information having all details of the product/label, when a barcode readable vending machine sees (through electronic eye or sensor) the barcode on the product. The barcode can be read from any ERP and CRM applications world wide through network.

Presently the catalogue numbers are being used for bar coding the medicines and related products which does not specifically contain any chemical property of the product as proposed in the method.

OBJECTIVES OF THE PRESENT INVENTION

The main objective of the invention is to propose a novel method of chromatographic finger printing, chemical and therapeutic standardization and bar coding of organic and organo-metallic molecules from a plant, animal or a naturally available or man made materials used as medicines.

Another objective of the present invention is to provide a novel chromatographic finger printing of herbal medicines and formulations which obviates the drawbacks detailed above.

Another objective of the present invention is to provide a complete chemical analysis of the constituents present in the medicine under study and their conjugative properties indicating the therapeutic efficacy as per the traditional concepts of the medicine using new software developed.

Still another objective of the present invention is to provide a novel method for chromatographic fingerprinting of herbal medicines useful for the quick identification of the actual profile of the compounds present in the medicine under use along with their therapeutic efficacy of the constituents.

In yet another objective of the present method is to provide a novel chromatographic finger printing of herbal medicines and formulations using the contour and 3-D chromatograms of the herbal medicines and formulations.

In yet another objective of the present invention is to provide a novel method for chromatographic finger printing of herbal medicines useful to check the adulteration of the compounds present in the medicine under use.

Yet another objective of the present investigation is to prepare a standard analytical parameters like extraction with same solvent ethyl alcohol, same run time 0–60min, same mobile phase acetonitrile along with phosphate buffer having a pH in the range of 5.5–7.5, and a same UV-Visible Range of 200–800 nm.

Yet another objective of the present invention is, to categorize and quantify the constituents of a medicine based on polarity and conjugation from 3-D and contour chromatograms and assess the therapeutic efficacy of the medicine on which humors it is going to act (vitiate).

Yet, another objective of the present invention is to provide a barcode for the selected peak of a molecule given in the image.

Yet another objective of the present invention is to prepare a database of barcodes for the fingerprints developed useful for all types of database applications.

Yet another objective of the present investigation is to generate display windows for all the samples of the fingerprints having the details of the samples like 3-D and Contour fingerprints, the barcode, details of the origin (Industry or Country), manufacturing date, date of expiry, reported dosha, individual constituents used, their assay, batch number, lot number, M.R.P (maximum retail price) etc.

Yet, another objective of the present invention is to attach the display windows with the respective barcodes, facilitating to deal with display windows in all applications whenever they are used as a source of data and information.

Yet another objective of the present invention is, to prepare a database of display windows thus generated and attached to the respective barcodes, to use in the Enterprise Resource Planning (ERP) and Customer Relationship Management (CRM) applications for all commercial networking transactions of the medicines and samples.

Yet another objective of the present investigation is to prepare a database of barcode and display windows and any information, specially required for the regulatory authorities to control the movement of the medicines in and out of the country.

Yet, another objective of the present invention the UV-Visible spectra of the compounds will provide the conjugative properties of the molecules and the concentration of the individual concentrations of the molecules along with the polarity of the molecules.

Yet another objective of the present invention the use of finger print of contour and 3-D chromatograms will be the basis for the identification of chemical constituents to limit the scope of the invention.

Yet another objective of the present invention is to develop a method of fingerprinting for the adulterated food and drug samples, substituted and contradictual food and drug samples and commercial samples of food and drug samples and to identify the pure and adulterated.

Yet, another objective of the present invention is to develop a method of fingerprinting for the organic and organo-metallic constituents in any type samples to identify the chemical constituents present in it for various purposes of quality control and process standardization.

Yet another objective of the present invention is to develop a method of fingerprinting for the Allopathic, Ayurvedic, Homoeo, Siddha, Unani, Chinese, Tibetan and, Kampo (Japanese) medicine samples for the quality control and chemical and therapeutic standardization.

Yet, another objective of the present invention is to develop a method of fingerprinting for the study of variation of chemical constituents in naturally occurring or synthetically prepared samples and to identify and standardize the chemical constituents in them.

Yet another objective of the present invention is to develop a method of fingerprinting for the study of variation of chemical constituents in naturally occurring or synthetically prepared samples and to identify and standardize the variation in chemical constituents in them due to Geological, Ecological, Genotypic and Phenotypic variation factors.

Yet, another objective of the present invention is to develop a method of fingerprinting for the study of chemical constituents in herbal products of single and formulated medicine samples and to identify the chemical constituents in them for chemical and therapeutic standardization.

Yet, another objective of the present invention is to develop a method of fingerprinting for the study of variation of chemical constituents in biological samples and to identify and standardize the chemical constituents in them.

Yet, another objective of the present invention is to prepare a large database, which will give many generalizations of the therapeutic efficacy of a particular group of plants, classified as a group for a particular disease or therapeutic classification.

Yet another objective of the present invention is to provide a method which enables to understand and standardize the Physico-Chemical properties of the medicines like color used in traditional method of therapeutic standardization using conjugative and polarity properties of the individual constituents and the whole medicine.

Yet another objective of the present invention is to provide a method which enables to understand and standardize the Physico-Chemical properties of the medicines like Taste (Rasa) namely Sour, Salty, Pungent, Bitter, and Astringent (Amla, Lavana, Katu, Tikta, and Kashaya as said in Ayurveda respectively) used in traditional method of therapeutic standardization using conjugative and polarity properties of the individual constituents and the whole medicine.

Yet, another objective of the present invention is to provide a method, which enables to understand and standardize the Physico-Chemical properties of the medicines like Quality, Potency, Metabolite after assimilation or such modifications and Specific properties like Chirality of the molecules (Guna, Veerya Vipaka, and Prabhava respectively as said in Ayurveda)

Yet another objective of the present invention is to provide a method which enables to understand and standardize the Physico-Chemical properties of the medicines like Heavy, Light, Cold, Hot, Soft Lubricated Supple, Dry, Slow, Sharp (Guru, Laghu, Sheeta, Ushna, Snigdha, Manda, Teekshna respectively as said in Ayurveda) used in traditional method of therapeutic standardization using conjugative and polarity properties of the individual constituents and the whole medicine.

SUMMARY OF THE INVENTION

This invention relates to a method for detection and identification of principles from extracts of plants or animal, natural or synthetic sources, using chromatographic finger printing techniques, said method comprising the steps of:

i.) extracting the organic or organo-metallic molecules using a suitable solvent;

ii.) subjecting the extract obtained in step (i) to the separation analysis, using High Pressure Liquid Chromatography techniques;

iii.) generating contour and 3D chromatograms of the ingredients eluted based on the pH and polarity;

iv.) converting the 3-D and contour chromatogram obtained into a colored image, analyzing the colored image for its individual colors using the co-ordinates denoting all its 3-dimensional properties of the said image by using an in-built software;

v.) denoting the concentrations of the various constituents eluted with time;

vi.) generating a chromatogram based on color analyzed, having peaks at various retention times along with conjugative properties of the molecules;

vii.) identifying the compounds in the said ingredients by the UV-Vis absorptive properties of the various constituents in the image;

viii.) identifying, determining and classifying the compounds eluted as polar, medium polar and less or non-polar based on the polarity and conjugative properties;

ix.) generating a barcode for a selected peak using the X axis as Retention Time, Y axis as Wavelength, R as number of Red Pixels, G as number of Green Pixels and B as number of Blue Pixels; and x.) generating a database of fingerprints and barcodes and identifying the respective compounds in the samples.

DETAILED DESCRIPTION OF THE PRESENT INVENTION

Accordingly, the novel basis of the present method is, presenting the spectral properties of the chemical constituents displayed in 3-D and contour chromatograms as a novel method of fingerprinting. The chromatogram generated by this method provides the conjugative and polarity properties of the individual molecules present in the medicines giving the therapeutic efficacy of the medicine.

In a molecule the UV-Visible absorbance capacity of the molecules depends on the structure of the molecules. When the double bonds or triple bonds are present in the molecules alternatively in the structure, it is called as conjugated. The more the molecule is conjugated the more it will be chemically and biologically active. Hence the more the molecule is conjugated the more it will be therapeutically active. Thus, the measurement of conjugative properties will give the therapeutic efficacy of a medicine. Hence, the use of conjugate property for the therapeutic standardization is the novelty of the present invention.

A novel method is proposed for the quality control of herbal medicines and formulations mostly useful for the fingerprinting and standardization (chemical and therapeutic) of Traditional Medicines unlike a method being used for analyzing only active ingredient (which is not known in many herbal medicines) for the analysis of medicines at a single wavelength. It gives the total profile of the chemical constituents present in the traditional medicines along with physical and chemical properties of the compounds (Say UV-Visible absorptive property and polarity property). In the first part of the method, an image of the fingerprint of the medicine will be generated. But as image cannot becomes analytical data, a computer-based method is developed to give the qualitative and quantitative data of the ingredients in the form of an analytical chromatographic report. The same is proposed as a novelty of the method of the invention.

The reactivity of any molecule will depend upon the number of double and triple bonds existing in the molecules along with the electrophilic and nucleophilic sites on the molecule. The moieties donating electron and accepting electron will create difference in the total electrical charge of the molecule. This makes the molecule polar. Hence polarity of the molecules will provide information about the capability of a molecule to donate or accept the electron with another molecule. This will control the activity of a molecule. Thus, the information of the polarity of a molecule will speak about the reactivity of the molecule. In the present method, the chromatogram provided by the method will give the conjugative and polarity properties of the constituents present in a medicine in the finger print. Thus, this method is used for the standardization of the medicines to know the therapeutic efficacy of a medicine using their conjugative and polarity properties of the medicines. This is the novelty of the proposed method.

As said above the UV-Visible spectra and polarity of the compounds will indicate the conjugative and polarity properties of the compounds and thus indicating the chemical / medicinal property of the medicines. This profile of spectra of all the constituents in a single picture, "the finger print" as proposed now will become the blue print of the constituents present in herbal medicines and formulations. This becomes a superior method of identification and standardization of herbal medicines than the existing, as the peaks will express the Uv-VIS. Properties or conjugative and polarity properties of the constituents, unlike in a conventional chromatogram taken at a single wavelength along with the quantification of the constituents.

As described in the traditional standardization methods the colors of the medicines were used to know and standardize their therapeutic efficacy. The colors of the molecules are understood by their absorptive properties of the radiation of the UV-Visible range of radiation. Based on the structure, functional groups, conjugation, and the extent of unsaturation the absorbance of a particular wavelength depends. The more the molecule is conjugated the longer the wavelength of absorption will be. Hence, the UV-Visible absorbance of any molecule is widely used in the qualitative and quantitative properties of the constituents. The colors and the therapeutic efficacy of various medicines were given in the ancient literature.

Ultimately the colors of the molecules are due to a specific chemical nature of the molecule. When the same is studied, the chemical property can also be understood. In ancient times the colors of the flames were used for the quality control of metals and related products this, involves the basic spectrophotometric principles. Thus, study and understanding of the interaction of the electromagnetic radiation will be useful to study the chemical nature and thus the therapeutic efficacy of the medicines. The same principle has been used in the present spectrophotometric method of fingerprinting and standardization. The main novelty of the present method involves in the "division of the fingerprint into different therapeutic zones based on the scales of wavelength (Conjugation) and retention time (Polarity) to understand the therapeutic efficacy (in traditional terms) of a single or a formulated medicine" using an instrumental and software based program.

Using the computer-based software developed, a barcode is generated for a selected peak of a molecule given in the image. Where, X is the Retention Time, Y is the Wave length in contour chromatograms and absorbance in 3-D chromatograms, R the red color indicating the highest concentration of the constituent, G the green color indicating the lesser concentration of the constituent and B Blue color indicating still lesser concentration of the constituent are the coordinates provided by the present software, is feed in any commercially available re-salable bar coding software, added in the present software generates a barcode for a single constituent, or for many constituents. The Image of the fingerprint is viewed on a display window attached to it. This will be displayed whenever the electronic eye of the vending machine reads the barcode. This makes the image (Finger print) and barcode proprietary for a product of an industry or a country. This is claimed as another novelty of the method of the invention.

When the polarity of the column is fixed and the polarity of mobile phase is varied constantly in an increased or decreased order, on a reverse phase column, the constituents present in the sample will elute in the order of high polar constituents eluting first the medium polar constituents next followed by non-polar constituents. Care is taken in eluting the constituents in the order of increased or decreased order of polarity such that no constituent of any polarity will be left un-eluted from the column achieving total elution. The order and properties of polarity and elution in the case of normal phase columns are applicable same as in the case of reverse phase column but in reverse. In a normal phase column the non-polar constituents will elute first and followed by polar constituents, based on order of polarity of the mobile phase used for elution.

Thus, a fingerprint developed having the chemical constituents arranged in the increased or decreased order of polarity will help to bring therapeutic generalizations about the medicines. This is another novelty of the proposed method.

The image of contour chromatogram developed after the analysis is divided in to three zones on X and Y-axis. The conjugative property (Absorption of a particular wavelength of radiation) is taken on Y-axis and polarity is taken on the X-axis, as the elution of the constituents is controlled using the polarity of the mobile phase composition. Now as reported in literature the Y axis is scaled as per, the therapeutic efficacy based on wavelength (color). The entire image is divided in to six chambers wherein the chemical constituents have specific conjugative and polarity properties. This in turn is proportional to the therapeutic efficacy of the constituents in the chamber. Thus when a medicine is fingerprinted, based on the color represented for the absorption of a specific wavelength and having a specific polarity, the total colors in that zone is calculated and interpreted for the therapeutic efficacy of the constituents present in it. Thus, the holistic therapeutic standardization and chemical standardization is achieved using this method.

Mostly the elution of the samples were done from high polarity mobile phase to low polarity mobile phase. Thus in the finger prints the constituents present in the first zone (Zone-1) will be of high polar in nature. The same pattern applies to the other zones, the medium polar constituents eluted in the medium polar zone (Zone-2) and the low or non-polar constituents eluted in the non-polar zone (Zone-3). This pattern reverse when a normal phase column is used due to its elution property as described above.

Most of the high polar molecules are highly reactive chemically, thus biologically. When they enter the first part of the digestive system mouth, they will immediately start acting on the biological system and the enzymes present there. Then the constituents will enter the stomach and intestine where they will under go different changes (Post assimilation effects, Vipaka in Ayurveda) due to the digestive juices and their enzymes present in the part. In the process of absorption, the moment the molecules of high activity (high polar) immediately start interacting with the biological system and show their therapeutic properties. This is compared that in Ayurveda, the intestinal part of the human body is classified as Pitta zone, where the high polar molecules are playing a major role. The heat causing mechanism will play an important role in the diseases and biological mechanisms related to. It indirectly indicates the molecules of high reactive, the high polar molecules. After the absorption, the blood with all the absorbed constituents will carry them to heart and the parts related to it. Then the blood will be sent to different parts of the body. In Ayurveda, the upper portion of the human body is defined as the Kapha zone, where the cold mechanism will be playing an important role. Thus, the molecules of medium polar molecules will play an important role in the mechanisms related to this zone.

The low polar and non-polar constituents will be able to enter to the human body only through blood transfer, Thus the body organs where the mechanism of availability of the chemical constituents is only by blood, will be coming in the last category of the polarity. The non-polar oils, fats and other such molecules and mechanisms in the human body are classified as Vata disorders and all such disorders are cure using the same type of materials.

The low and non-polar constituents will be eluting in the last zone of the fingerprint. Thus, this zone (zone-3) is considered as Vata zone. Thus, the basic humors of the molecules can be identified based on their polarity, which facilitates to know on what disorder (dosha) it is going to act upon. Thus, the present method is useful for the therapeutic standardization of the medicines.

Thus the total constituents present in the Zone-1 Pitta zone, Zone-2 Kapha zone, Zone-3 Vata zone are present in the form of a pie diagram which represents the ratio of the efficacy of the medicine on each of the disorder. Thus, medicines having constituents in the order of 50:20:30 will be medicines of tridoshahara of the order of 50%: 200%: 30%.

Thus, the therapeutic efficacy is standardized quantitatively. The increase or decrease of any one or two of the other doshas is done by formulating medicine by adding other medicines and prepare a suitable formulation needed to cure a specific individual. Thus, a fingerprint having the scales of conjugation, absorbance and polarity the 3-D chromatogram will give information about the therapeutic efficacy of the medicine. Analyzing it using all its three dimensional properties of the said image will do quantification of 3-D chromatograms of the medicine. For example if the 3-D chromatogram is considered as a 'cap with a hood' the matching of the entire cap 3 dimensionally, with another sample of different qualitative and quantitative properties, the extent it matched will be presented as an analytical report qualitatively and quantitatively. Here the hood of the Cap is compared to the peak of the molecule at a particular wavelength. A sample with more number will like a cap with many hoods. Thus the matching of the three dimensional coordinates will provide a foolproof method of comparison and analysis. The coordinate it matched will give qualitative and the extent it matched will give the quantitative data of the sample understudy. This is made possible by special software prepared for this purpose. This becomes an ultimate method of quality control. This is another novelty of the method of the invention.

The invention also relates to a software based data processor of 3D chromatograms and color contour image of an ingredient, said processor comprising computing means and capable of a. an analyzer (extracting colors) for analyzing the colored contour image based on the selection of various colors (with standards mentioned in release notes, life cycle, processing) denoting the concentrations of the various constituents eluted with time, and polarity based on retention time;

b. an analyzer for analyzing the 3-D chromatograms of the medicine using all its 3 dimensional properties of the image;

c. a means for generating a chromatogram having peaks at various retention times along with conjugative properties of the molecules eluted with time in a specified order of polarity;

d. an identifier for identifying the compounds in the said molecules by the UV-Vis absorptive properties of the various constituents in the image;

e. a means for correlating the reported biological, therapeutic activity of the of various constituents present in the medicines understudy based on the polarity and the conjugative properties of the molecules by dividing the fingerprint into therapeutic zones on X and Y axis;

f. a means for generating a barcode for a selected peak(s) using the image coordinates viz., X for retention time, Y for wavelength, R for number of red pixels, G for number of green pixels and B for number of blue pixels, provided by the proposed software;

g. a means for generating a database of fingerprints and barcodes for the samples, facilitating all kinds of database utilities like Enterprise Resource Planning (ERP) and Customer Resource Management (CRM) applications; and h. a means for generating a database of the 'display widows' for all the samples to be used by the ENTERPRISE RESOURCE PLANNING (ERP) and CUSTOMER RELATIONSHIP MANAGEMENT (CRM) type of business applications.

Abbriviations Used in the Patent Document

1. ERP: Enterprise Resource Planning
2. CRM: Customer Relationship Management
3. UV-Visible: Electromagnetic radiation in the range of 200 nm to 800 nm
4. Organic molecule: A molecule having basic elements of C, H, N, O, S in its structure.
5. Organo-Metallic molecule: A molecule having a metal along with basic elements of C, H, N, O, S in its structure
6. Contour Chromatogram: A type of chromatogram displayed in the data generated from a Photo Diode Array detector, which scans the sample with electromagnetic radiation in the range of 200 nm to 800 nm. The chromatogram thus generated will provide Retention time on X-axis, range of absorbance (nm) on Y-axis. Different colors will be used to represent different concentrations of the individual constituents.
7. 3-D chromatogram: This is also generated using the same set of equipment as given above. It will be more informative providing the UV-Vis spectra of each of the in-gradients after separation from a mixture. It helps to identify the constituents using the spectrum.
8. Ayurveda: An Indian philosophy written by Indian sages explaining organized science of medicine and health discipline.
9. Oshadisukta: a chapter in Rigveda giving the details of the properties of the medicines used as medicines.
10. Rasa, Guna, Veerya, Vipaka, and Prabhava: Different Physico-Chemical properties of the medicines and materials used to understand the efficacy of the medicines used in Indian system of medicine.
11. Lokapurusha Samanya: Law of Uniformity of Nature 12. Tri doshas: three humors using which the human body is studied viz., Pitta, Kapha and Vata used in Indian system of medicine.
13. Prakriti-Purusha: The first one is compared to Mother Nature (woman) and the second to person (man) used in Indian system of medicine
14. Pitta: A term used in Indian system of medicine for one of the humors in the body in Indian system of medicine to denote the personality or a disease which denotes the digestion and chemical functions or rasa kriya in general in the human body.
15. Kapha: A term used in Indian system of medicine for one of the humors in the body in Indian system of medicine to denote the personality or a disease which denotes the factors providing form, stability, and cohesion and lubrication factors in the human body.
16. Vata: A term used in Indian system of medicine for one of the humors in the body in Indian system of medicine to denote the personality or a disease which denotes the neurological and endocrinological, and nervous activities in the human body.
17. Geological factors: Global variation in soil nature and ground water constitution etc related to earthly components.
18. Ecological Factors: Global variation in tropical regions, monsoon conditions and temperatures.
19. Organoleptic methods: Methods of identification of the properties of medicines like 1. Taste (like Sour (Amla), Salty (Lavana), Pungent (Katu), Bitter (Tikta), Astringent (Kashaya)) 2. Color, 3. Odor and 4. Texture etc., using human sensory organs.
20. Tastes (Rasa Physico-Chemical properties) Properties visibly seen (Color, Size) and felt (Texture) and all physical properties and properties like taste and medicinal related to the chemistry of the individual constituents present in the medicines.
21. The medicines were standardized using their properties like Taste (Rasa), Quality (Guna) Potency (Virya), Post assimilative status and effect of the constituents (Vipaka) and Special action (Prabhava,)
22. Saptadhatus: The 7 elements like Rasa (Body fluids), Rakta (Blood), Mamsa (Muscle), Majja (Bone marrow), Asthi (Skeleton System), Medas (Fat) and Shukra (Reproductive) constituents present in the human body used in Indian system of medicine.
23. Panchbhutas: The 5 natural elements like Prithivi (Earth), Ap (Water), Teja (Fire), Vayu (Air) and Akasha (Space) present in the world used in Indian system of medicine
24. Nadisastra: A science, which explains the health status in the human body, used in Indian system of medicine by studying the pulse of the person.
25. In Indian System of Medicine, Factors causing disease are explained as Agantavaha (accidental), Sarirah (body born), Manasah (Mind born) and Swabhavikah (natural)
26. The diseases were classified into three classes as per Indian System of Medicine They are Curable (Sadhya), Mitigateable or manageable (Yapya), The incurable (Asadhya)
27. Conjugative property: If a molecule has alternative single and double bond and electron donating and accepting property it is called conjugative. This is seen in the UV-Visible spectrum of a molecule. Based on the energy absorbed for the excitation of Sigma and Pi electrons in a molecule from the electromagnetic radiation, the molecule will absorb a specific wavelength of radiation. The absorbance maxima of a molecule will thus indicate the conjugative property of the molecule under study.
28. Polarity property: If a molecule has difference in its electrochemical property, it is called polar. This depends on the atoms attached to the molecule with electron donating (nucleophilic) or electron accepting (electrophilic) moieties or functional groups the molecule will have a difference in its electrical charge on its molecular orbital. This makes the molecule to have a positive end and negative ends. This type of molecules is called polar molecules. The extent and type of electrical charge will make the molecule polar, medium polar and non-polar in nature.
29. Gradient or ternary system of HPLC: A HPLC instrument having two or three liquid pumps to vary the ratio of the aqueous or non-aqueous solvents. This will help to control the total polarity of the mobile phase as per the requirement.

Some abbreviations used in software:
1. JDK: Java Development Kit
2. Con: Contour Chromatogram
3. 3-D: 3-Dimensional Chromatogram
4. WOS: Without Scale
5. X: Represents the Retention Time of the chromatogram
6. Y: Represents the absorbance in the 3-D chromatogram and wave length range in contour chromatogram
7. R: Intensity of red color at a particular pixel position
8. G: Intensity of green color at a particular pixel position
9. B: Intensity of blue color at a particular pixel position

EMBODIMENTS

One of the present embodiments of the present invention relates to a method for chromatographic finger printing, chemical and therapeutic standardization and bar coding of organic and organo-metallic molecules from a plant, animal or a naturally available or man made materials.

Another embodiment of the present invention relates to a novel method for chromatographic finger printing of herbal medicines and formulations, which obviates the drawbacks detailed above.

Still another embodiment of the present invention relates to a method for a complete chemical analysis of the constituents present in the medicine under study and their conjugative properties indicating the therapeutic efficacy as per the traditional concepts of the medicine using new software developed.

Still another embodiment of the present invention, relates to a method of novel chromatographic finger printing of medicines that is useful for the quick identification of the actual profile of the compounds present in the medicine under use along with their therapeutic efficacy of the constituents.

In yet another embodiment of the invention, an embodiment of a novel concept of chromatographic finger printing of herbal medicines and formulations using the contour and 3-D chromatograms of the herbal medicines and formulations is proposed. They were developed on a Photo Diode Array detector (PDA) of a High Pressure Liquid Chromatograph. This delineates the data of the spectral properties of the constituents present in the herbal medicines eluted under experimental analytical conditions.

In yet another embodiment of the present invention relates to a method for the chromatographic finger printing of extract from a medicine of any nature containing molecules that absorb Ultraviolet and Visible range of radiation (200–800) or of any range of electromagnetic radiation.

In another embodiment of the present invention, the UV-Visible spectra of the compounds provide the conjugative properties of the molecules and the concentration of the individual concentrations of the molecules.

In another embodiment of the present invention the fingerprints developed for a same medicine extracted under different pH values are helpful to understand the drug release in the intestine system at different pH values of an individual.

In yet another embodiment of the present invention, the UV_VIS spectra of all the constituents are shown in a single image "The Chromatographic Fingerprint"

In yet another embodiment of the present invention the finger print becomes the blue print of the constituents present in a herbal medicine or formulation for an assay and quick identification of the medicine understudy.

In yet another embodiment of the present invention, the fingerprint using the contour and 3-D chromatogram is the basis for the identification of chemical constituents existing and/or formed new.

In yet another embodiment the UV-Vis spectra and polarity of the compounds indicates the conjugative and polarity properties of the compounds and thus indicating the chemical/medicinal property of the medicines. This profile of spectra of all the constituents in a single picture, "The Finger Print" as proposed now becomes the blue print of the constituents present in herbal medicines and formulations. This becomes a superior method of identification and standardization of herbal medicines than the existing, as the peaks express the UV-VIS. Properties or conjugative and polarity properties of the constituents, unlike in a conventional chromatogram taken at a single wavelength along with the quantification of the constituents.

In yet another embodiment of the present method the "division of the fingerprint into different therapeutic zones based on the scales of wavelength (Conjugation) and retention time (Polarity) to understand the therapeutic efficacy (in traditional terms) of a single or a formulated medicine" is done by using an instrumental and software based program.

In yet another embodiment of the present invention, from a large database prepared using this method, it gives many generalizations of the therapeutic efficacy of a particular group of plants, therapeutically classified as a group for a particular disease.

In yet another embodiment of the present invention using the X, Y, R, G, B as coordinates of a selected peak in the fingerprint, a barcode is generated using a bar coding software, which makes the medicine proprietary for an industry.

In yet another embodiment of the present invention, 3-D chromatogram of the medicine is analyzed using all its 3 dimensional properties of the said image. If the 3-D chromatogram is considered as a cap with a hood, the matching of the entire cap 3 dimensionally, with another sample of different qualitative and quantitative properties, the extent it matched is presented as an analytical report qualitatively and quantitatively. Here the hood of the Cap is compared to the peak of the molecule at a particular wavelength. A sample with more number will like a cap with many hoods. Thus the matching of the three dimensional coordinates will provide a foolproof method of comparison and analysis. The coordinate it matched will give qualitative and the extent it matched will give the quantitative data of the sample under study. This is made possible by special software prepared for this purpose. This becomes an ultimate method of quality control.

In yet another embodiment of the present invention relates to a method to provide a novel chromatographic finger printing of herbal medicines and formulations using the contour and 3-D chromatograms of the herbal medicines and formulations is proposed. They are developed on a Photo Diode Array detector (PDA) of a High Pressure Liquid Chromatograph. This delineates the data of the spectral properties of the constituents present in the herbal medicines presented in a specific order of polarity under experimental analytical conditions.

In yet another embodiment of the present invention relates to a to use UV-Visible spectra of the compounds which provides the conjugative properties of the molecules and the concentration of the individual concentrations of the molecules along with the polarity of the molecules.

In yet another embodiment of the present invention relates to a method to provide the UV_VIS spectra of all the constituents shown in a single image "The Chromatographic Fingerprint". The fingerprint thus becomes the blue print of the constituents present in a single medicine or formulation for an assay and quick identification of the medicine understudy.

In yet another embodiment of the present invention relates to use of fingerprint of contour and 3-D chromatograms as a basis for the identification of chemical constituents to limit the scope of the invention.

In yet another embodiment of the present invention relates to the method having standard analytical parameters like Extraction with ethyl alcohol, maintaining same run time 0–60min, using same mobile phase acetonitrile along with phosphate buffer having a pH in the range of 5.5–7.5, and a same UV-Visible Range of 200–800 nm.

In yet another embodiment of the present invention, a method uses a standard analytical parameter like Extraction with same solvent ethyl alcohol for all samples for the finger printing of a particular therapeutic group of samples to make therapeutic generalizations.

In yet another embodiment of the present invention relates to a method of fingerprinting for the adulterated food, drug and chemical samples and to identify the pure and adulterated.

In yet another embodiment of the present invention relates to a method of fingerprinting for the substituted food, drug and chemical samples and to identify the pure and the substituted.

In yet another embodiment of the present invention relates to a method of fingerprinting for the contradictual food, drug and chemical samples and to identify the pure and the substituted.

In yet another embodiment of the present invention relates to a method of fingerprinting for the commercial samples of food and drug and to identify the pure and the substituted.

In yet another embodiment of the present invention relates to a method of fingerprinting for the organic and organometallic constituents in any type samples to identify the chemical constituents present in it for various purposes of quality control and process standardization.

In yet another embodiment-of the present invention relates to a method of fingerprinting for the Allopathic, Ayurvedic, Homoeo, Siddha, Unani, Chinese medicine, Tibetan and Kampo (Japanese) medicine samples for the quality control and chemical and therapeutic standardization.

In yet another embodiment of the present invention relates to a method of fingerprinting for the study of variation of chemical constituents in Naturally occurring samples and to identify and standardize the chemical constituents in them.

In yet another embodiment of the present invention relates to a method of fingerprinting for the study of variation of chemical constituents in Naturally occurring samples and to identify and standardize the variation in chemical constituents in them due to geological and Ecological factors.

In yet another embodiment of the present invention relates to a method of fingerprinting for the study of variation of chemical constituents in Naturally occurring samples and to identify and standardize the variation in chemical constituents in them due to Genotypic and Phenotypic variation factors.

In yet another embodiment of the present invention relates to a method of fingerprinting for the study of chemical constituents in Synthetically prepared samples and to identify and standardize the chemical constituents in them for chemical and therapeutic standardization which ever is applicable.

In yet another embodiment of the present invention relates to a method of fingerprinting for the study of chemical constituents in herbal products of single and formulated medicine samples and to identify the chemical constituents in them for chemical and therapeutic standardization.

In yet another embodiment of the present invention relates to a method of fingerprinting for the study of variation of chemical constituents in biological samples and to identify and standardize the chemical constituents in them.

In yet another embodiment of the present invention relates to a method of fingerprinting for the study of variation of chemical constituents in different brands of products of single and formulated food and medicine samples and to identify the chemical constituents in them for chemical and therapeutic standardization.

In yet another embodiment of the present invention relates to a method of preparing a database giving many generalizations of the therapeutic efficacy of a particular group of plants, classified as a group for a particular disease or therapeutic classification.

In yet another embodiment of the present invention relates to a method to develop fingerprinting and to categorize and quantify the constituents of a medicine, based on polarity and conjugation from 3-D and contour chromatograms.

In yet another embodiment of the present invention relates to a method, which provides a barcode for the selected peak of a molecule given in the image, wherein X—the retention time, Y—the wavelength, R—the number of red pixels, G the number of green pixels and B the number of blue pixels are the coordinates provided by the present computer based (Microchip, Dongle switch, hardware and software locked) software and is feed to any commercially available re-salable bar-coding software resident in the proposed software, generates a barcode. Some examples of images displaying the X—retention time, Y—wavelength, R—number of red pixels, G—number of green pixels and B—number of blue pixels the coordinates of a particular peak (s), which is specific to the product and the barcodes thus, generated are enclosed.

In yet another embodiment of the present invention relates to a method, to prepare a database of barcodes for the fingerprints developed useful for all types of database applications.

In yet another embodiment of the present invention relates to a method to generate display windows for all the samples the fingerprints are developed. In the 'display window' all details of the samples like both 3-D and Contour fingerprints, the barcode, details of the origin (Industry or Country), manufacturing date, date of expiry, reported dosha, individual constituents used, their assay, batch number, lot number, M.R.P and other information on the label), are displayed. When the barcode on the label is shown to the vending machine, it will display the attached display window. This helps to know the chemical and therapeutic authenticity of the medicine being sold/purchased in all types of regulatory and commercial applications.

In yet another embodiment of the present invention relates to a method to attach the display windows with the respective barcodes, facilitating to deal with display windows in all applications whenever they are used as a source of data and information.

In yet another embodiment of the present invention relates to a method to prepare a database of display windows thus generated and attached to the respective barcodes, to use in the ENTERPRISE RESOURCE PLANNING (ERP) and CUSTOMER RELATIONSHIP MANAGEMENT (CRM) applications for all commercial networking transactions of the medicines and samples for which the database was prepared.

In yet another embodiment of the present invention relates to a method to prepare a database of barcodes and display windows and any information, specially required for the regulatory authorities to control the movement of the medicines in and out of the country.

In yet another embodiment of the present invention relates to a method for chromatographic fingerprinting which enables to understand and standardize the Physico-Chemical properties of the medicines like color for the therapeutic standardization of the medicines and humors.

In yet another embodiment of the present invention relates to a method for chromatographic fingerprinting which enables to understand and standardize the Physico-Chemical properties like Taste (Rasa) like Sour (Amla), Salty (Lavana), Pungent (Katu), Bitter (Tikta), Astringent (Kashaya) of the medicines, for the therapeutic standardization of the medicines and humors.

In yet another embodiment of the present invention relates to a method for chromatographic fingerprinting which enables to understand and standardize the Chemical properties of the medicines like Cold, Hot, Slow in action, Sharp in action, Heavy, Light, Soft, Lubricated, Supple, Dry (Guna's like Sheeta, Ushna, Manda, Teekshna, Guru, Laghu, Snigdha and Rooksha as described in Ayurveda) of the medicines for the therapeutic standardization of the medicines.

In yet another embodiment of the present invention relates to a method for chromatographic fingerprinting which enables to understand and standardize the Physico-Chemical properties of the medicines like Potency, Metabolite formation after assimilation and Specific properties like Charlotte of the molecules (Described as Veerya, Vipaka and Prabhava) for the therapeutic standardization of the medicines and humors.

In yet another embodiment of the present invention provides a software based data processor of 3-D chromatograms and contour image of an ingredient.

The method of the invention is described in steps with reference to the accompanying tables, drawings, flow charts and examples, which are provided to illustrate some of the embodiments of the invention, and the same should not be construed as limitations on the inventive concept embodied herein.

DESCRIPTION OF THE ACCOMPANYING TABLES AND FIGURES

The following examples are given by way of illustrations and these should not be construed to limit the scope of the invention.

I. Tables

1. Table showing different philosophies and various terminology used in different medicines
2. Table showing Relation of Humors, Properties, and different parts of the human body—An Ayurvedic approach.
3. Table showing Division in terms of the Macrocosm in Chinese medicine
4. Table showing Division in terms of the Microcosm in Chinese medicine
5. Table showing the relation of five natural elements and their relation
6. Table showing the meaning of Yin and Yang used in Chinese Medicine
7. Table showing the basis of color for the therapeutic classification of the medicines
8. Table showing the effect of different colors on different diseases
9. Table showing Properties of the six tastes (Rasas in Ayurveda) and their properties and efficacy
10. Table of Colors and The Relation with Wavelengths.
11. Table showing the role of acidity and alkalinity in human body
12. Table showing the comparison of different analytical techniques being used for the finger printing and chemical standardization.
13. Table showing the parameters used for developing fingerprints of some of the medicines
14. Table showing the therapeutic classification of medicines reported in the proposed invention.
15. Table of medicines shown as thumbnails.
16. Table showing the division of the fingerprint in to therapeutic zone based on the conjugation and polarity.

II. FIGURES

FIGS. 1 A&B shows the five basic elements in Chinese medicine and the relationship between them. Imbalance (excess or deficiency) of any one element leads to disturbance in other elements and becomes the root cause of a disease. The health of human body is achieved by managing and controlling the above elements in Chinese medicine.

FIG. 2 shows the effect of colors on the basic humors based on which the medicines of the same colors were selected for vitiating the corresponding humor. The color of a medicine is due to the chemical properties of the constituents present in it, and thus indirectly the chemical properties are used for the therapeutic standardization.

FIGS. 3 and 4 shows the fingerprints of Shilajit of two different brands. The chemical profile in the fingerprint shows the therapeutic efficacy due to the presence of a greater number of molecules with wide conjugative properties. The chemical profile varies with the age of the sample and the amount of time it spent in the earth. The older the sample, the more it will be therapeutically active. This may depend on the place of collection and purification process.

FIG. 5 shows chromatograms of a commercial Turmeric powder at different wavelengths. This is the existing method.

FIG. 6 shows chromatograms of a Furazolidine medicine at different wavelengths. This is the existing method.

FIG. 7 shows chromatograms of the herbal formulation *Krimikutara Ras* at different wavelengths. This is the existing method.

FIG. 8 shows chromatograms of herbomineral medicine Shilajit (good by efficacy) at different wavelengths. This is the existing method.

FIG. 9 shows chromatograms of herbomineral medicine Shilajit (poor by efficacy) at different wavelengths. This is the existing method.

FIG. 10 shows chromatograms of herbal formulation Suryavarti at different wavelengths. This is the existing method.

FIG. 11 shows chromatocirams of herbal food product Tea at different wavelengths. This is the existing method.

FIG. 12 shows chromatograms of herbal formulation Trikatu (a formulation of Pippali, Maricha and Shunti) at different wavelengths. This is the existing method.

Figure 22A:
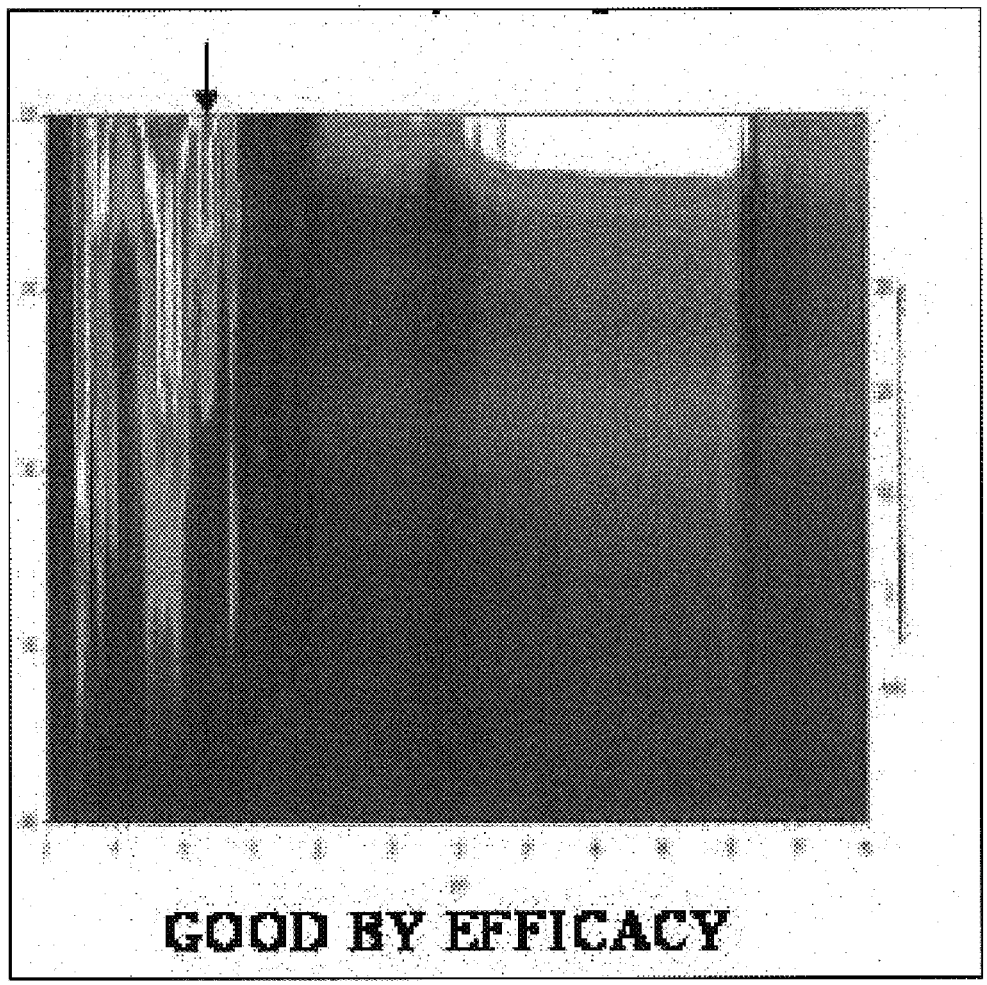
Figure 22B:
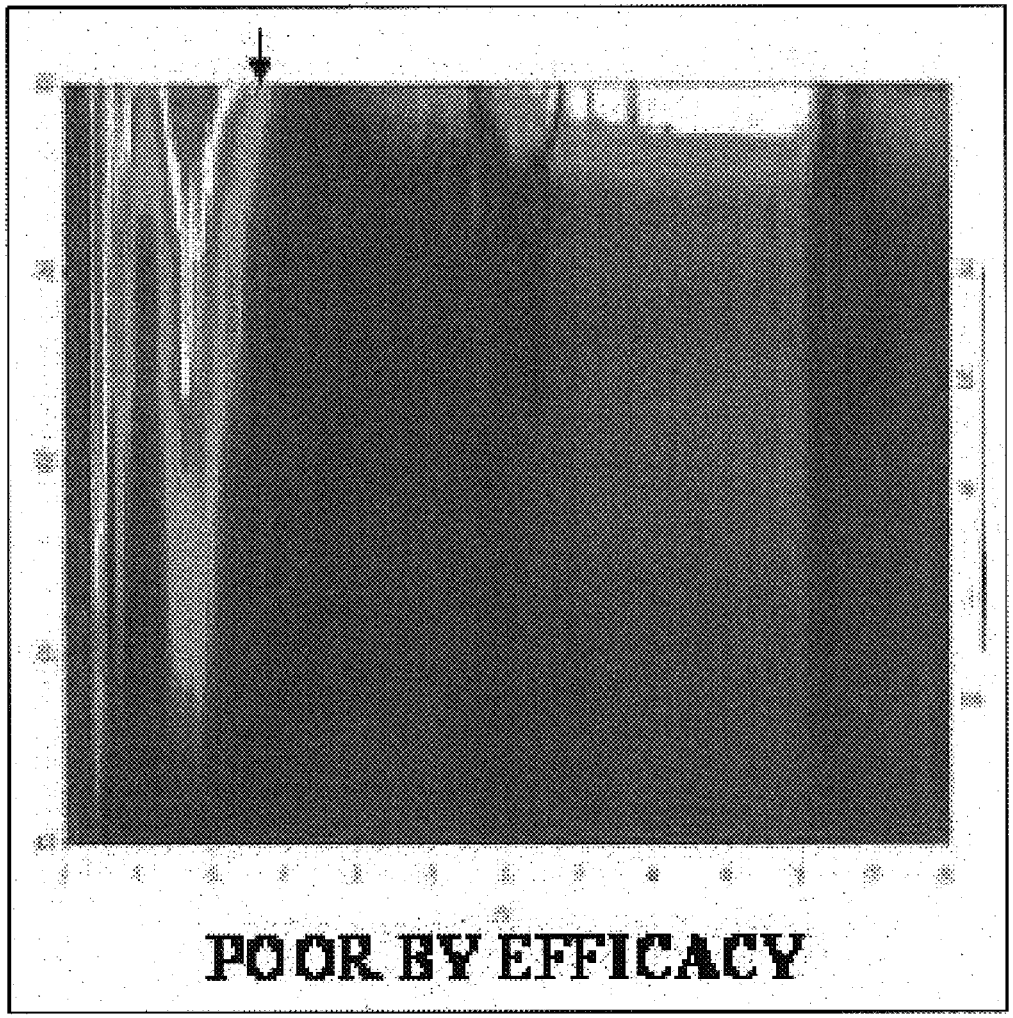

FIG. 22 (A and B) shows fingerprints of different samples of Citrallus Colosynthis. The fingerprint shows the lack of some constituents due to which this method is used for standardization of the extraction process of homoeo mother tinctures from plants. This supports the claim of taste identification used for therapeutic standardization.

Figure 23A:
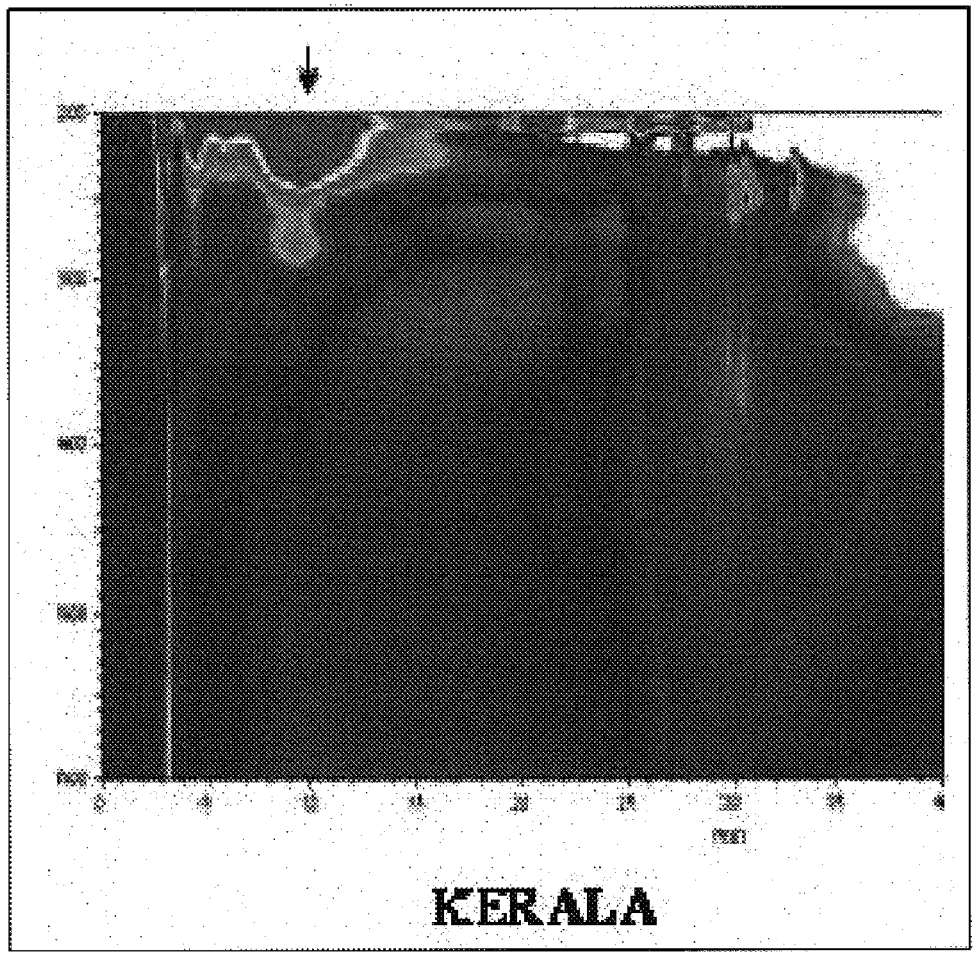
Figure 23B:
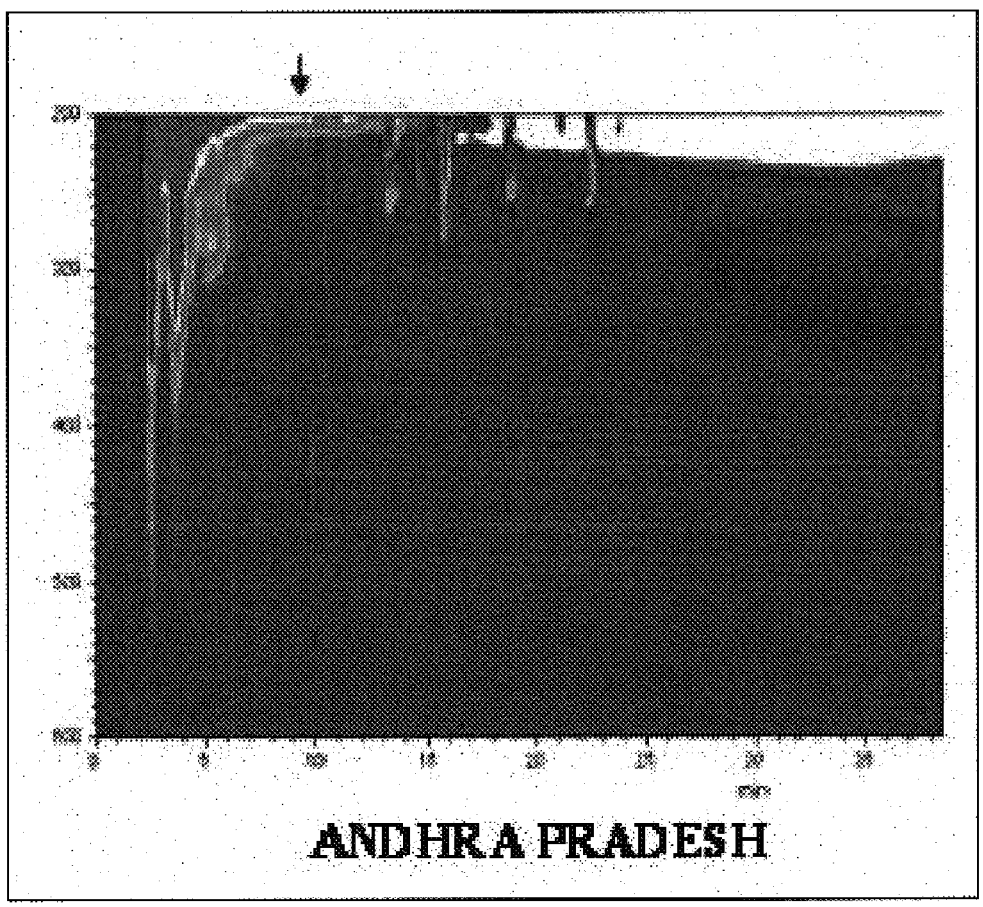

FIG. 23 (A and B) shows fingerprints of different samples of Holarrena Antidyssentric collected from different places of the country. The fingerprint shows the influence of ecological factors on the chemical constituent of the plant material. This constituent is basic in nature because the basic or alkaline amines elute stretched or elongated. Acid compounds elute fast as illustrated in a sharp peak.

Figure 24A:
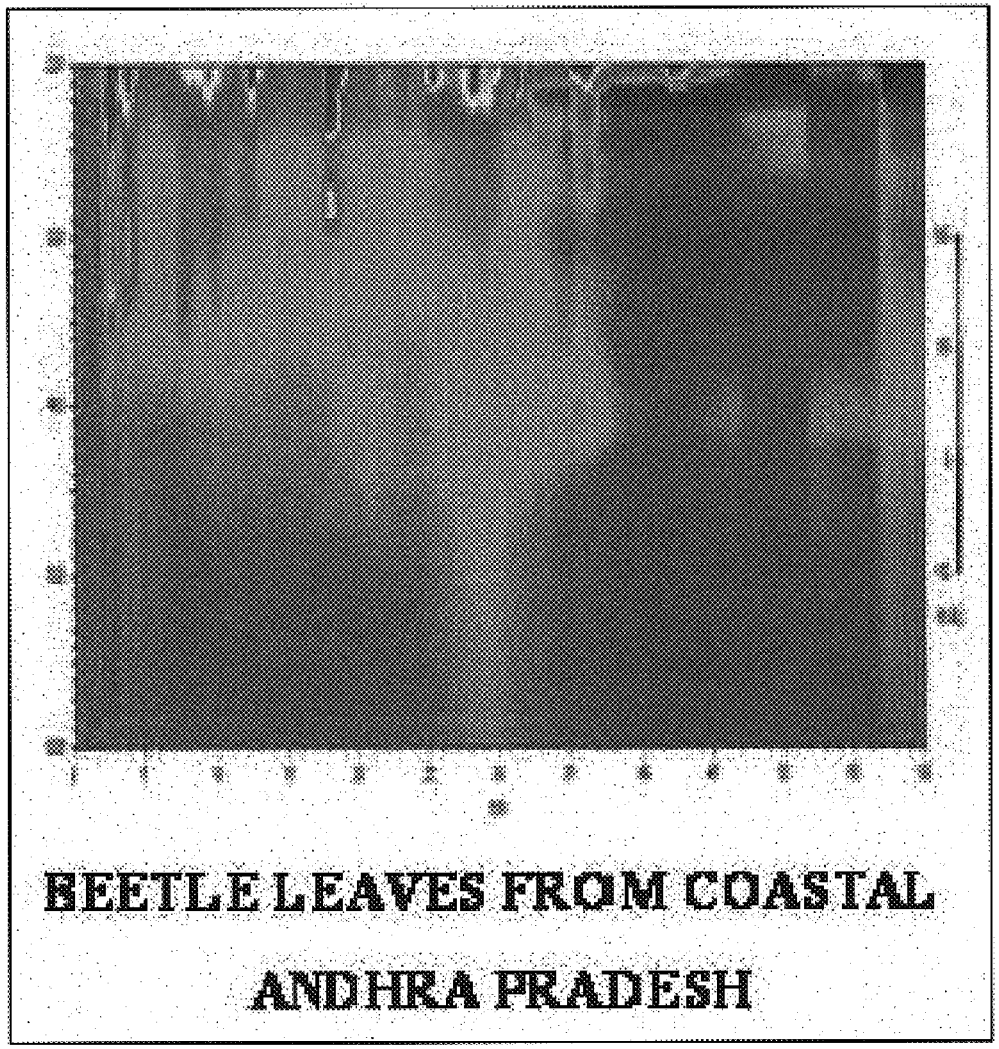
Figure 24B:
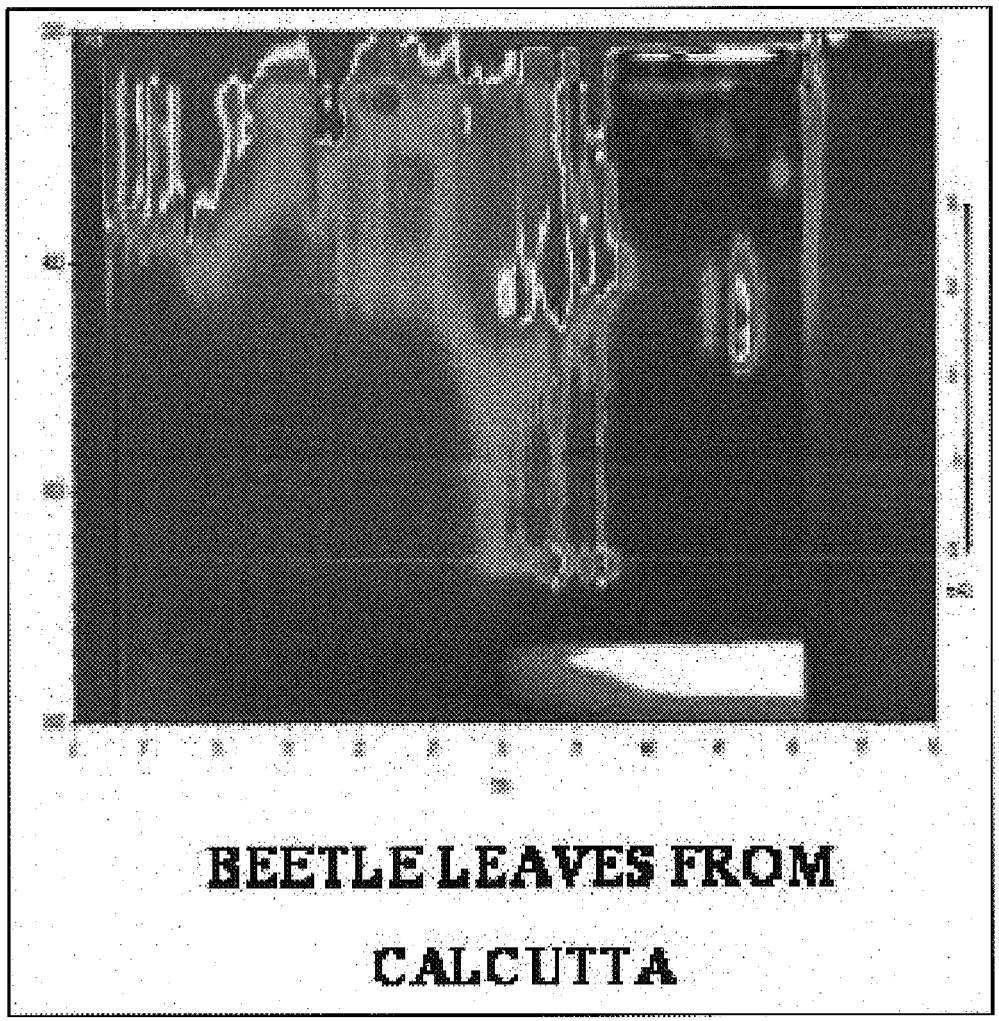

FIG. 24 (A and B) shows the fingerprints of two samples of *Piper Beetle* leaves from different places. The flavonoids present in the time range of 30–40 min shows the influence of genotypic, phenotypic variations and ecological factors on the chemical constituents of the plant material. Aurones and Chareones (flavoinids) are antioxidants.

FIG. 25 shows the satellite images of India. These satellite images indicates that India has different tropical zones.

Figure 26A:
Figure 26B:
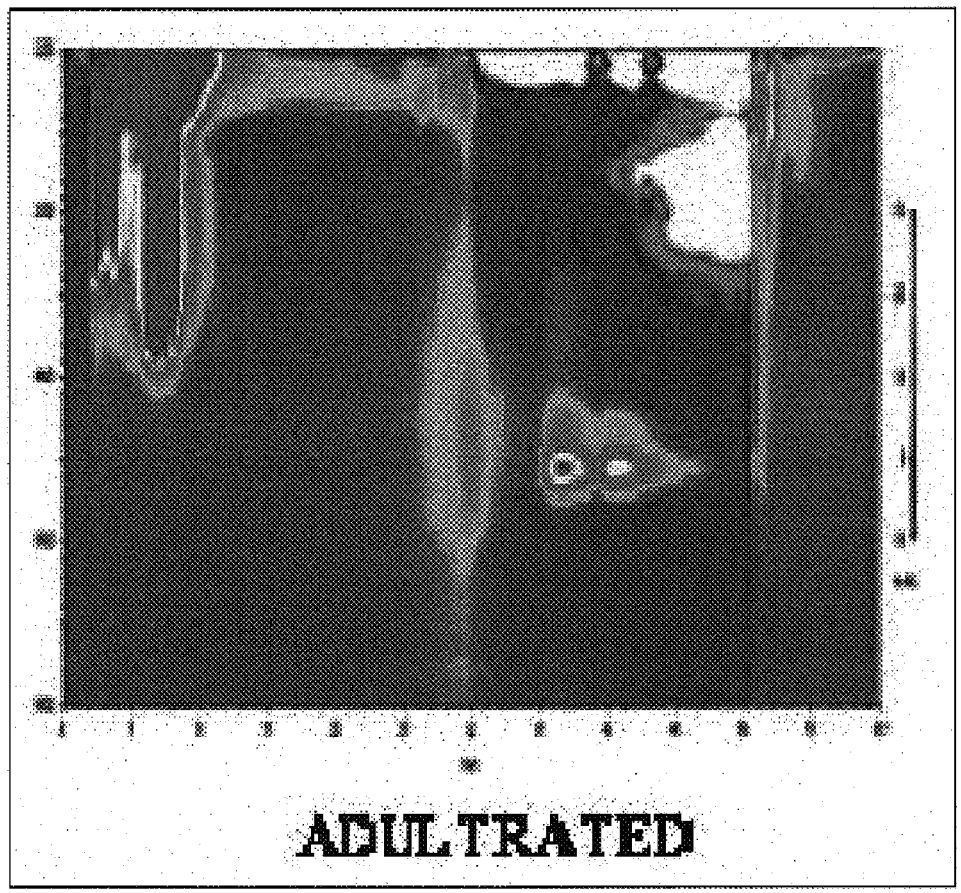
Figure 26C:
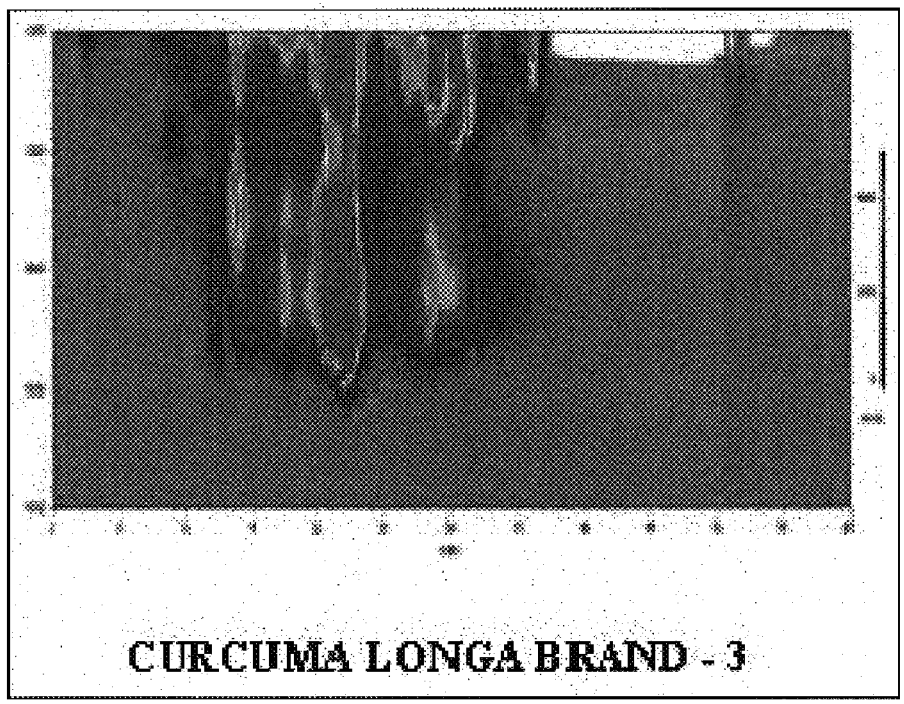

FIG. 26 (A and B) shows the fingerprints of two formulations used as cosmetics like Herbal head Bath powders. These fingerprints show the adulteration of detergents in the identified herbal cosmetic product. Thus fingerprinting helps to monitor the adulterations in various commercial herbal products. Constituents at 35–40 minutes are highly basic and soapy in nature. The pure detergent samples are eluting at the same time.

Figure 27A:
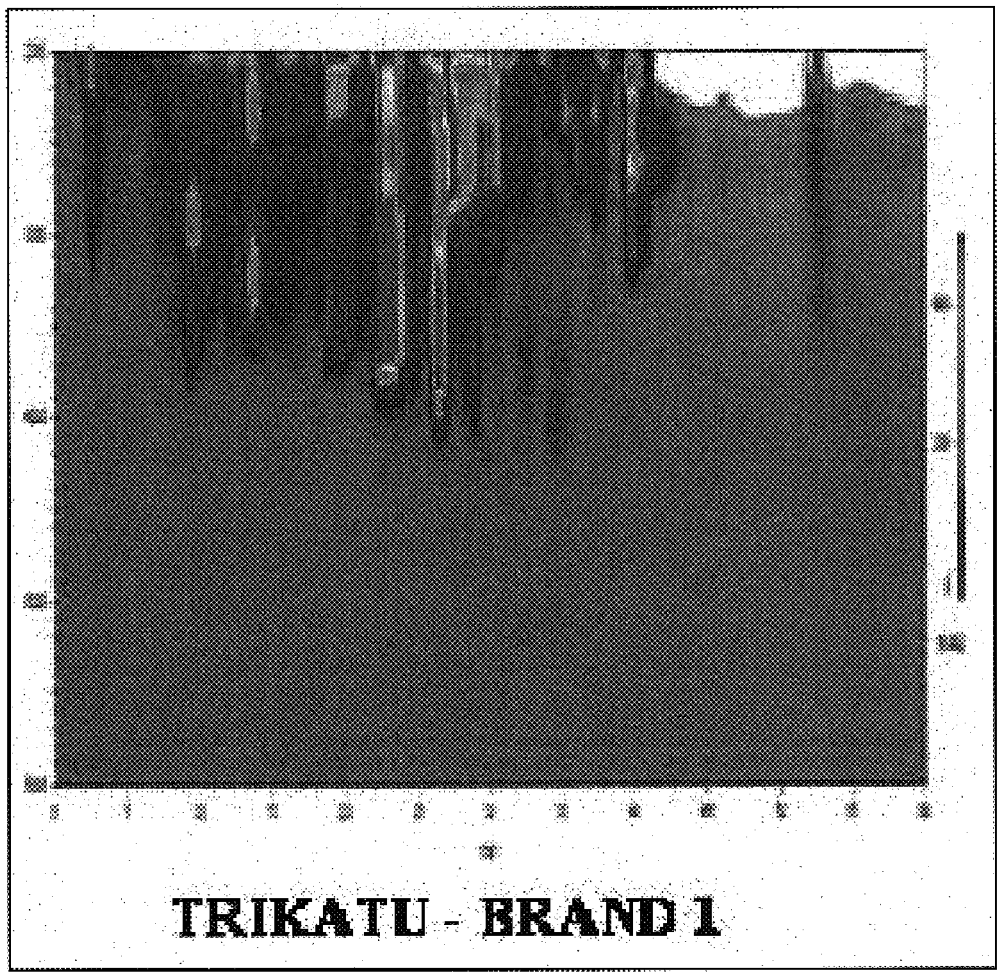
Figure 27B:
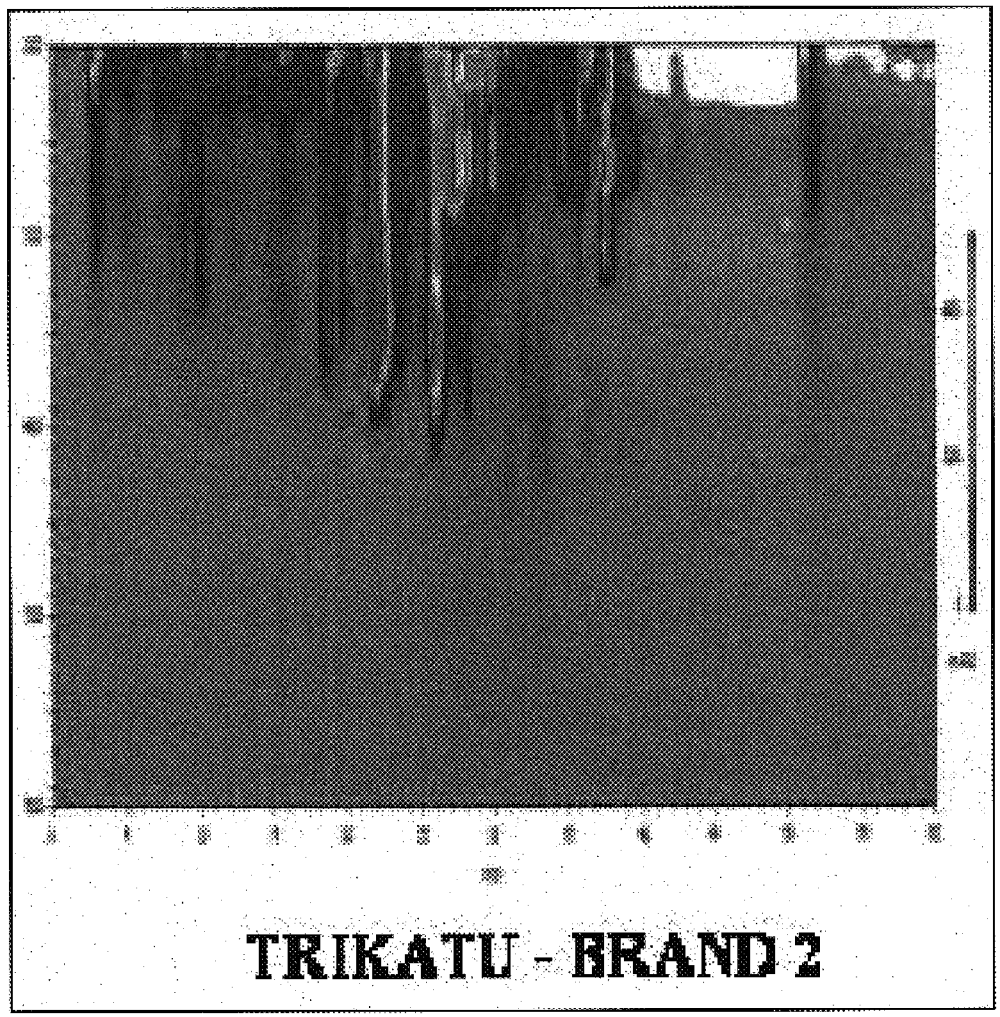

FIG. 27 (A and B) shows the fingerprints of TRIKATU of two different brands. The difference in their assay may be due to variations in the constituent elements of TRIKATU. These examples of TRIKATU show differences in the assay and variations in the chemical constituents. The reason may be due to the variations in the single medicines used to prepare the formulations.

Figure 28A:
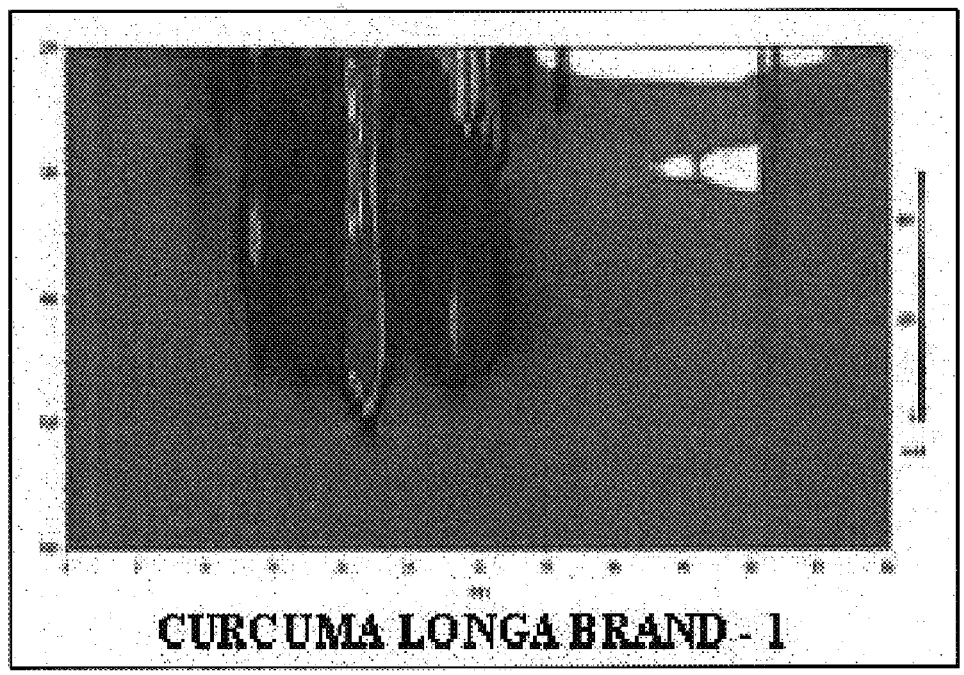
Figure 28B:
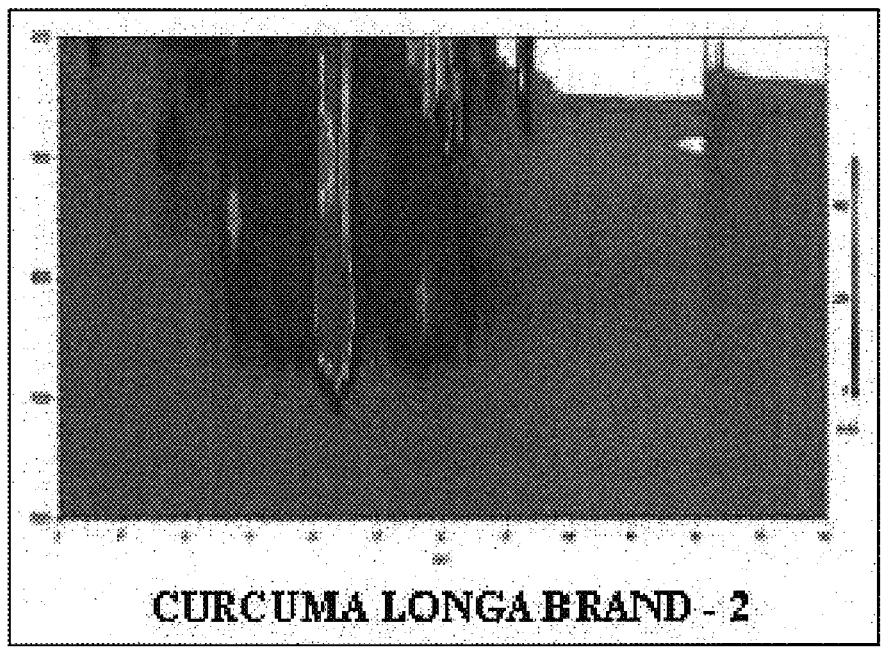
Figure 28D:
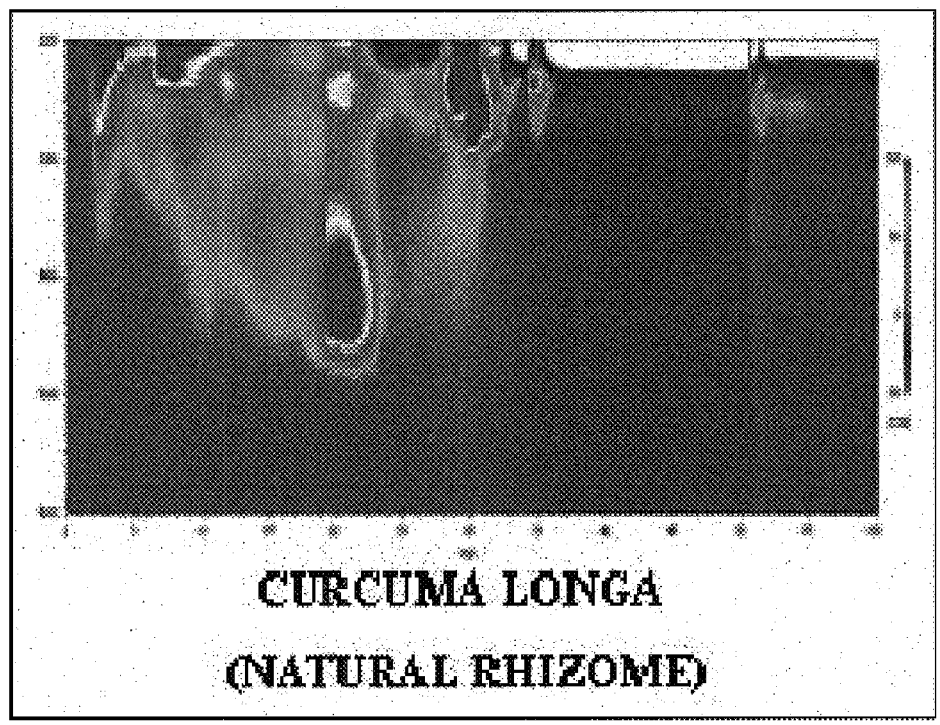

FIG. 28 (A through D) shows the fingerprints of turmeric and its three different commercial products. A common peak occurs at 20 minutes in all of these fingerprints. The fingerprints of the same herbal product in different forms help in the guality control of the natural substances. The common peaks at 20 mm in natural and commercial products indicate the presence of the yellow colored molecules in all.

Figure 29A:
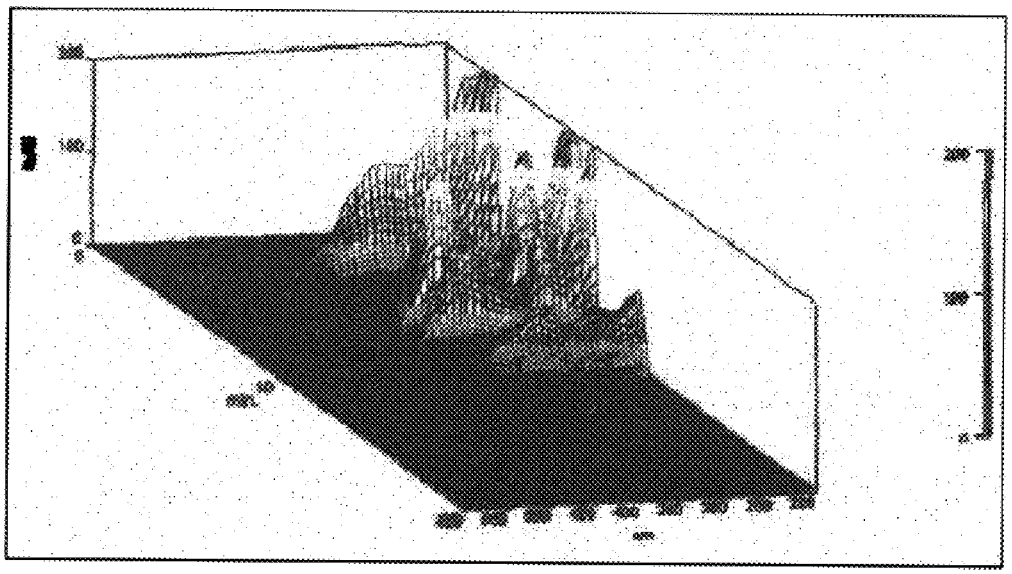
Figure 29B:
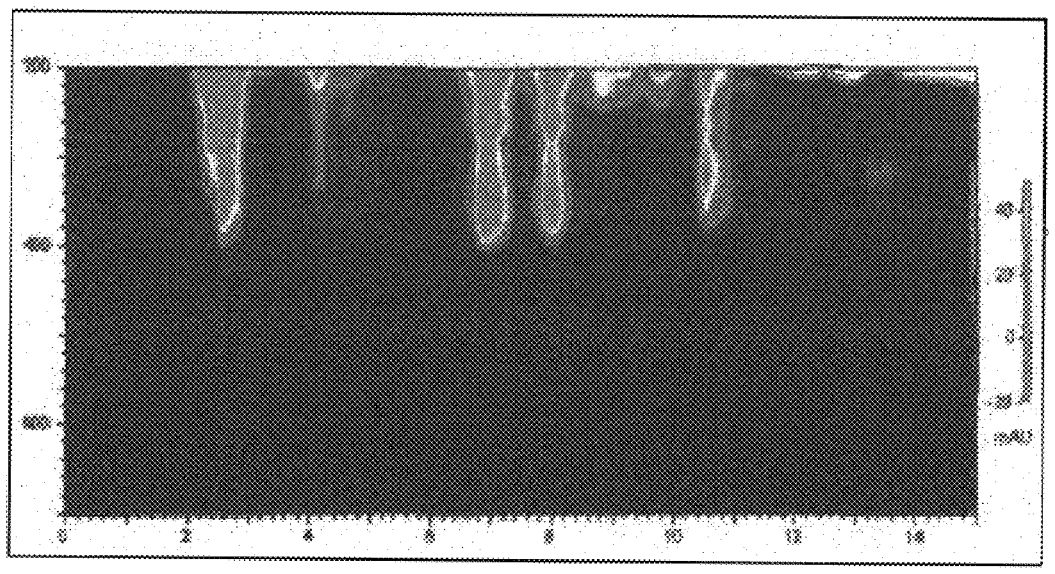

FIG. 29 (A and B) shows both fingerprints of whole plant of *Abel moschus, Moschatus medicum*.

Figure 30A:
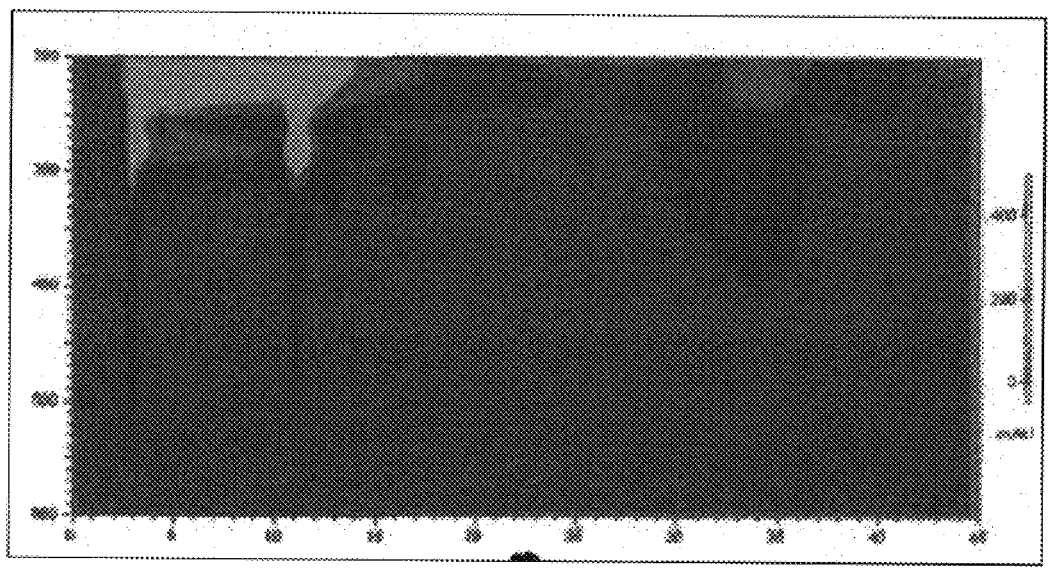
Figure 30B:
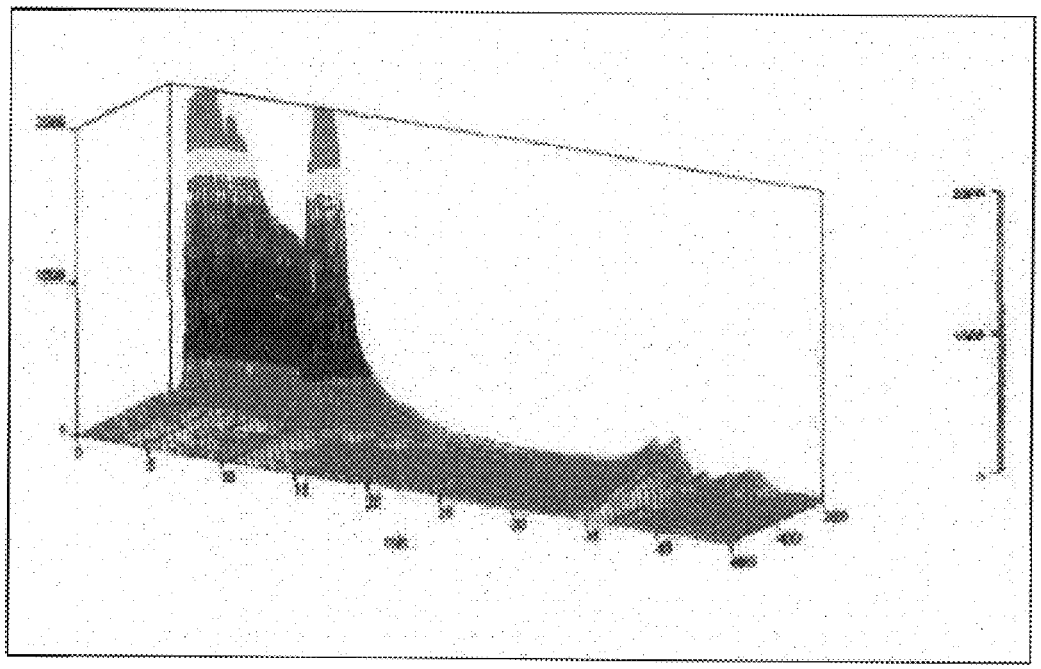

FIG. 30 (A and B) shows both fingerprints of bark of *Acacia suma*.

Figure 31A:
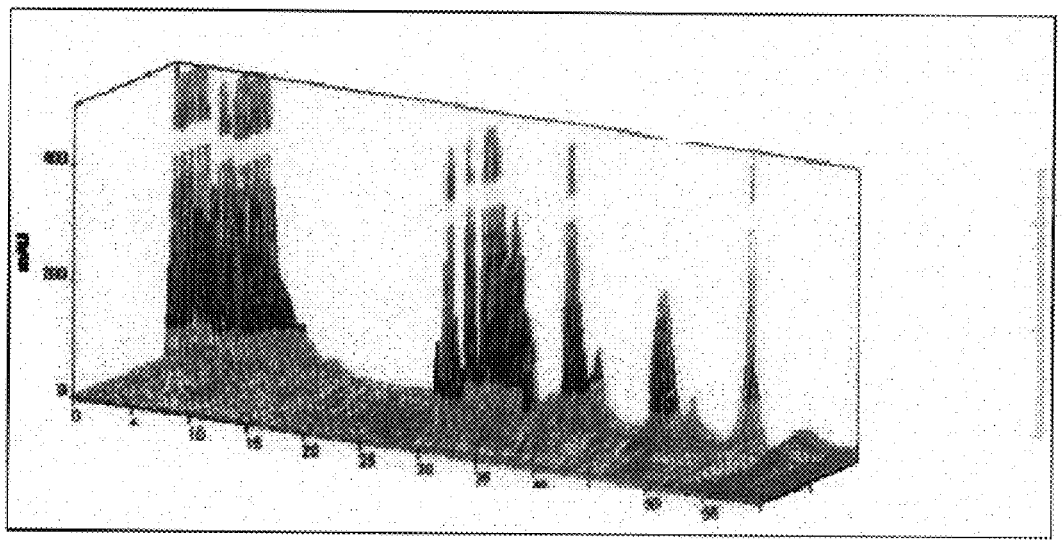
Figure 31B:
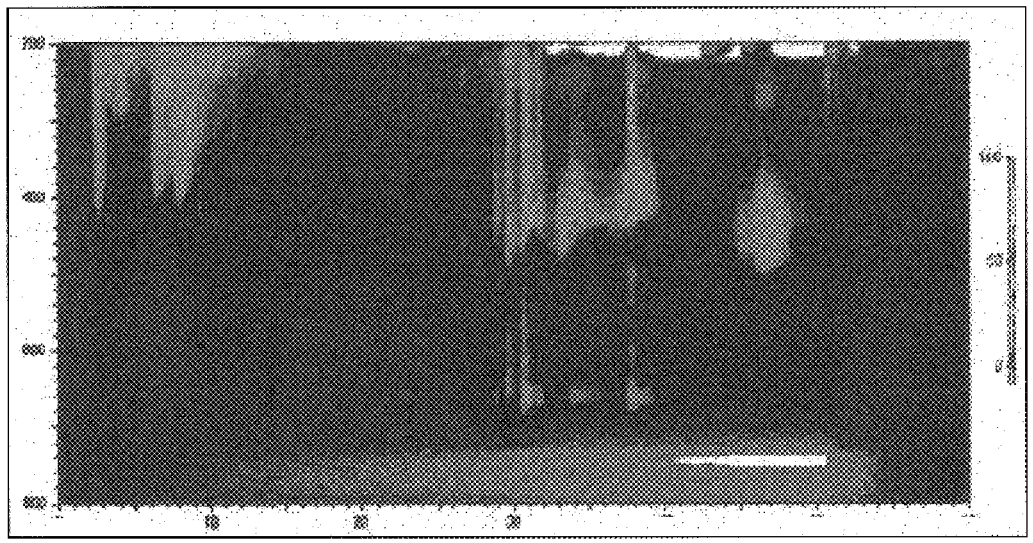

FIG. 31 (A and B) shows both fingerprints of leaflets of *Acalypha indica*.

Figure 32A:
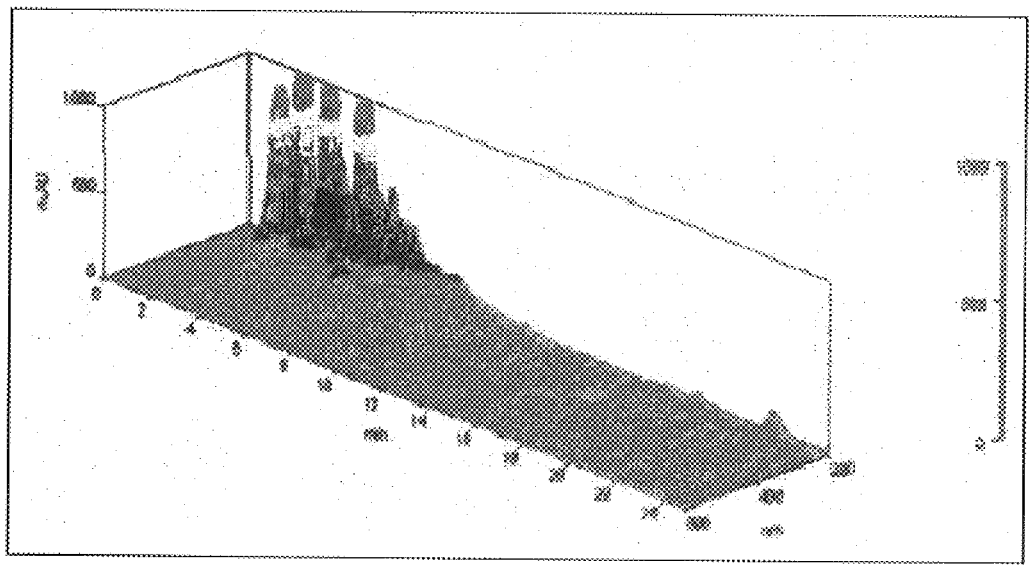
Figure 32B:
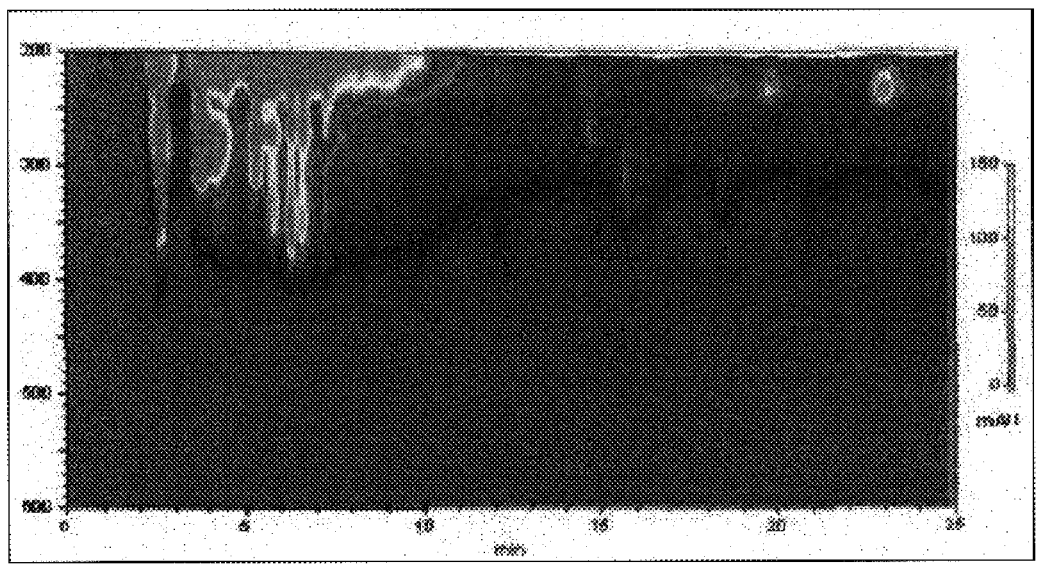

FIG. 32 (A and B) shows both fingerprints of leaves of *Adhatoda vasaka*.

Figure 33A:
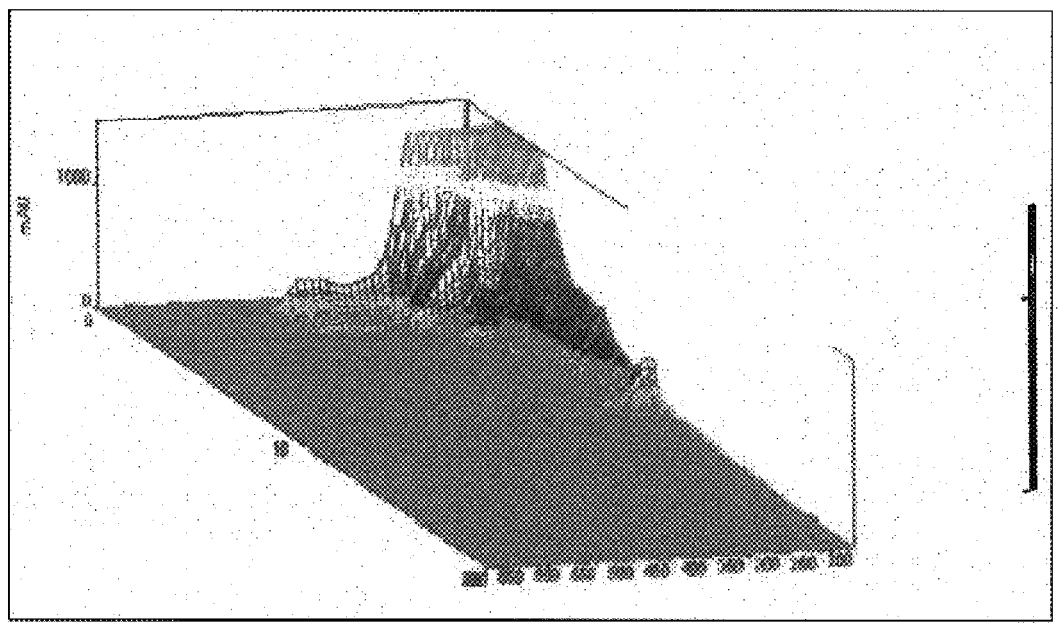
Figure 33B:
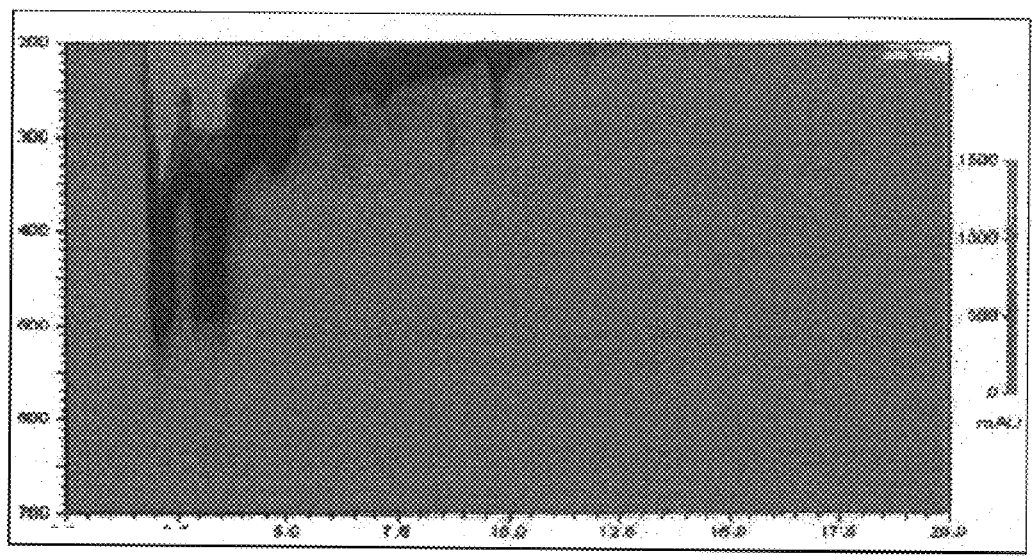

FIG. 33 (A and B) shows both fingerprints of leaves of *Adiantum caudatum*.

Figure 34A:
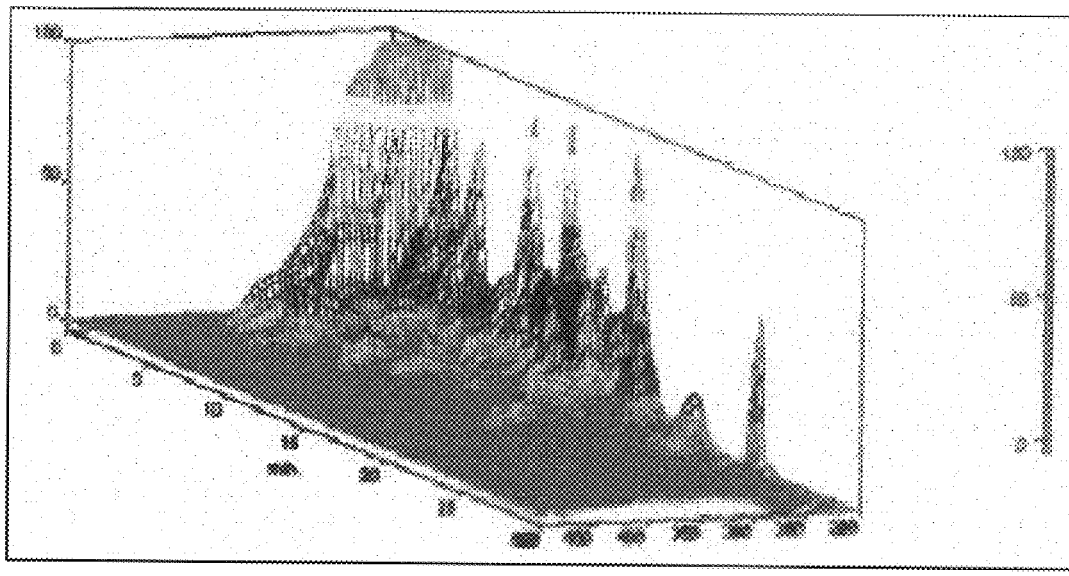
Figure 34B:
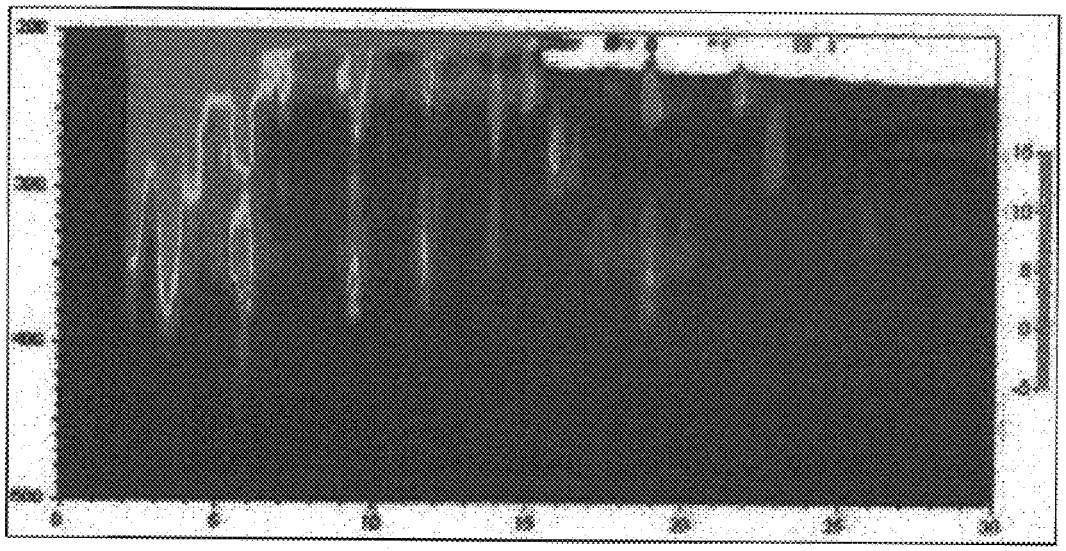

FIG. 34 (A and B) shows both fingerprints of stem bark of *Ailanthus excelsa*.

Figure 35A:
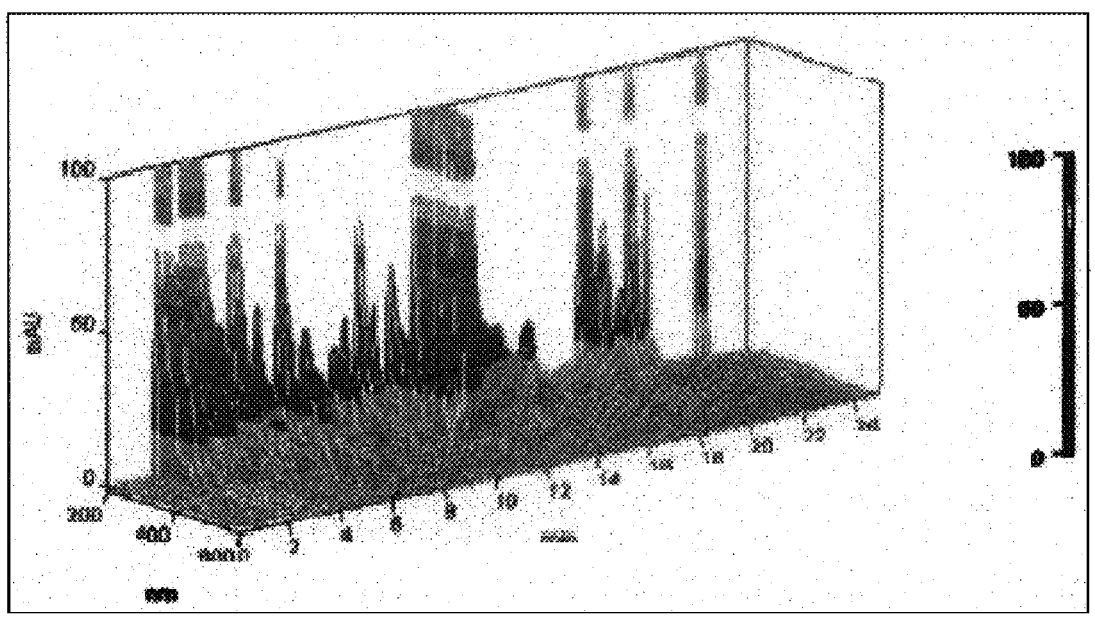
Figure 35B:
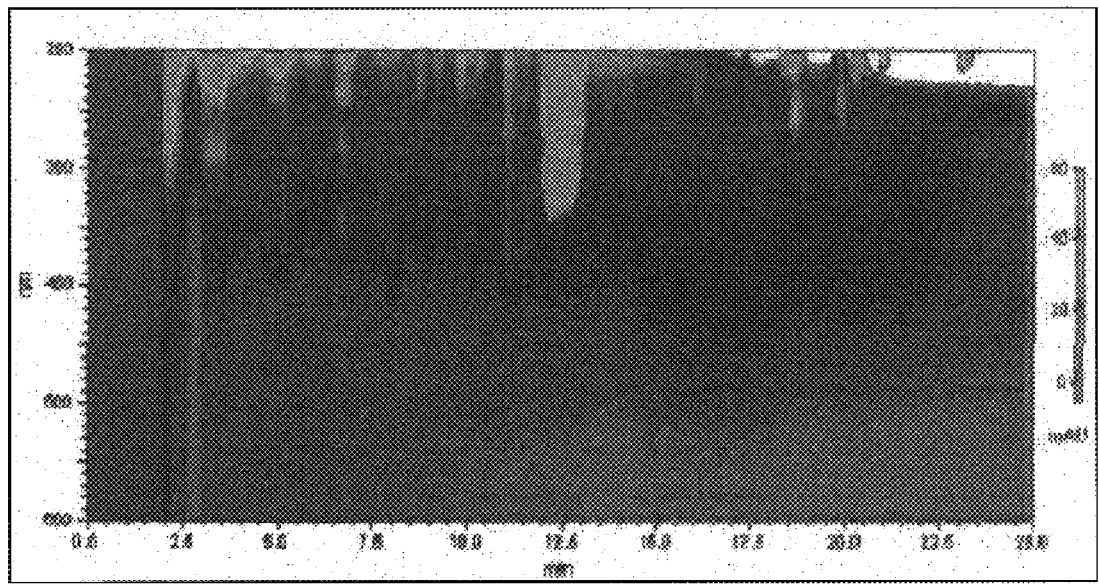

FIG. 35 (A and B) shows both fingerprints of rhizome of *Acorus calamus*.

Figure 36A:
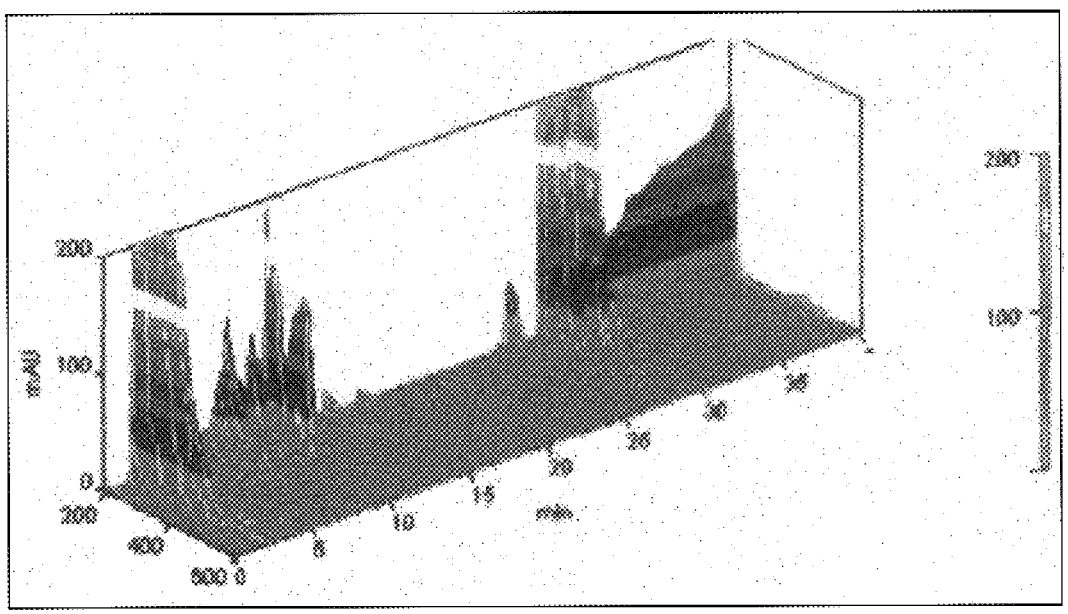
Figure 36B:
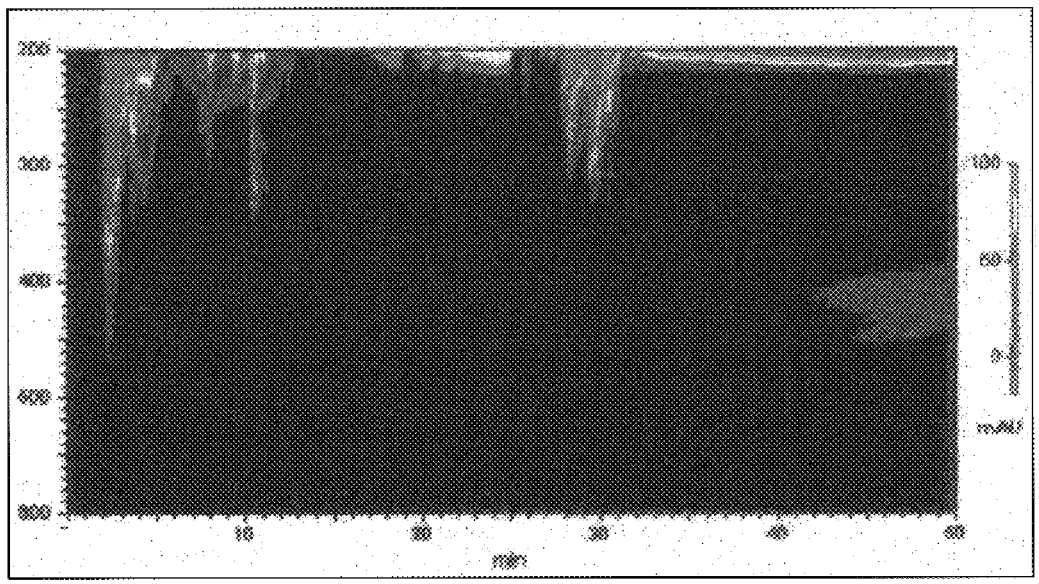

FIG. 36 (A and B) shows both fingerprints of big single cloves of *Allium porum*.

Figure 37A:
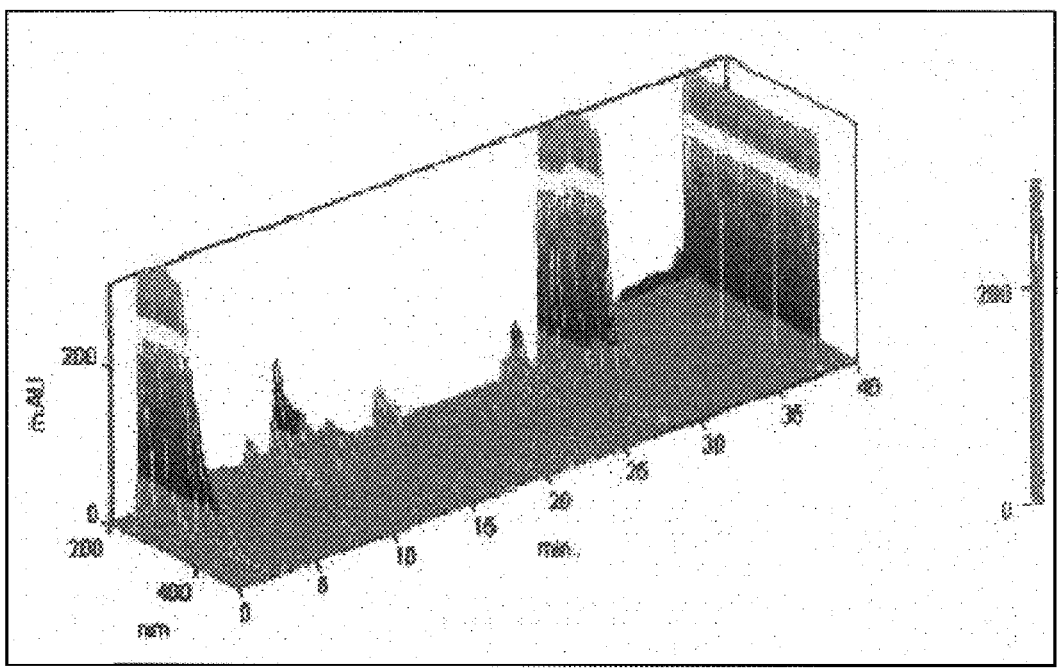
Figure 37B:
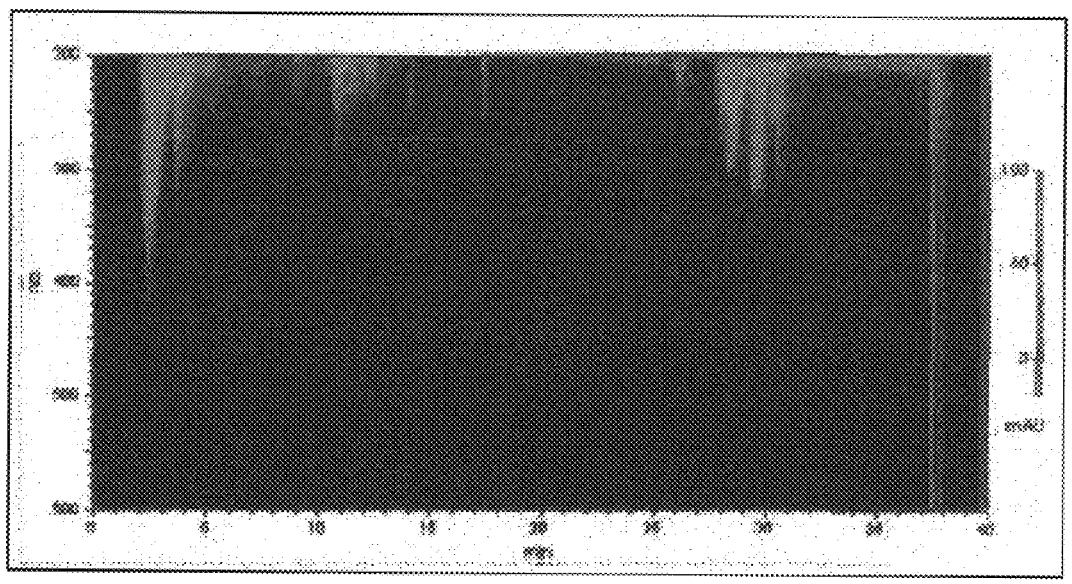

FIG. 37 (A and B) shows both fingerprints of small cloves of *Allium sativam*.

Figure 38A:
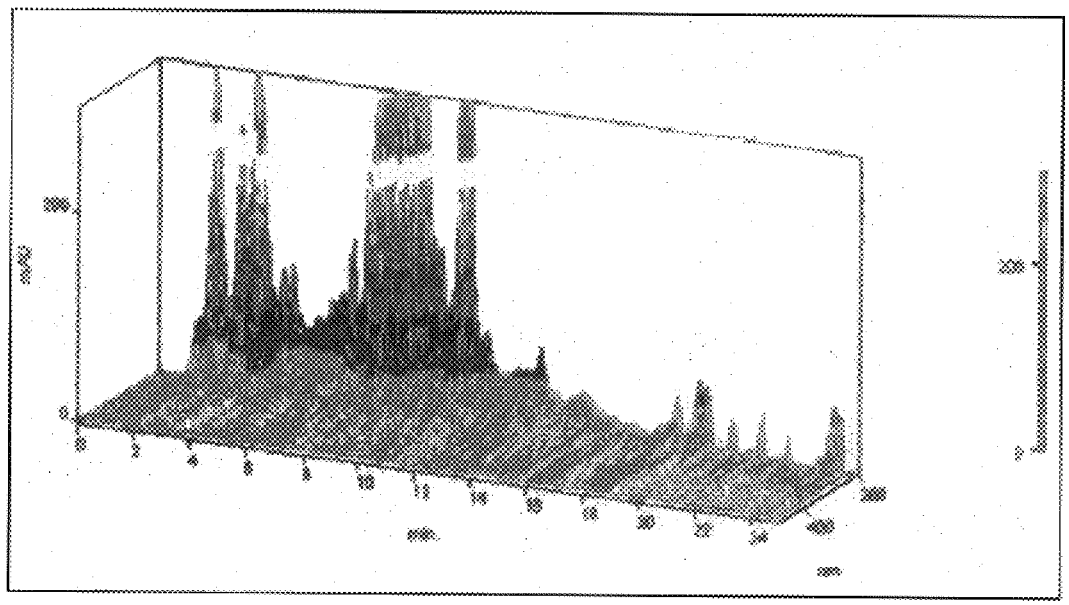
Figure 38B:
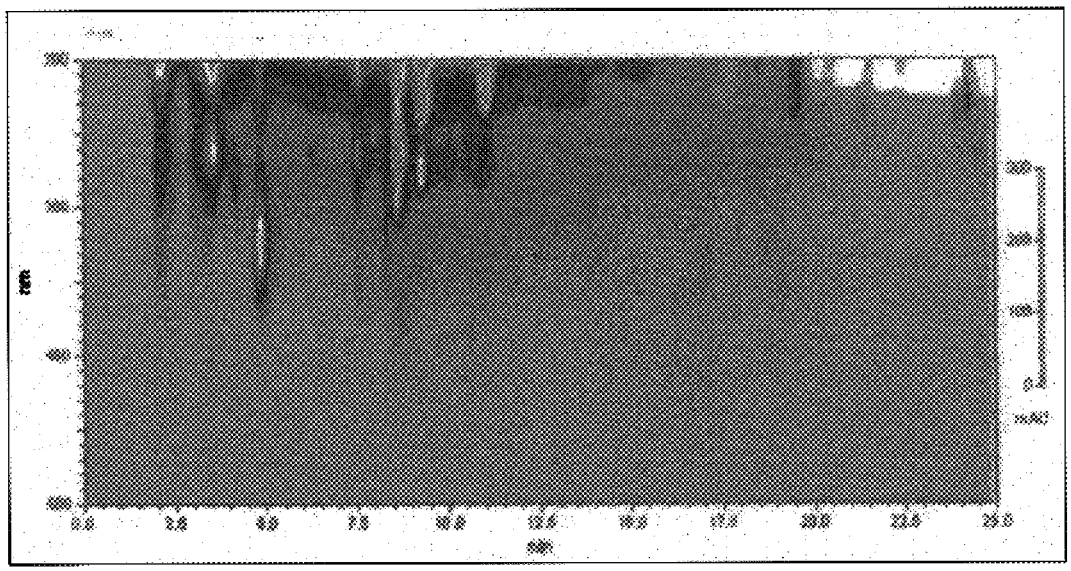
Figure 38A:
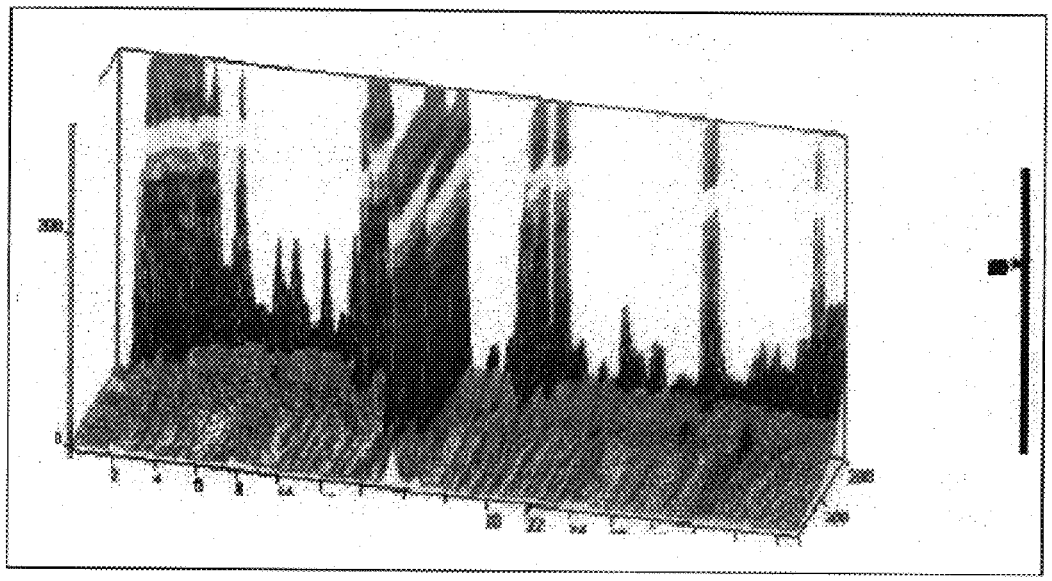

FIG. 38 (A and B) shows both fingerprints of rhizome of *Alpinia galanga*.

Figure 39B:
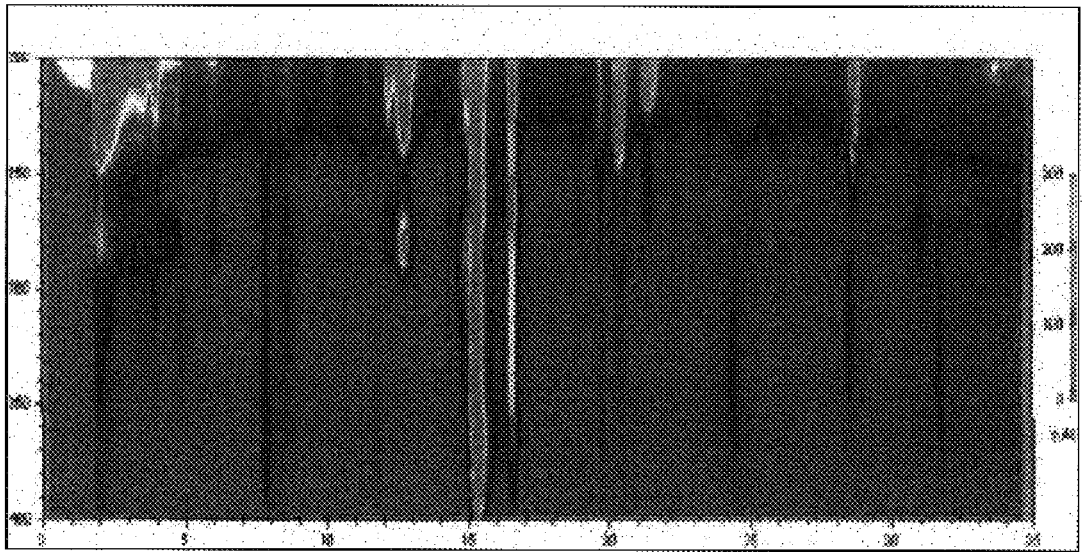

FIG. 39 (A and B) shows both fingerprints of rhizome of *Alpinia officinarum*.

Figure 40A:
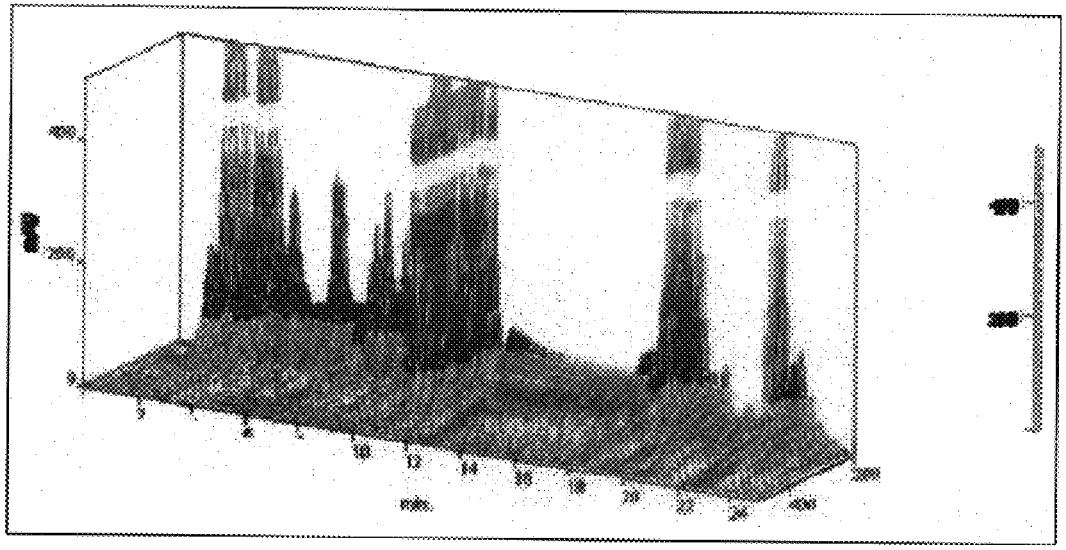
Figure 40B:
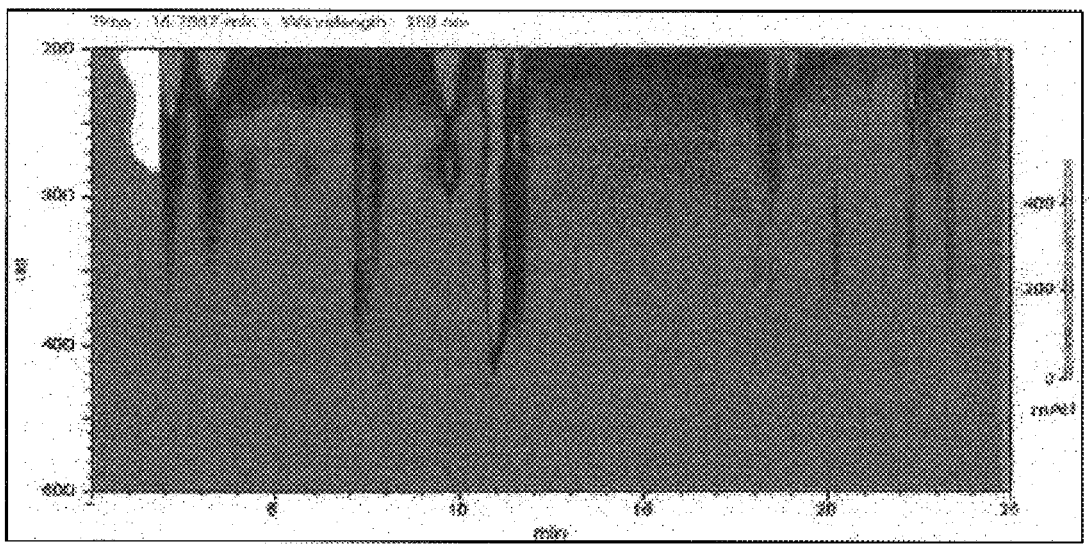

FIG. 40 (A and B) shows both fingerprints of rhizome of *Alpinia speciosa*.

Figure 41A:
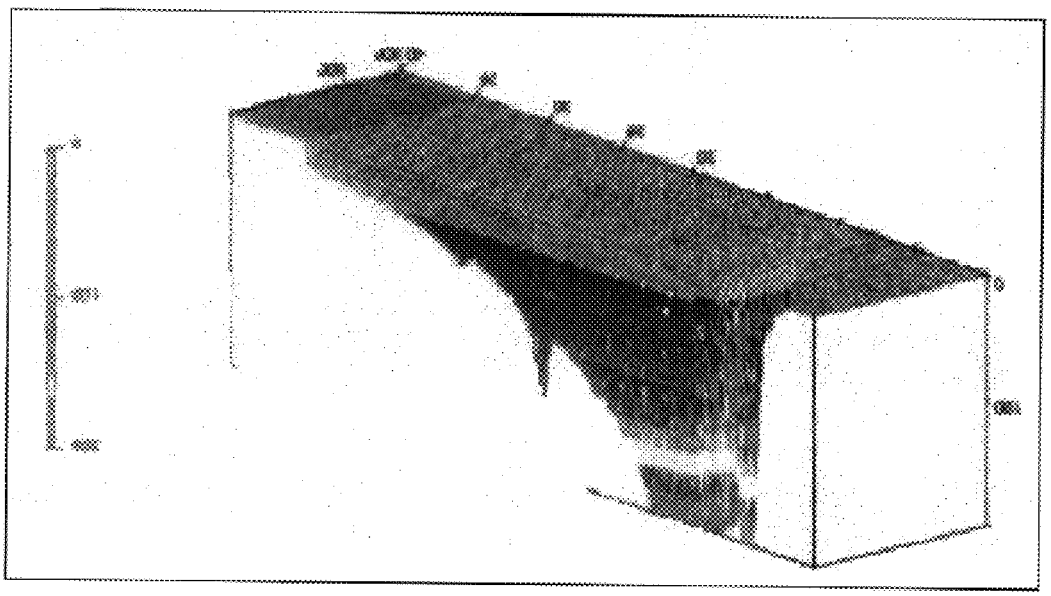
Figure 41B:
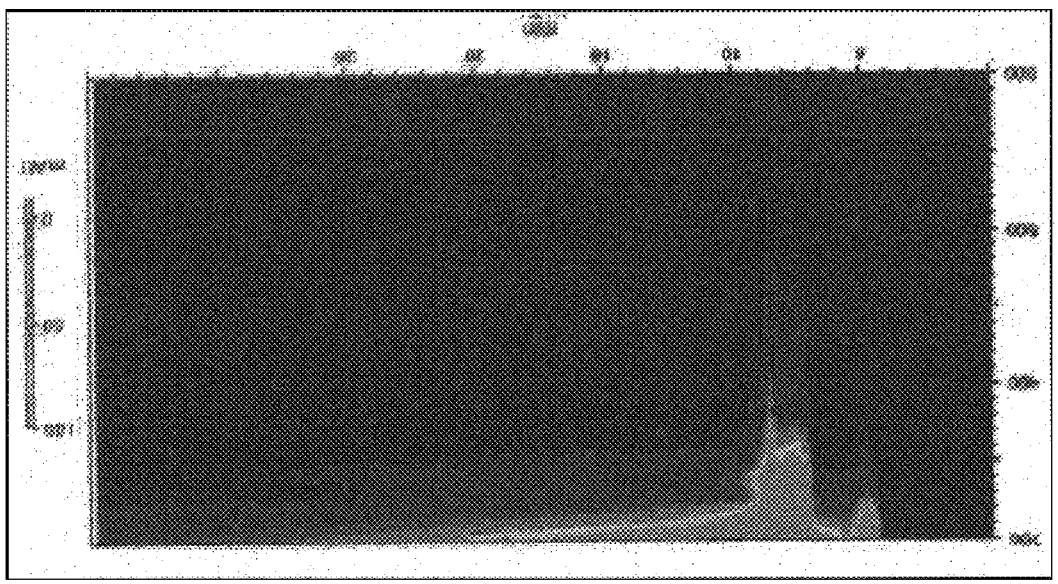

FIG. 41 (A and B) shows both fingerprints of unprocessed raw fruit nut of *Areca catechu*.

Figure 42R:
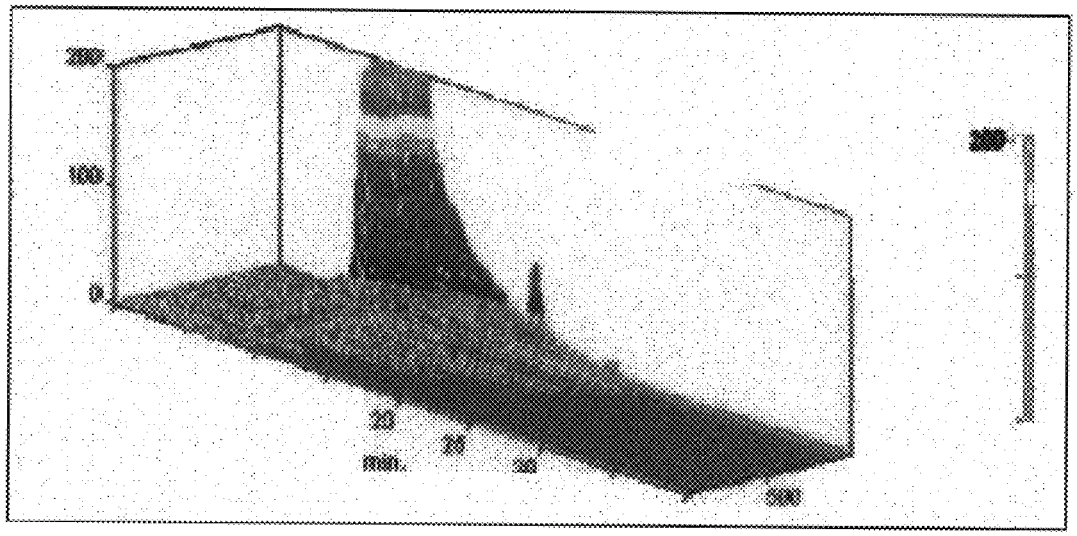
Figure 42B:
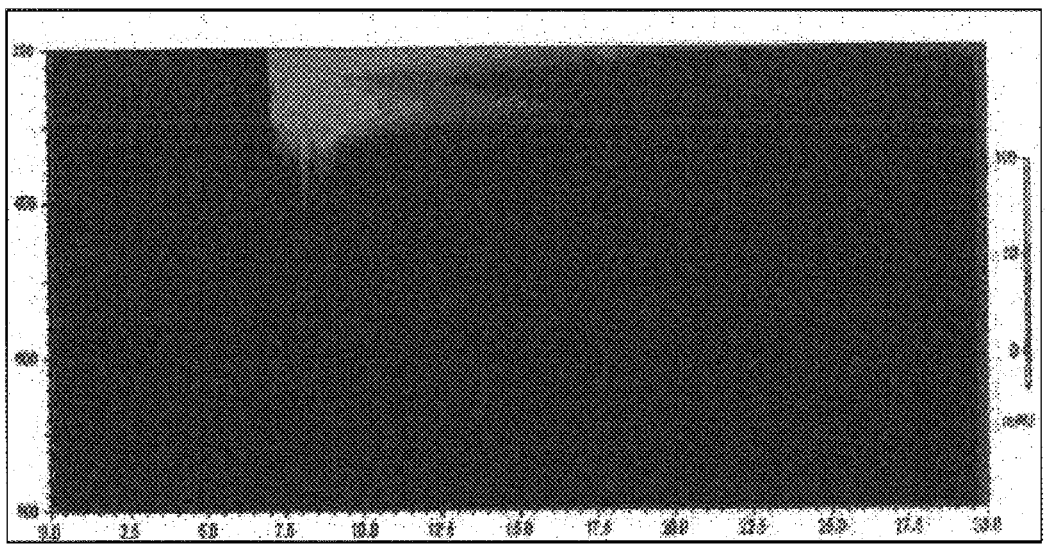

FIG. 42 (A and B) shows both fingerprints of milk processed nut of *Areca catechu*.

Figure 43A:
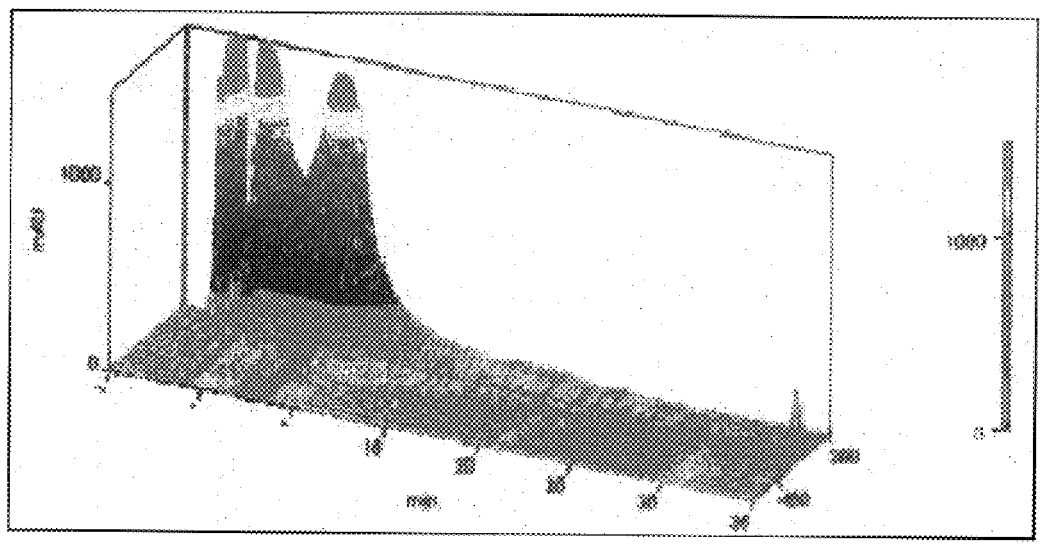
Figure 43B:
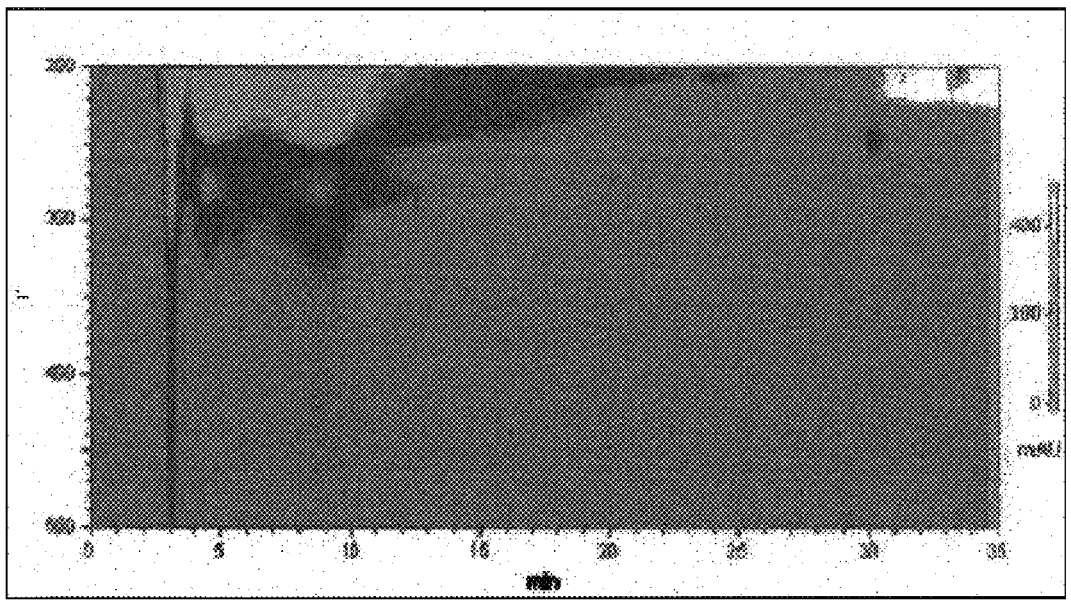

FIG. 43 (A and B) shows both fingerprints of stem bark of *Areca kateeh*.

Figure 44A:
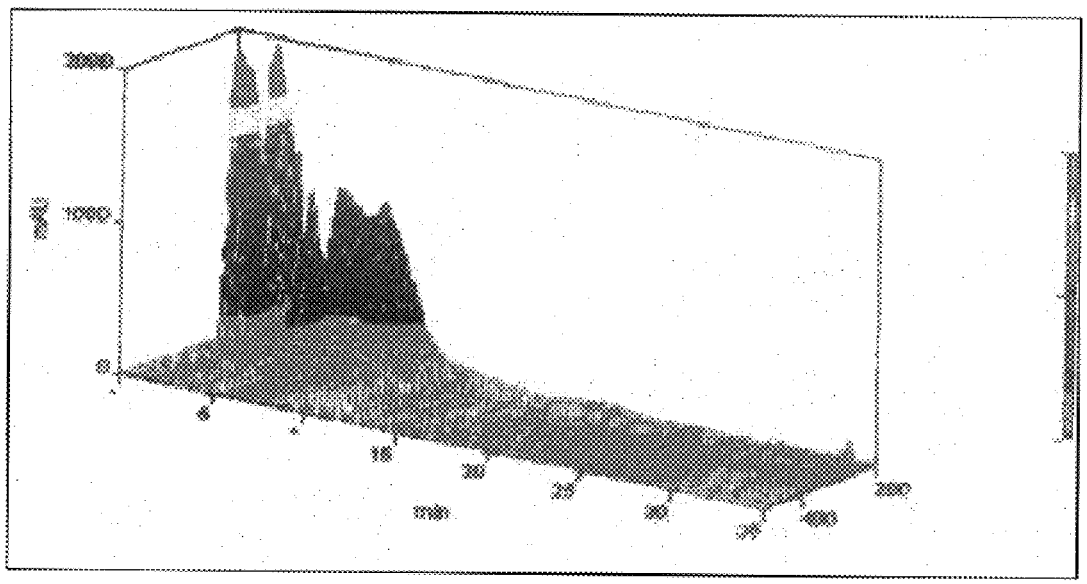
Figure 44B:
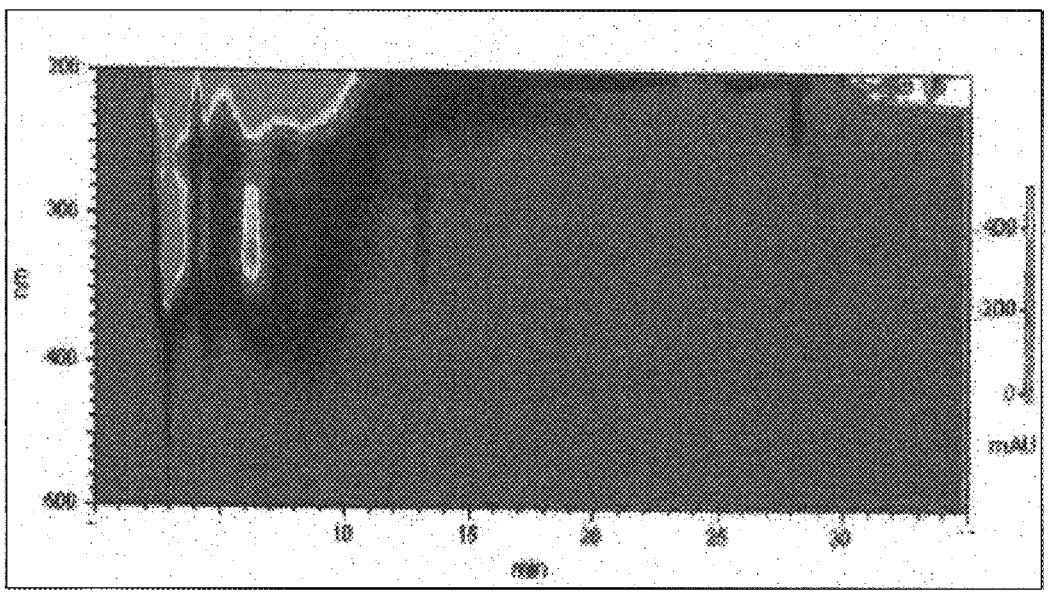

FIG. 44 (A and B) shows both fingerprints of Homoeo mother tincture of *Arnica*.

Figure 45A:
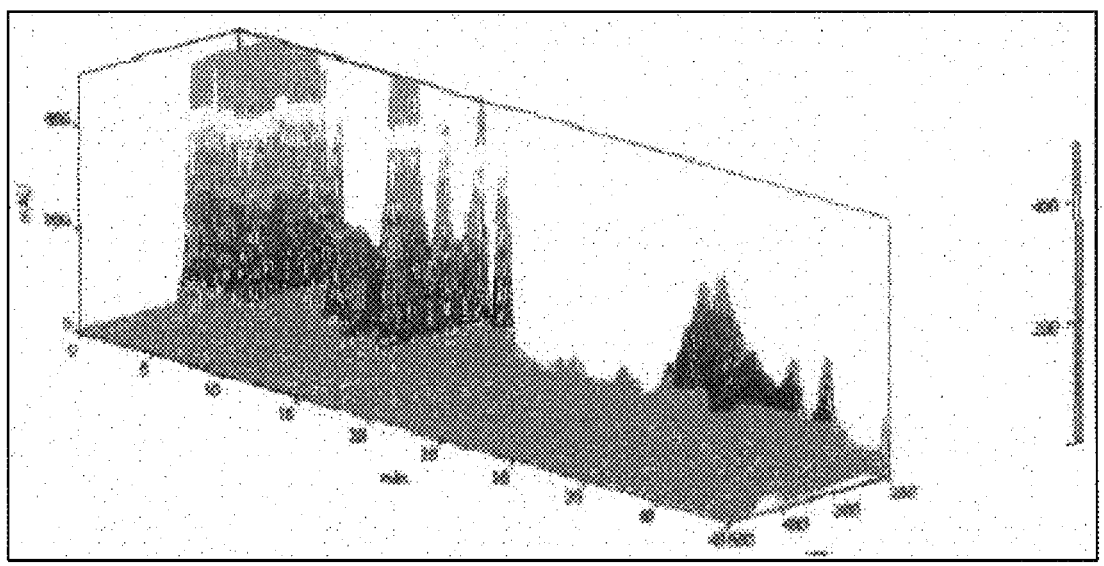
Figure 45B:
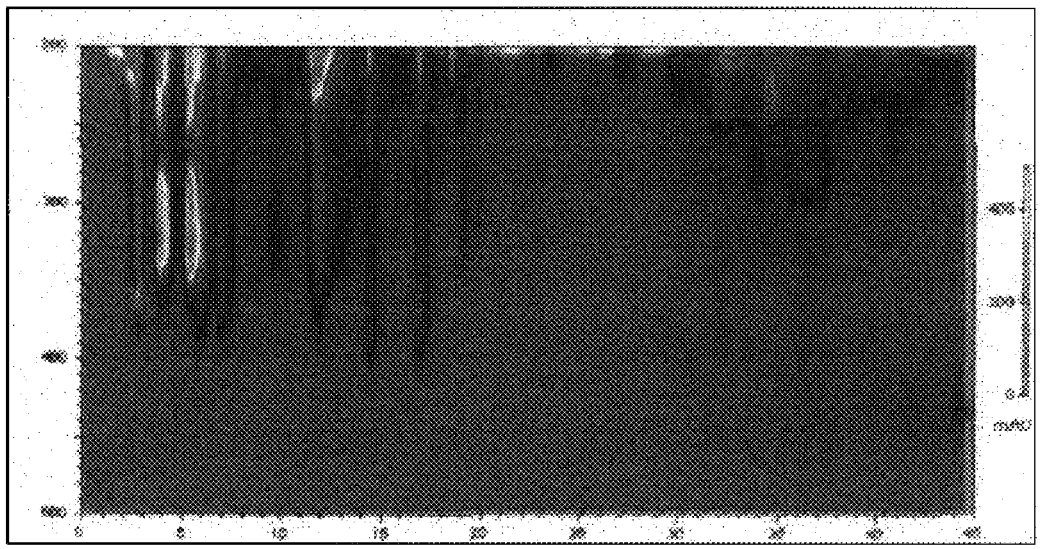

FIG. 45 (A and B) shows both fingerprints of whole herb of *Bacopa monneri*.

Figure 46A:
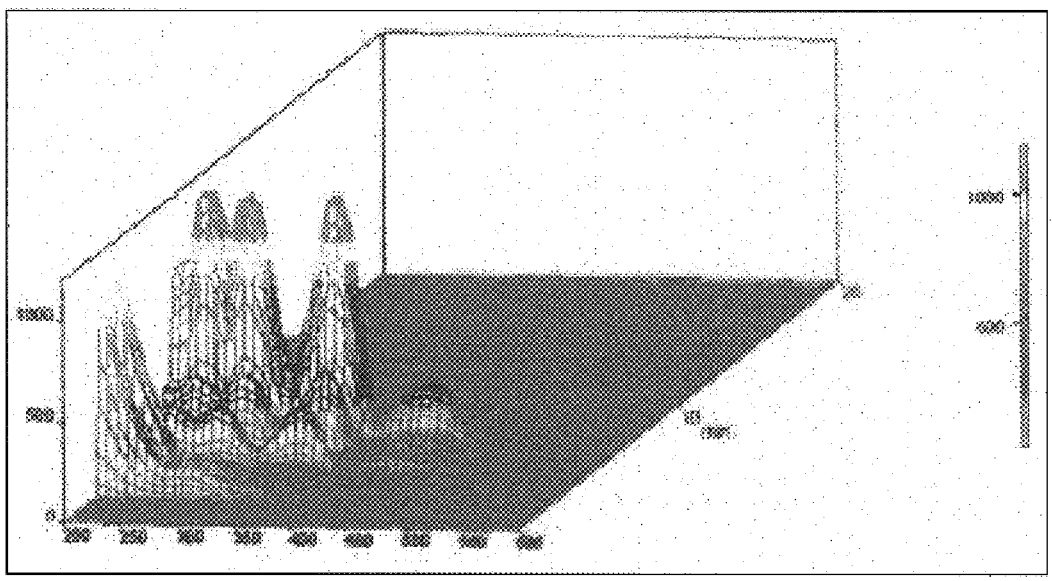
Figure 46B:
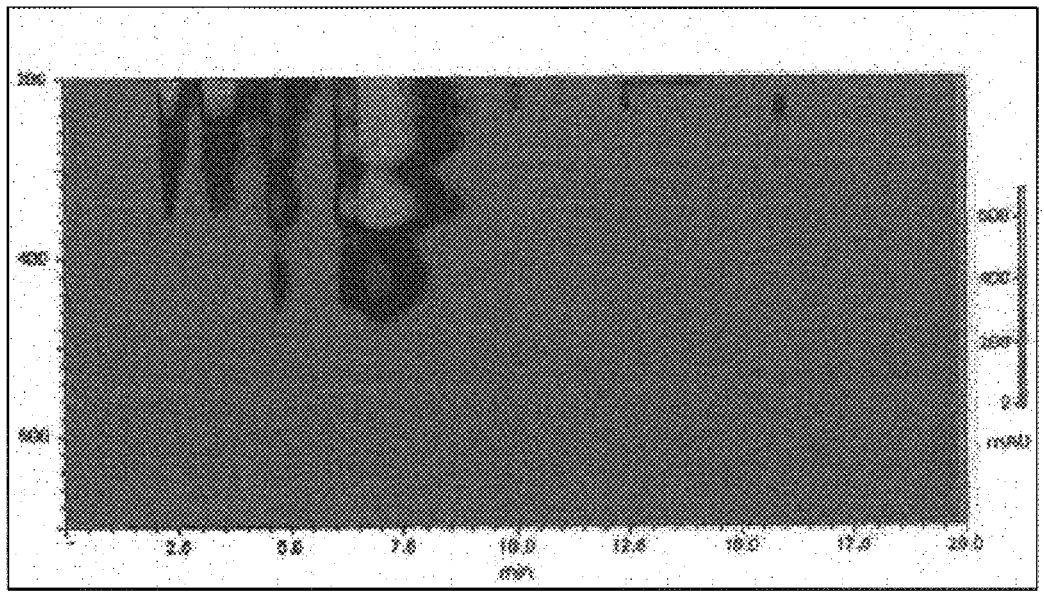

FIG. 46 (A and B) shows both fingerprints of stem bark of *Berberis aristata*.

Figure 47A:
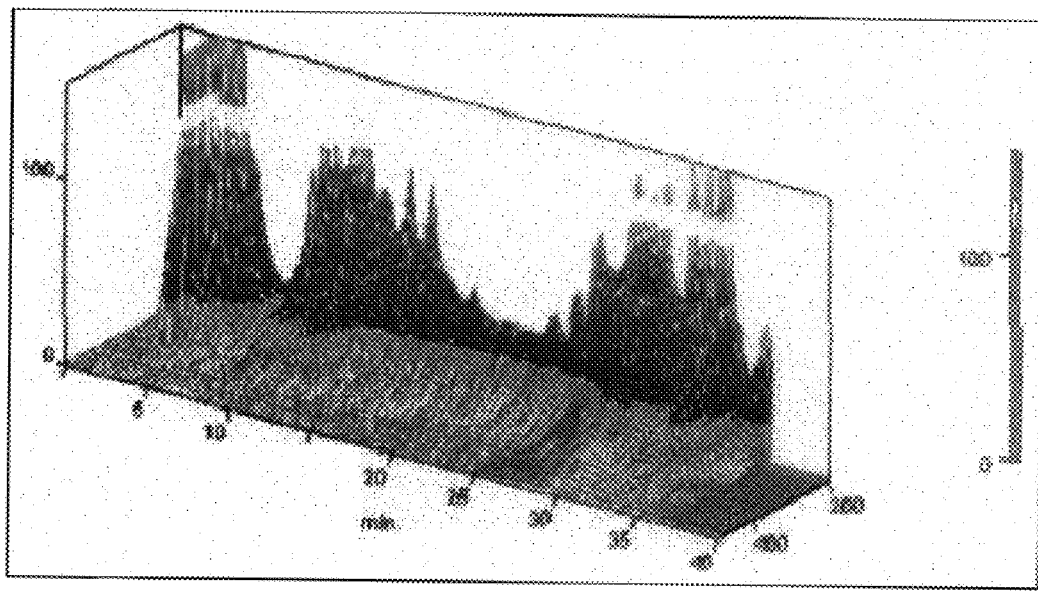
Figure 47B:
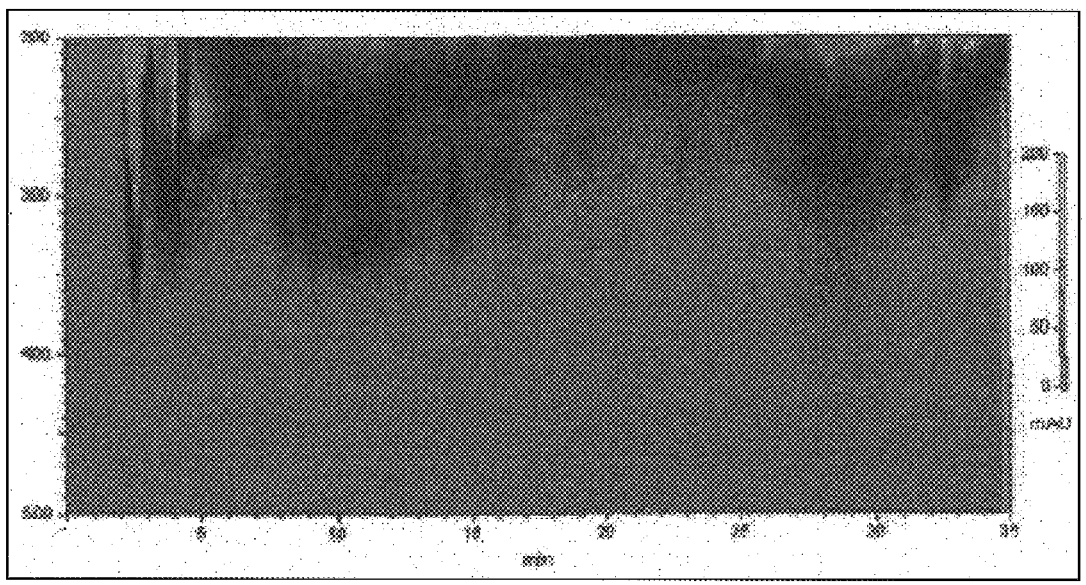

FIG. 47 (A and B) shows both fingerprints of whole plant of *Borrhievia diffusa*.

Figure 48A:
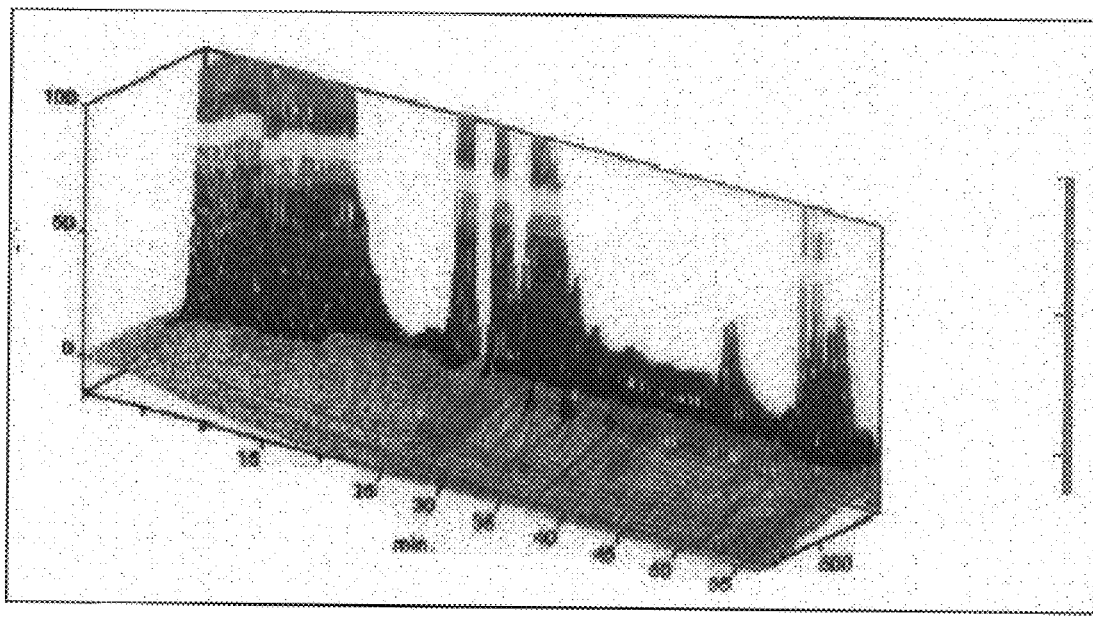
Figure 48B:
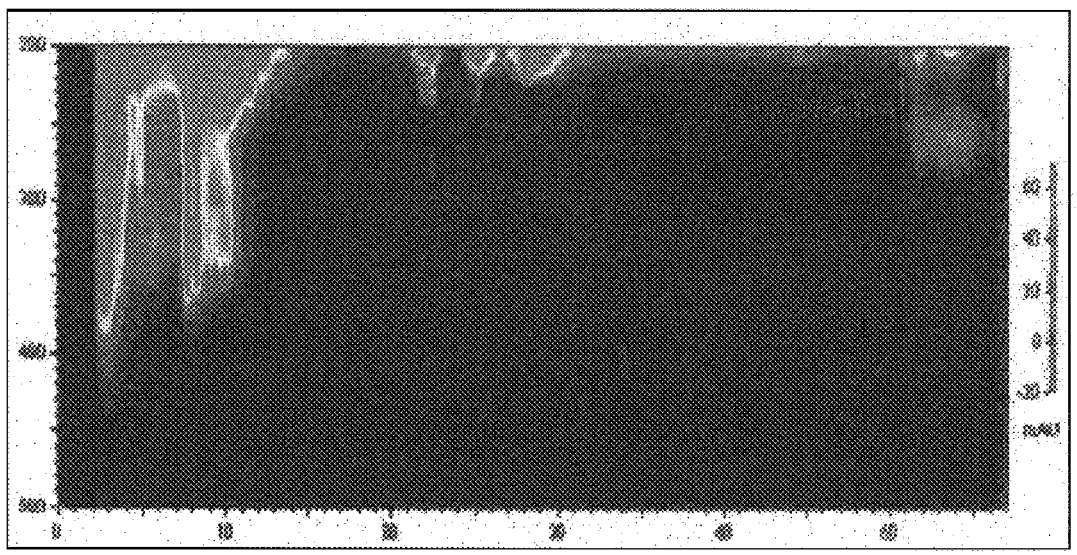

FIG. 48 (A and B) shows both fingerprints of big, ripened fruit of *Capscicum Annum linn*.

Figure 49A:
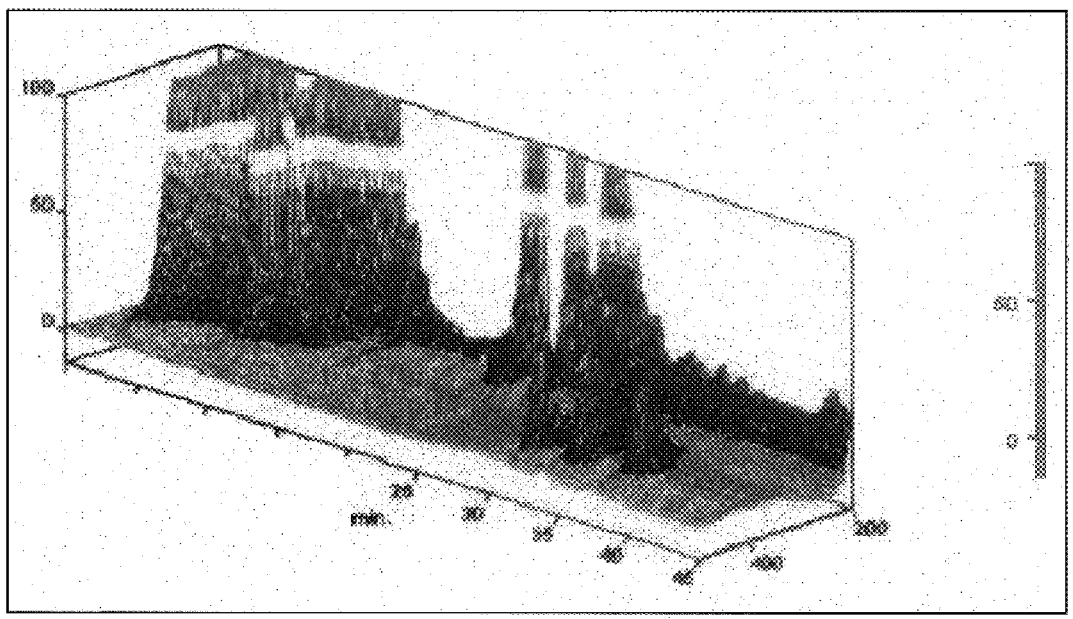
Figure 49B:
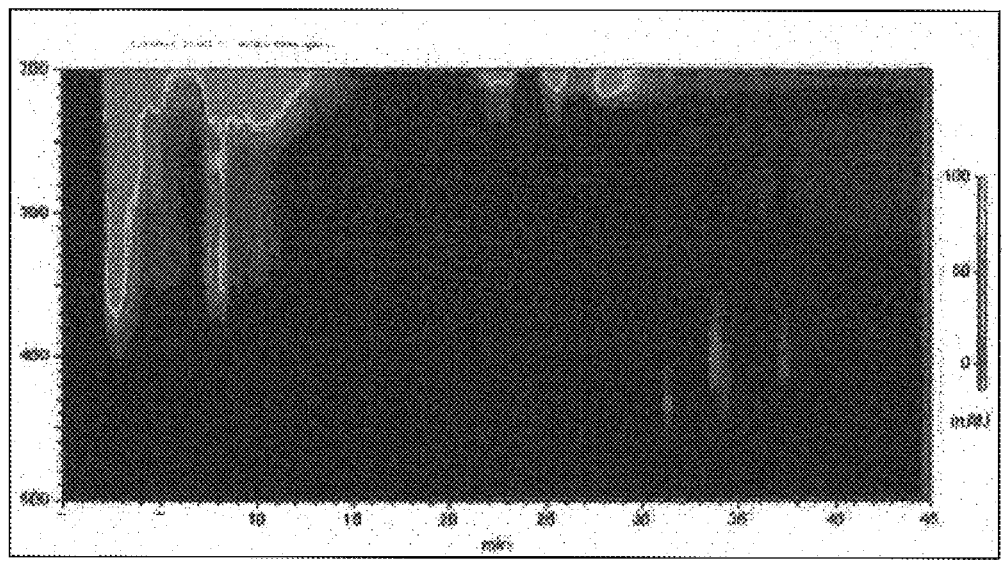

FIG. 49 (A and B) shows both fingerprints of big, un-ripened fruit of *Capscicum annum linn*.

Figure 50A:
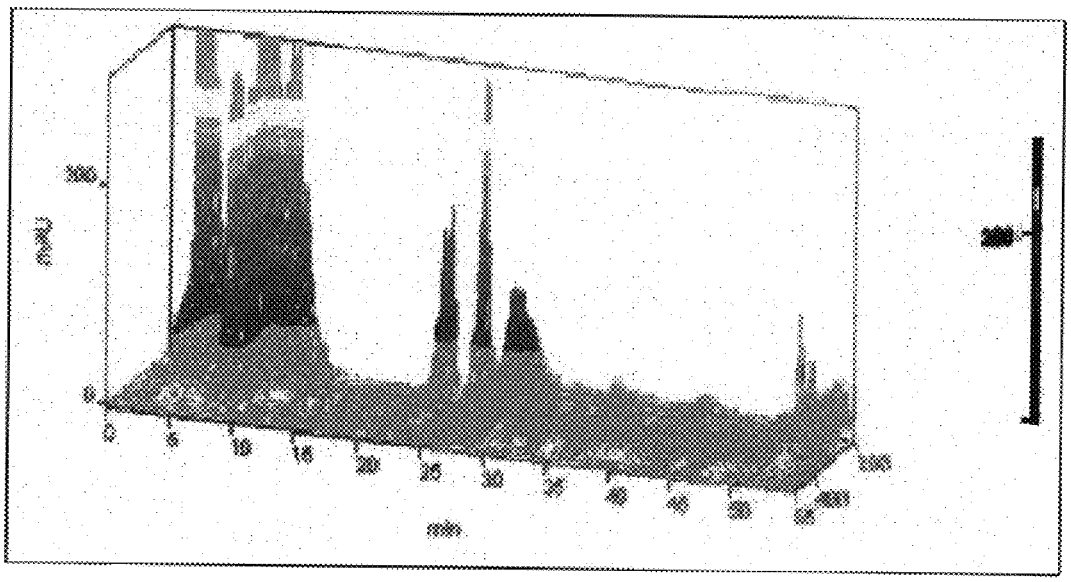
Figure 50B:
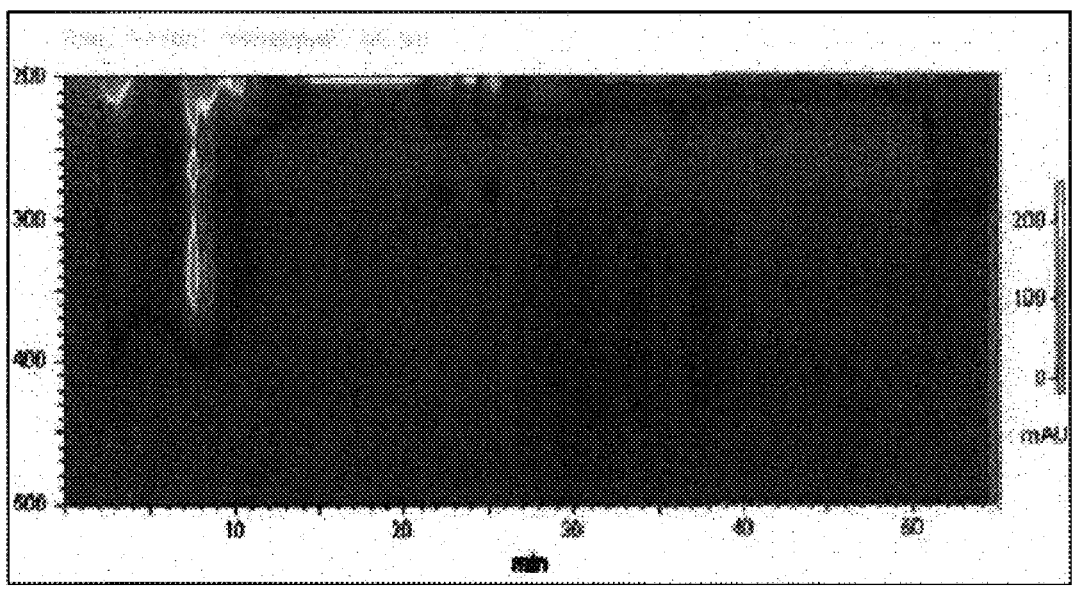

FIG. 50 (A and B) shows both fingerprints of small, un-ripened, fruit of *Capscicum annum linn*.

Figure 51A:
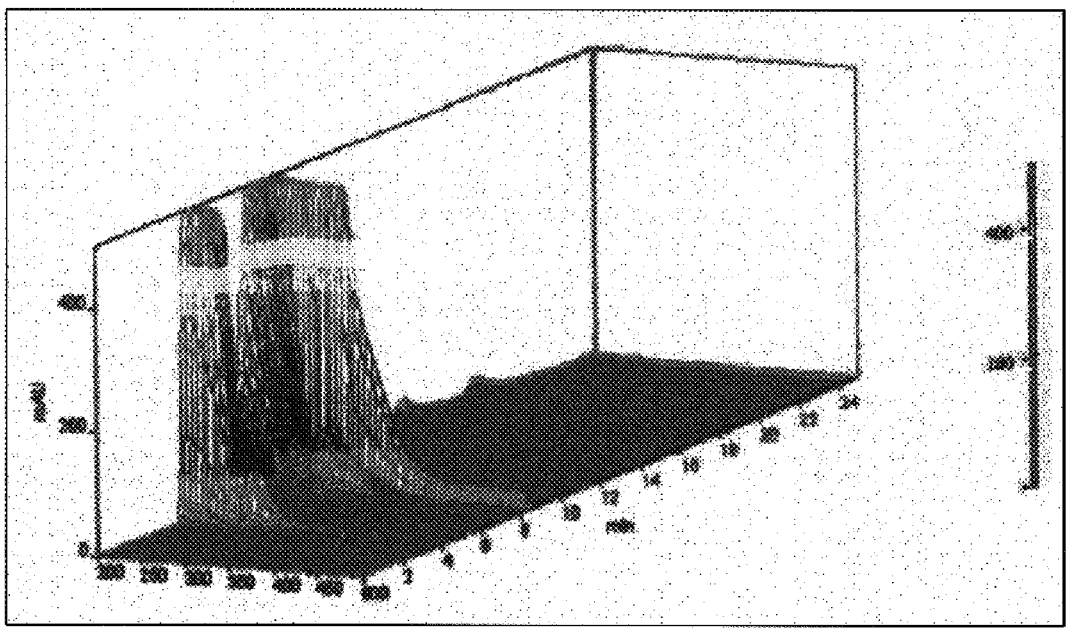
Figure 51B:
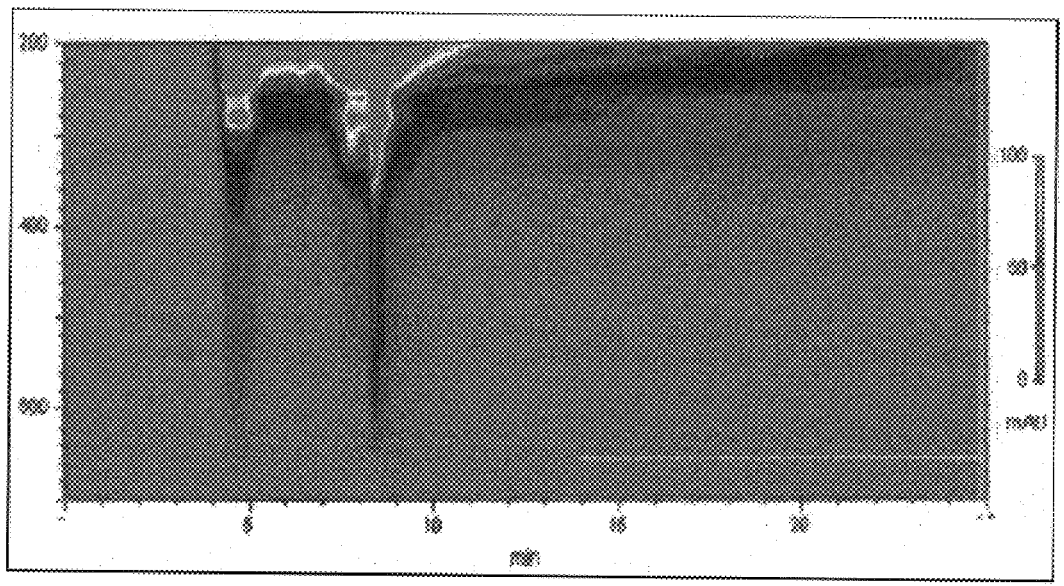

FIG. 51 (A and B) shows both fingerprints of stem bark of *Coscinium fenestratum*.

Figure 52A:
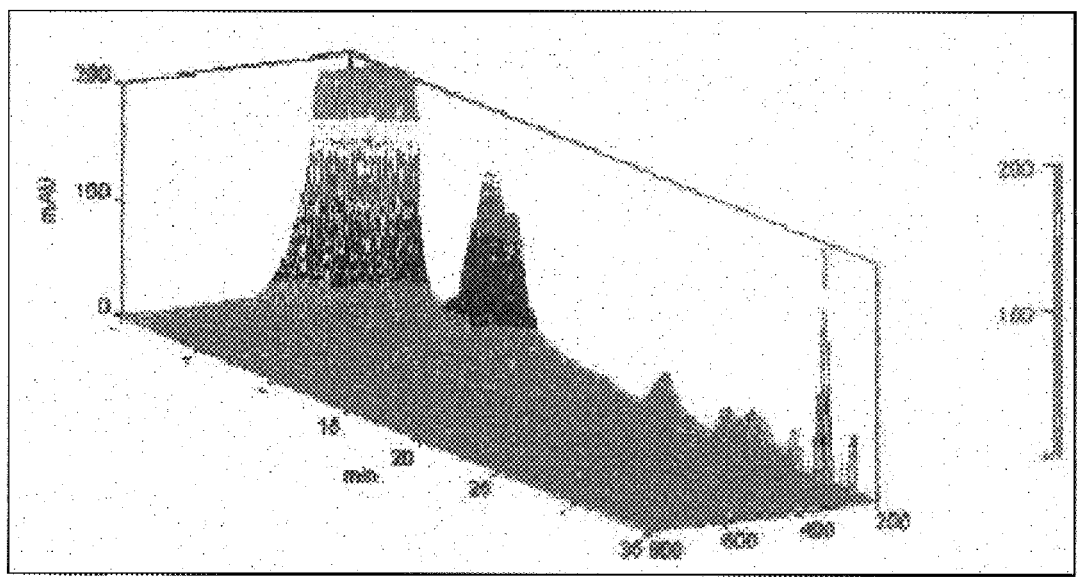
Figure 52B:
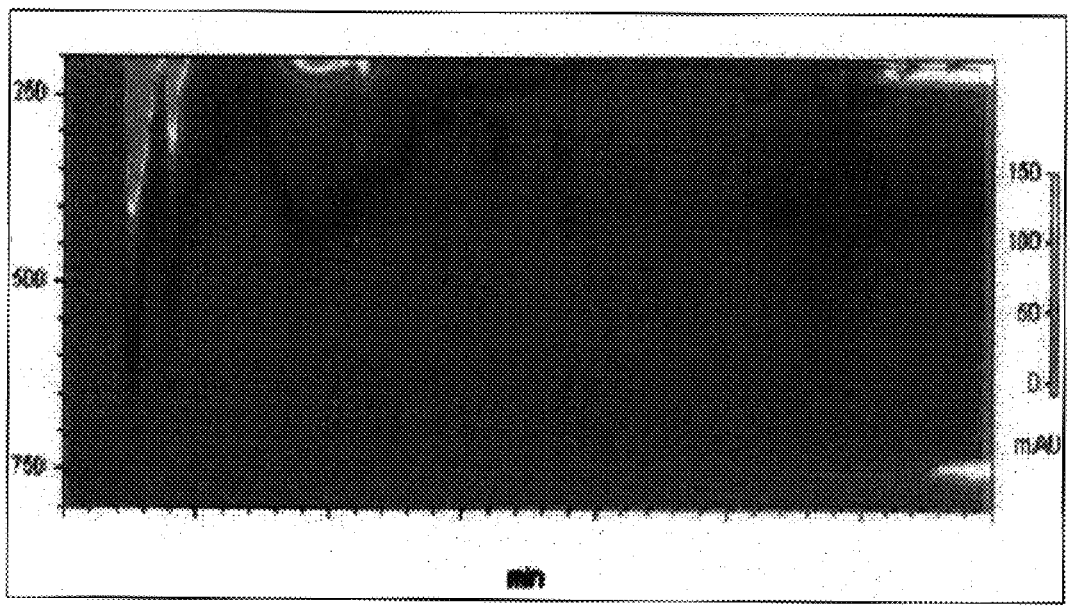

FIG. 52 (A and B) shows both fingerprints of root and leaf of *Coccinidium grandis*.

Figure 53A:
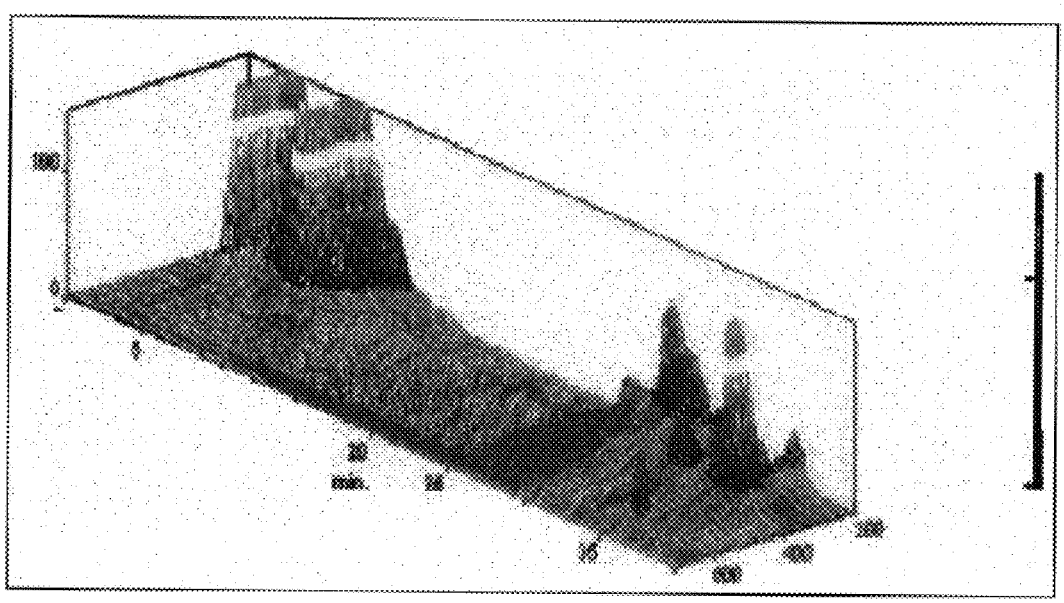
Figure 53B:
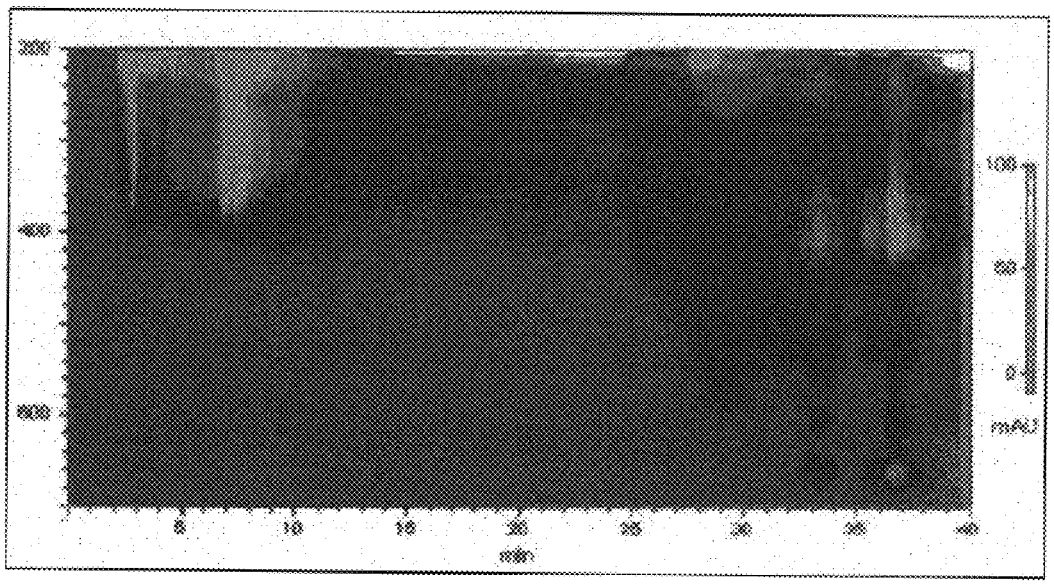

FIG. 53 (A and B) shows both fingerprints of leaf of *Dactlylactinium Aegyptium* (erect).

Figure 54A:
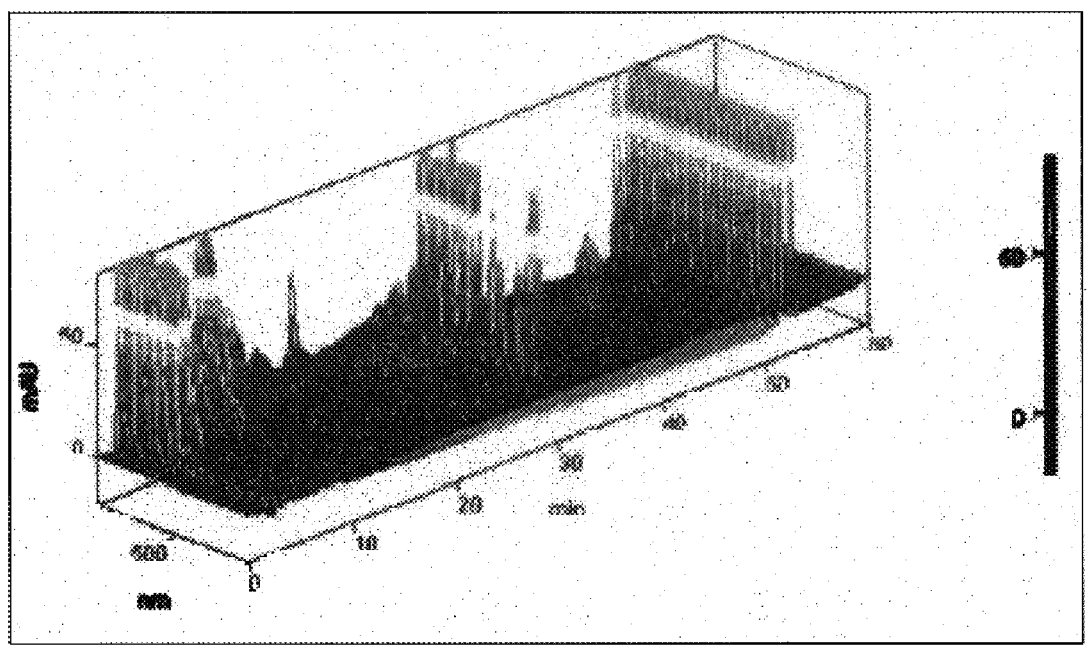
Figure 54B:
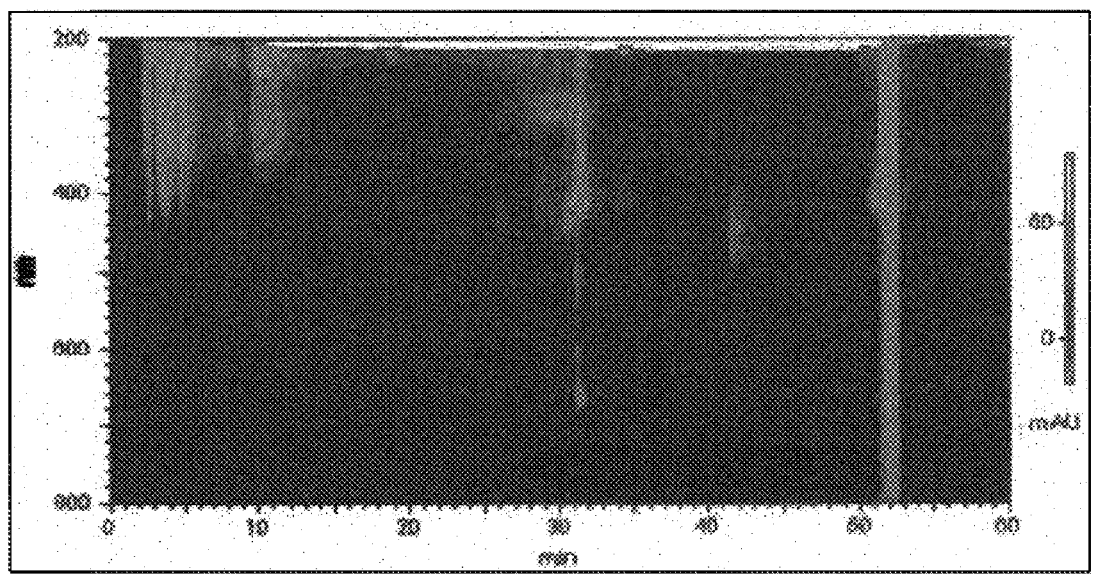

FIG. 54 (A and B) shows both fingerprints of leaf of *Dactlylactinium Aegyptium* (prostrate).

Figure 55A:
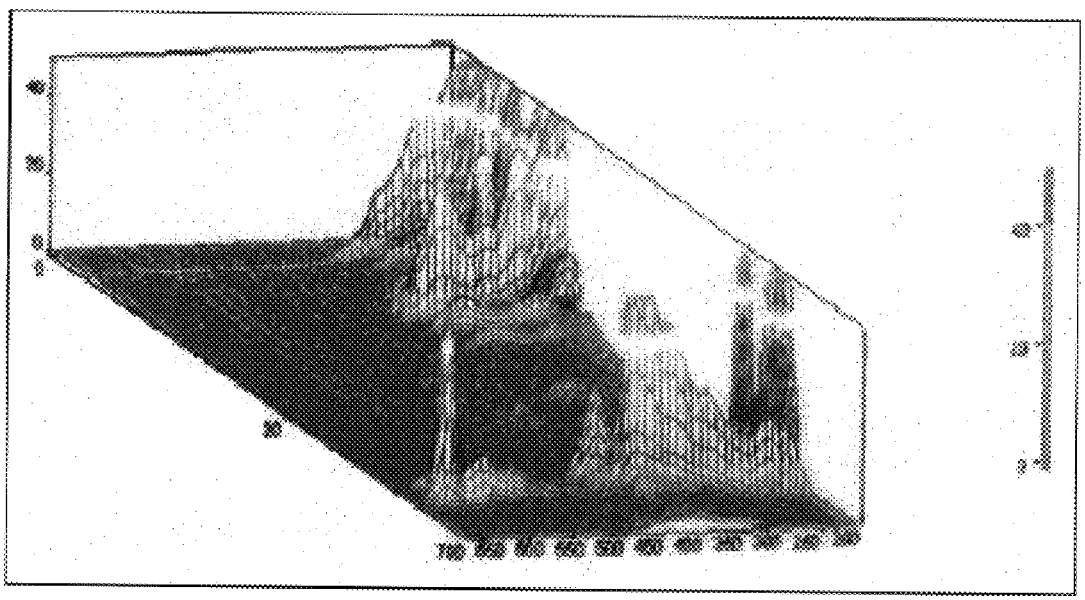
Figure 55B:
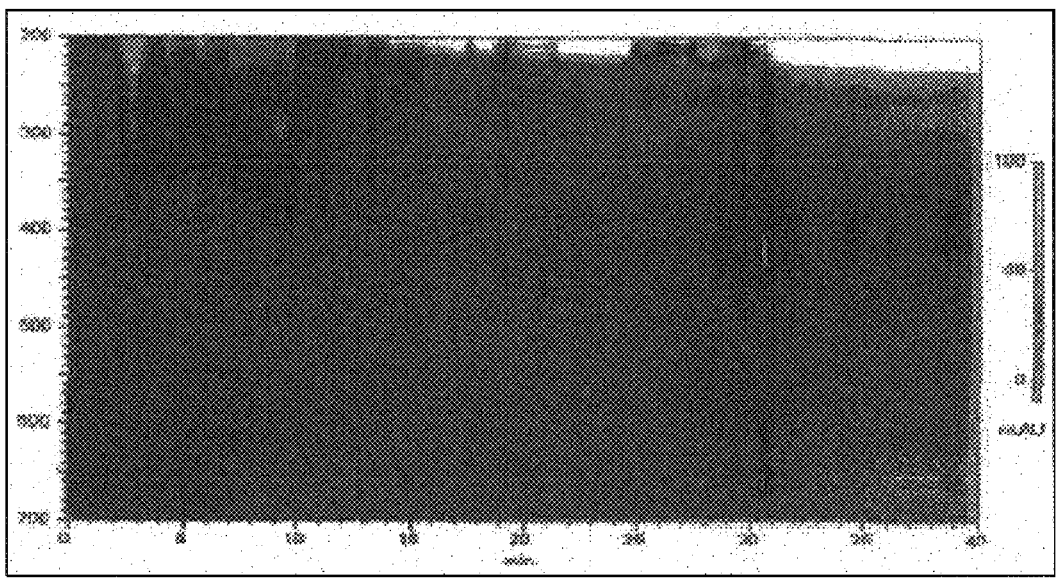

FIG. 55 (A and B) shows both fingerprints of leaf and bark of *Diristachis cineraria*.

Figure 56A:
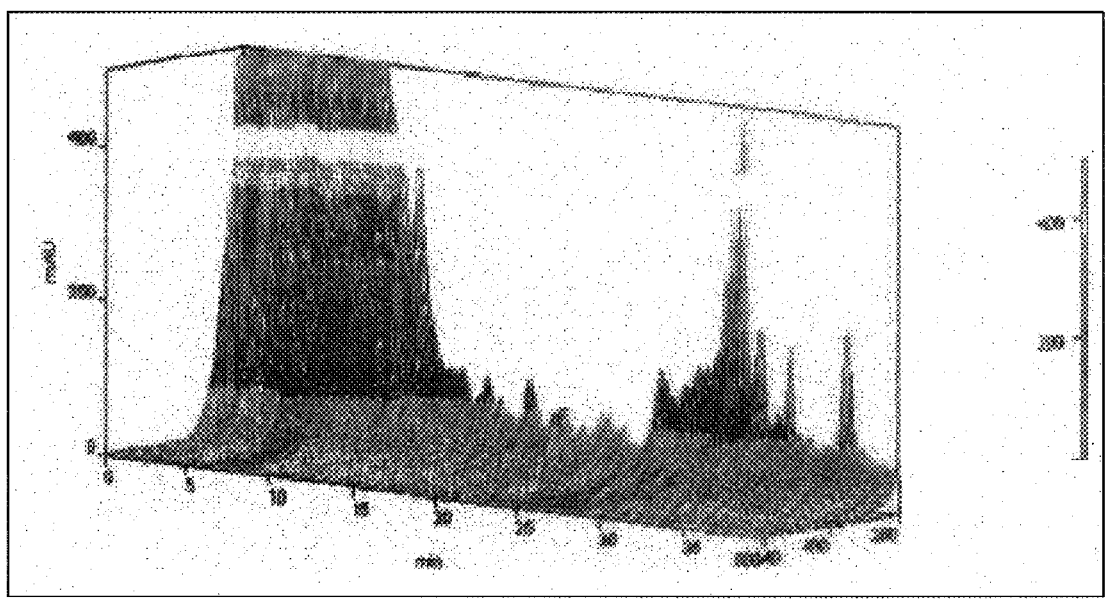
Figure 56B:
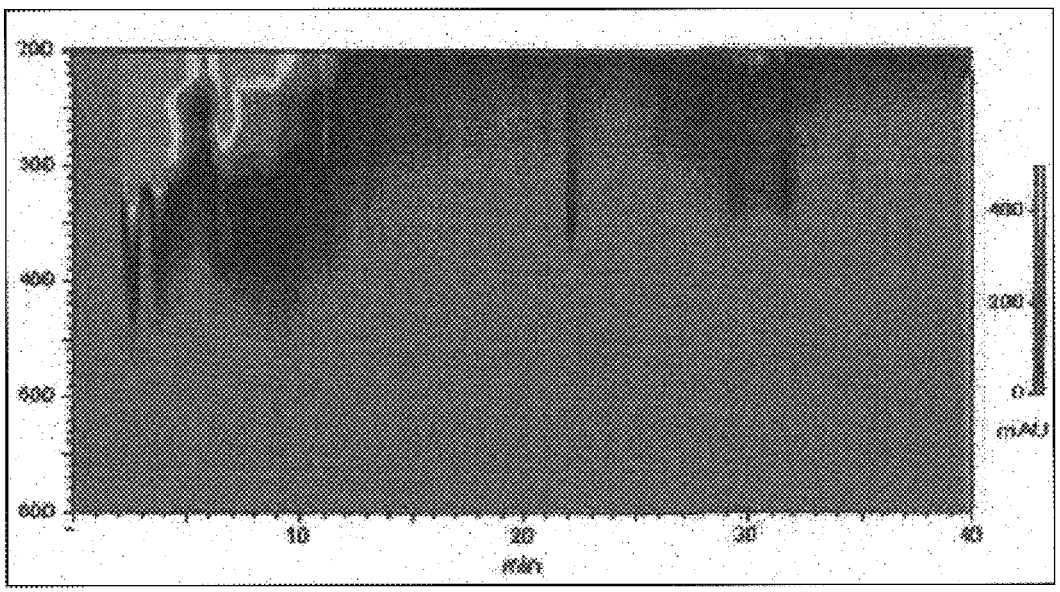
Figure 56A:
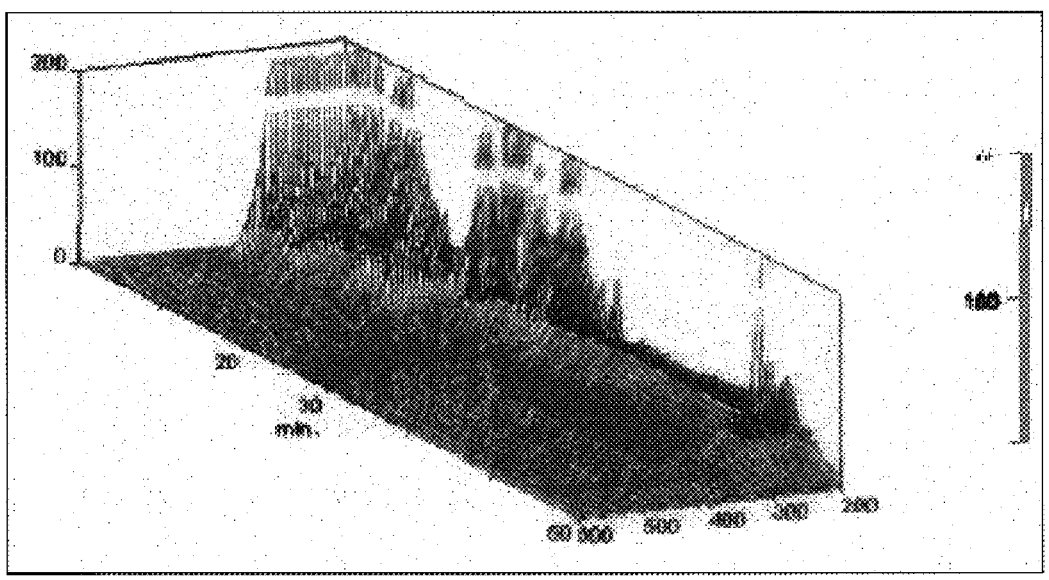

FIG. 56 (A and B) shows both fingerprints of fruit epicarp of *Emblica officinalis*.

Figure 57A:
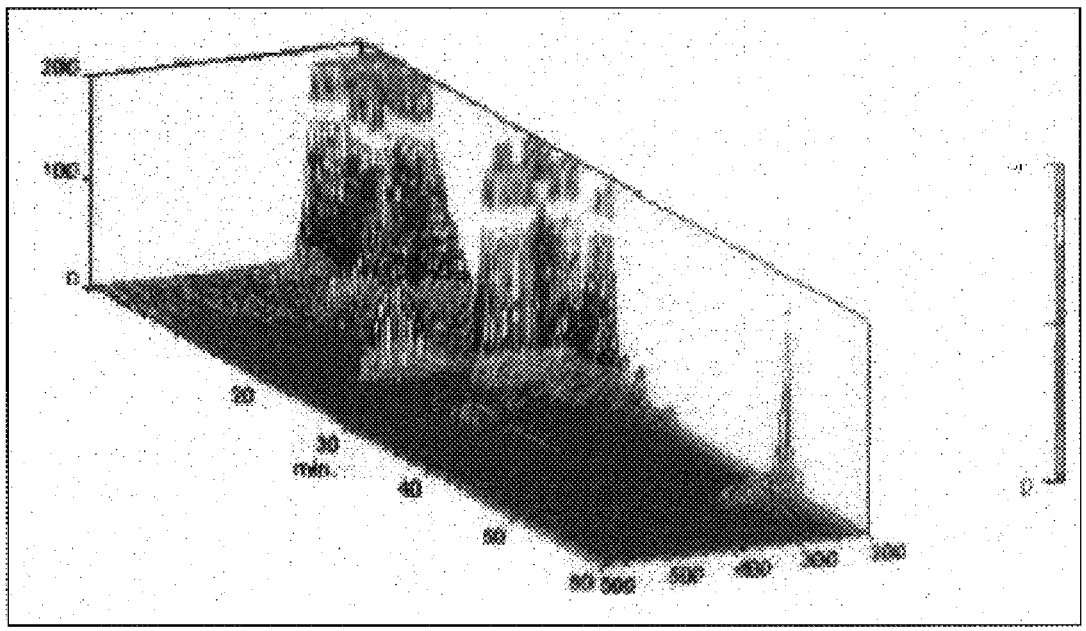
Figure 57B:
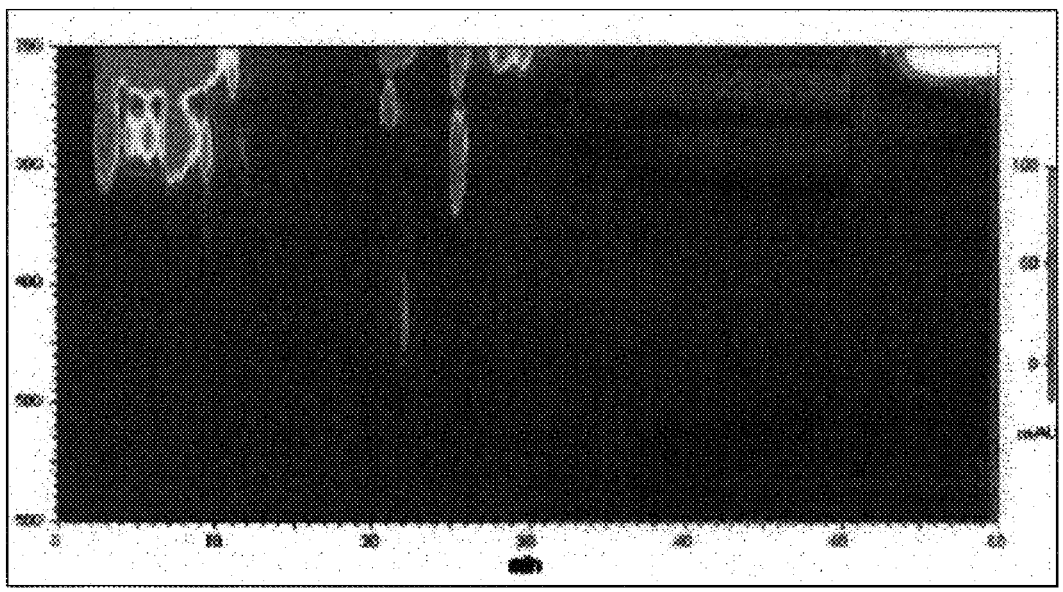

FIG. 57 (A and B) shows both fingerprints of formulation of a face pack.

Figure 58B:
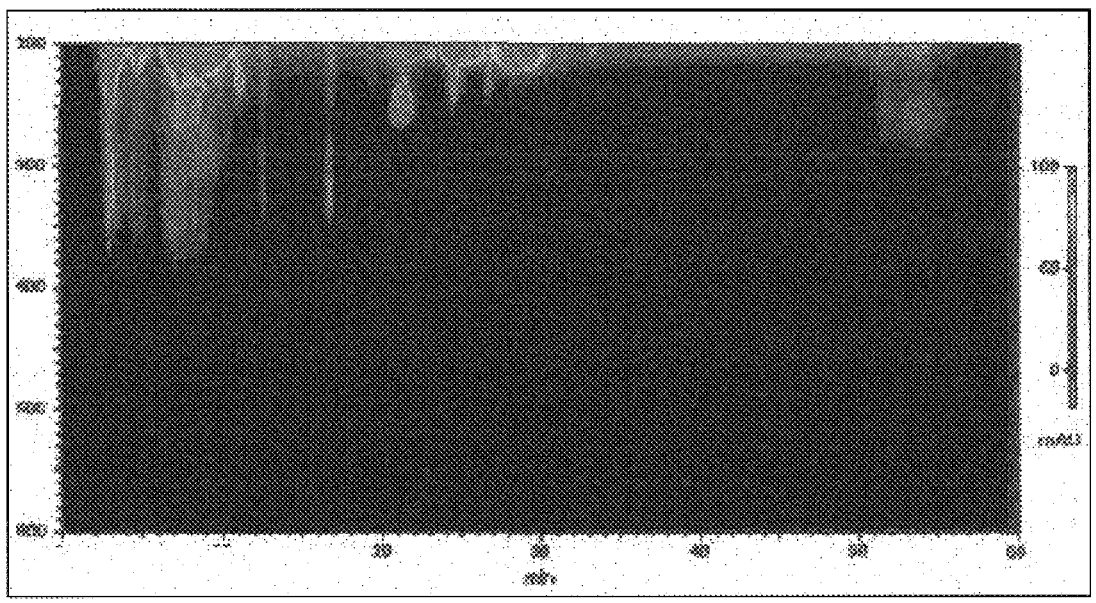

FIG. 58 (A and B) shows both fingerprints of formulation of a face pack.

Figure 59A:
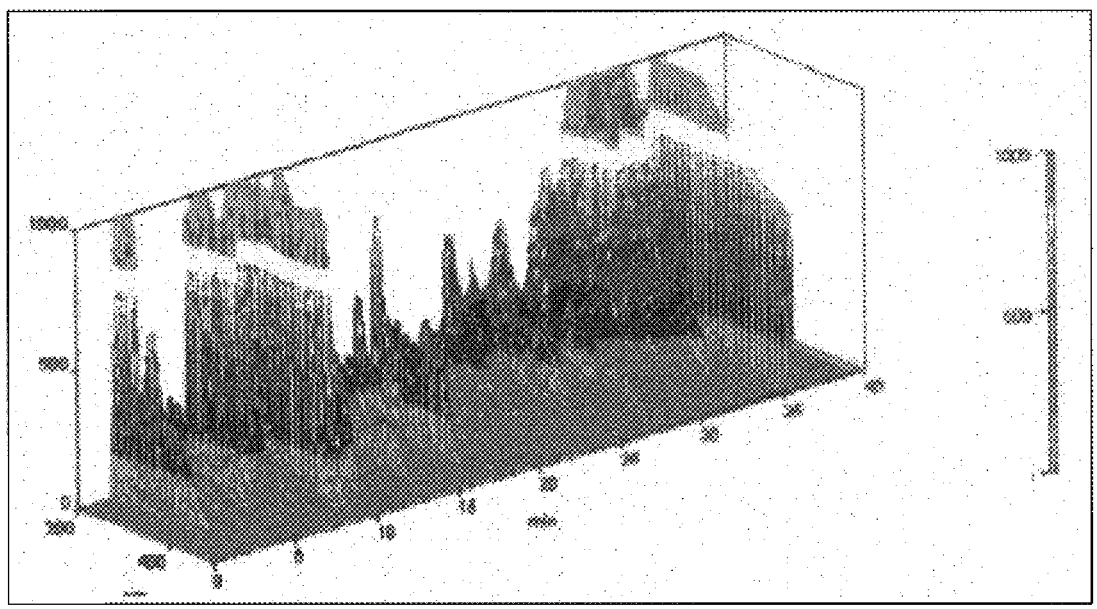
Figure 59B:
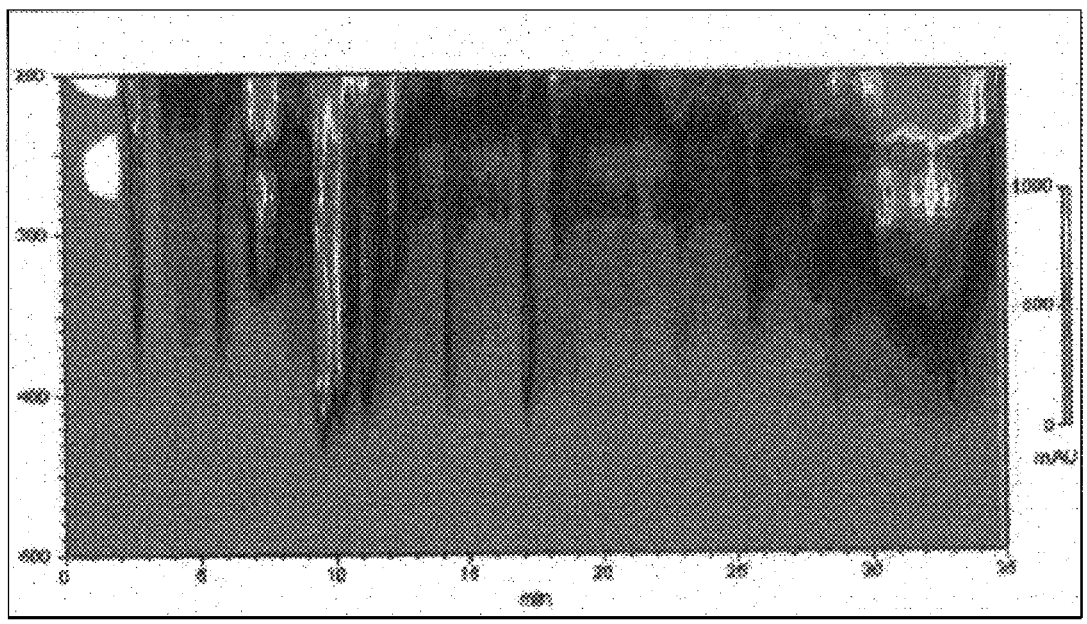

FIG. 59 (A and B) shows both fingerprints of root bark of *Glycerrhzia glabra*.

Figure 60A:
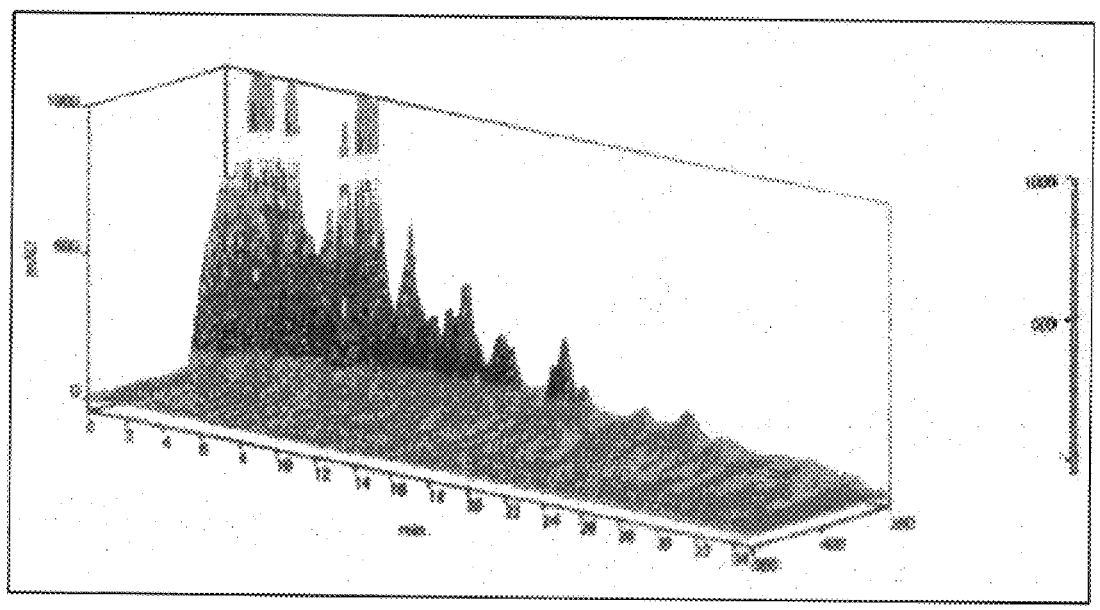
Figure 60B:
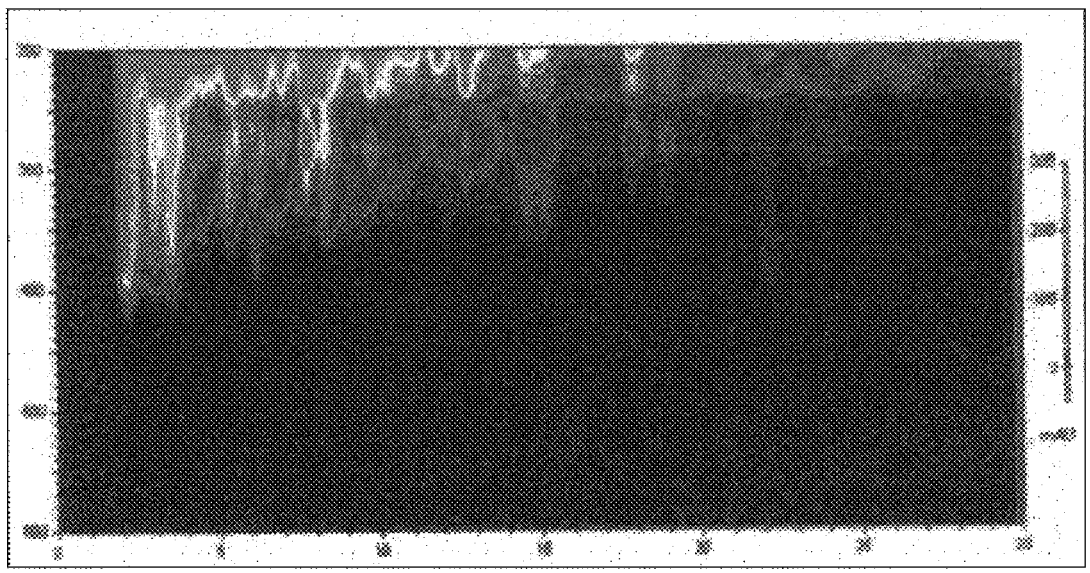

FIG. 60 (A and B) shows both fingerprints of powder of whole plant of *Glycerrhzia glabra*.

Figure 61B:
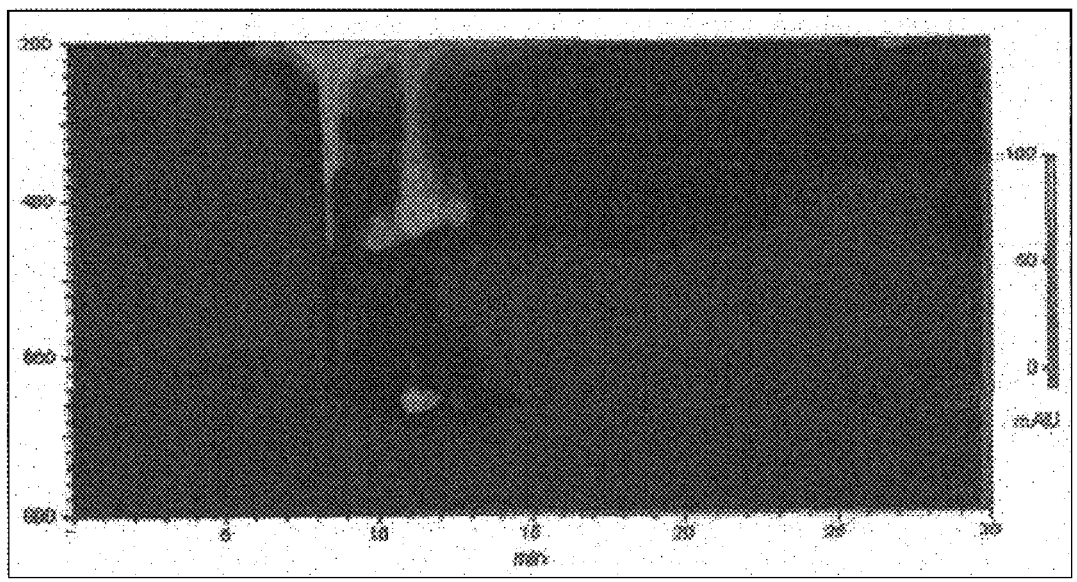

FIG. 61 (A and B) shows both fingerprints of whole plant of *Gymnema sylvestrae*.

Figure 62A:
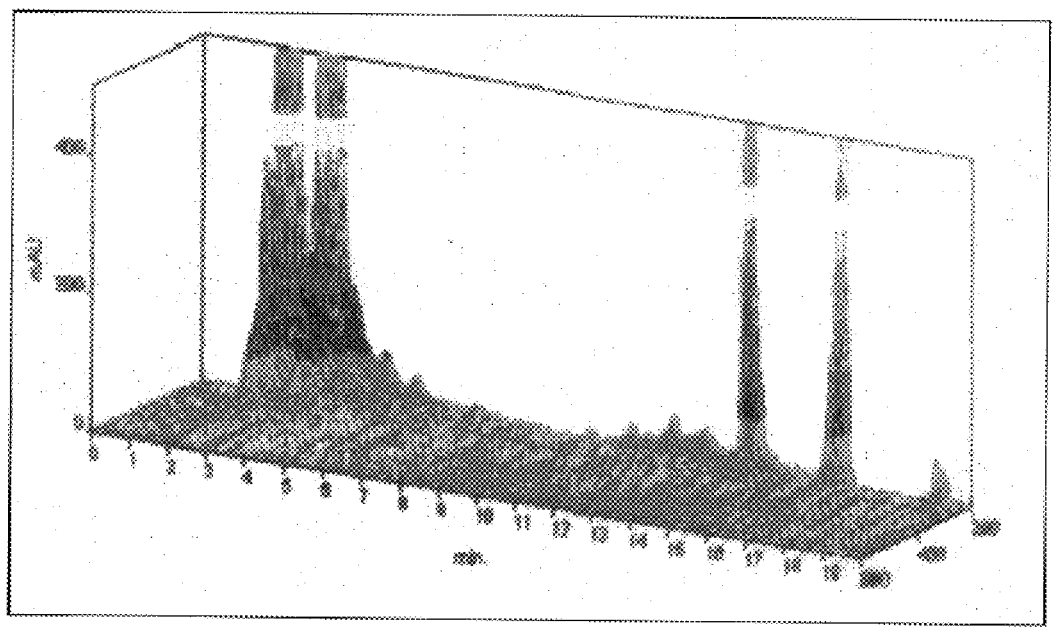
Figure 62B:
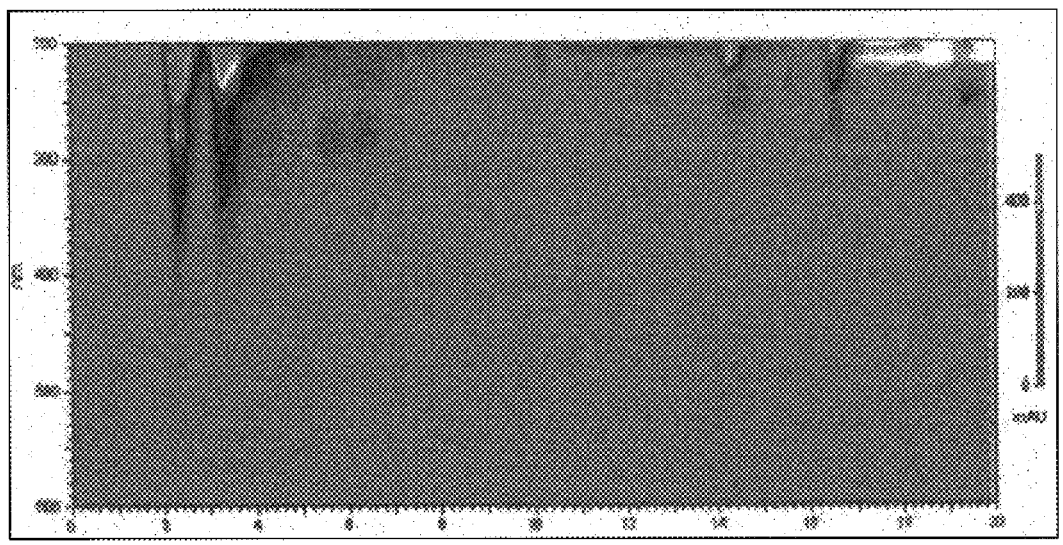

FIG. 62 (A and B) shows both fingerprints of stem bark of *Hollerona Antidysentrica*.

Figure 63A:
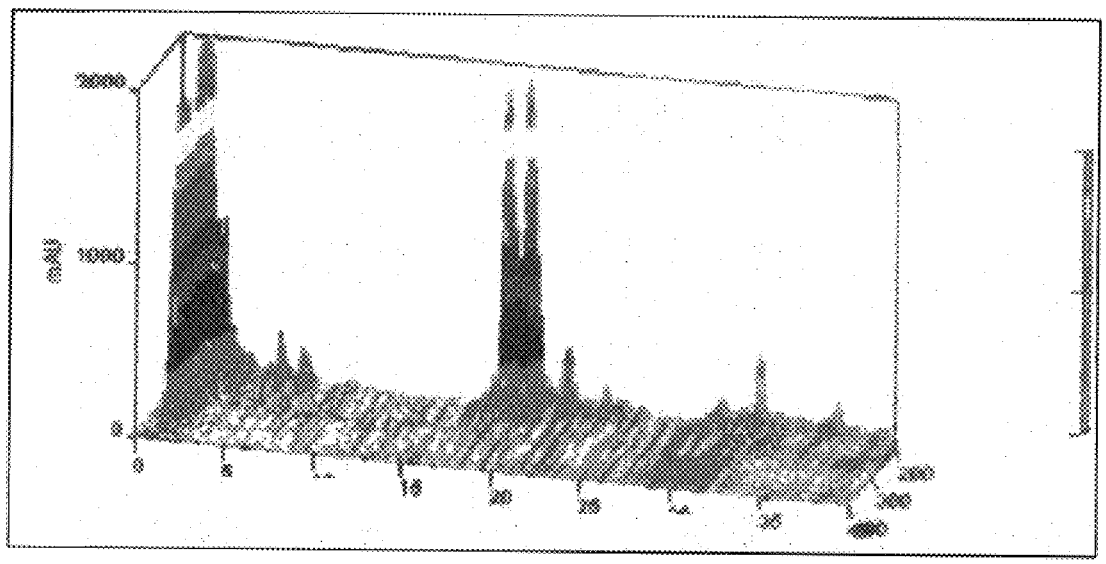
Figure 63B:
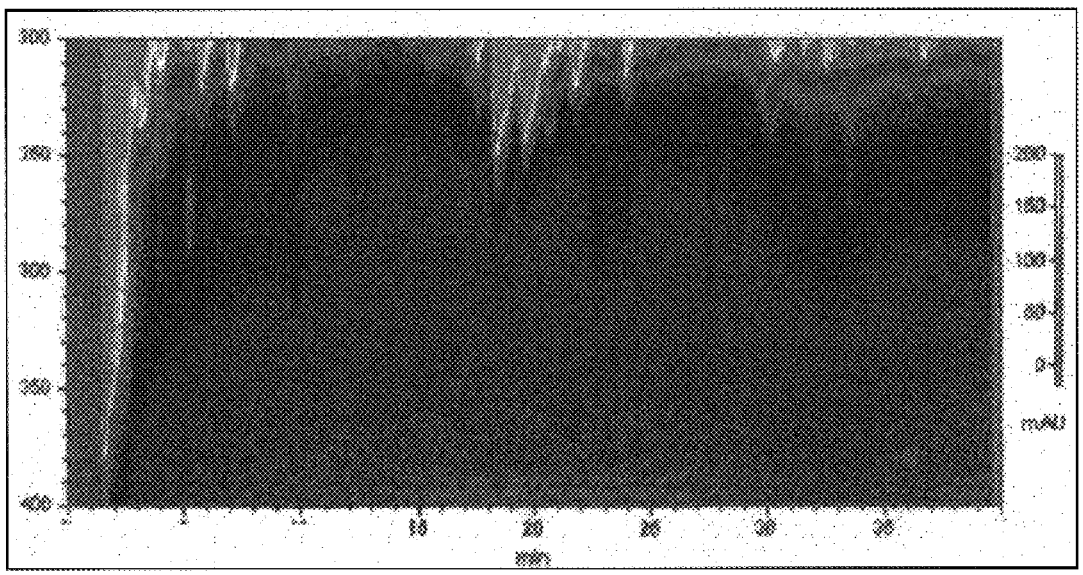

FIG. 63 (A and B) shows both fingerprints of root of *Innula recemosa*.

Figure 64A:
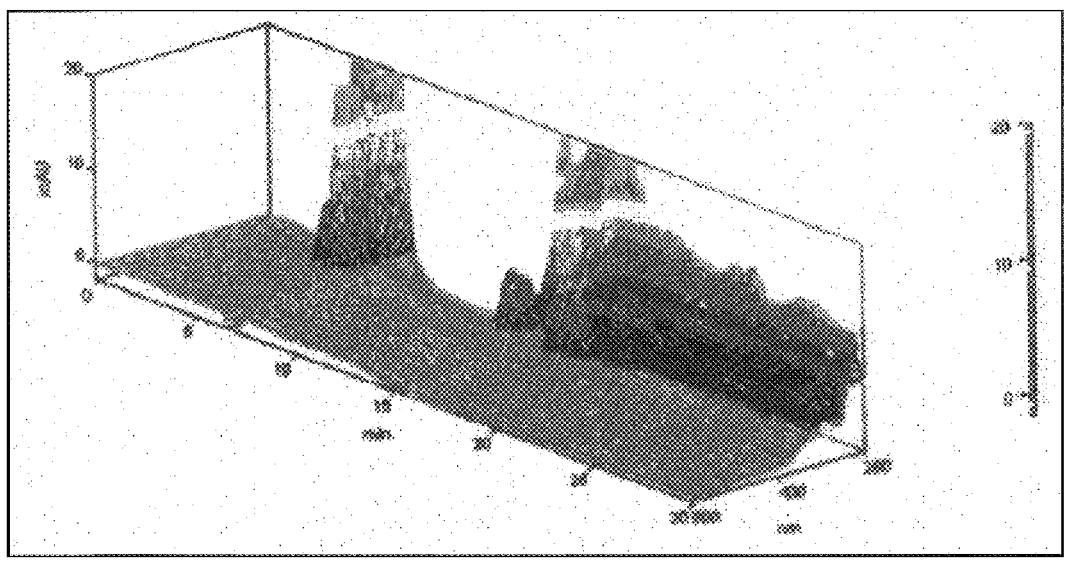
Figure 64B:
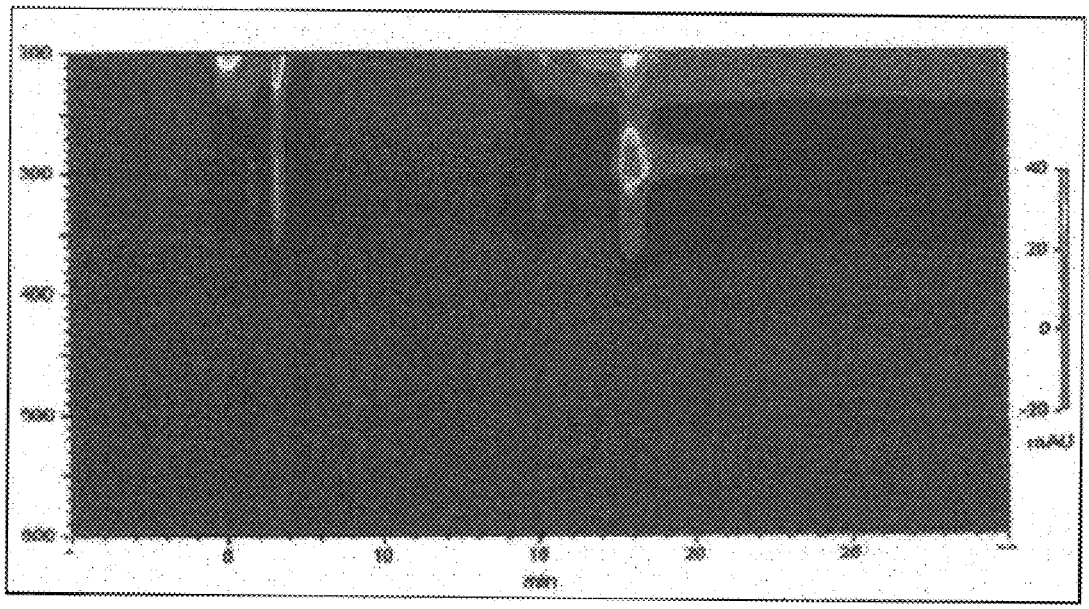

FIG. 64 (A and B) shows both fingerprints of flower of *Michellia champaka*.

Figure 65B:
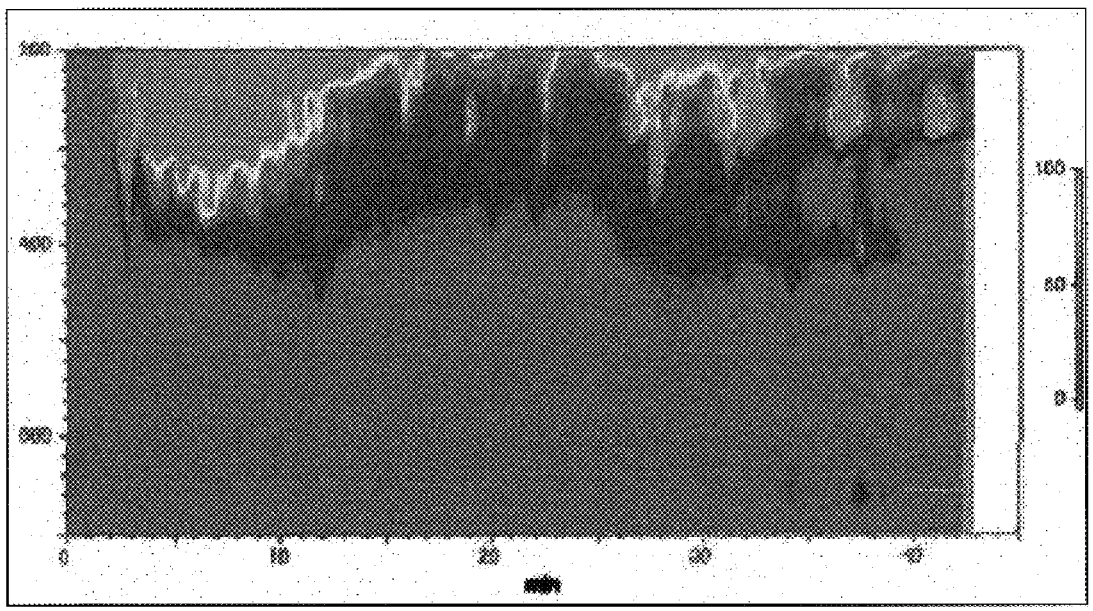

FIG. 65 (A and B) shows both fingerprints of leaf of *Moringa olifera*.

Figure 66A:
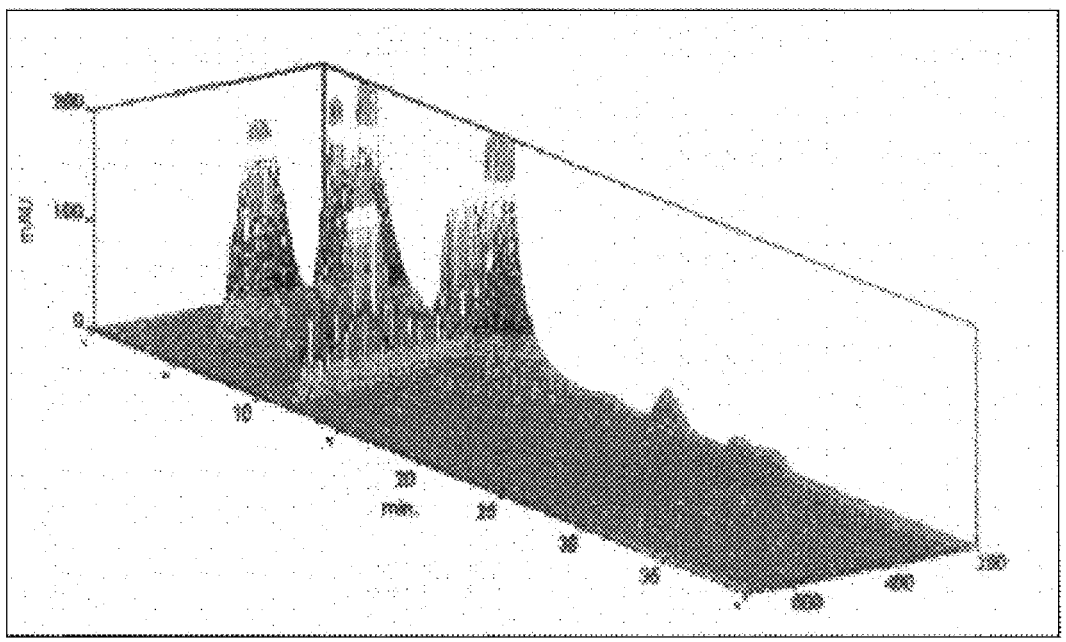
Figure 66B:
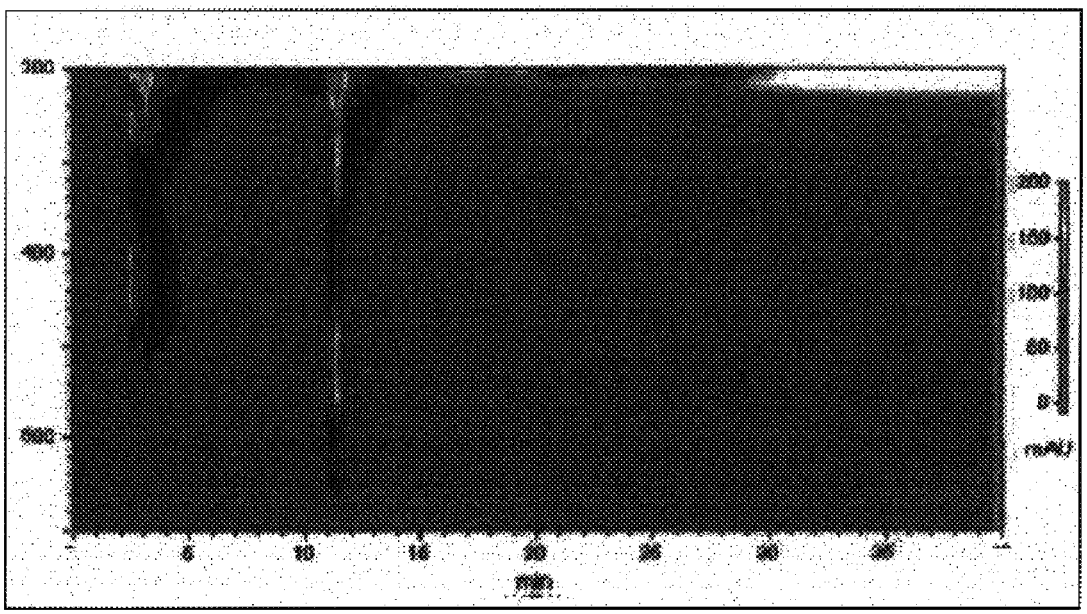

FIG. 66 (A and B) shows both fingerprints of homeopathic mother tincture of *Myrica cerefera*.

Figure 67B:
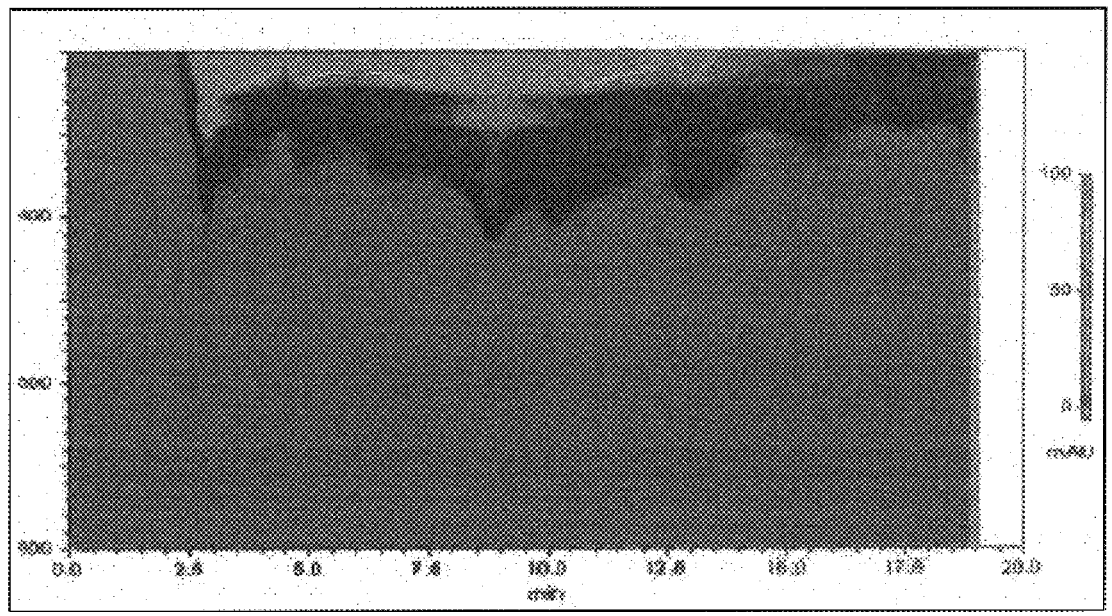
Figure 67A:
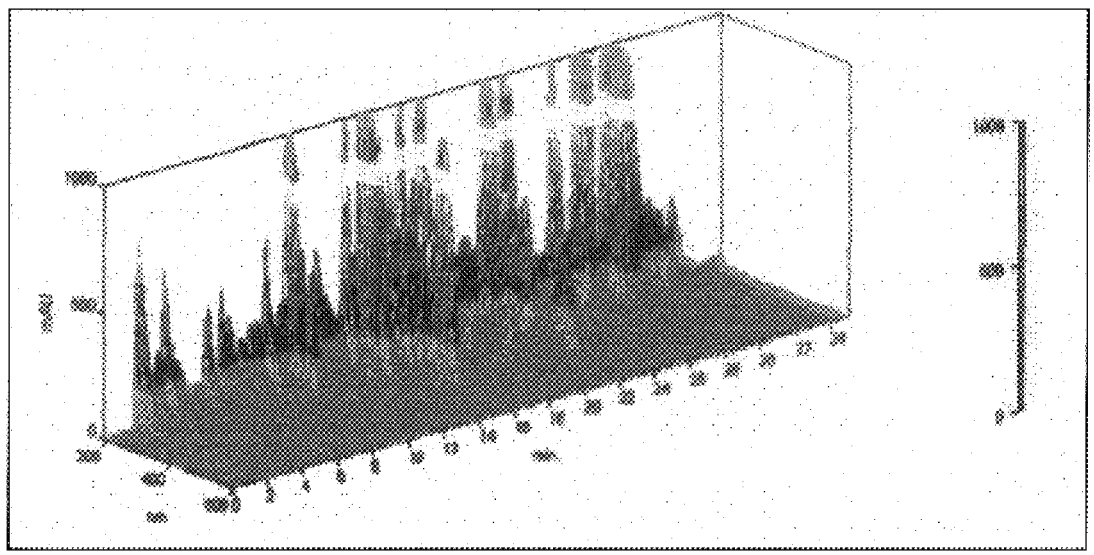

FIG. 67 (A and B) shows both fingerprints of a whole plant of *Nahi axillae*.

Figure 68A:
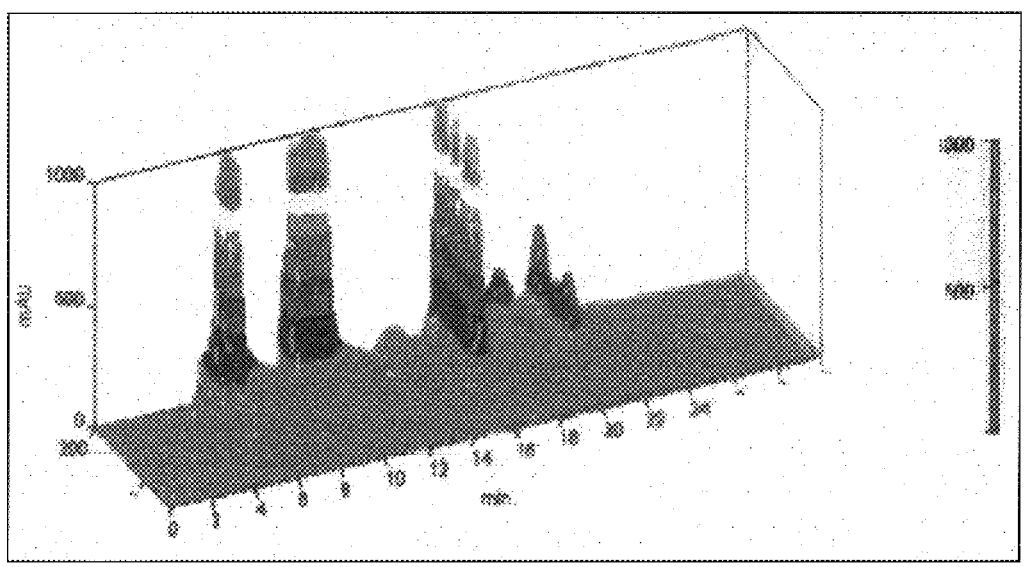
Figure 68B:
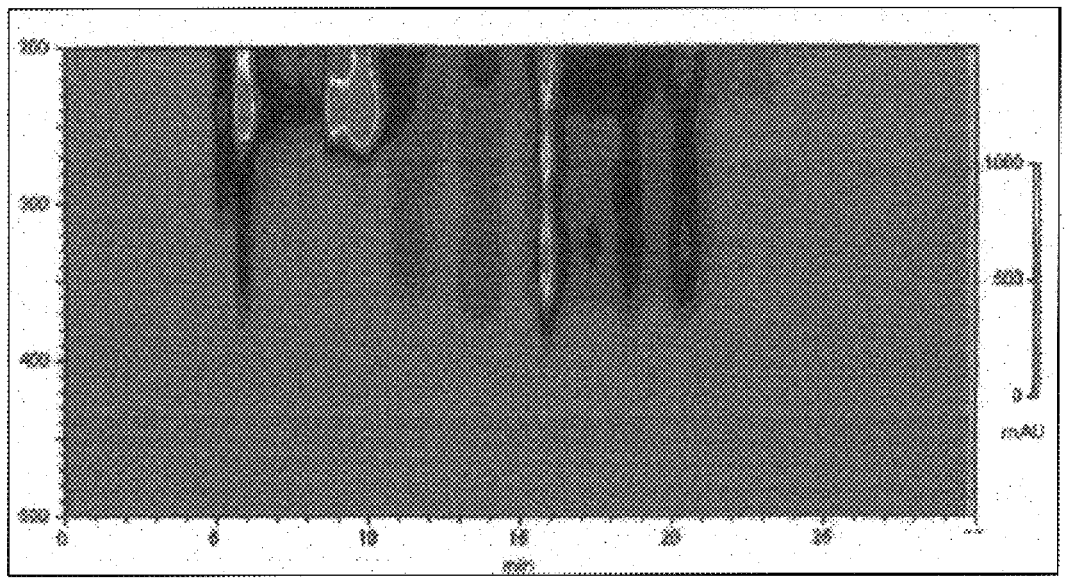

FIG. 68 (A and B) shows both fingerprints of stem bark of *Oroxylum indicum*.

FIG. 69 shows both fingerprints of leaf of *Ocimum sanctum*

FIG. 70 shows both fingerprints of leaf of *Pluchea lanceolata*

FIG. 71 shows both fingerprints of stem bark of *Picrorrhiza kurroh*

FIG. 72 shows both fingerprints of leaf of *Piper beetle*.

FIG. 73 shows both fingerprints of seeds of *Psoralia corilifolia*

FIG. 74 shows both fingerprints of leaf of *Raphanus sativus*

FIG. 75 shows both fingerprints of root of *Ricinus cummunis*

Figure 76A:
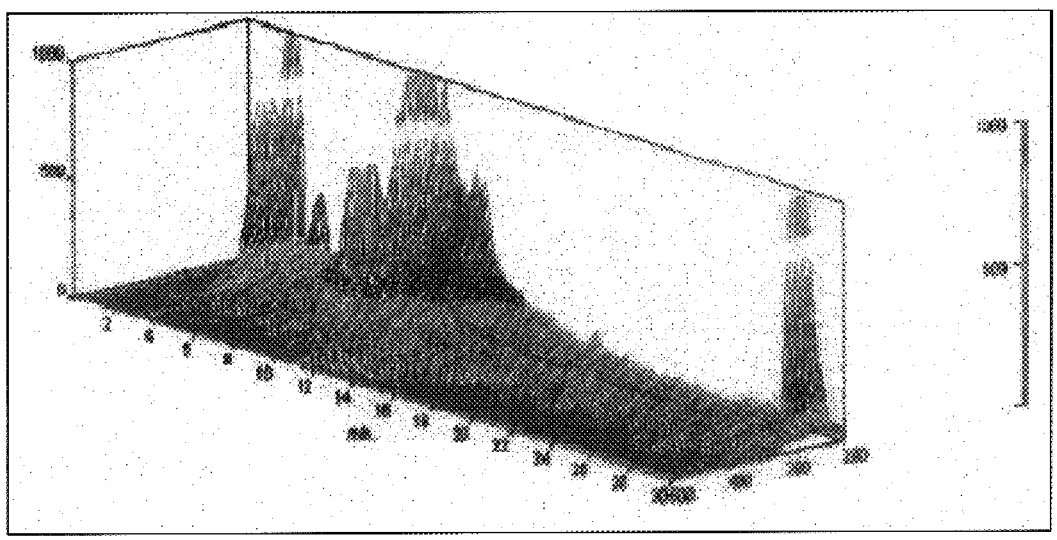
Figure 76B:
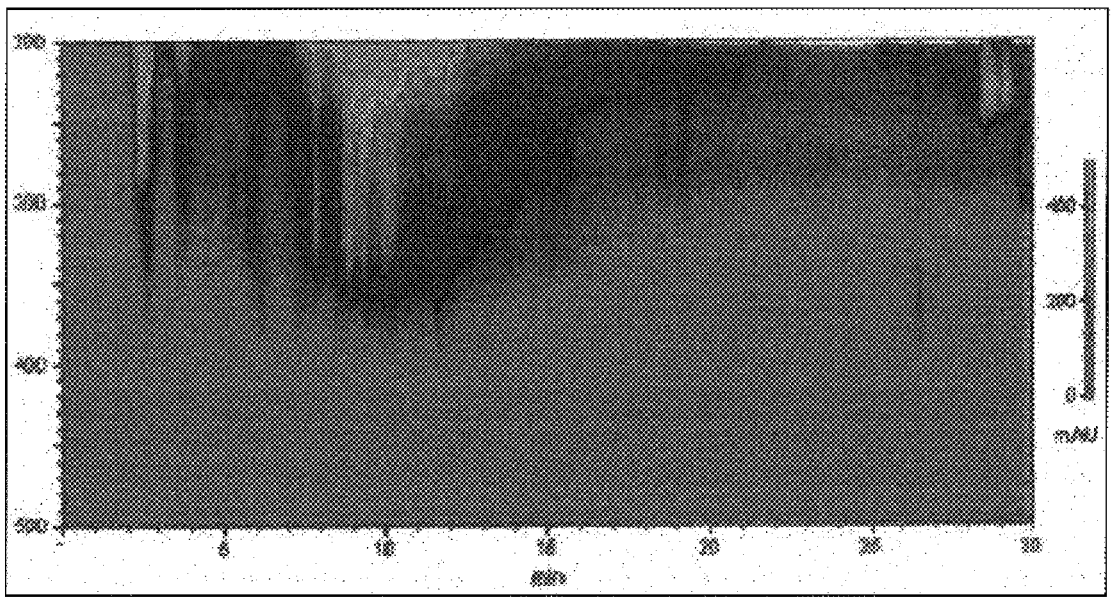
Figure 76B:

FIG. 76 (A and B) shows both fingerprints of stem and root of *Rubia cordifolia*.

Figure 77A:
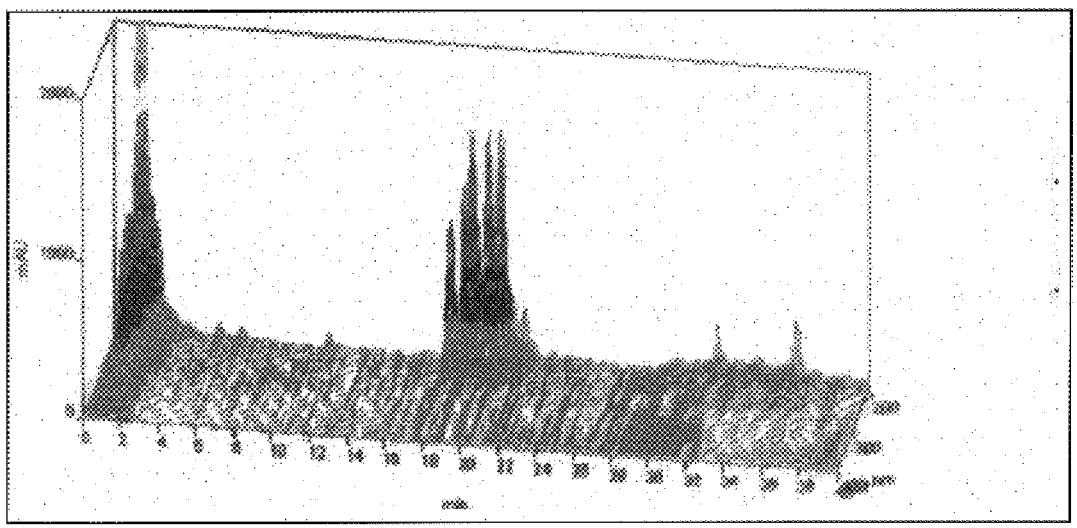
Figure 77B:
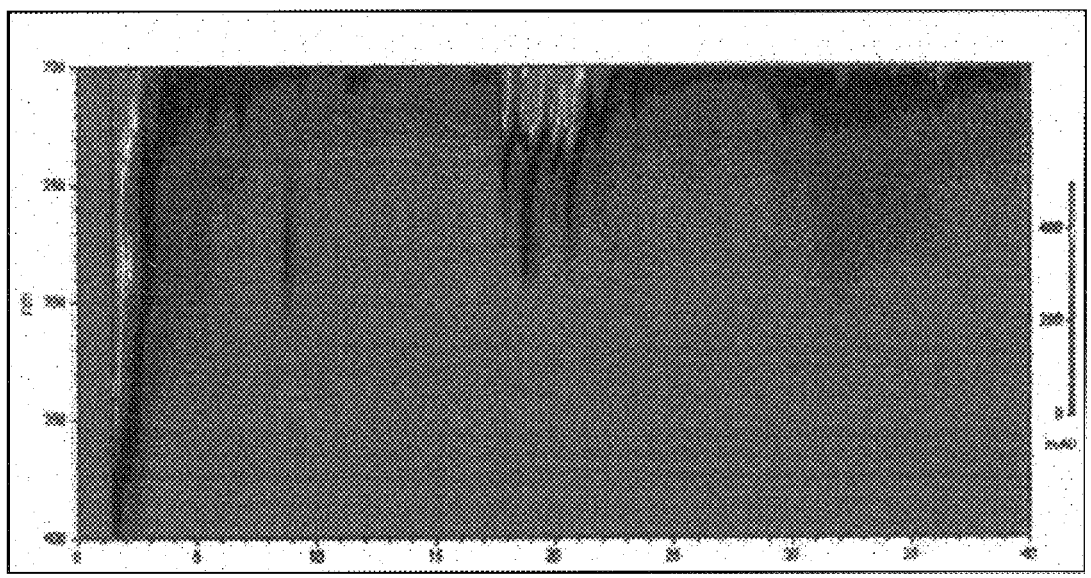

FIG. 77 (A and B) shows both fingerprints of root of *Saussrea lappa*.

Figure 78A:
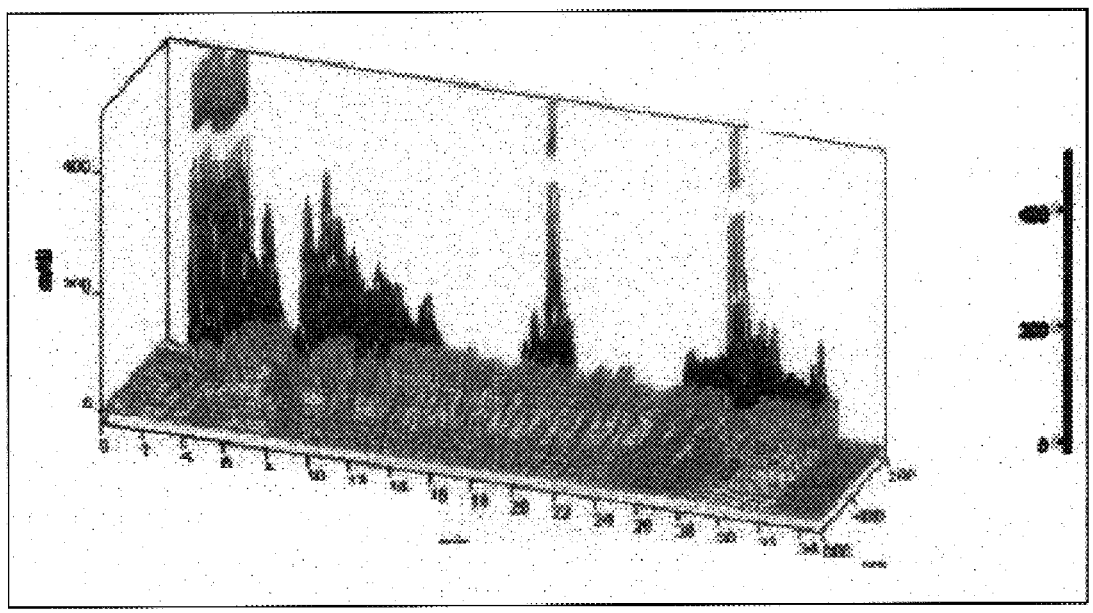

FIG. 78 (A and B) shows both fingerprints of whole herb of *Spheranthus indicus*.

Figure 79A:
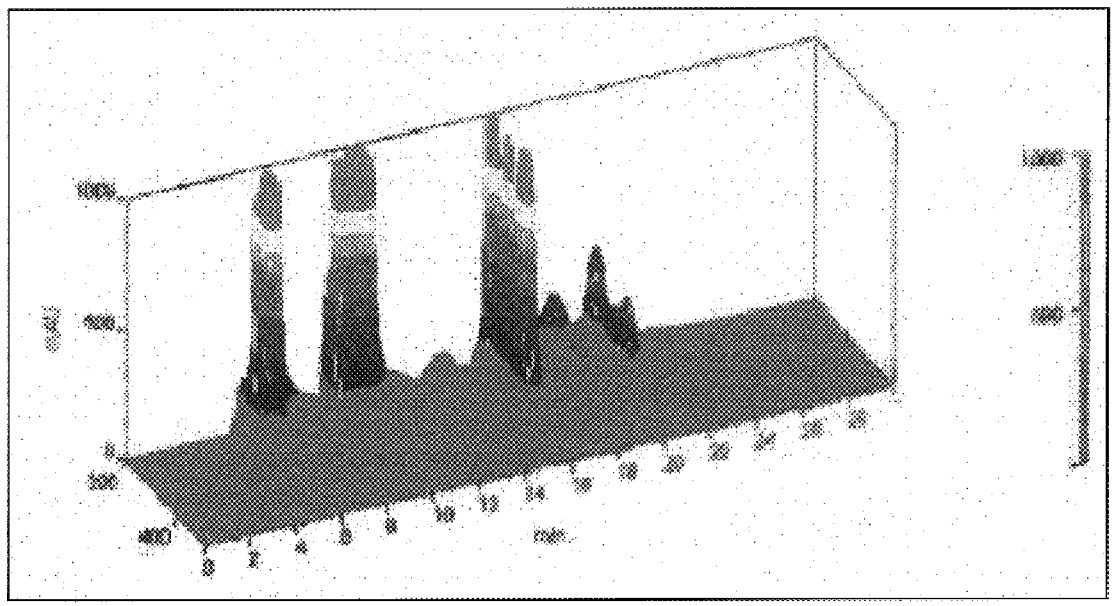
Figure 79B:
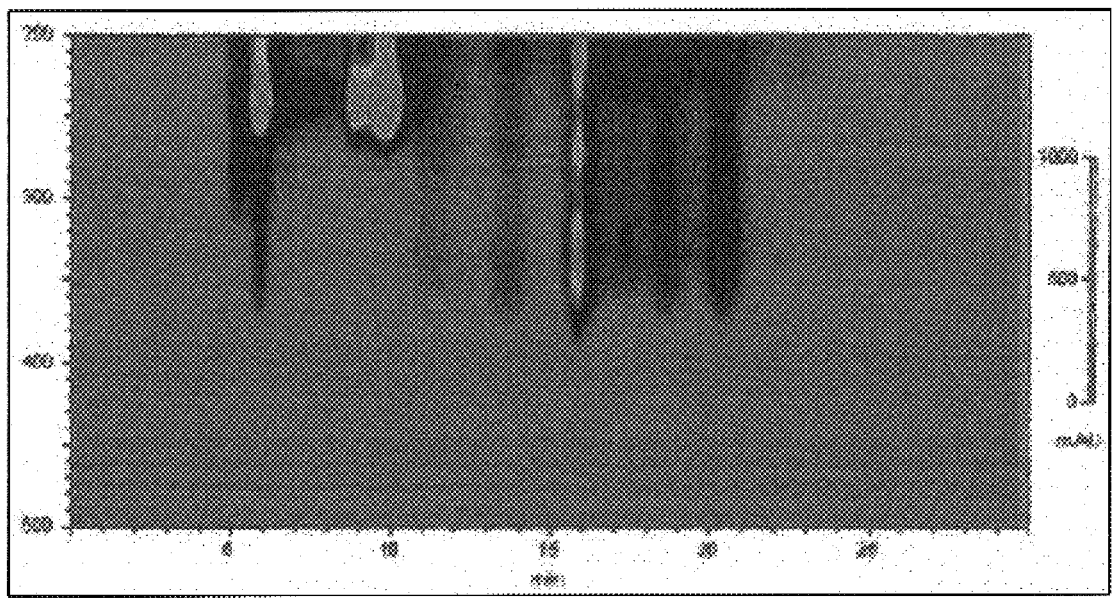

FIG. 79 (A and B) shows both fingerprints of stem bark of *Symplocus racemosus*.

Figure 80A:
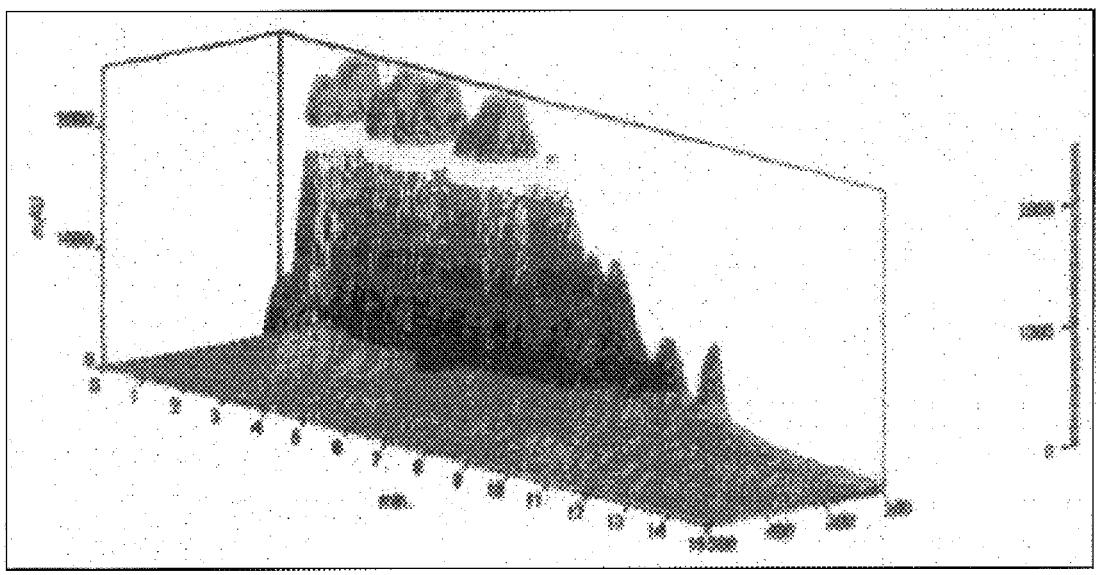
Figure 80B:
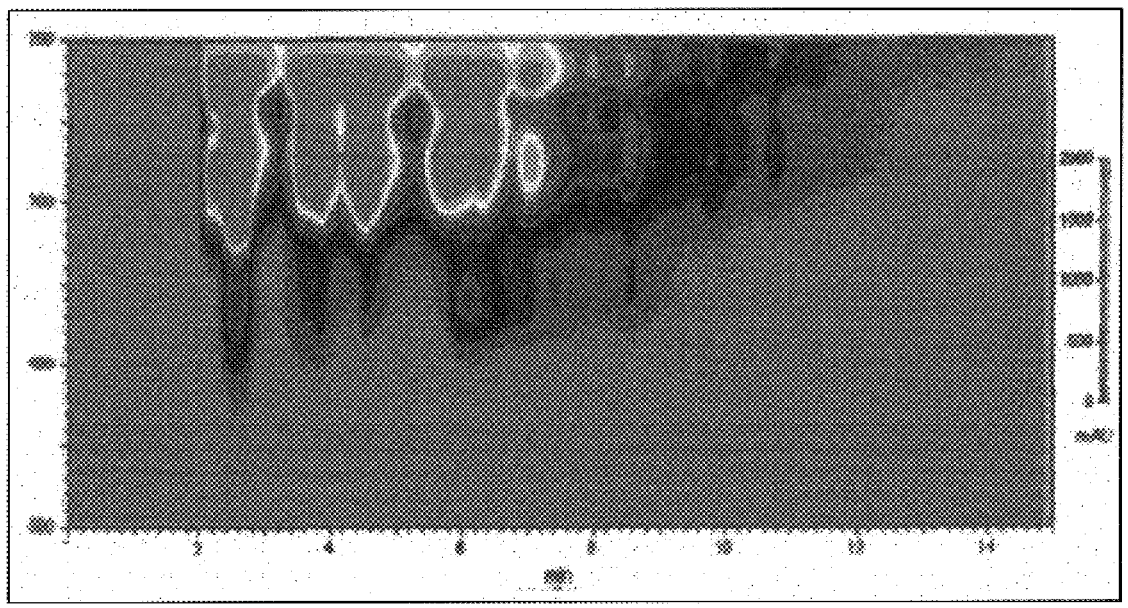

FIG. 80 (A and B) shows both fingerprints of fruit of *Terminalia chebula*.

Figure 81A:
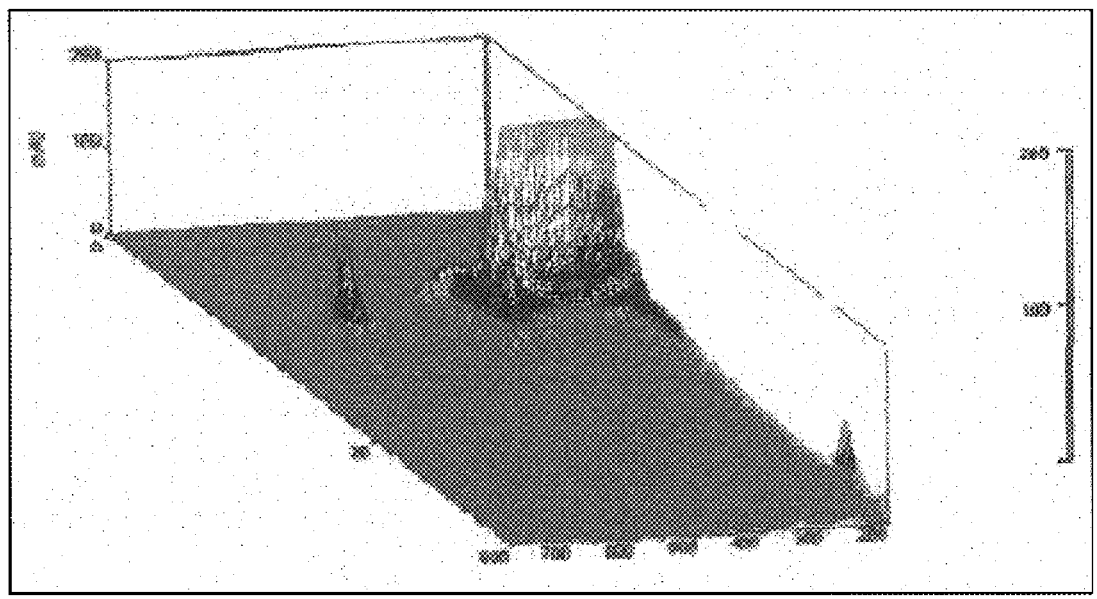
Figure 81A:
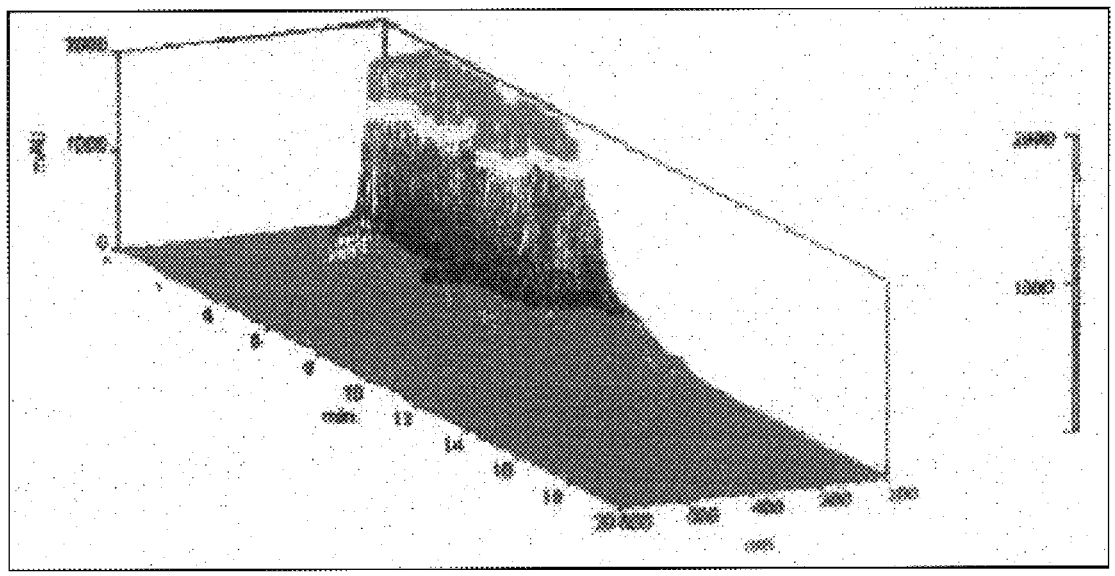
Figure 81B:
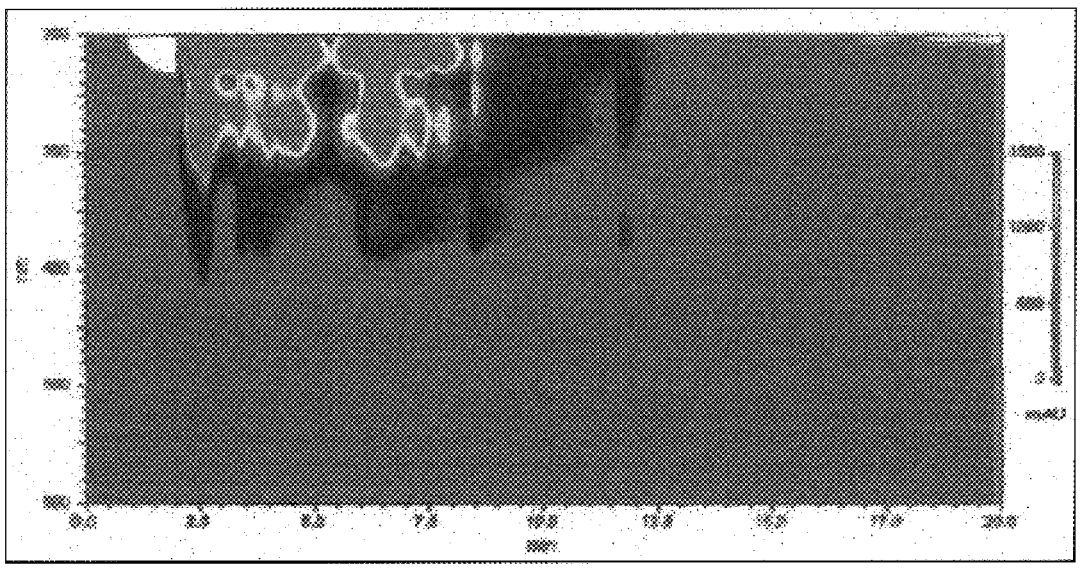

FIG. 81 (A and B) shows both fingerprints of fruit of *Terminalia bellerica*.

Figure 82A:
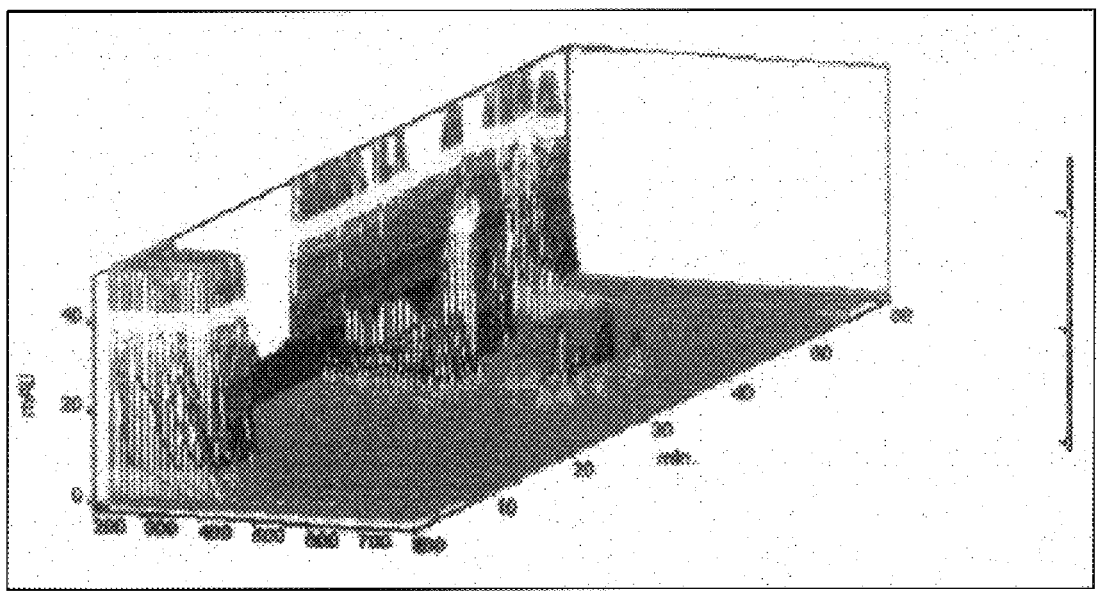
Figure 82B:
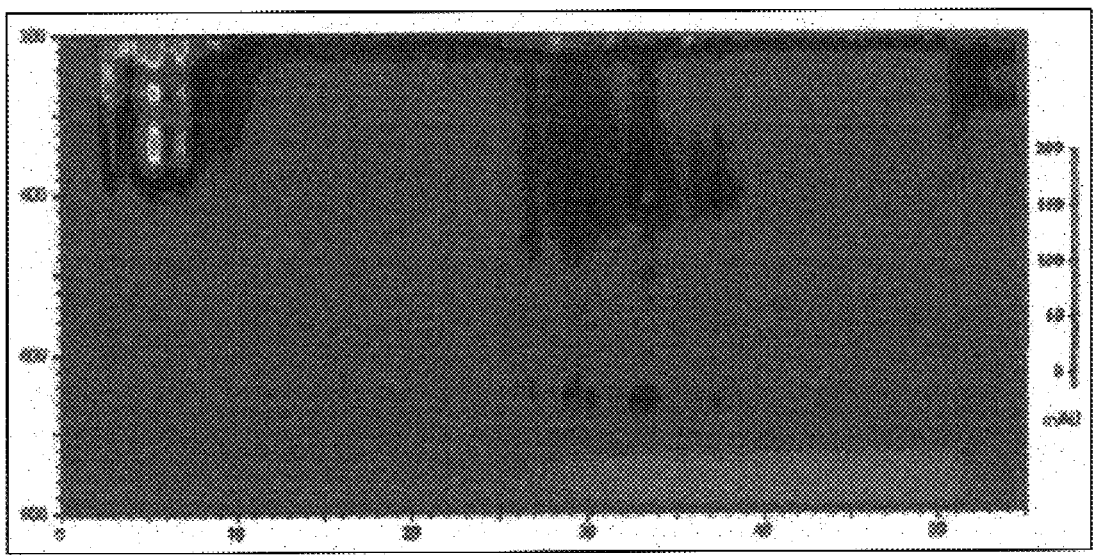

FIG. 82 (A and B) shows both fingerprints of a whole plant *Trigonella faenum g*.

Figure 83A:
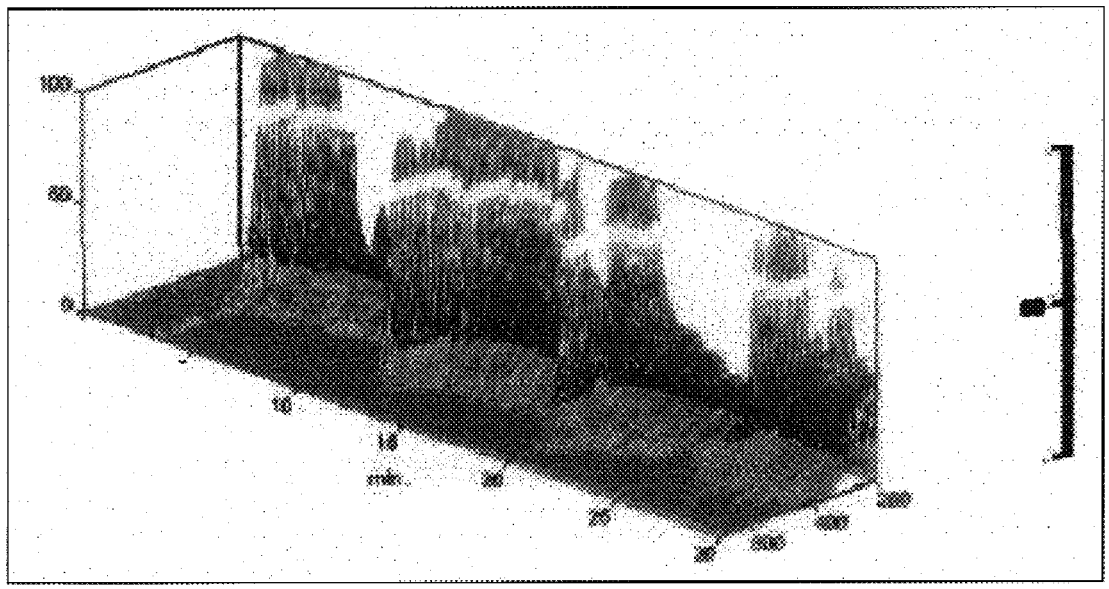
Figure 83B:
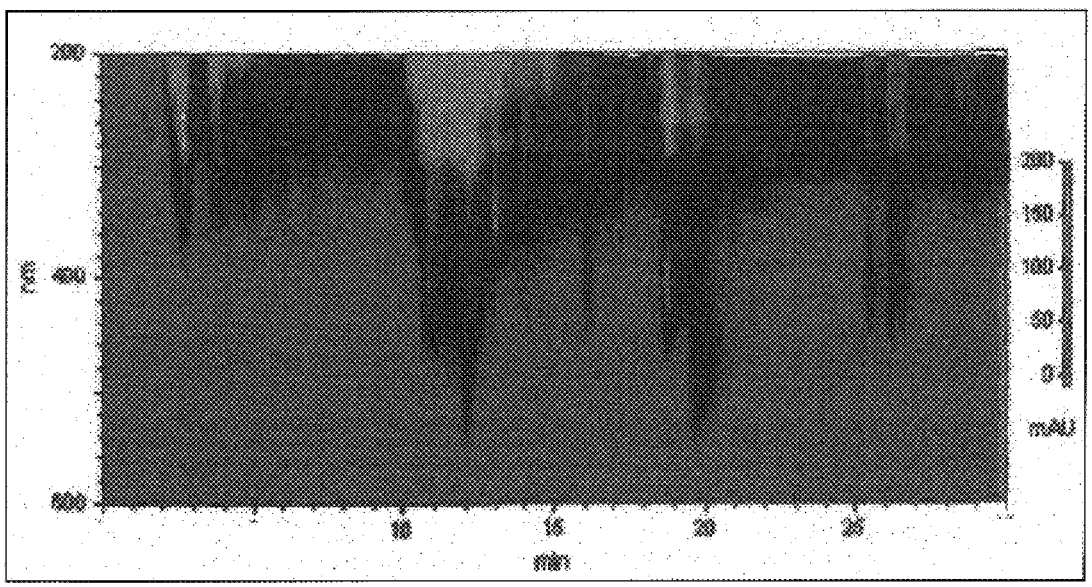

FIG. 83 (A and B) shows both fingerprints of a stem and root of *Tribulus terrestrias*.

Figure 84A:
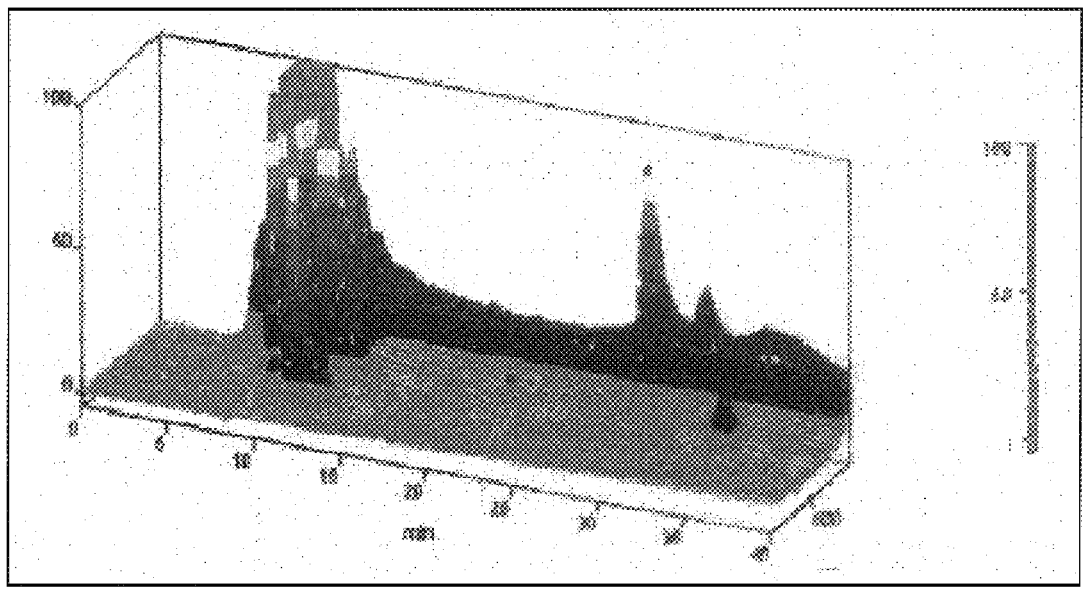
Figure 84B:
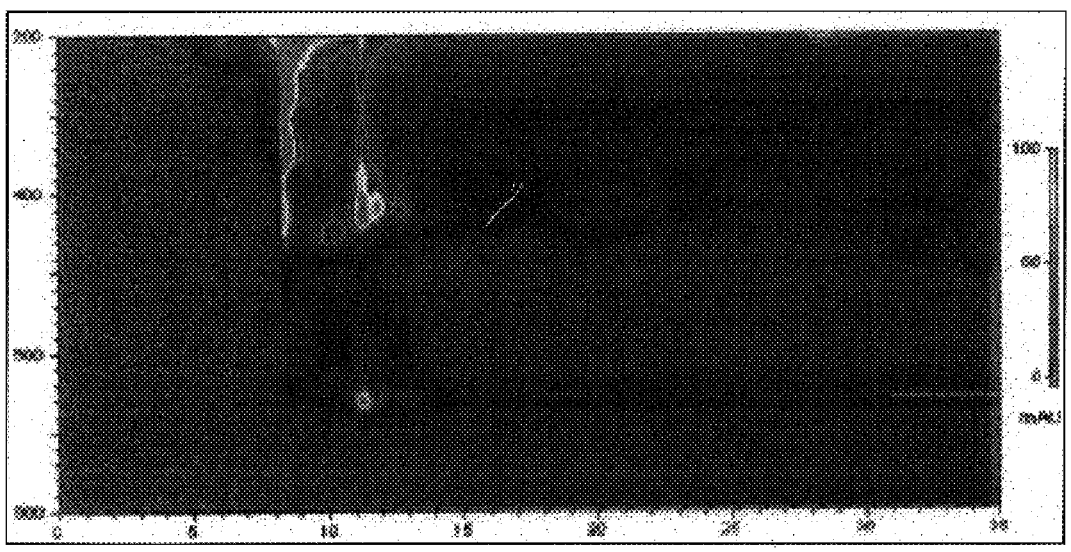

FIG. 84 (A and B) shows both fingerprints of leaves of *Tylophora asthmatica*.

Figure 85A:
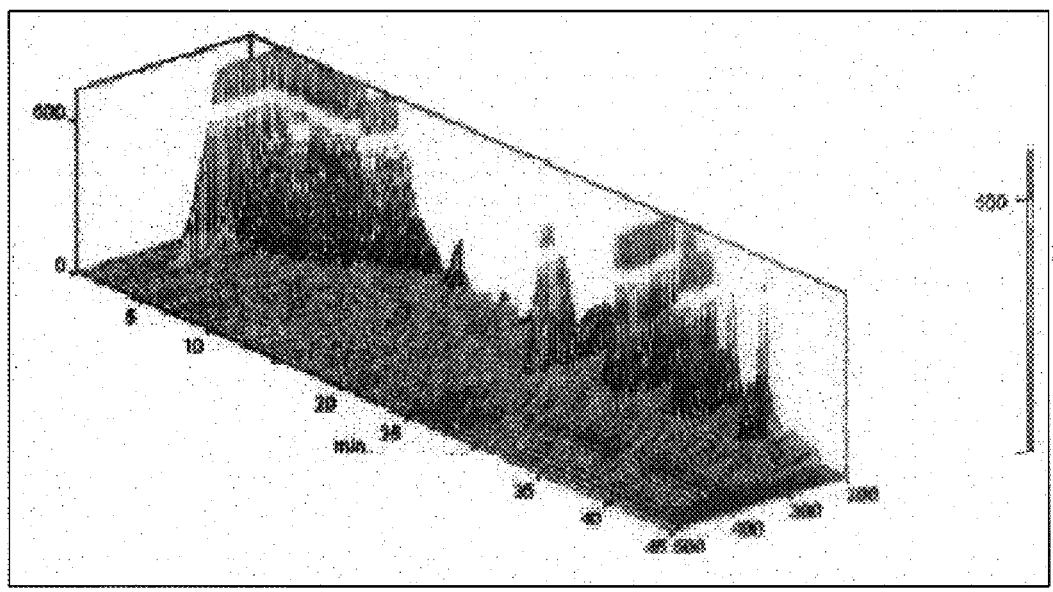
Figure 85A:
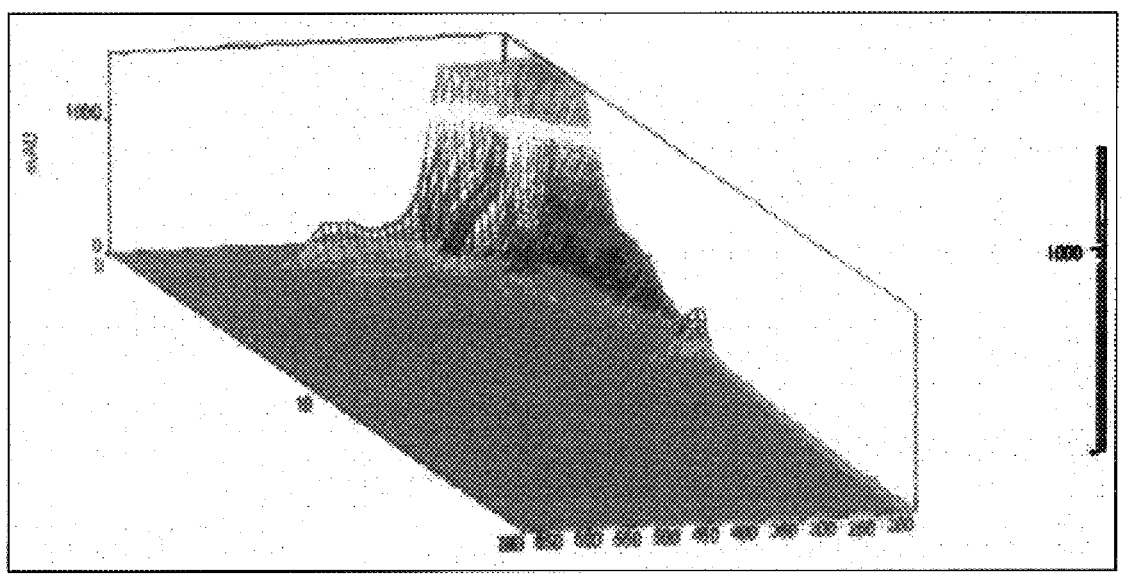
Figure 85B:
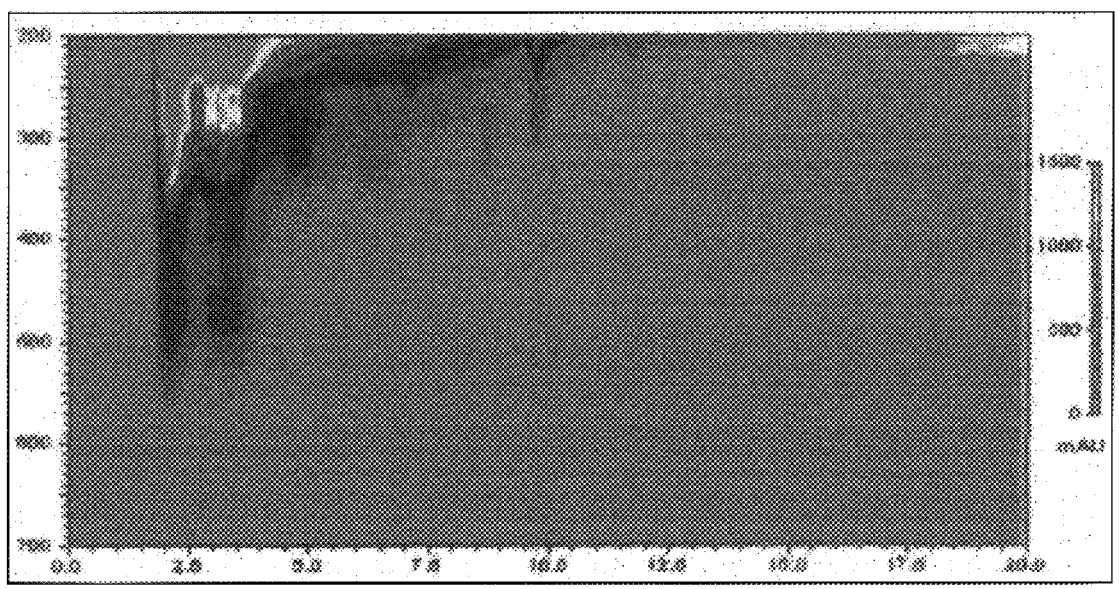

FIG. 85 (A and B) shows both fingerprints of mother tincture of Homoeo medicine *Viburnum*.

Figure 86A:
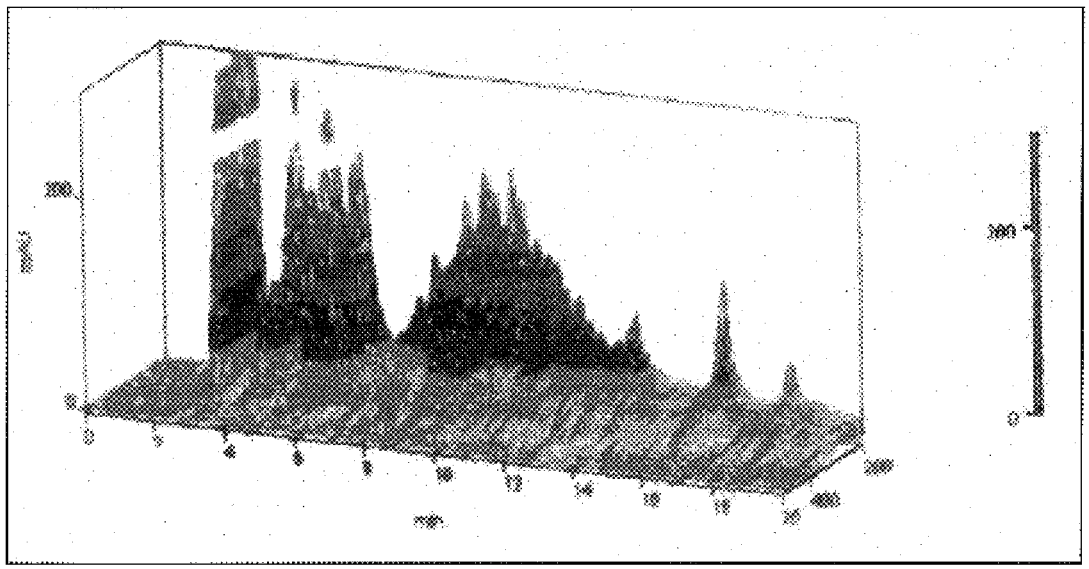
Figure 86B:
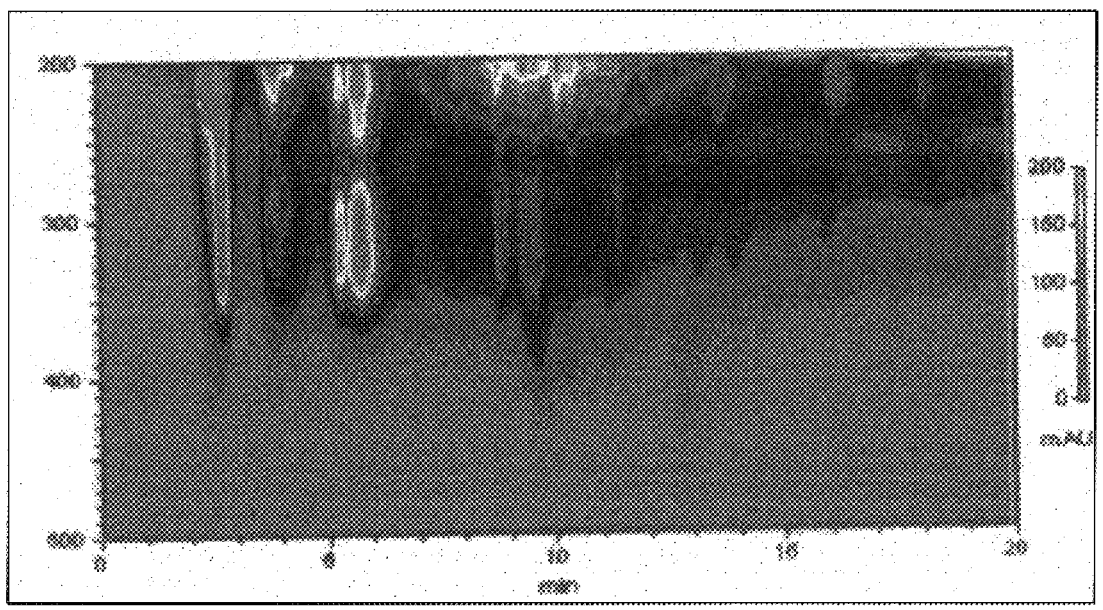

FIG. 86 (A and B) shows both fingerprints of root of *Withinia somnifera*.

Figure 87A:
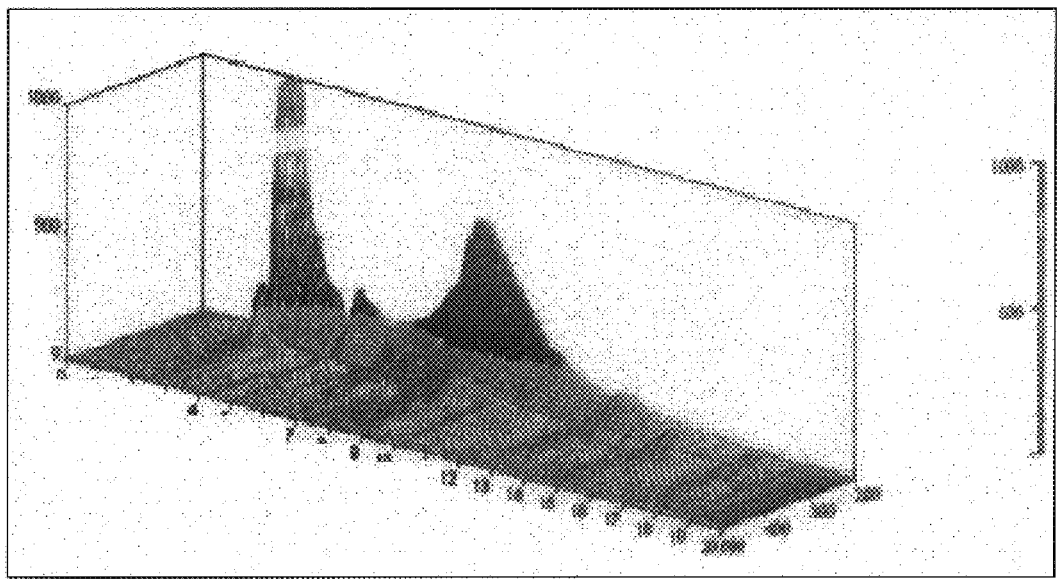
Figure 87B:
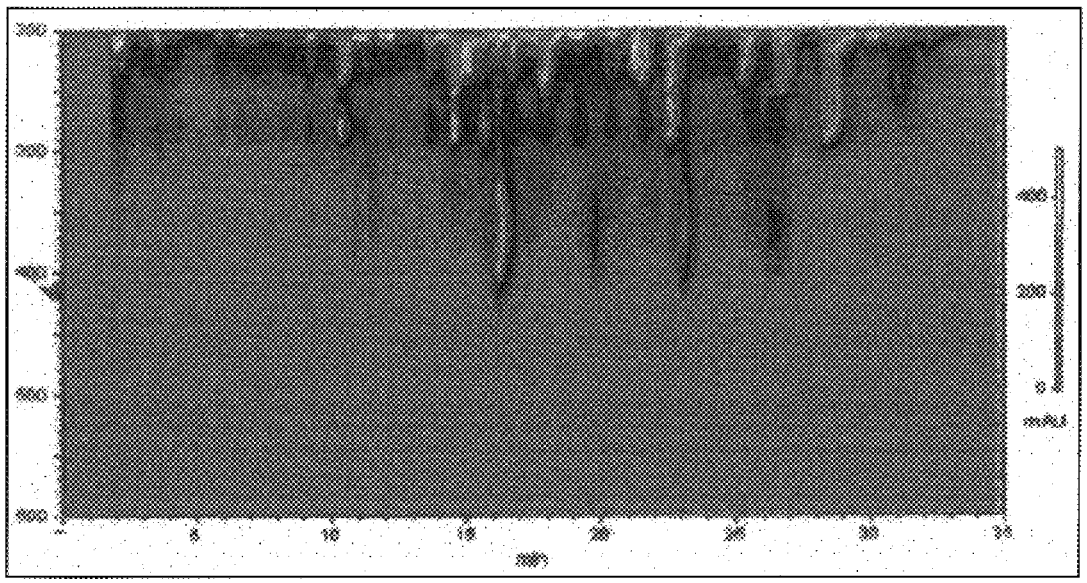

FIG. 87 (A and B) shows both fingerprints of rhizome of processed *Zinziber officinalis*.

Figure 88A:
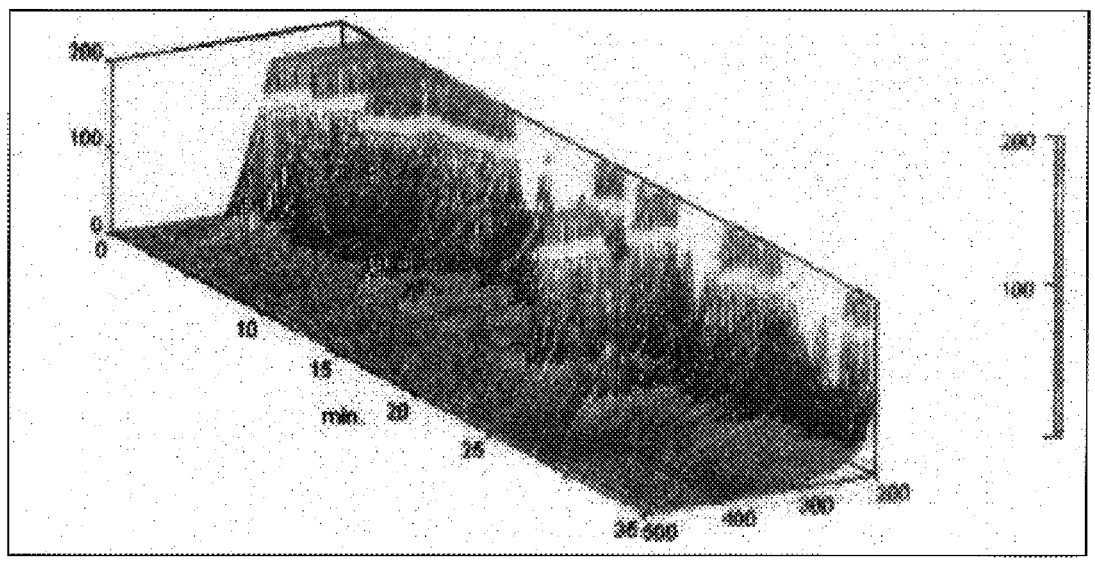
Figure 888:
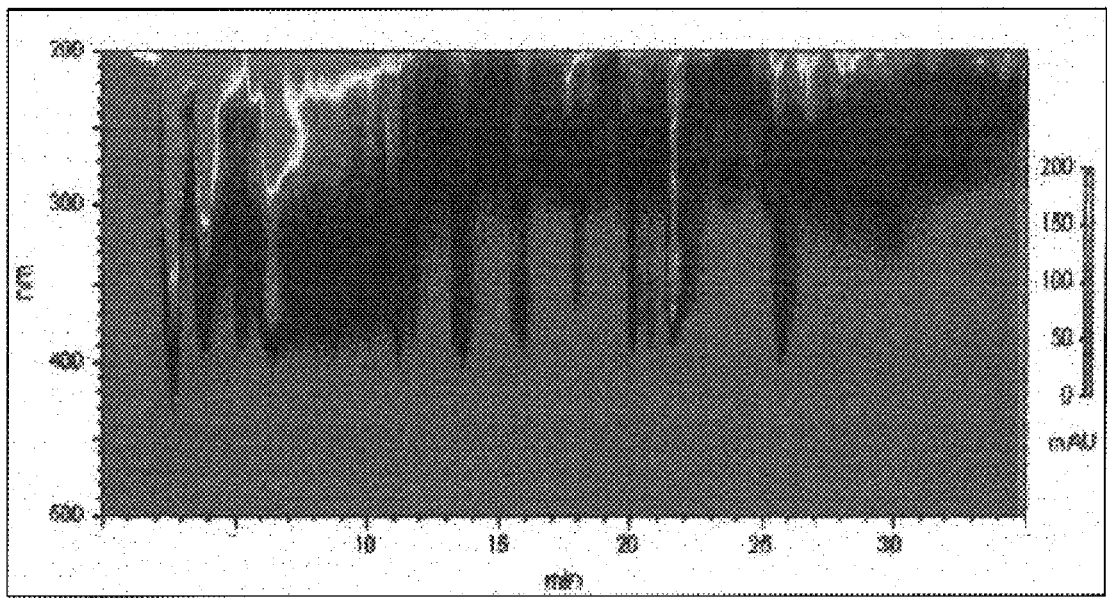

FIG. 88 (A and B) shows both fingerprints of powder of *Avipattakara churna*.

Figure 89A:
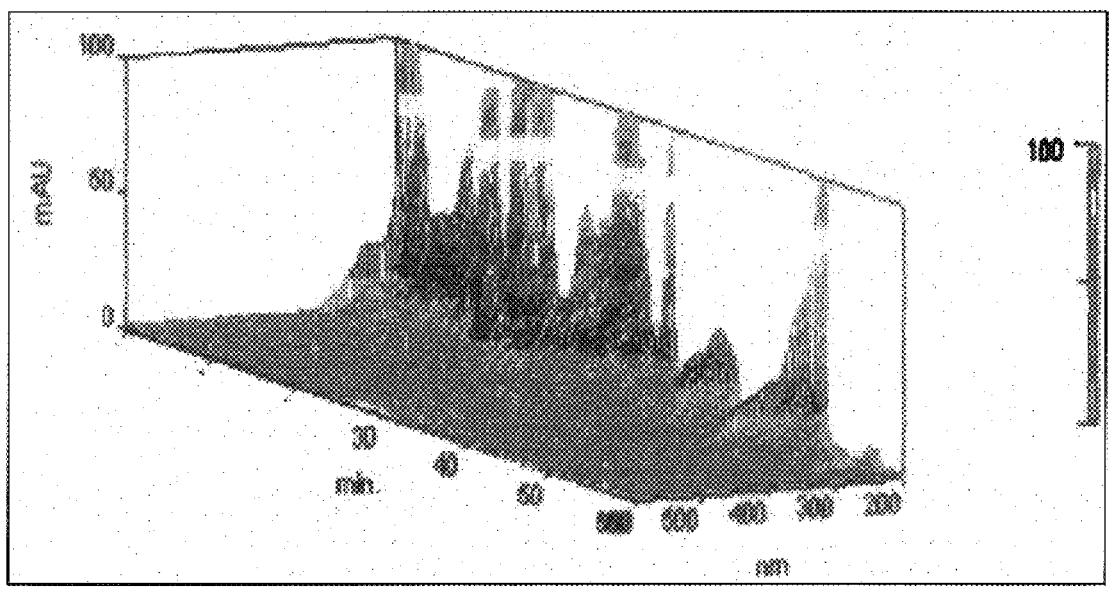
Figure 89B:
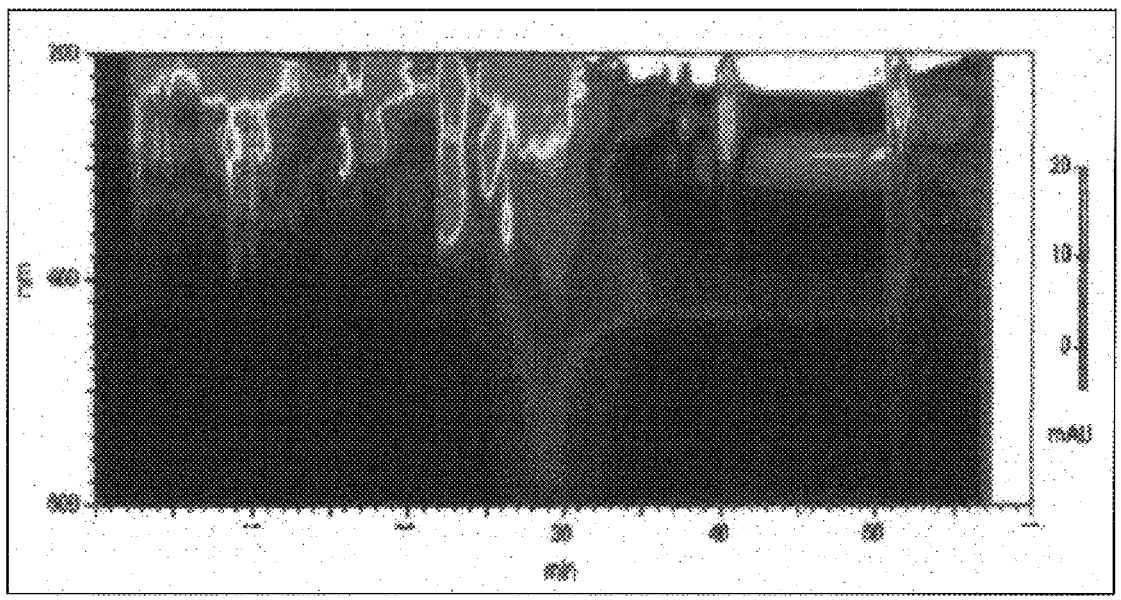

FIG. 89 (A and B) shows both fingerprints of an herbal formulation of *Kamaduga Ras*.

Figure 90A:
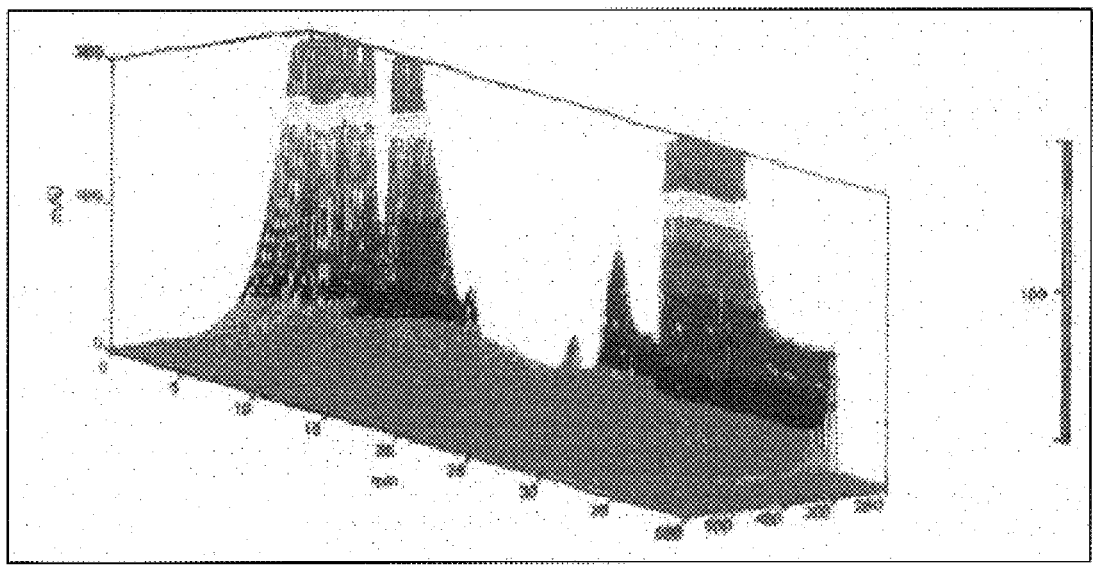
Figure 90B:
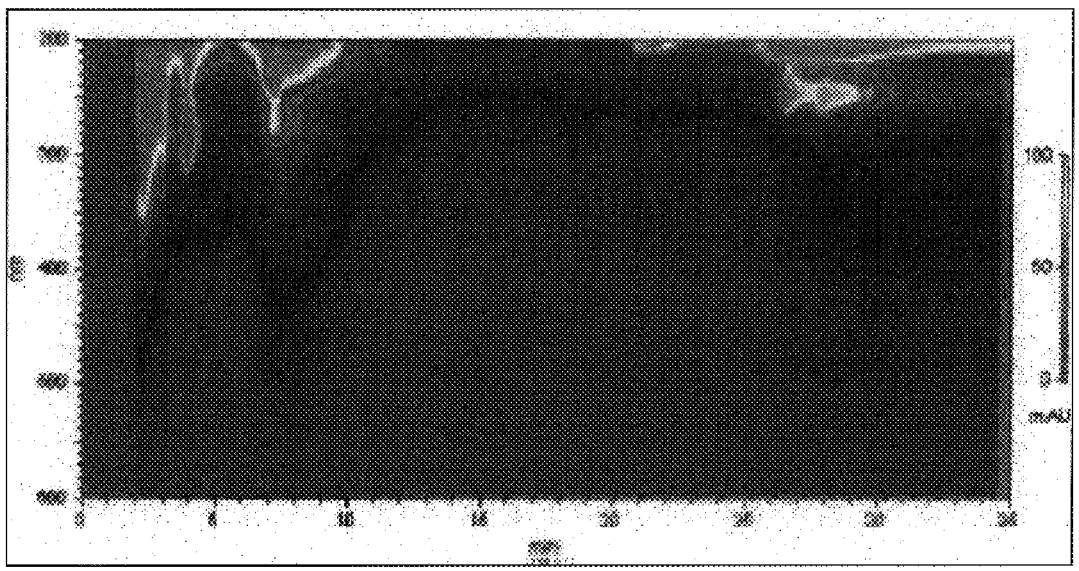

FIG. 90 (A and B) shows both fingerprints of a *Kumarayasava*, an herbal medicine produced by a fermentation process.

Figure 91A:
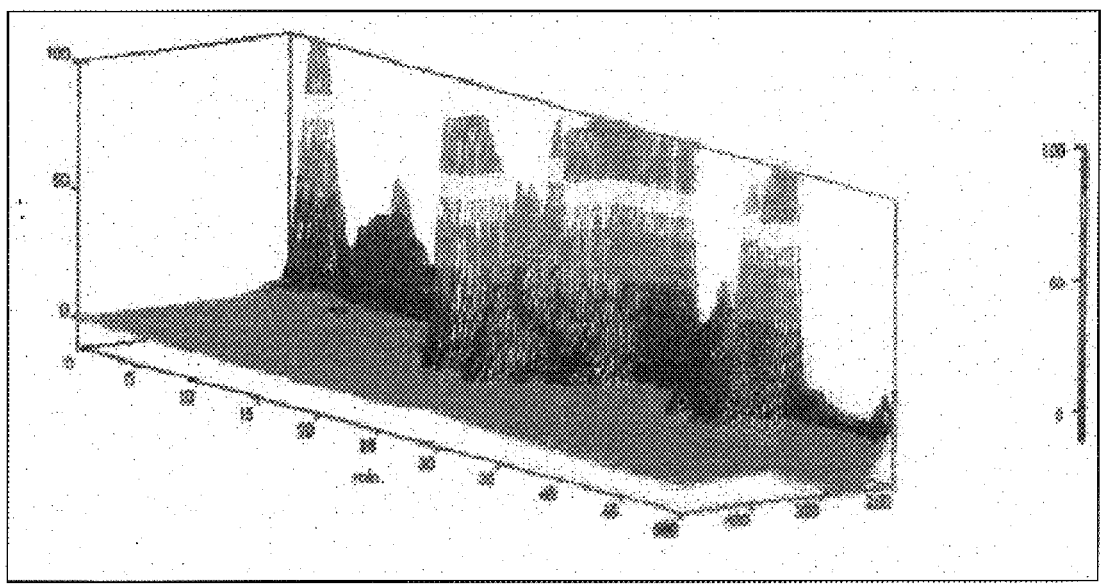
Figure 91B:
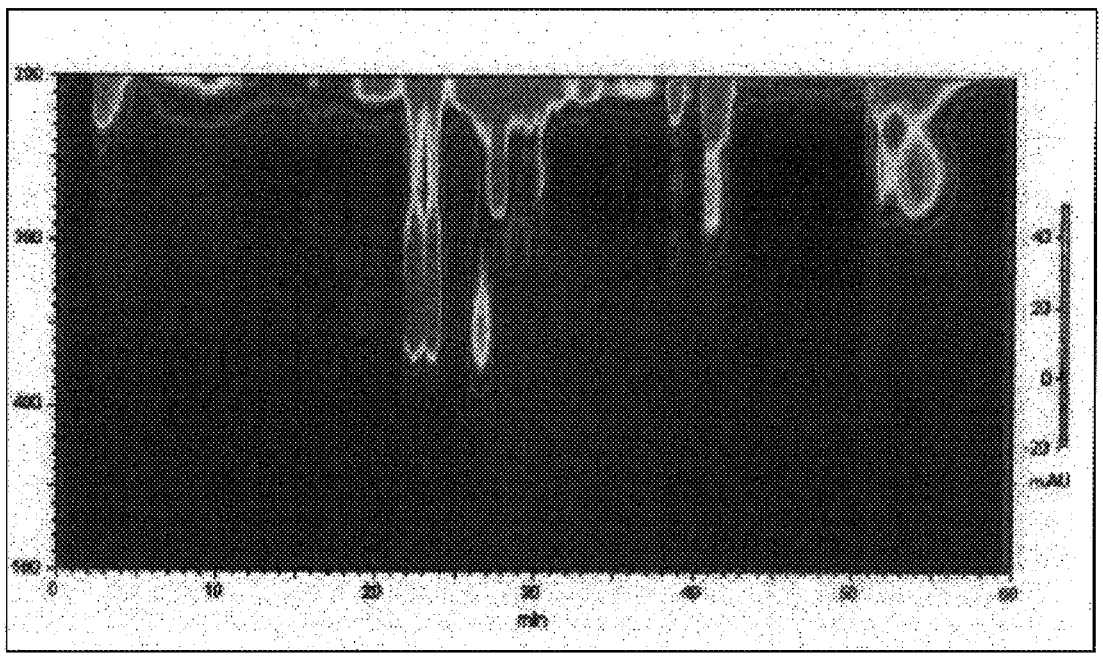

FIG. 91 (A and B) shows both fingerprints of an herbal formulation of *Mahalakshmi vilas ras*.

Figure 92A:
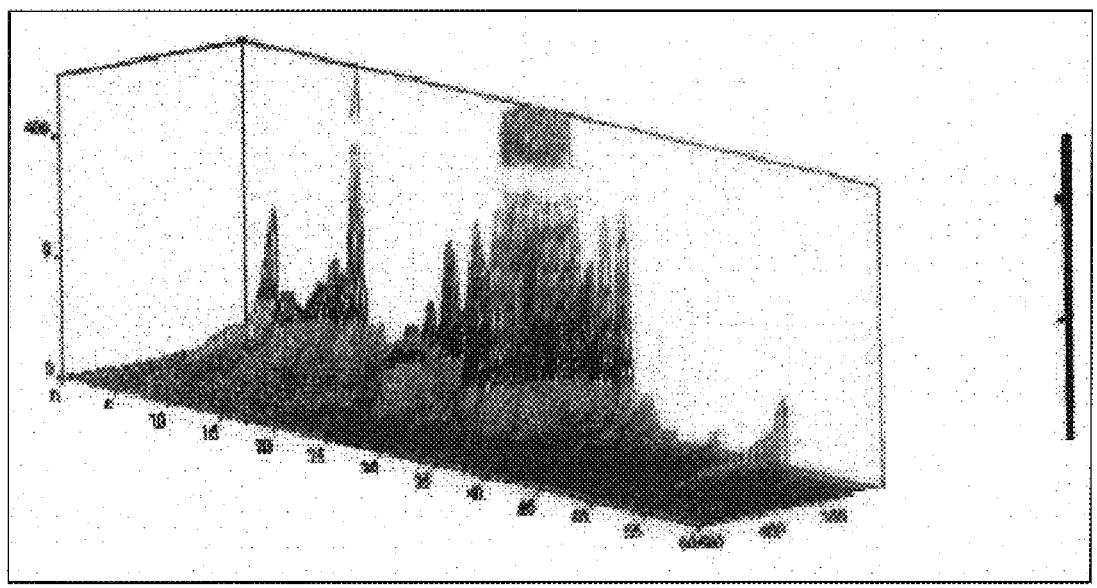
Figure 92B:
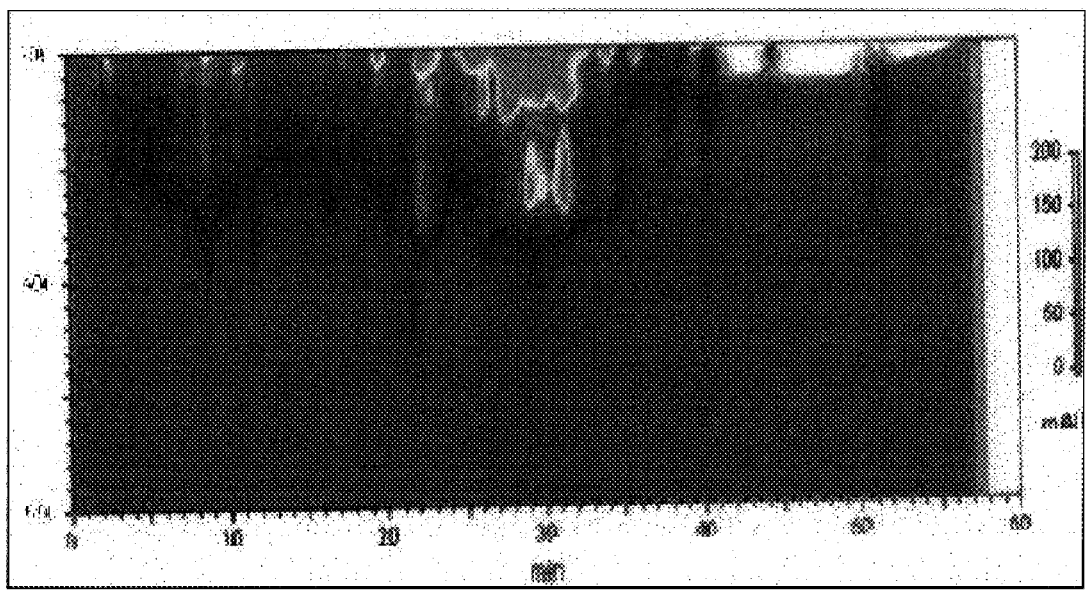

FIG. 92 (A and B) shows both fingerprints of an herbal formulation of *Suvarna yogaraja Guggulu*.

Figure 93:
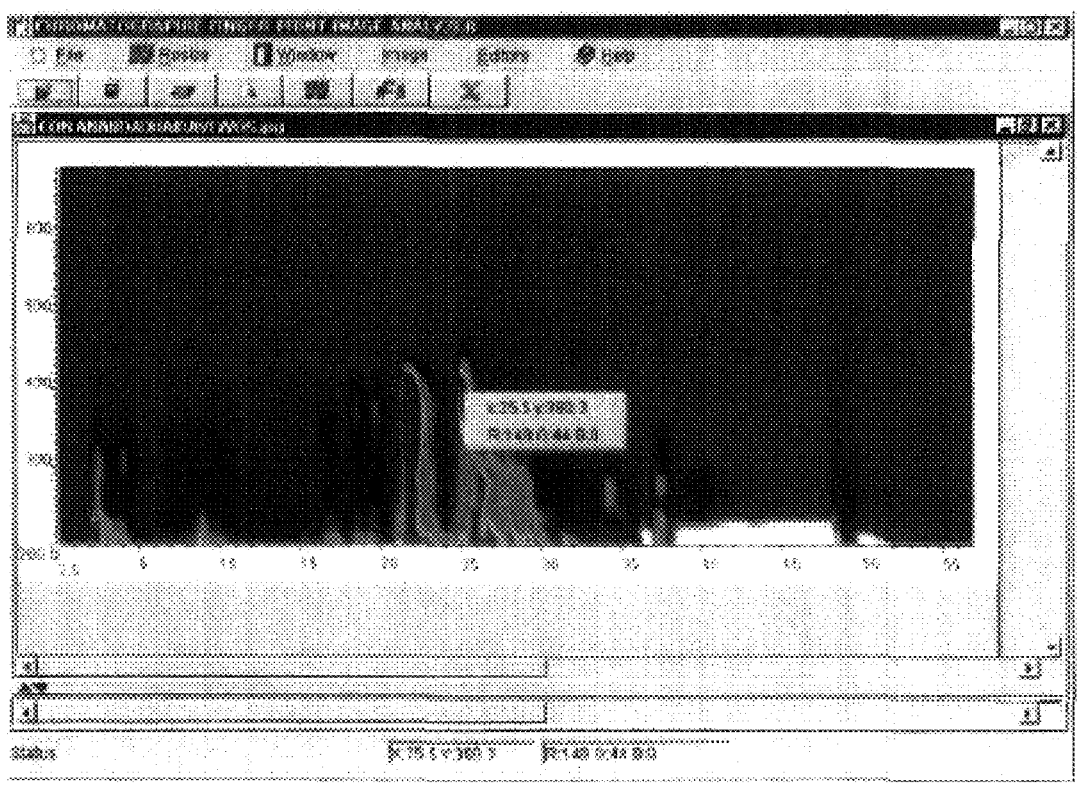

FIG. 93 shows the fingerprint of *Anandabhairavi Ras*. Right clicking on any particular peak, the image software will display the X, Y, R, G and B coordinates of the peak, which are used for bar coding. These coordinates are shown inside a box (near the peak) and in the tool bar. The image software displays the bar code values of a particular peak. The coordinates will be exported to barcoding software which generates a barcode for these values.

Figure 94:
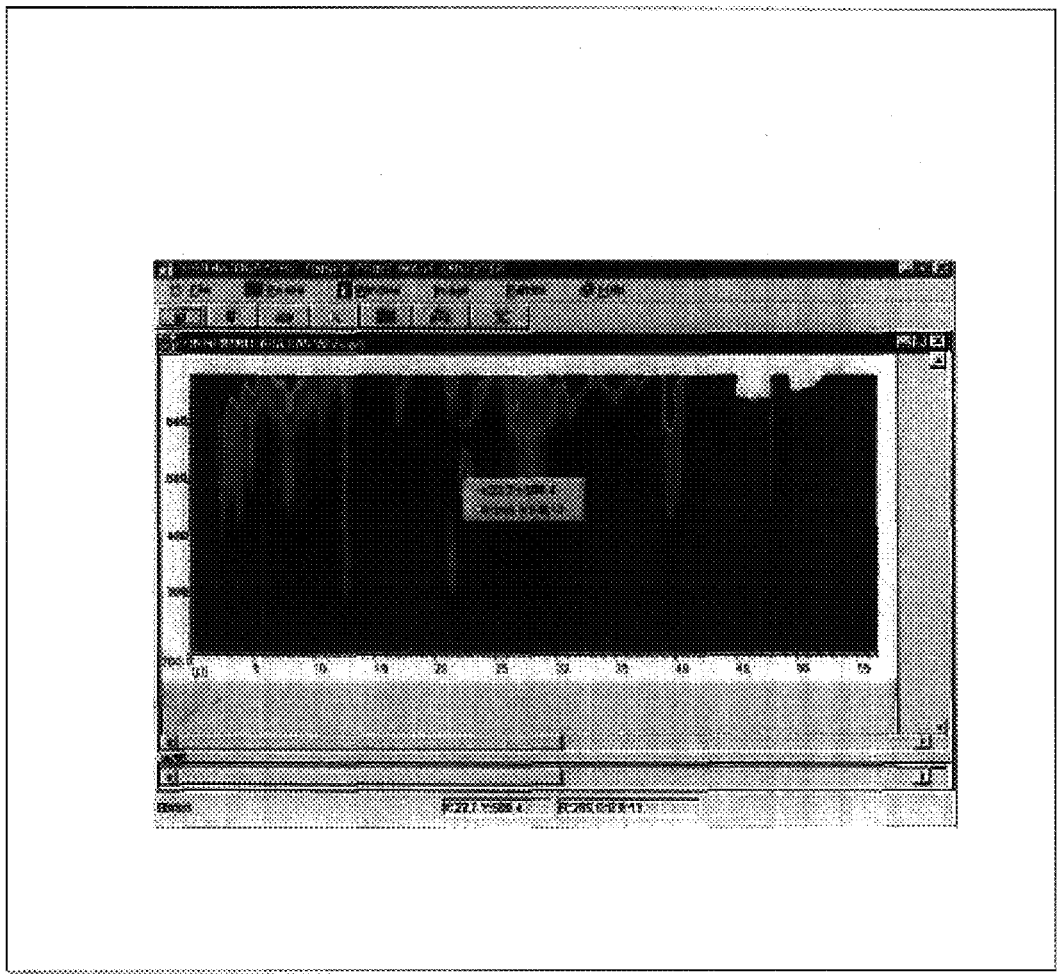

FIG. 94 shows the fingerprint of *Krimikutara Ras*. The image software displays the bar code values of a particular peak. The same mechanism as described above with respect to FIG. 93 is used.

Figure 95:

FIG. 95 shows the barcode generated for *Anandabhairavi Ras*

Figure 96:
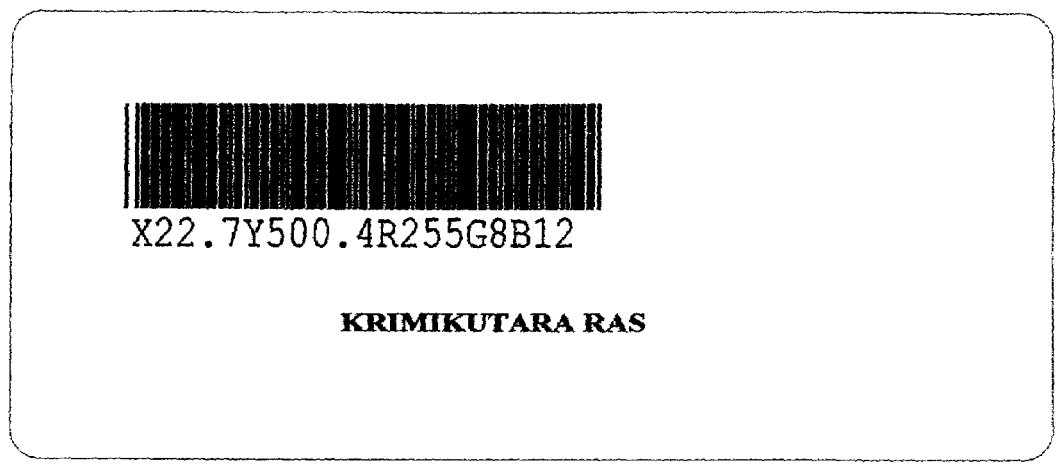

FIG. 96 shows the barcode generated for *Krimikutara Ras*.

Figure 97:
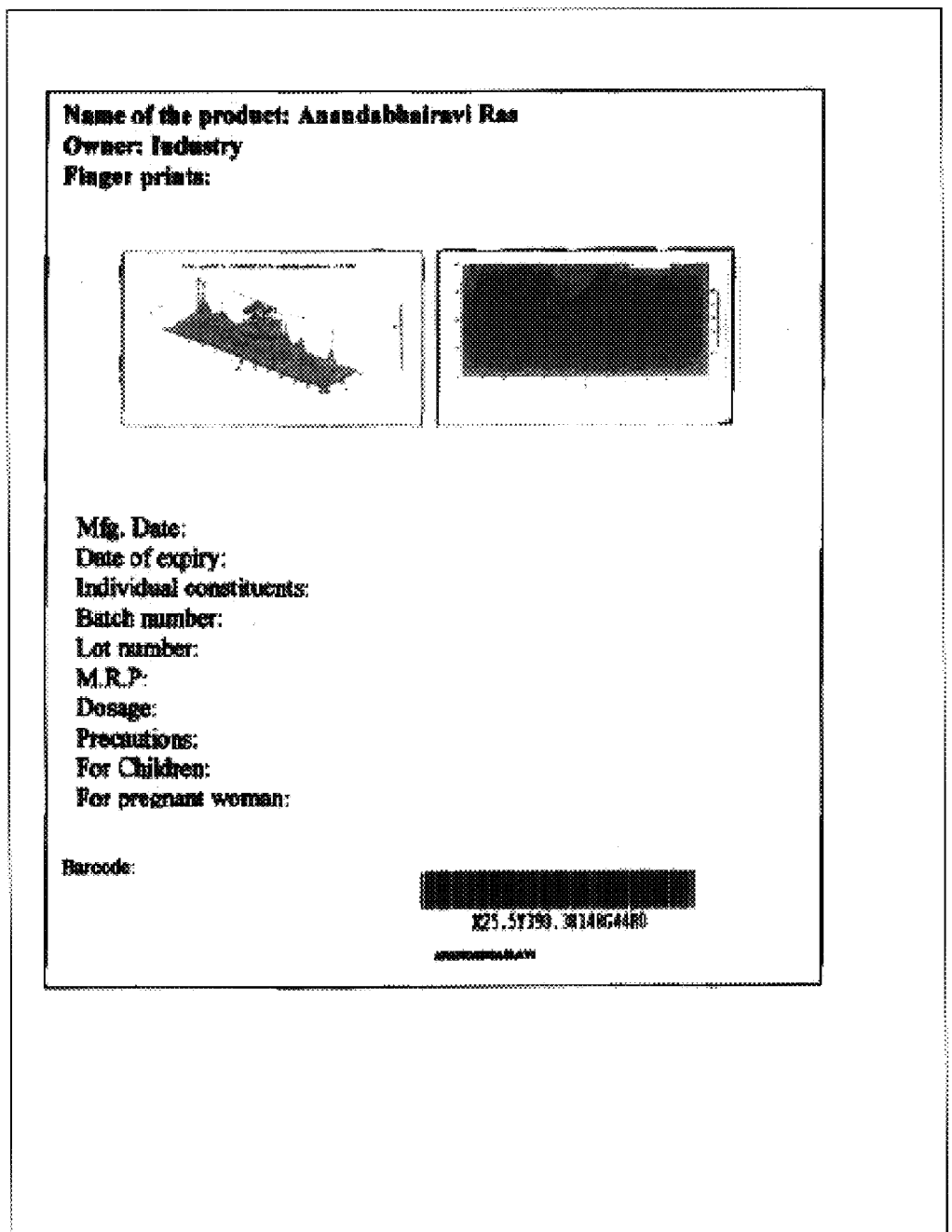

FIG. 97 shows the display window for *Anandabhairavi Ras*. The display windows for all medicines will be done. This becomes a database for ERP CRM application.

FIG. 98 shows the display window for *Krimikutara Ras*

Figure 99:
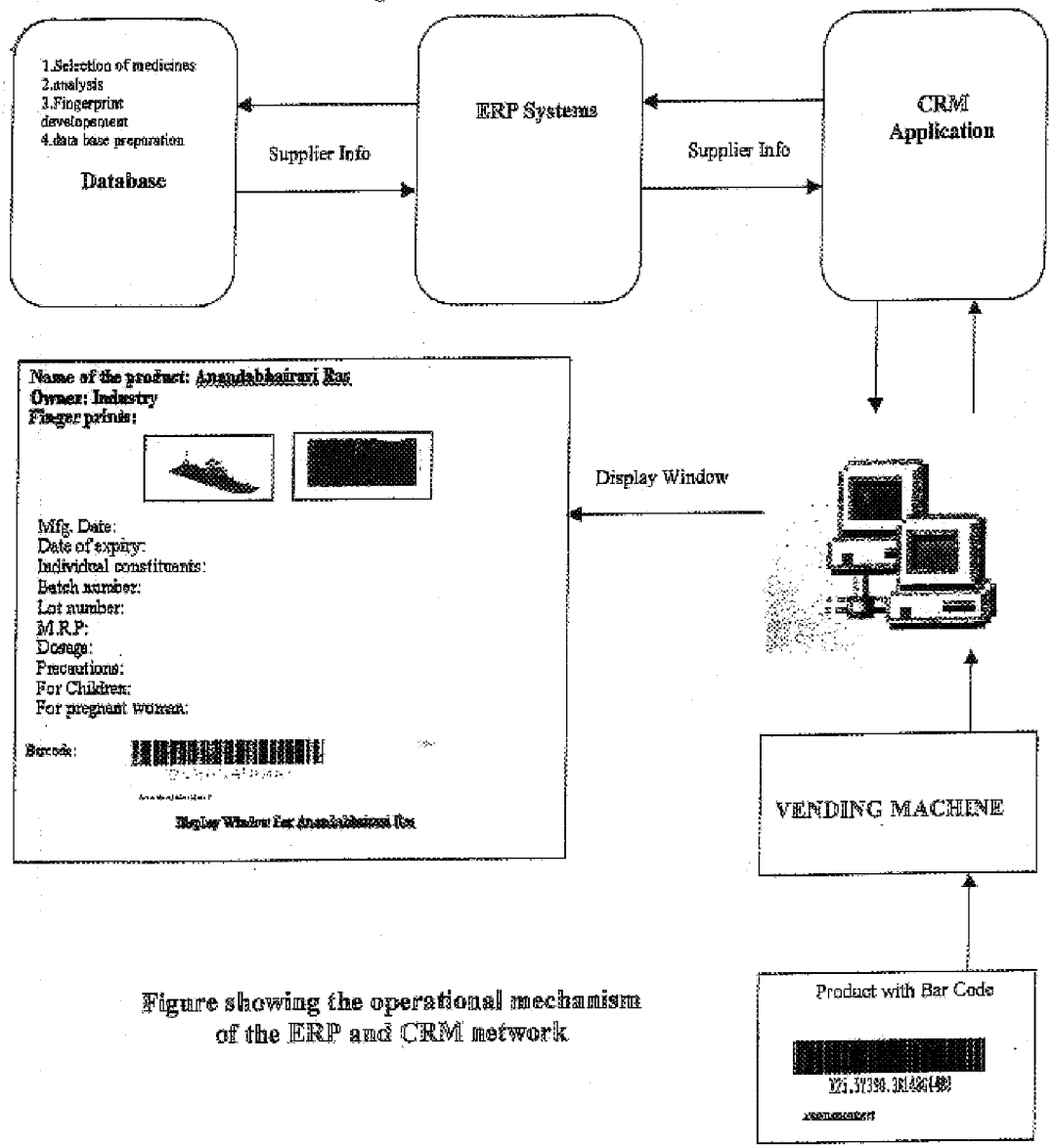

FIG. 99 shows how the network works in an Enterprise Resource Planning and Customer Relationship Management applications networked using the database prepared by the proposed method.

Figure 100:
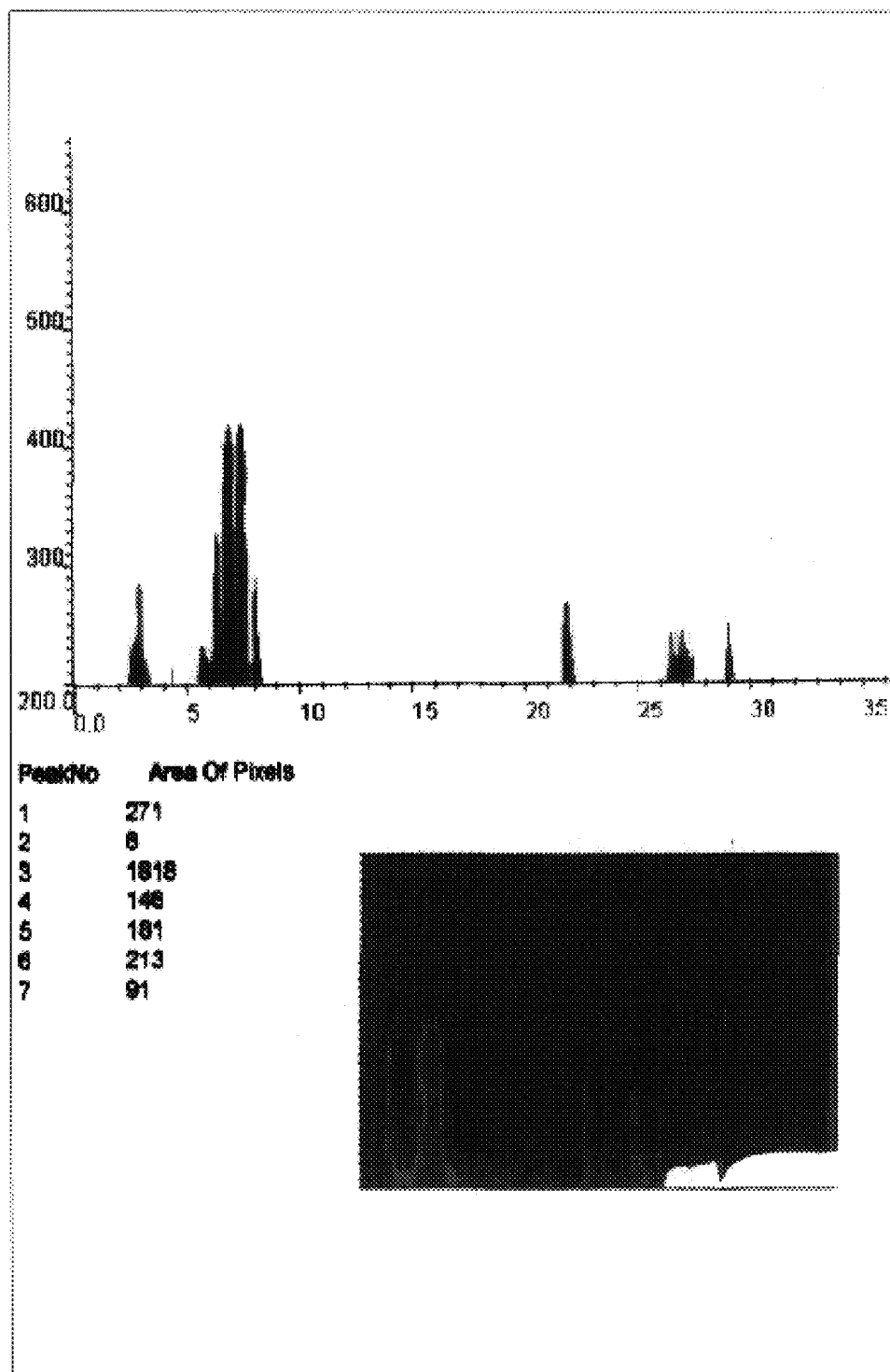
Figure 101:
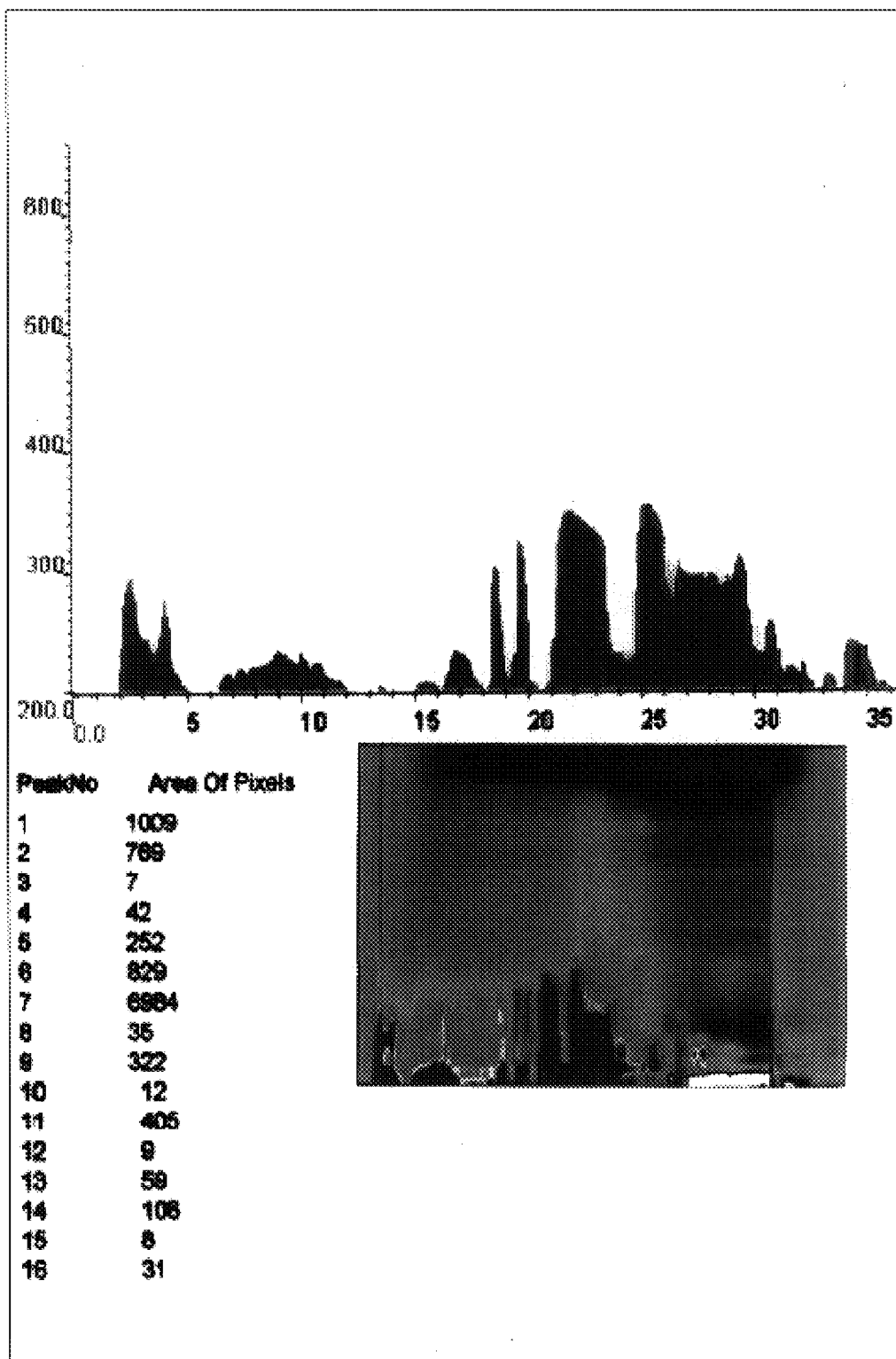

FIG. 100 shows a new chromatogram in the form of a colored bar chart for the tender leaves of *Azadiracta indica* collected in February FIG. 101 shows a new chromatogram in the form of a colored bar chart for the medicine of *Anandabhairavi Ras* an herbal formulation.

Figure 102:
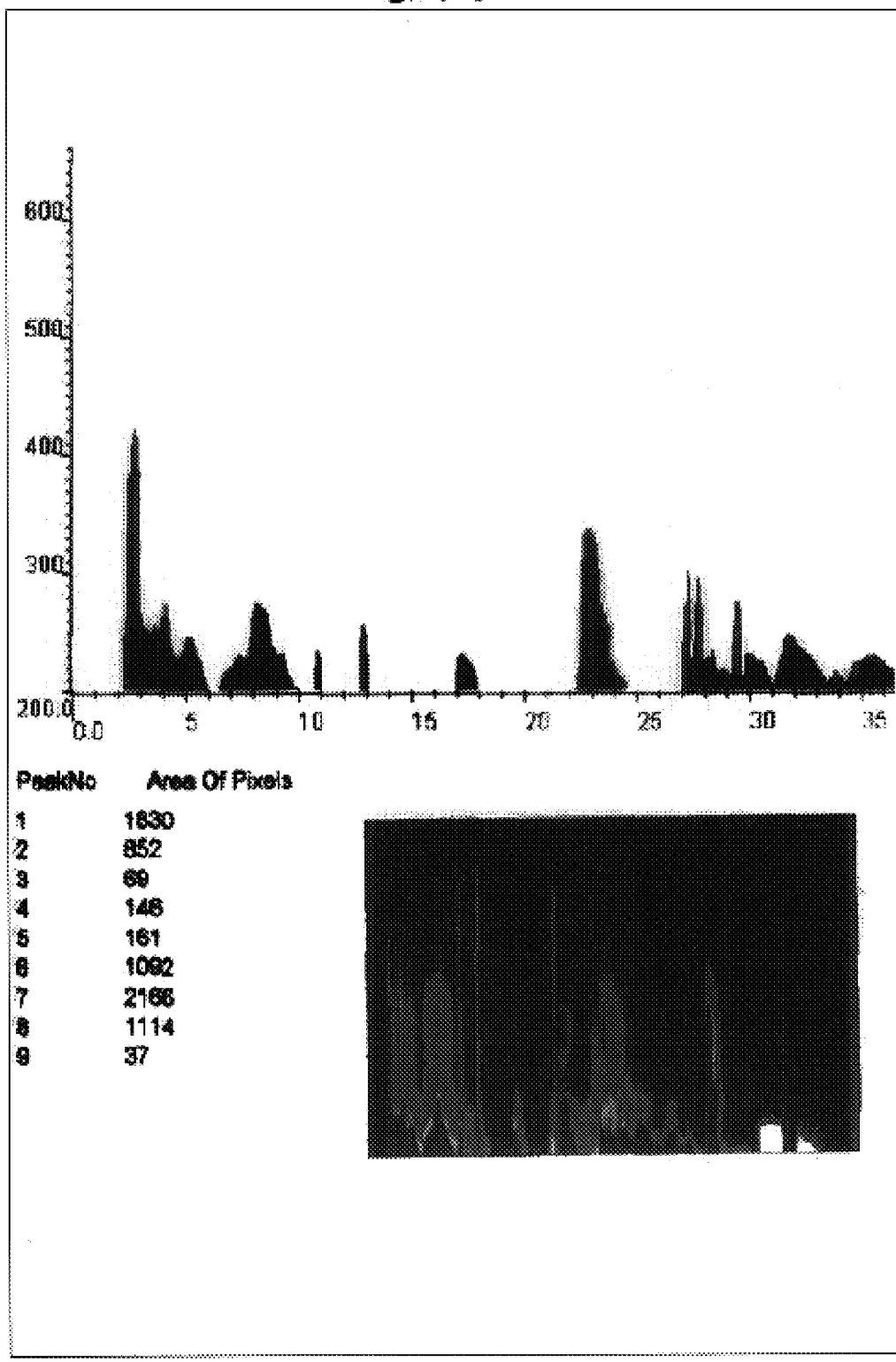

FIG. 102 shows a new chromatogram in the form of a colored bar chart for the medicine of *Krimikutara Ras,* an herbal formulation.

Figure 103:
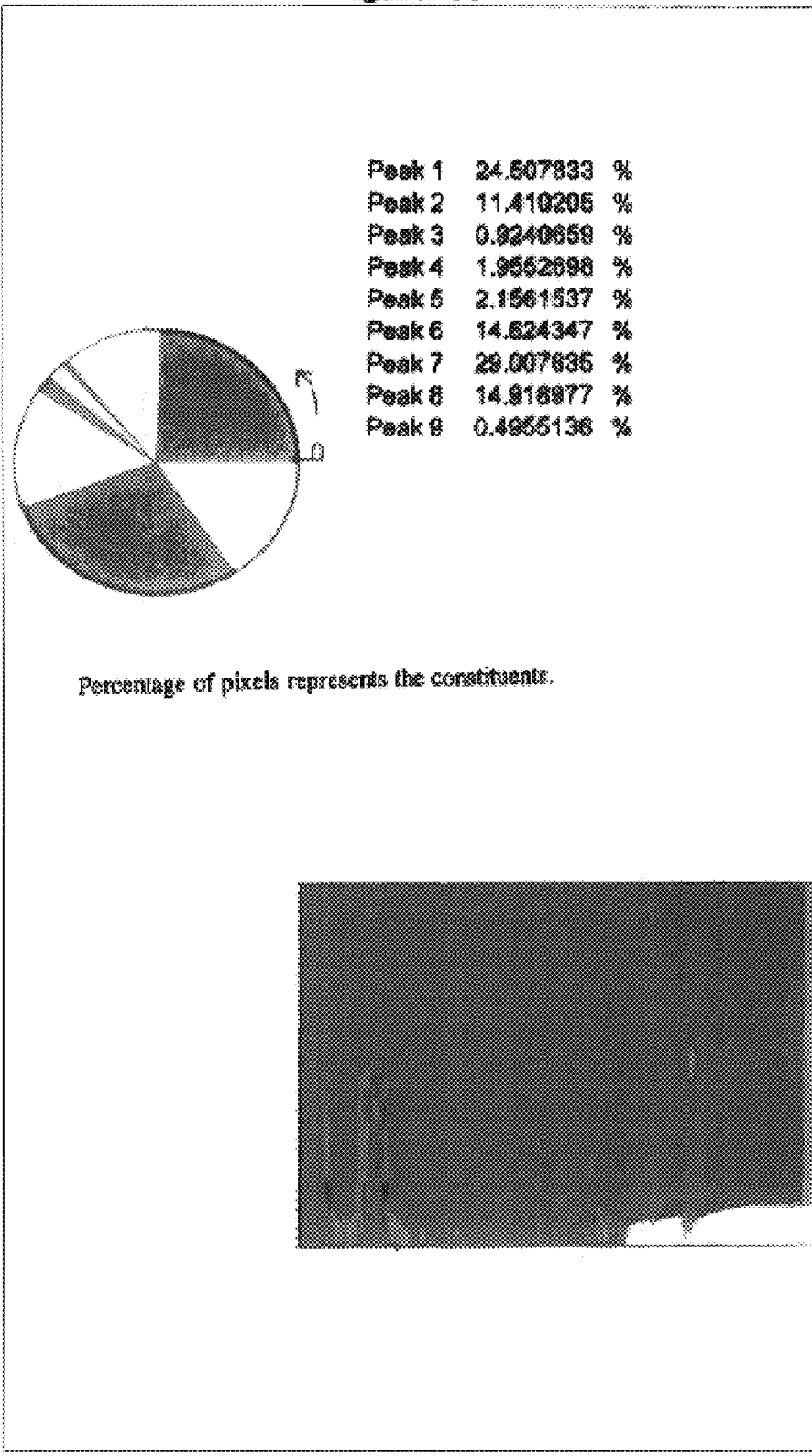

FIG. 103 shows the Pie diagram for the chromatogram of *Azadiracta indica*

Figure 104:
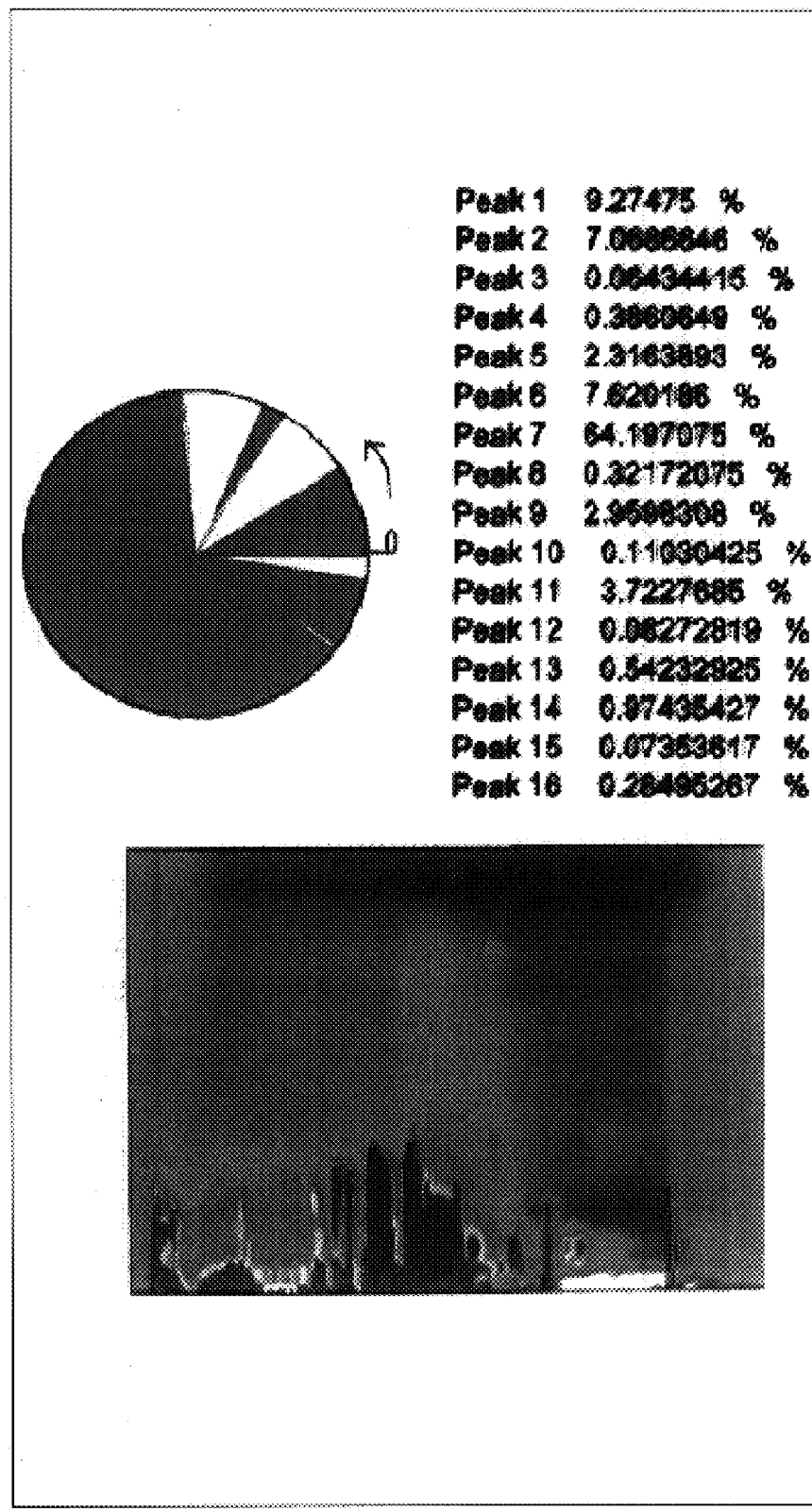

FIG. 104 shows the Pie diagram for the chromatogram of *Anandabhairavi Ras*

Figure 105:
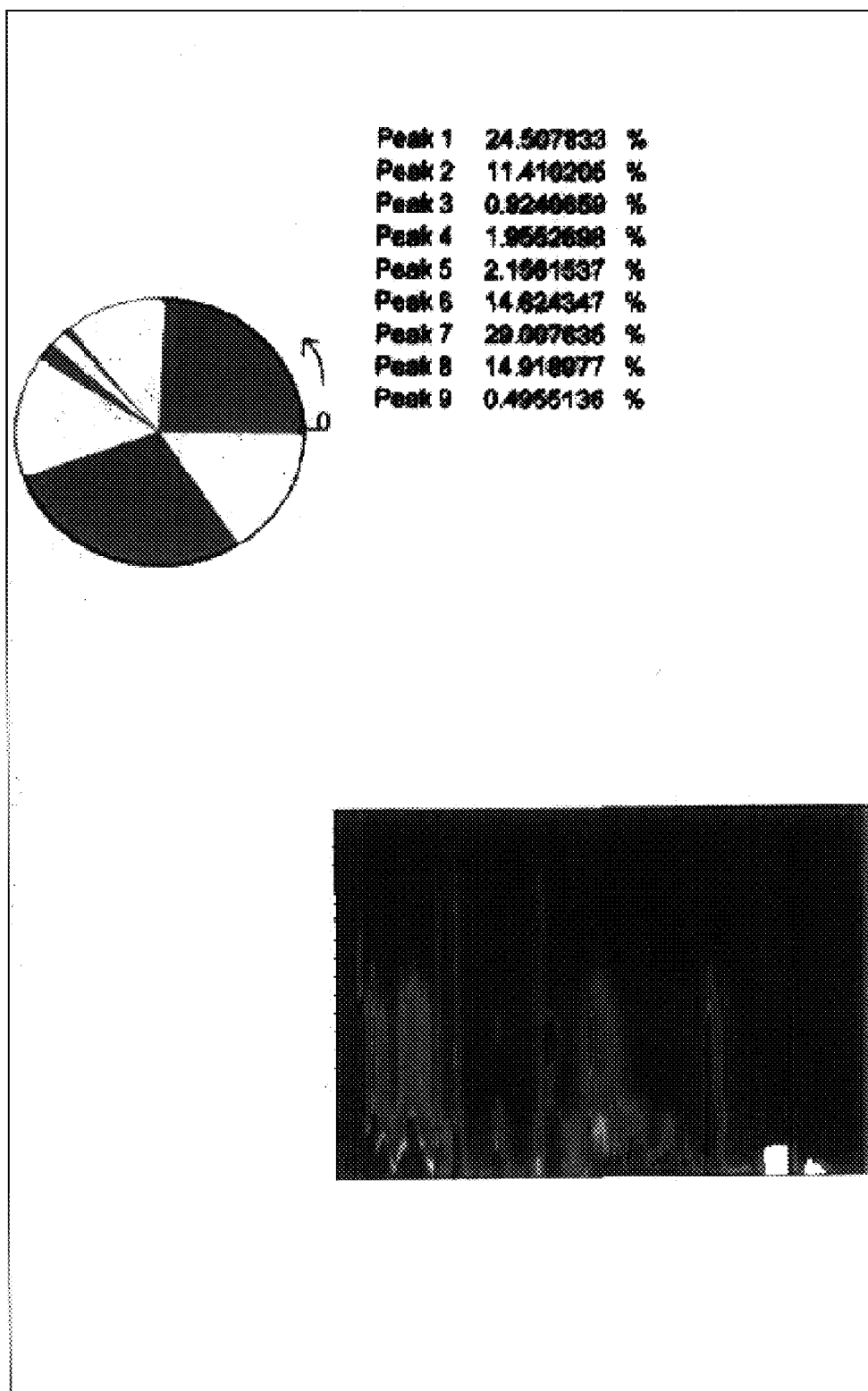

FIG. 105 shows the Pie diagram for the chromatogram of *Krimikutara Ras*

Figure 106:
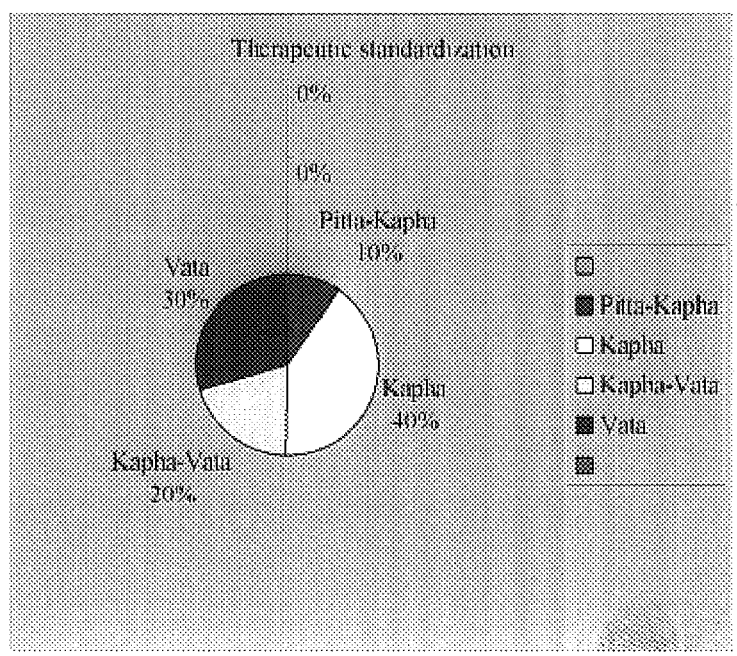

FIG. 106 shows the Pie diagram of vitiation disorders (dosha) quantitative. The pixel values or percentage values from graphs are illustrated. This gives the efficacy of the medicine due to the constituents present in various zones of the fingerprint. The values of pixels were taken generally and are not for a chromatogram. This figure only shows how it appears.

Figure 107:
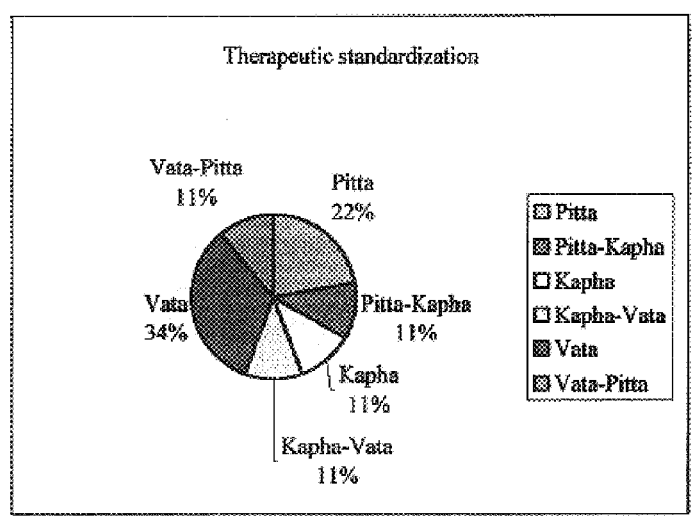

FIG. 107 shows the Pie diagram of vitiation disorders (dosha) quantitative.

Figure 108:
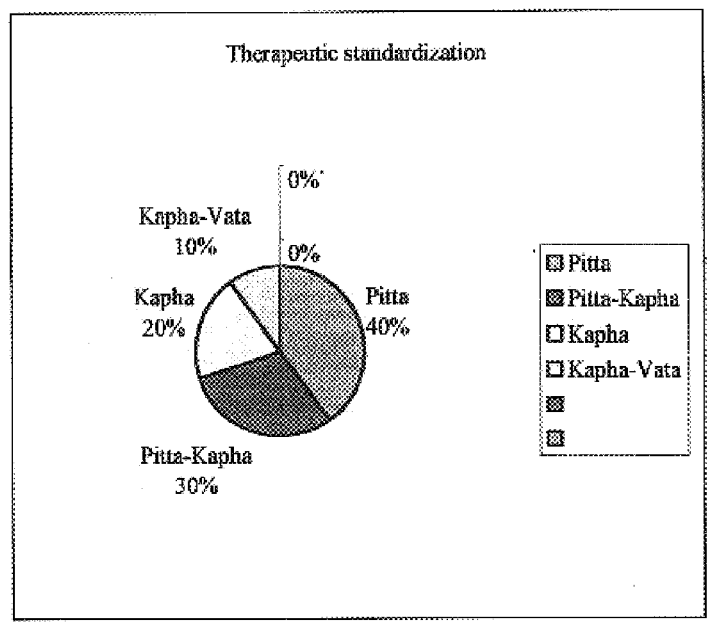

FIG. 108 shows the Pie diagram of vitiation disorders (dosha) quantitative.

Figure 109:
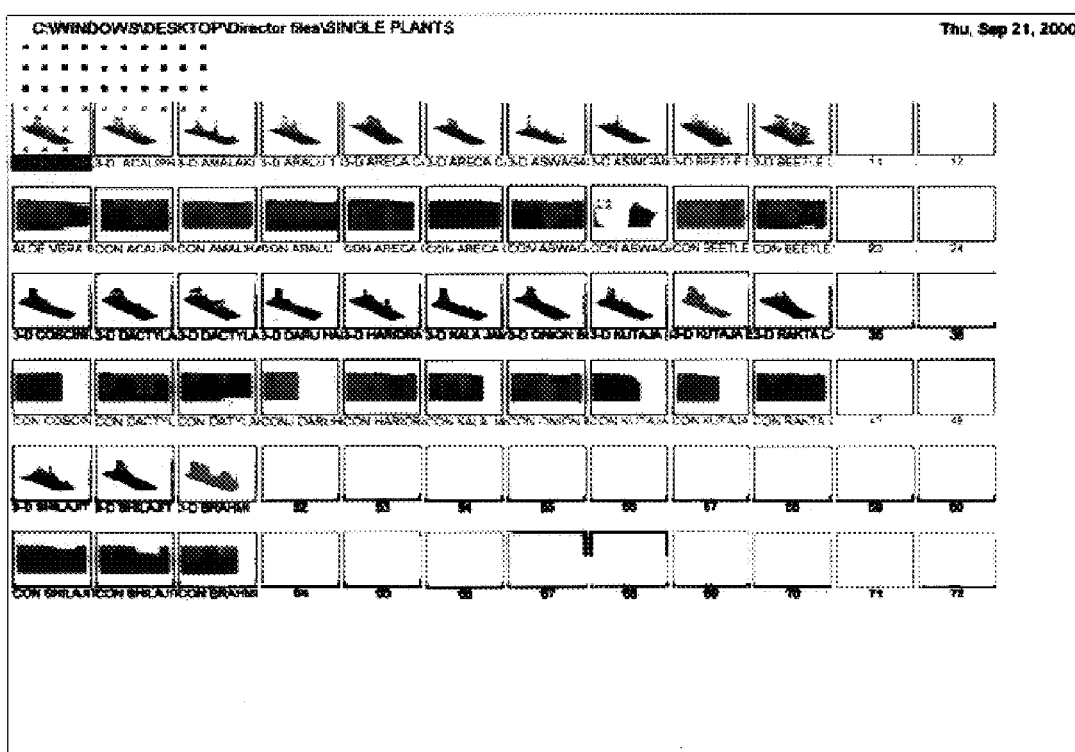

FIG. 109 shows the fingerprints as 3D and contour images of several herbal medicines, which are fed into a database and are used for various ERP and CRM applications. The 3D and contour chromatograms are given in top and bottom lines. Databases based on color, taste, odor, therapeutic value, phytochemical parameters can be prepared to understand the therapeutic efficacy of a specific batch or class of medicines.

Figure 110:
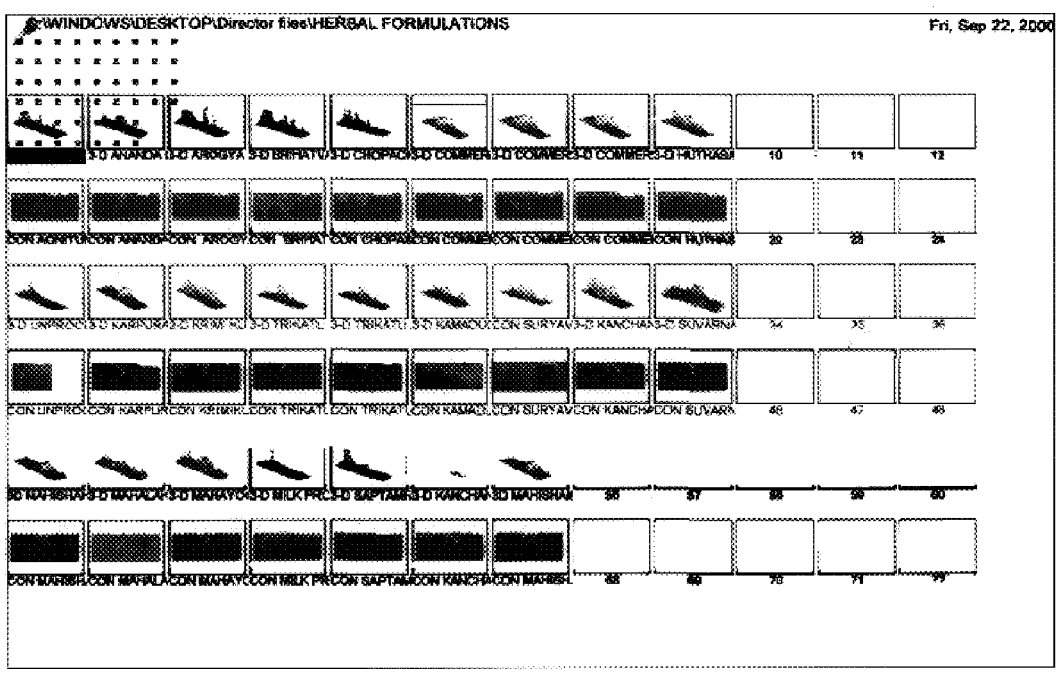

FIG. 110 shows the fingerprints as 3D and contour images of several herbal medicines, which are fed into a database and are used for various ERP and CRM applications. These will help the industry to monitor their product profile for the market and also for proper standardization in the preparation of a formulation.

Figure 111:
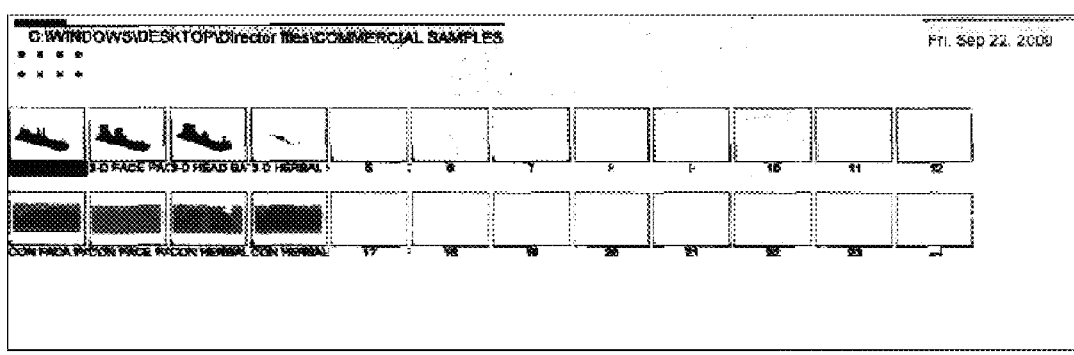

FIG. 111 shows the fingerprint of adulterated cosmetic samples as 3D and contour images.

Figure 112:
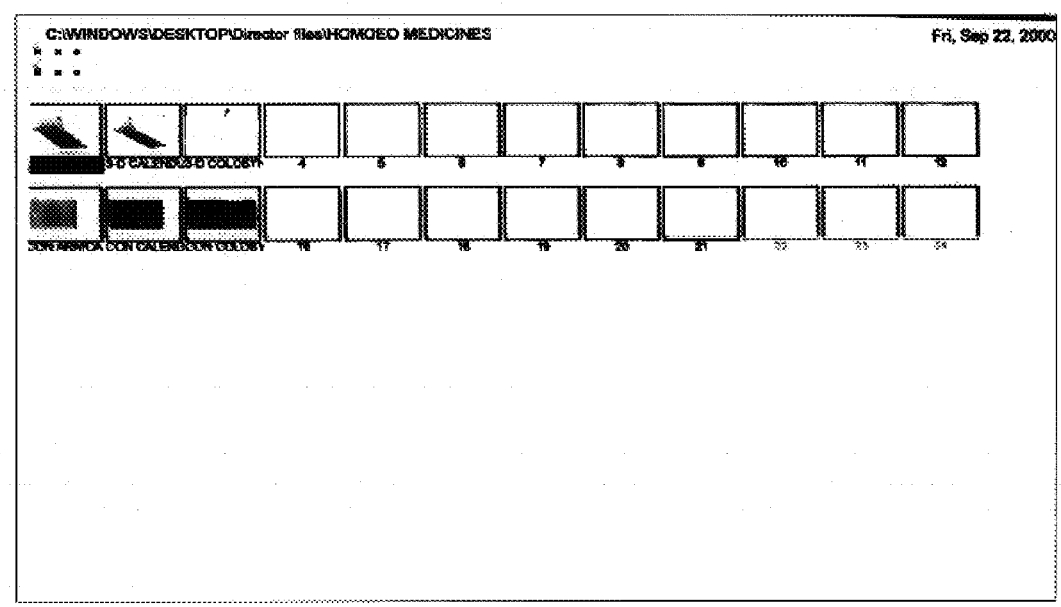

FIG. 112 shows the fingerprints of Mother tincture as 3D and contour images. These can be used to find out the dilution of Mother tincture. The fingerprint of Mother tincture only were done. They can be done to the level of Femto pram level as the PDA detectives are very sensitive. Hence dilution can also be fingerprinted.

Figure 113:
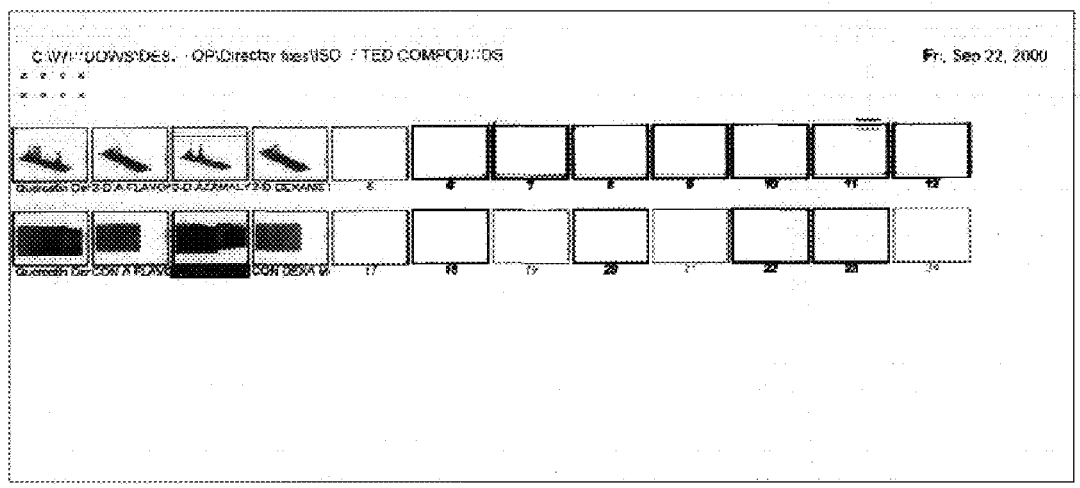

FIG. 113 shows the fingerprints of isolated medicines and their UV spectra as 3D and contour images. This assists in ascertaining the purity after isolation and to know the UV spectra of an unknown molecule.

Figure 114:
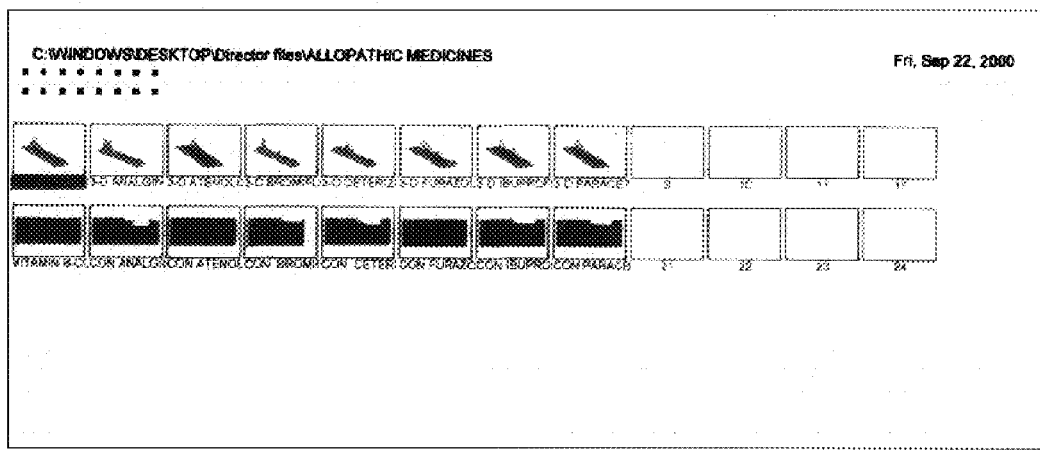

FIG. 114 shows the fingerprints of allopathic medicines as 3D and contour images. This method can also be used for all allopathic medicines for chemical and therapeutic standardization.

Figure 115:
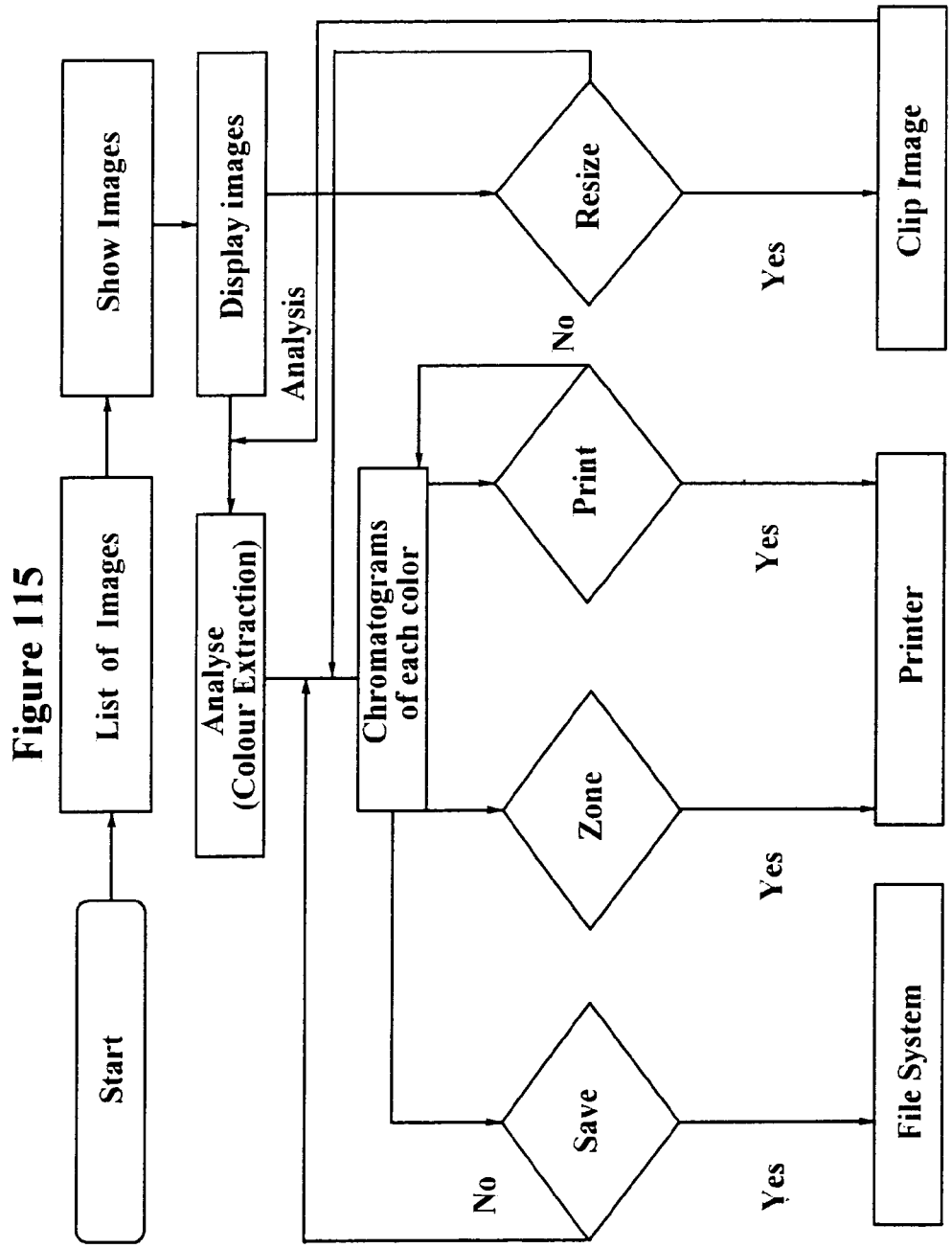

FIG. 115 shows a diagram with operational sequence of the software with various Functionality's.

The invention is described in detail below with reference to the accompanying drawings, flow charts and examples, which are provided to illustrate some of the embodiments of the invention, and the same should not be construed as limitations on the inventive concept embodied herein.

Method of Chemical Standardization:

Hence unlike a method currently under use, where in a chromatogram is given at a single wavelength, a novel method of chromatographic standardization, finger printing and bar coding is proposed, using contour and 3-D chromatograms. It provides the total chemical profile (properties like polarity and conjugation, there in) of the chemical constituents present in complex medicines like herbal medicines and formulations or any medicine. Further, bar coding the finger prints thus generated will provide many commercial features in dealing such medicines using the ERP and CRM applications.

Figure 1A:
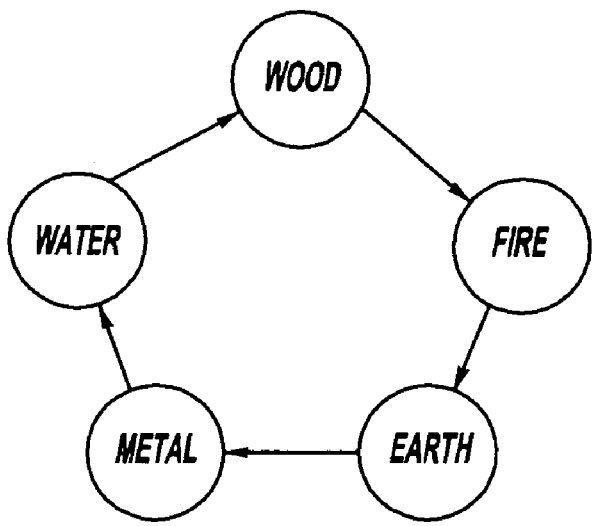
Figure 1B:
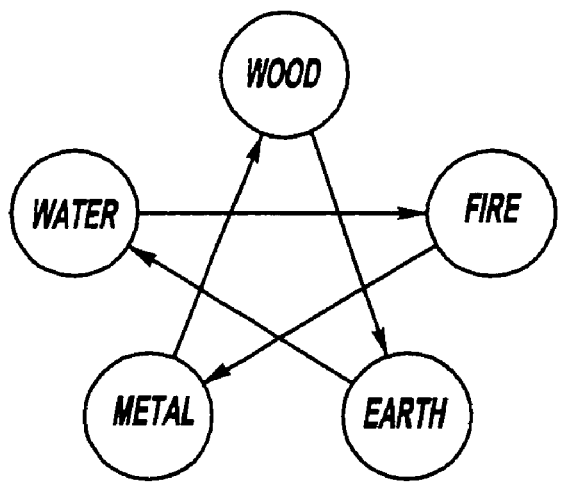
Figure 3:
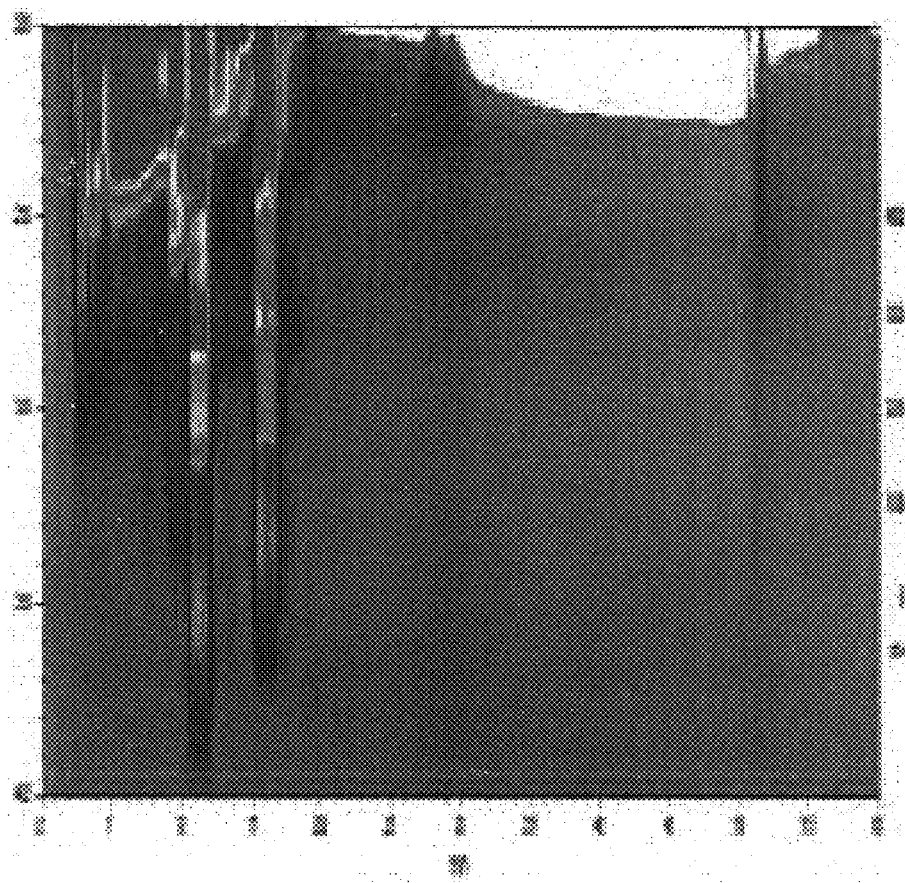
Figure 4:
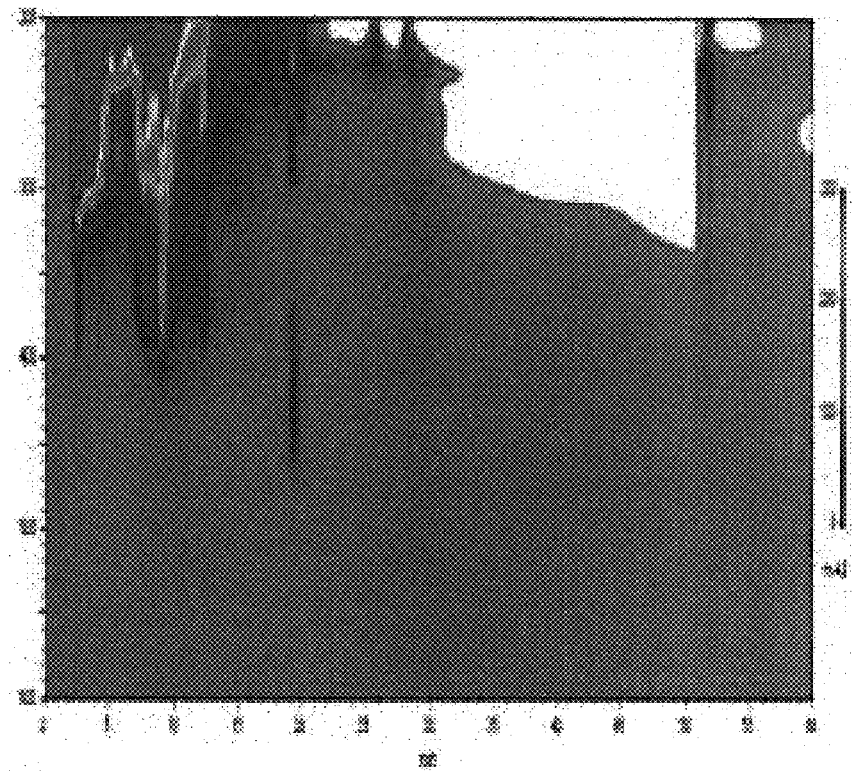
FIG. 4 shows the existing use of chromatographic fingerprints on a label.
Figure 13A:
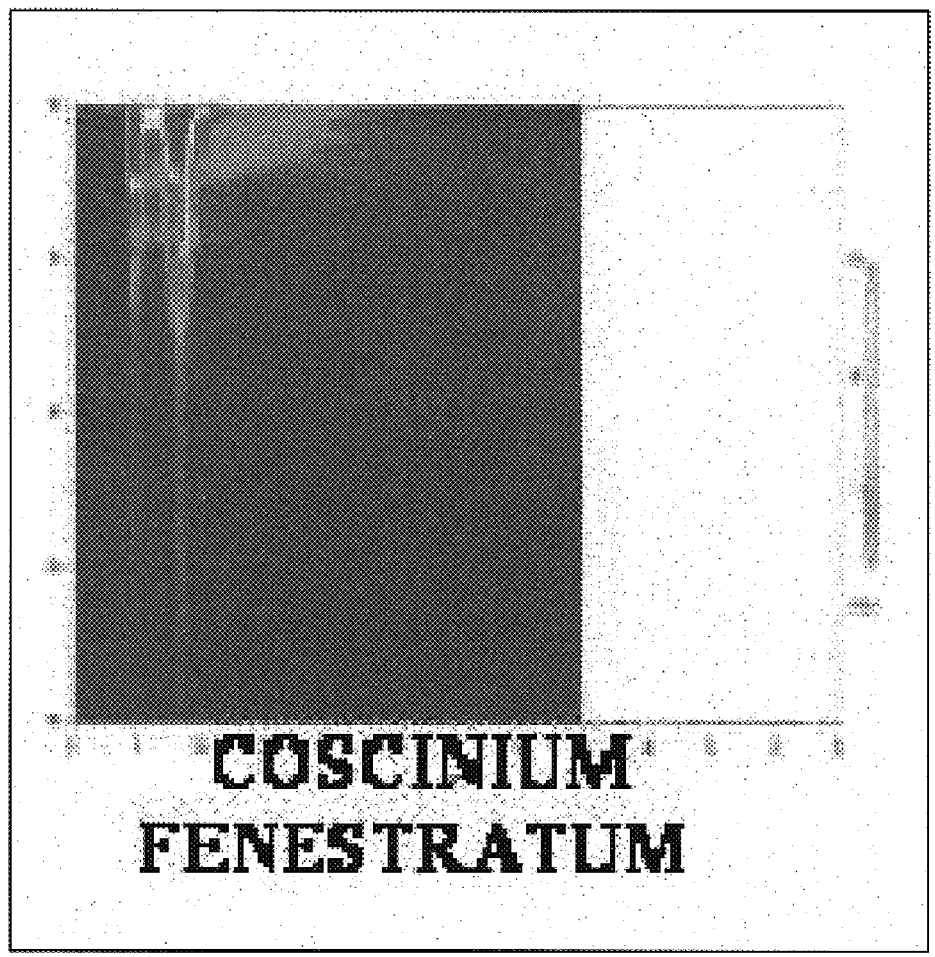
FIG. 13 (A through F) shows the fingerprints of all yellow medicines. Here the fingerprint of Sandigdha Dravyas (a contraversial drug) shows a clear difference in appearance, making the identification more easy.
Figure 13B:
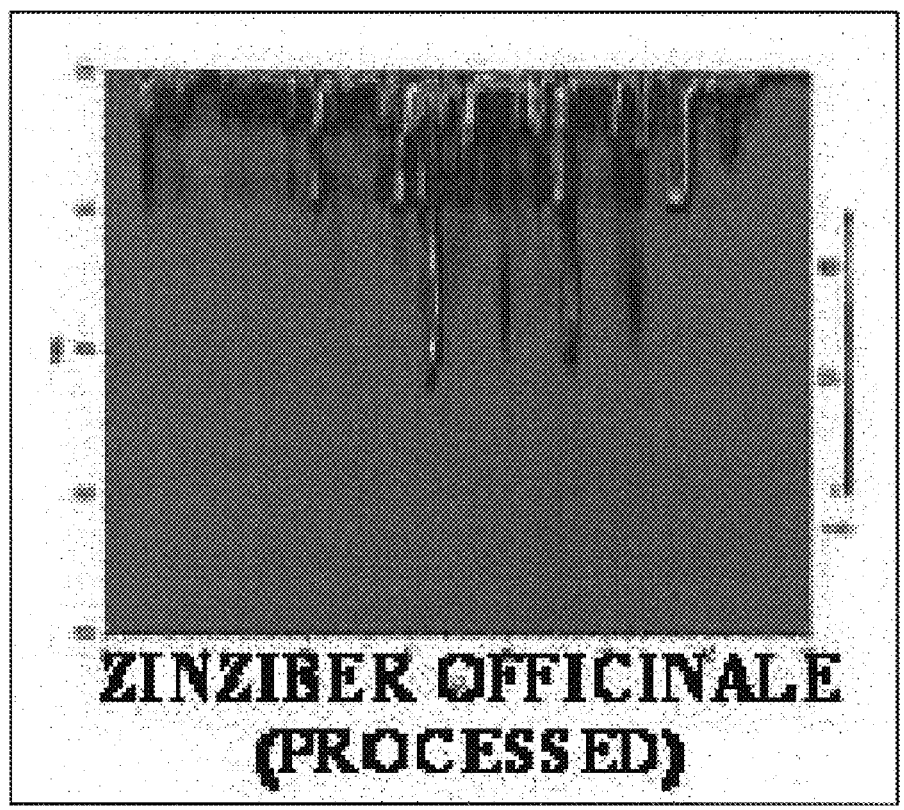
Figure 13C:
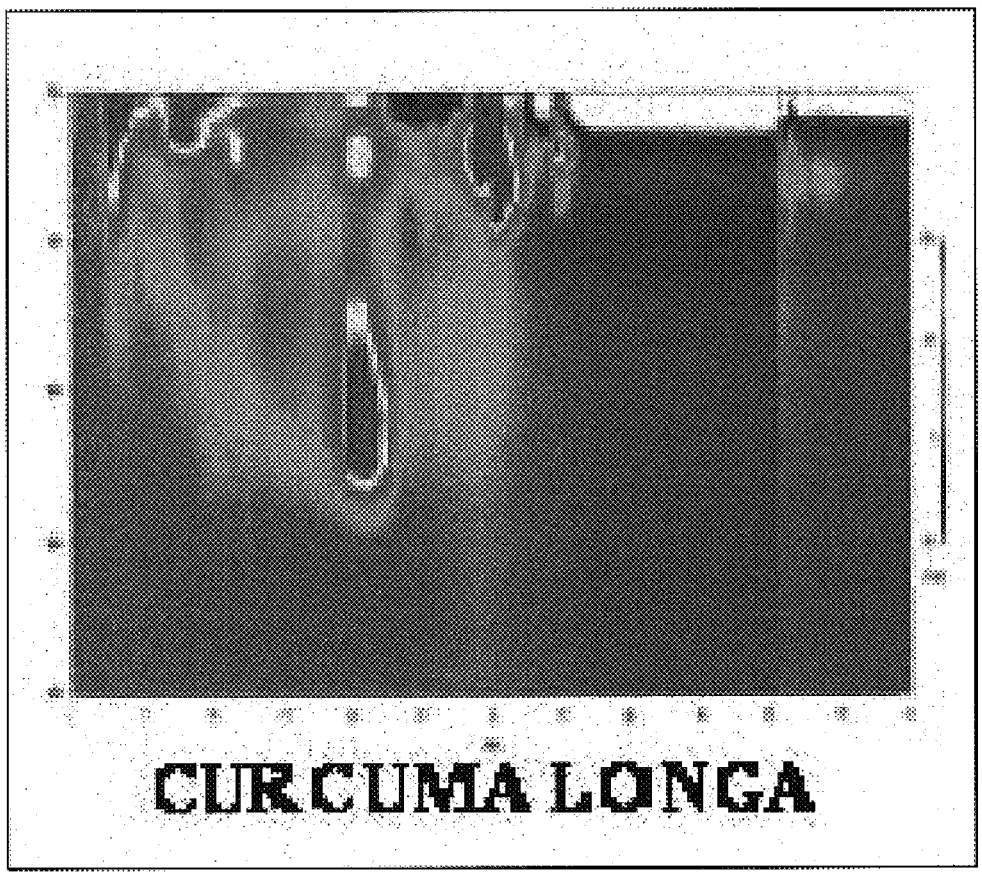
Figure 13D:
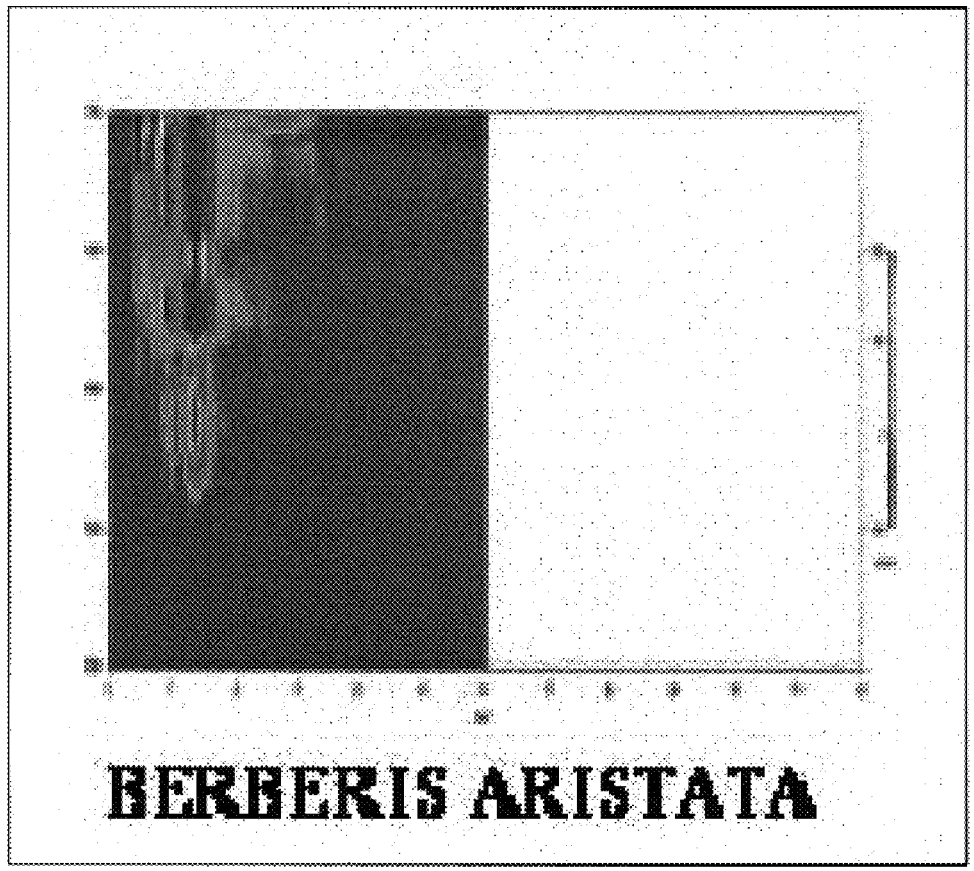
Figure 13E:
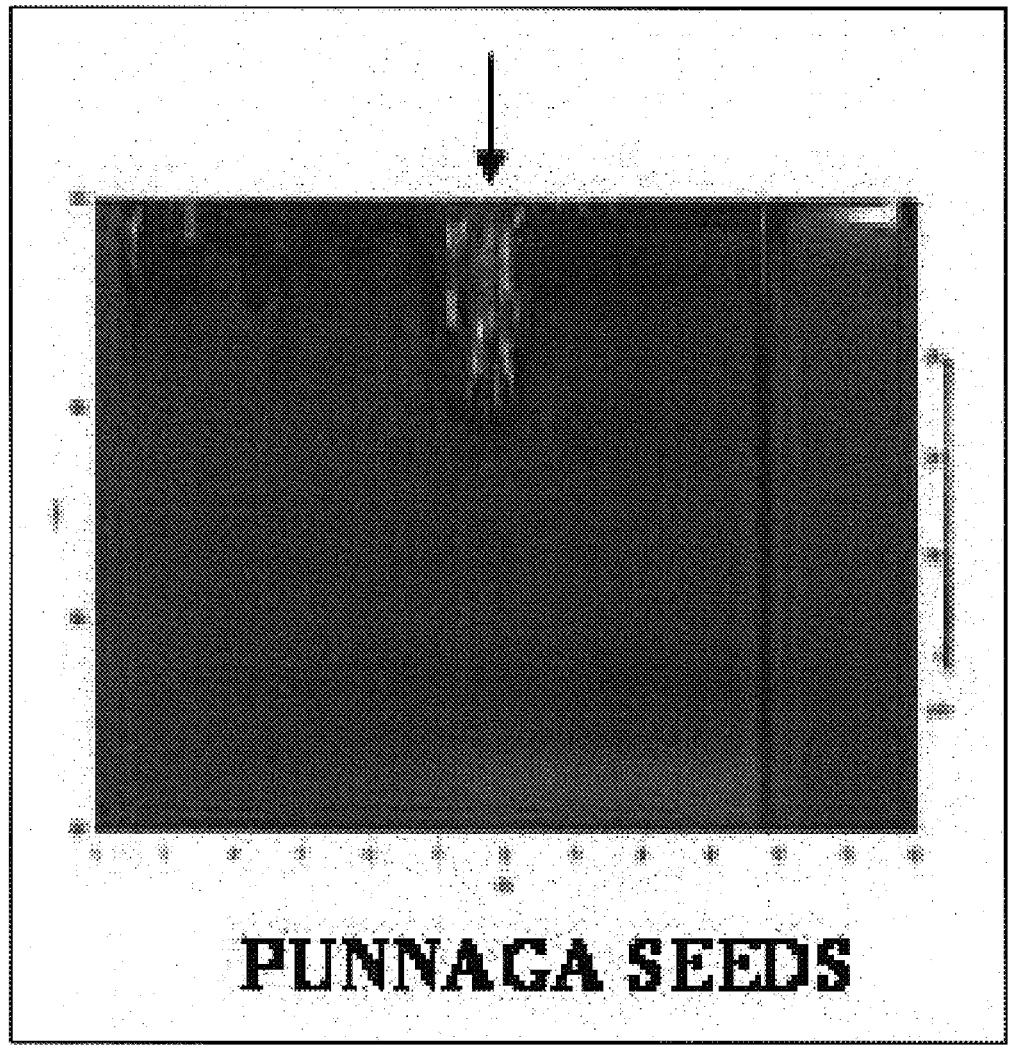
Figure 13F:
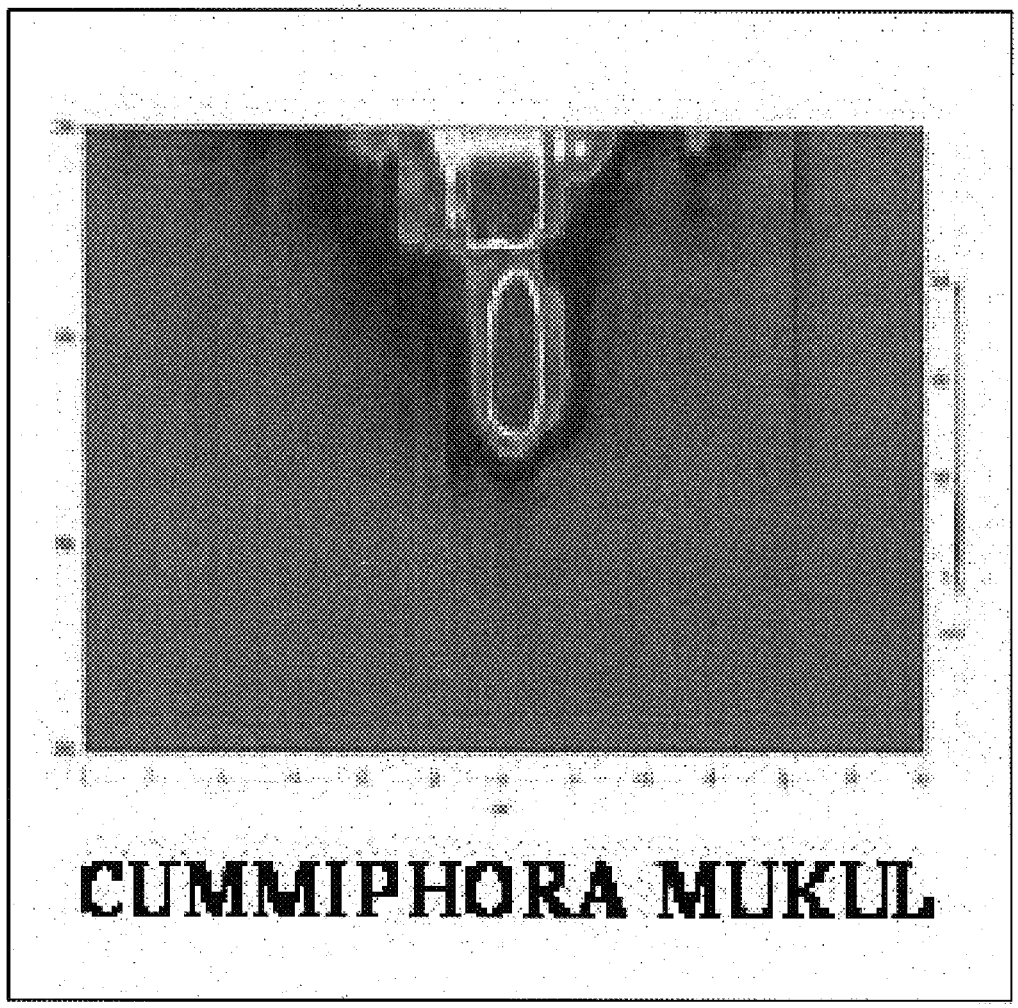
Figure 14A:
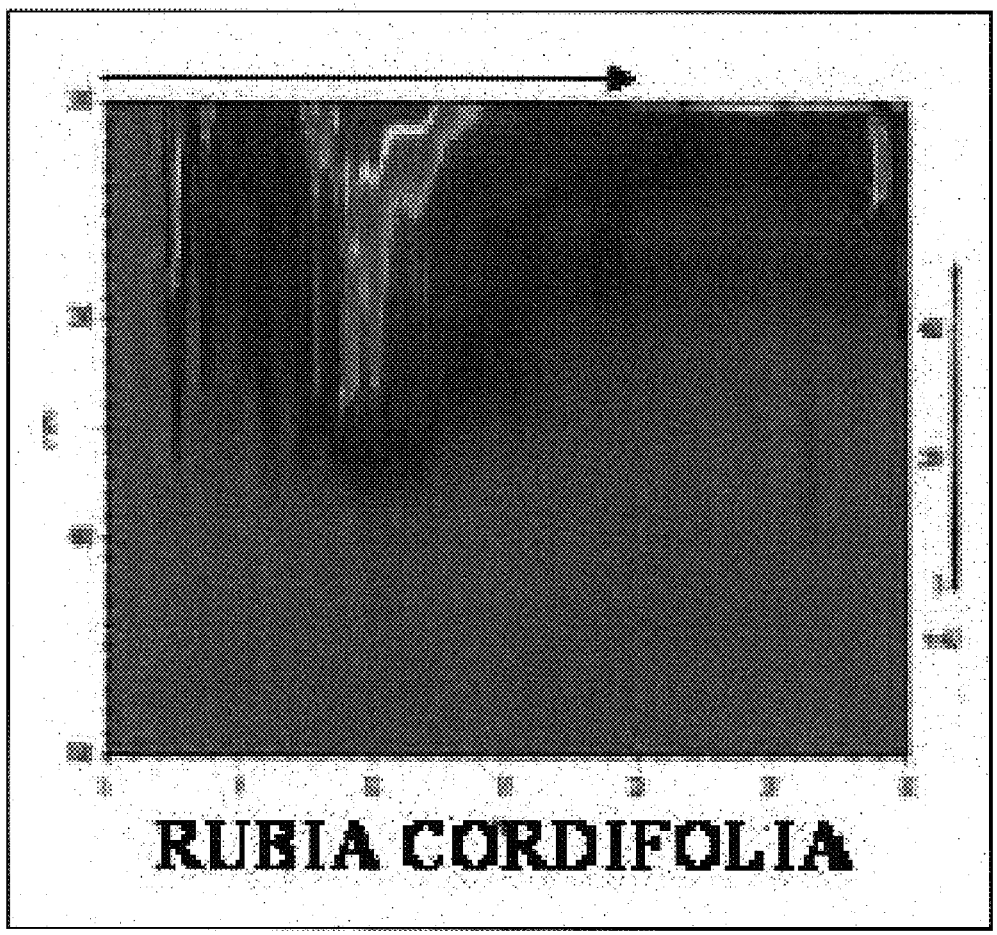
FIG. 14 (A through F) shows the fingerprints of all medicines of PITTA HARA in nature. The presence of constituents in zone-1 indicates the efficacy of the medicine.
Figure 14B:
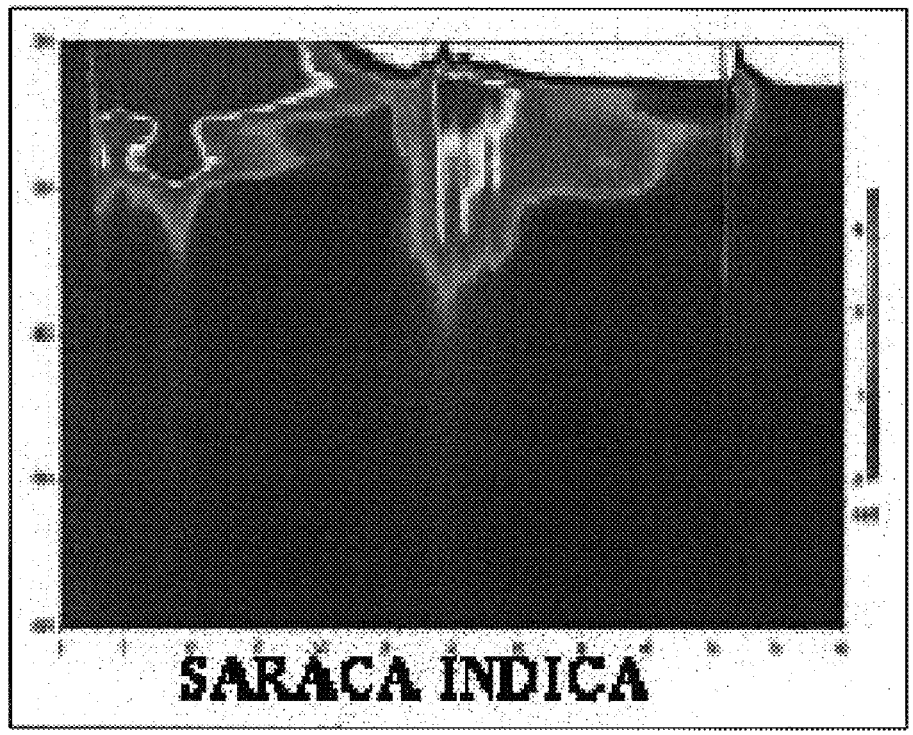
Figure 14C:
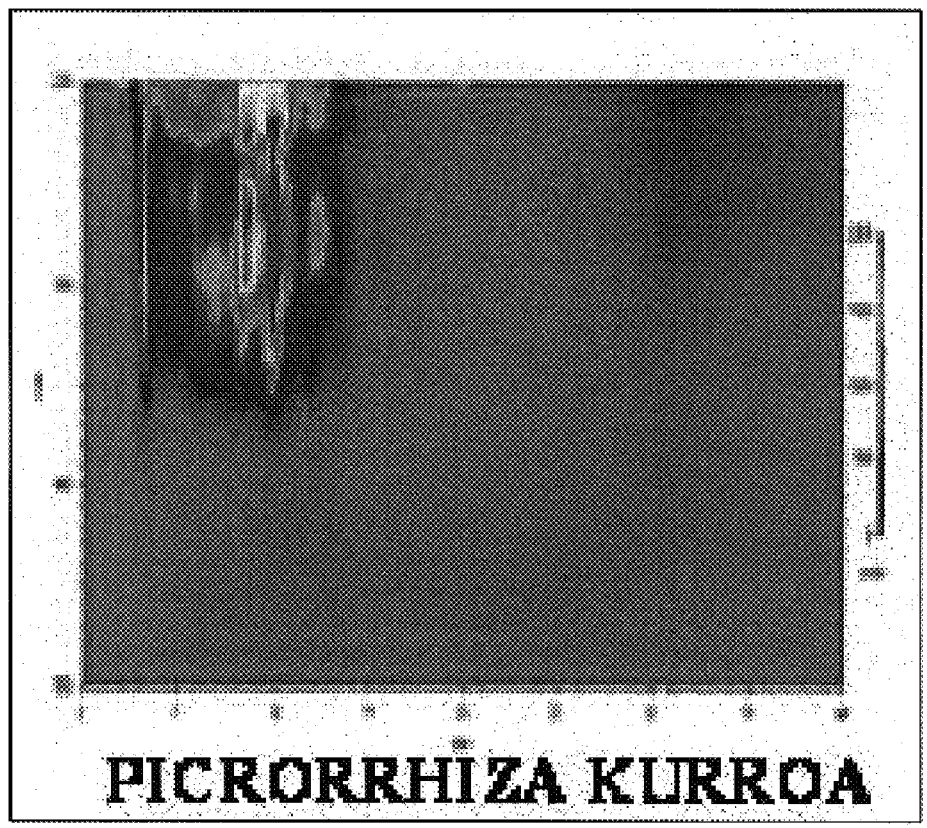
Figure 14B:
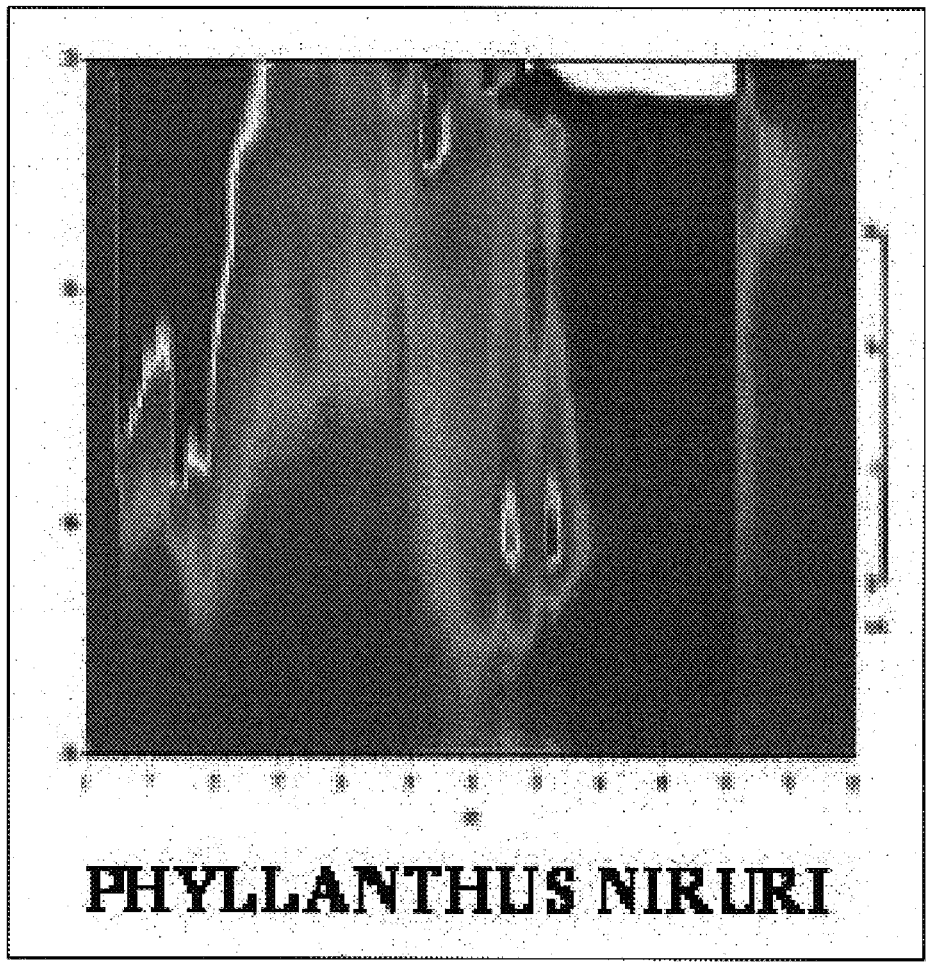
Figure 14E:
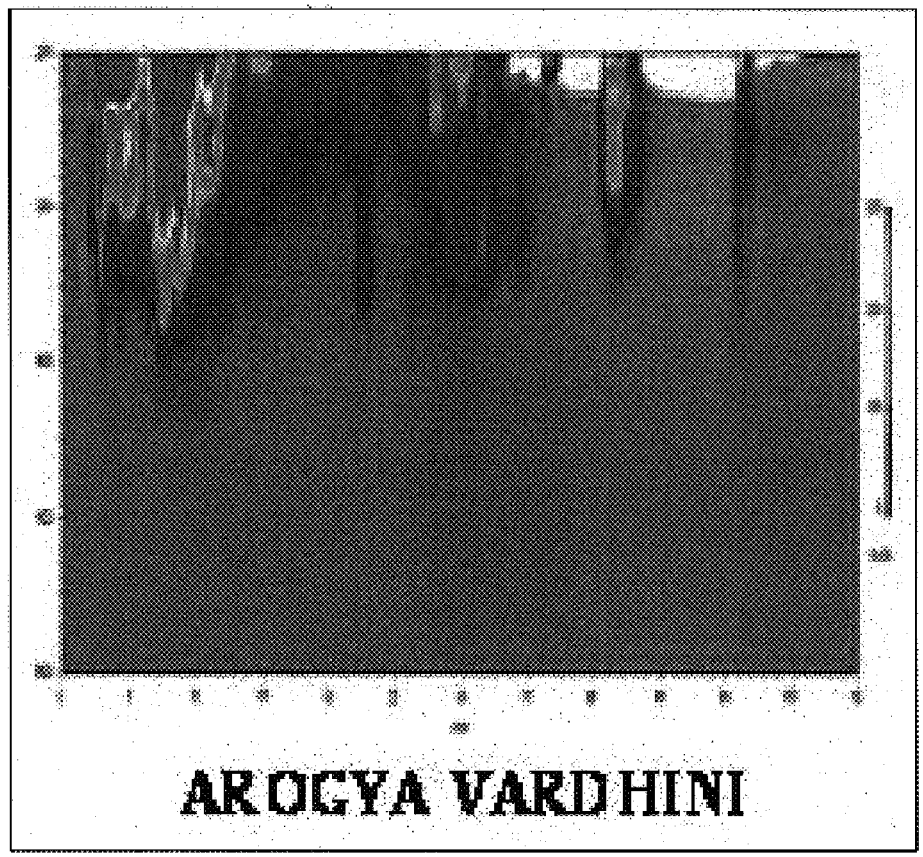
Figure 14F:
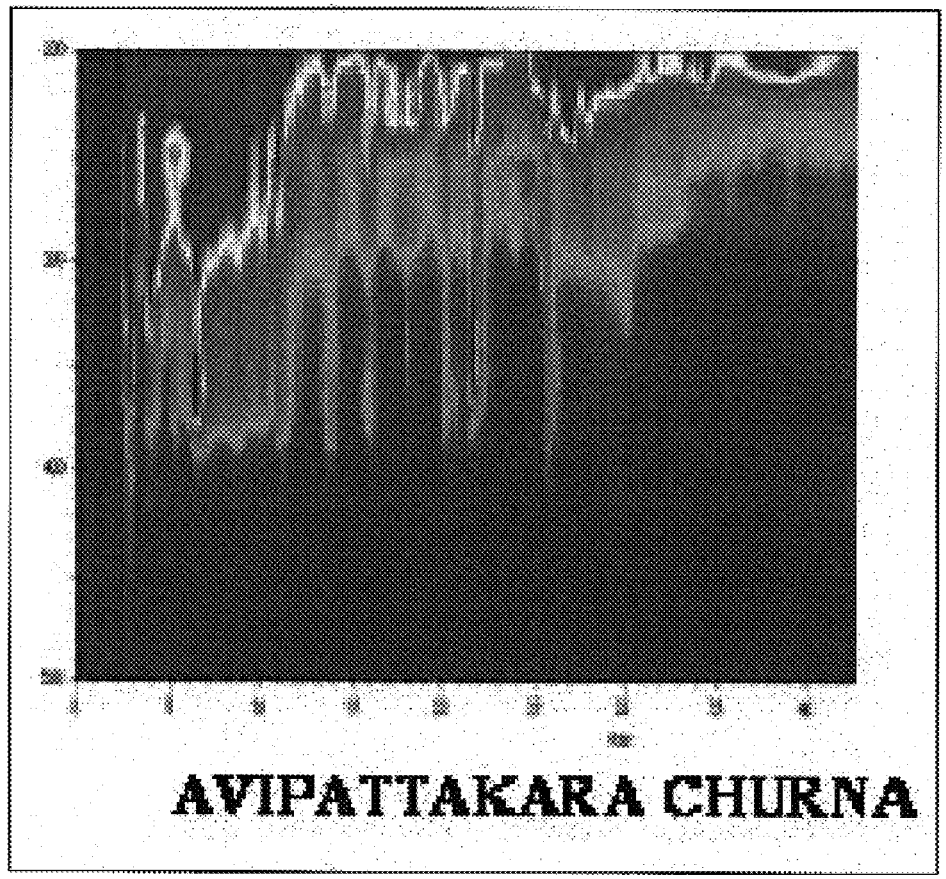
Figure 15A:
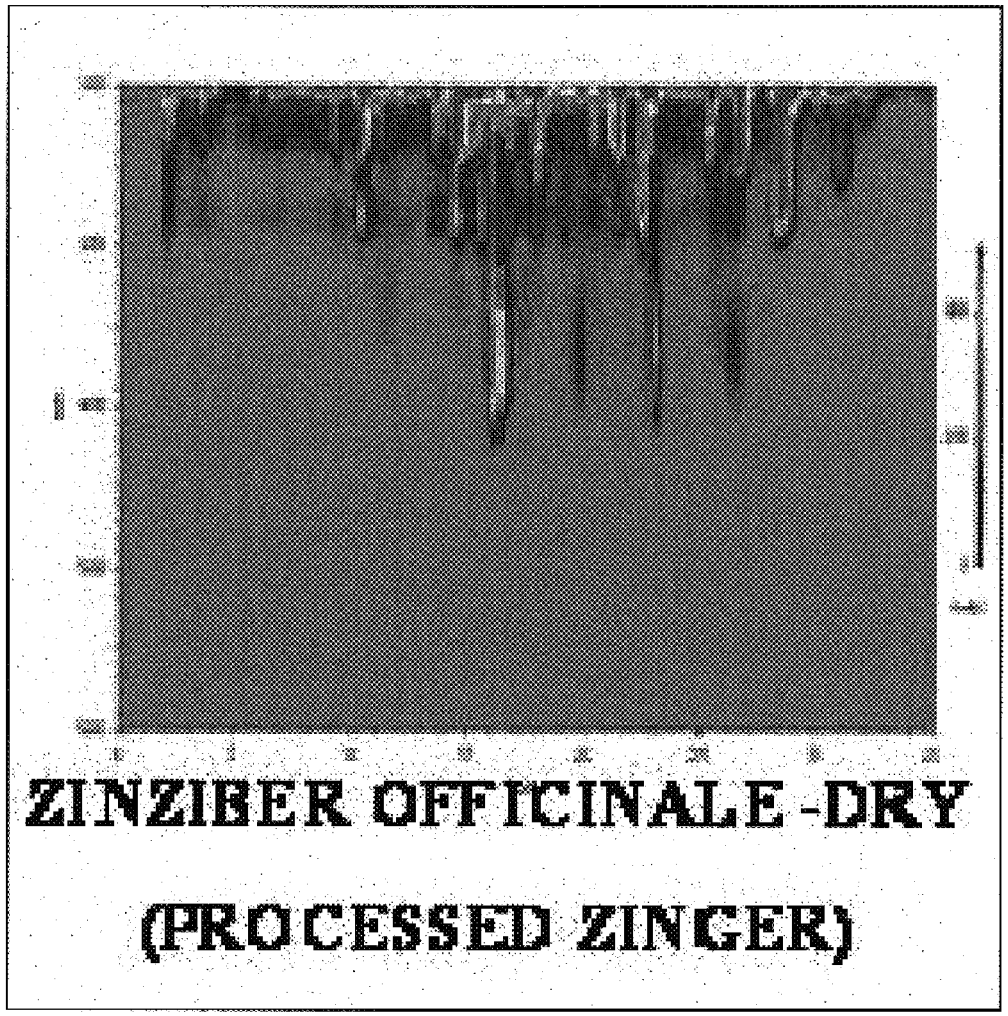
FIG. 15 (A through F) shows the fingerprints of all medicines of KAPHA HARA in nature. The presence of constituents in zone-2 indicates the efficacy of the medicine.
Figure 15B:
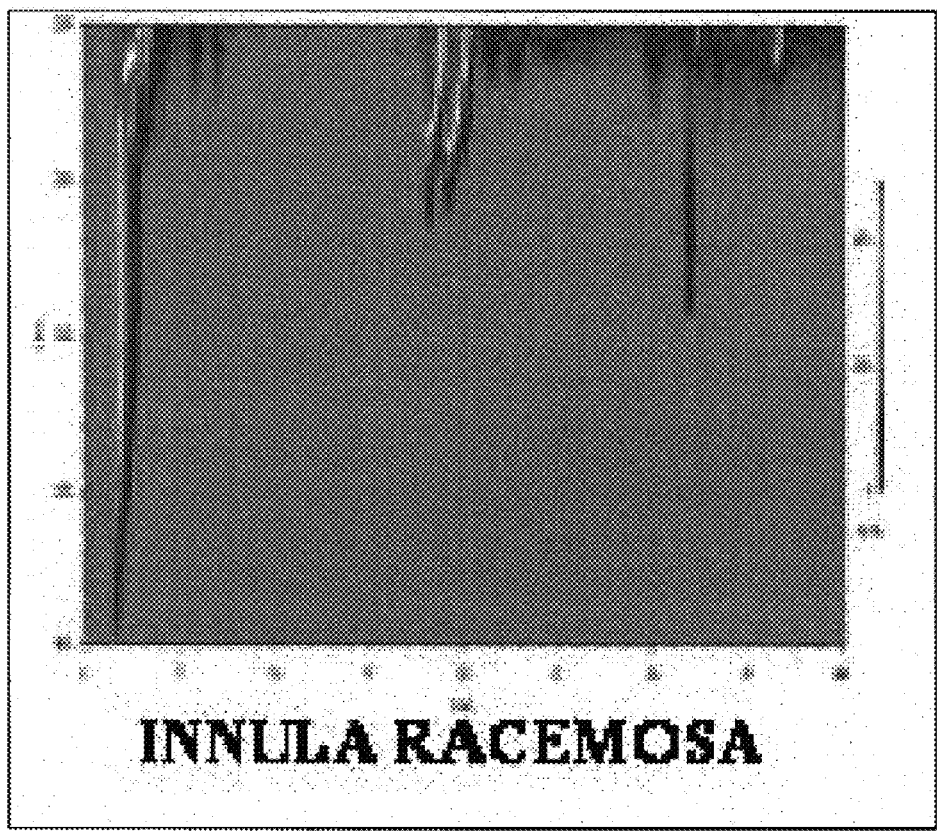
Figure 15C:
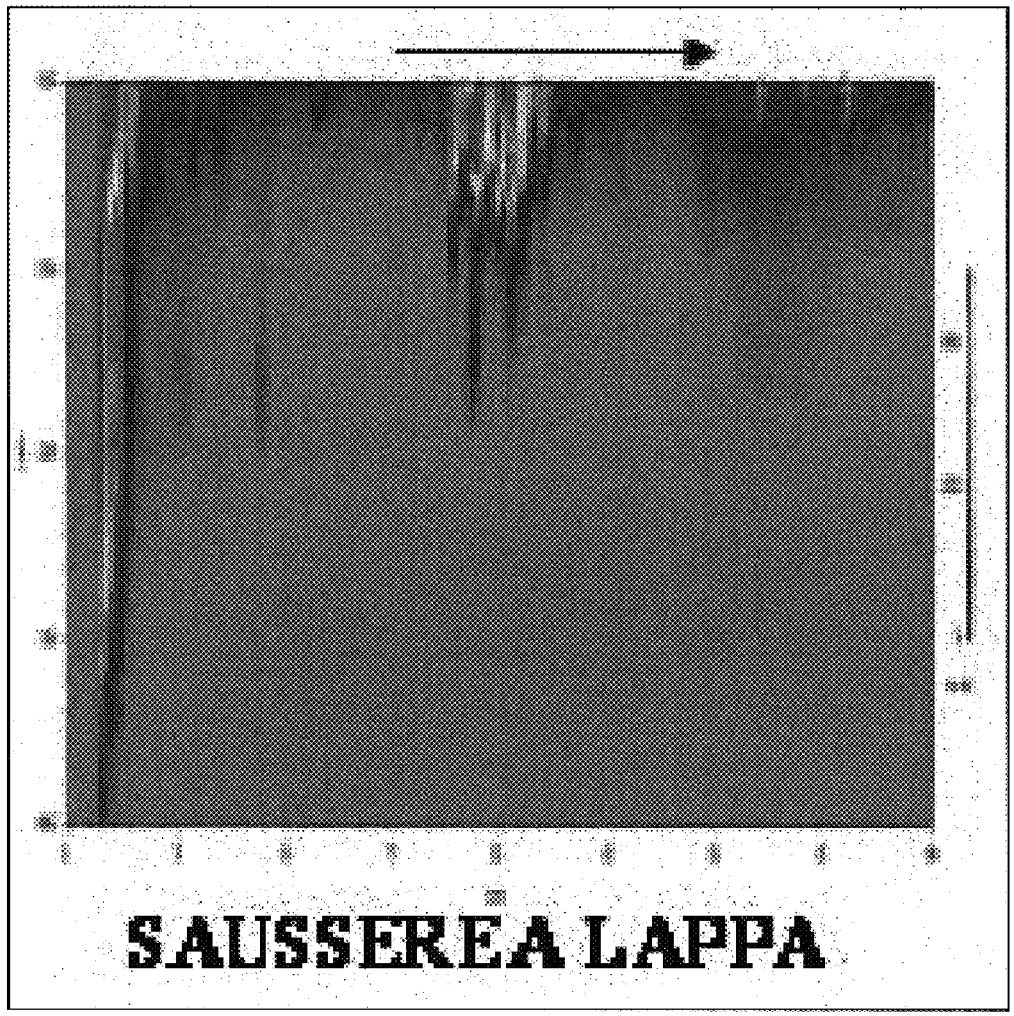
Figure 15D:
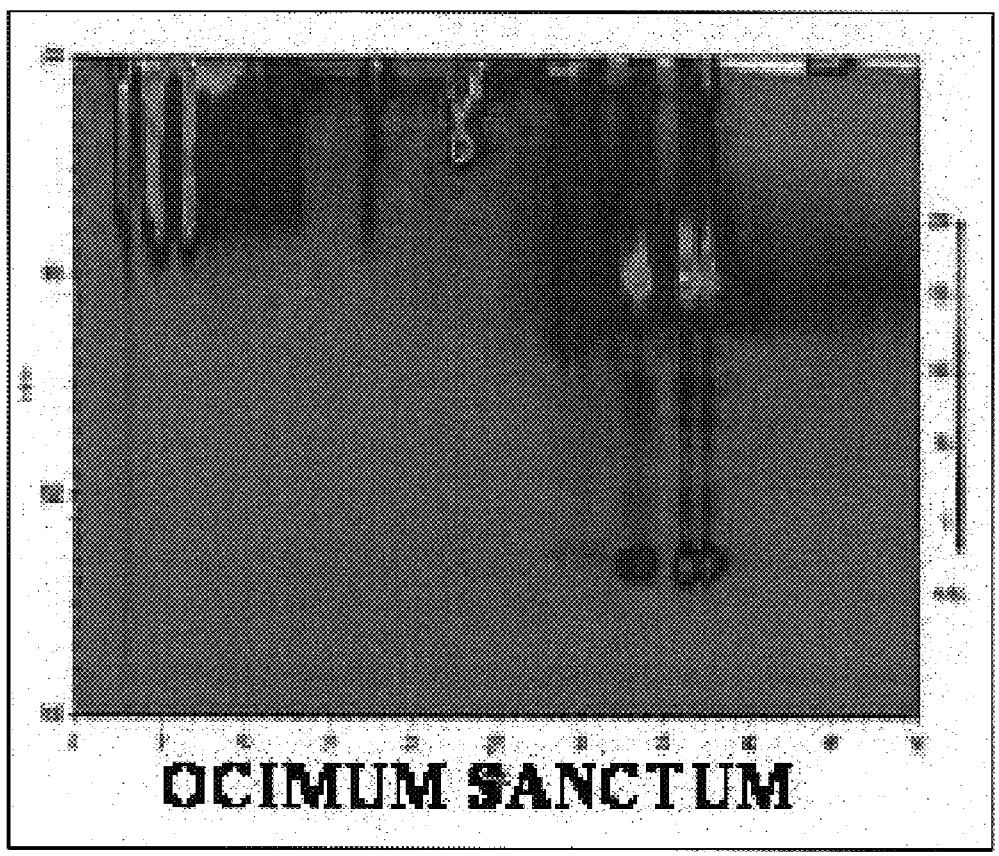
Figure 15E:
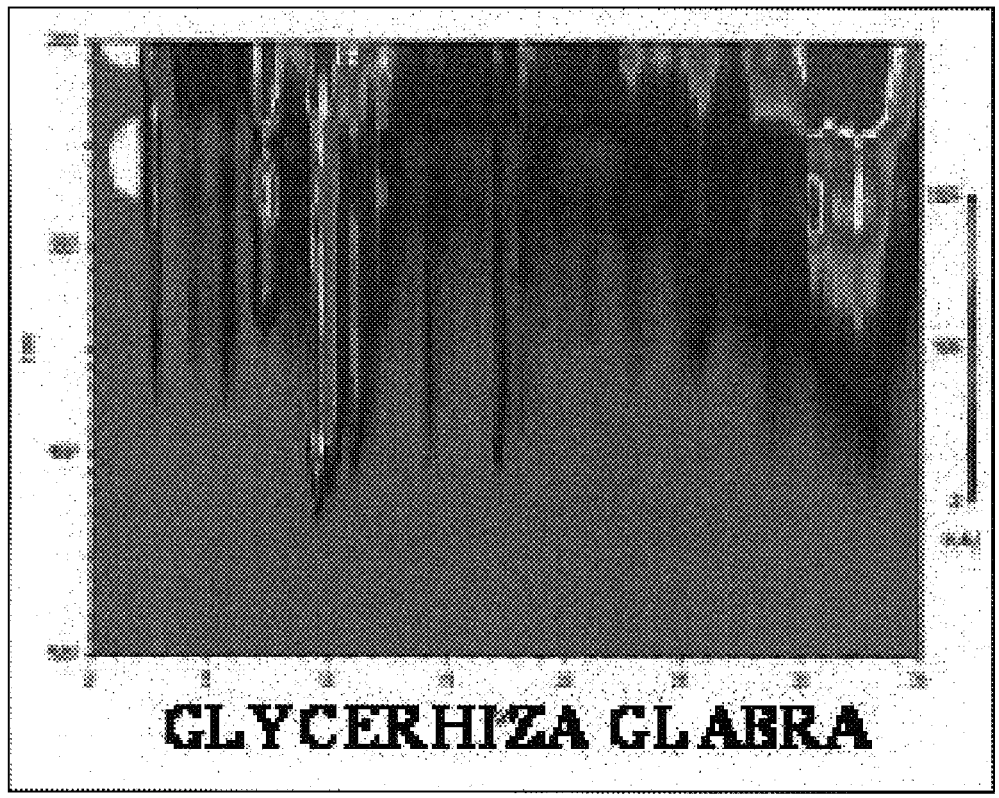
Figure 15F:
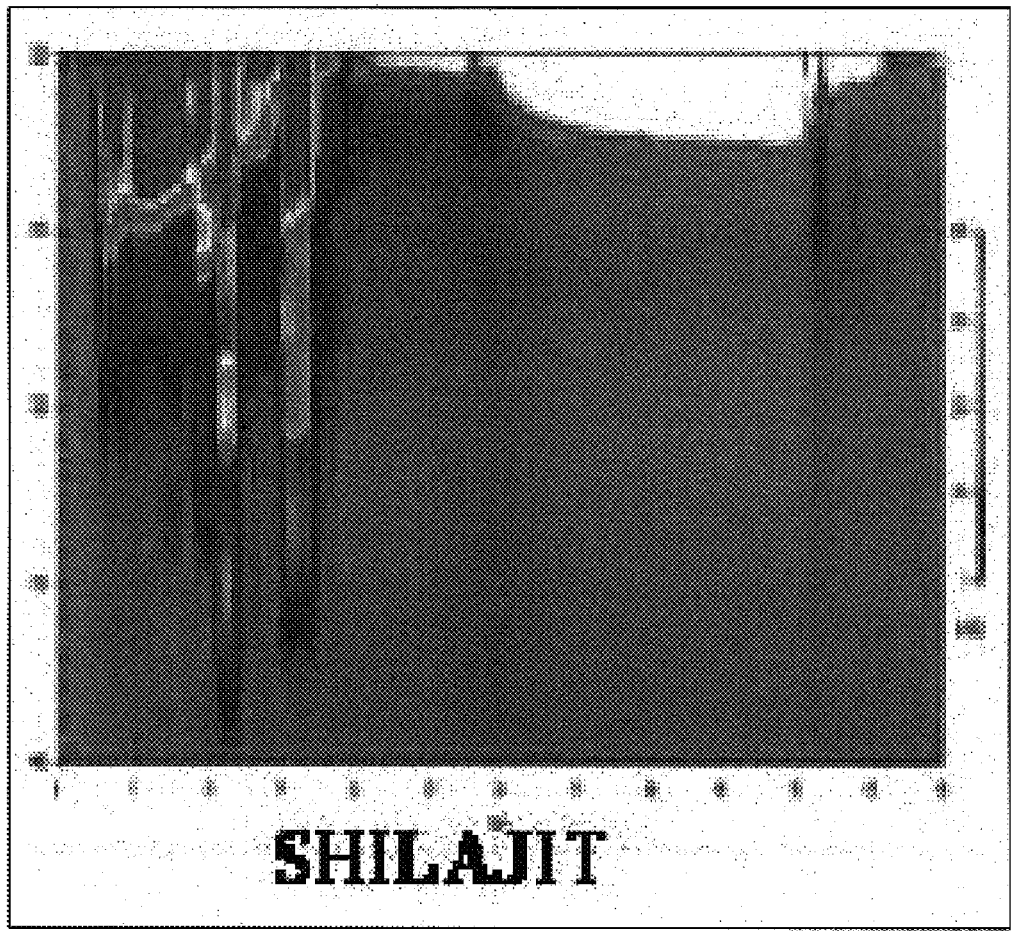
Figure 16A:
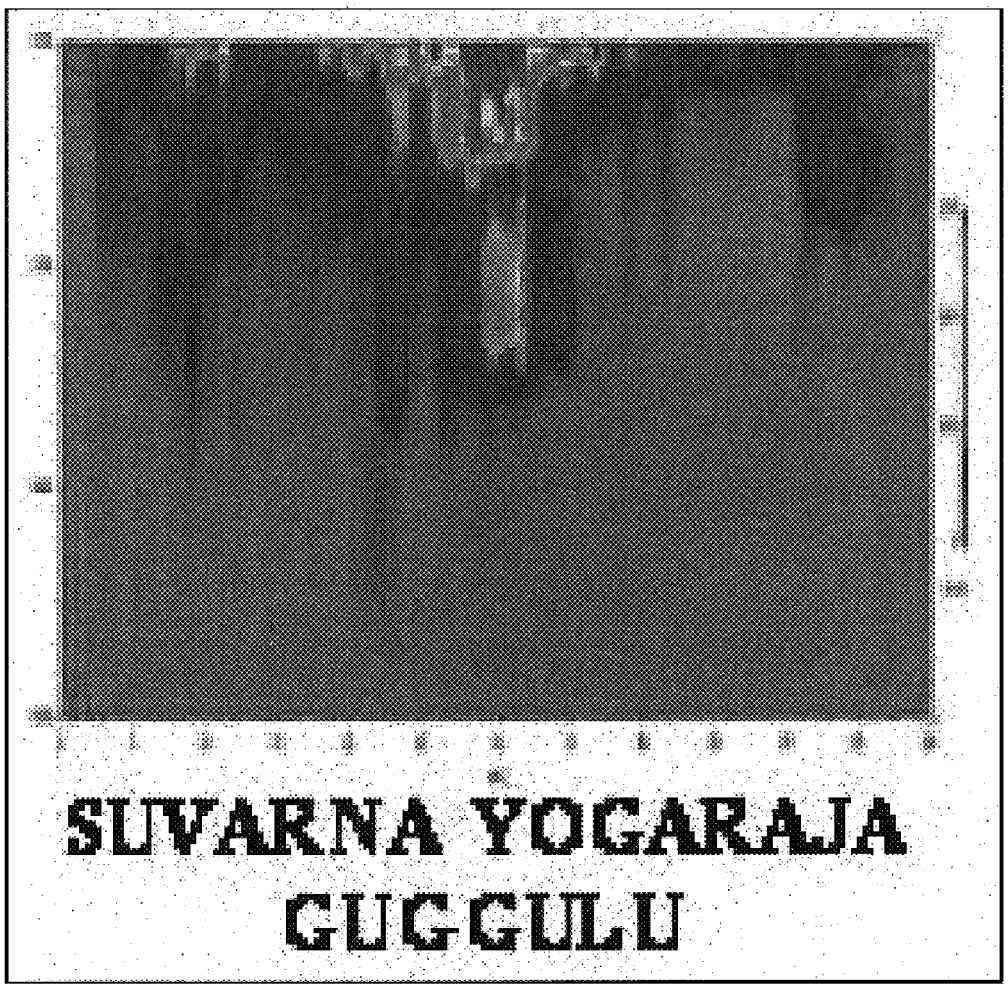
FIG. 16 (A through F)shows the fingerprints of all medicines of VATA HARA in nature. The presence of constituents in zone-3 indicates the efficacy of the medicine.
Figure 16B:
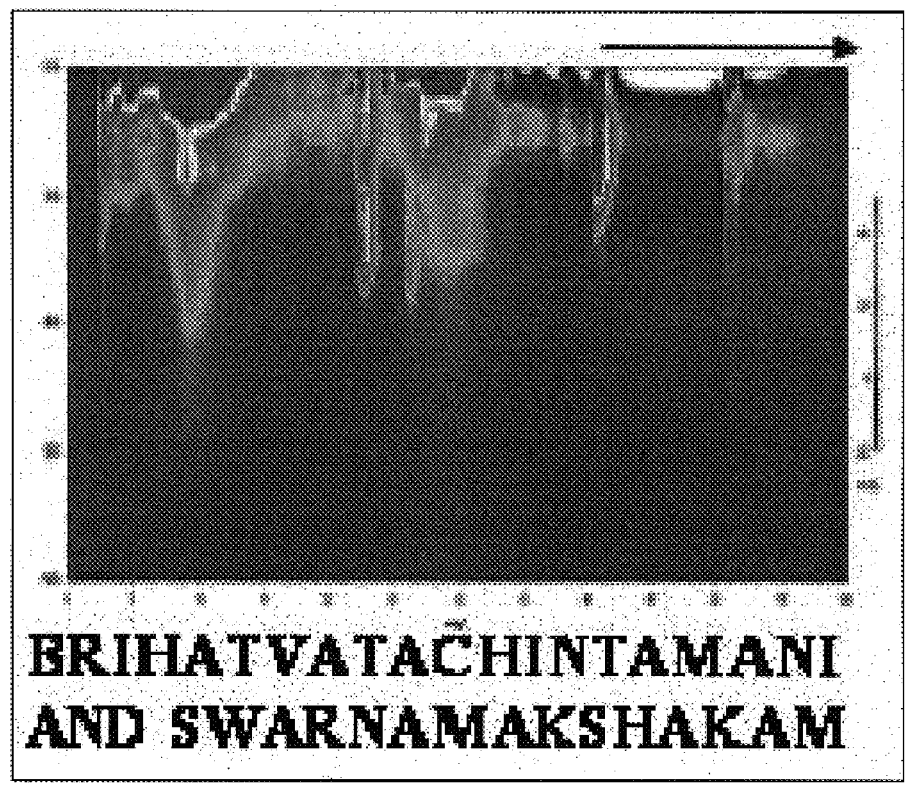
Figure 16D:
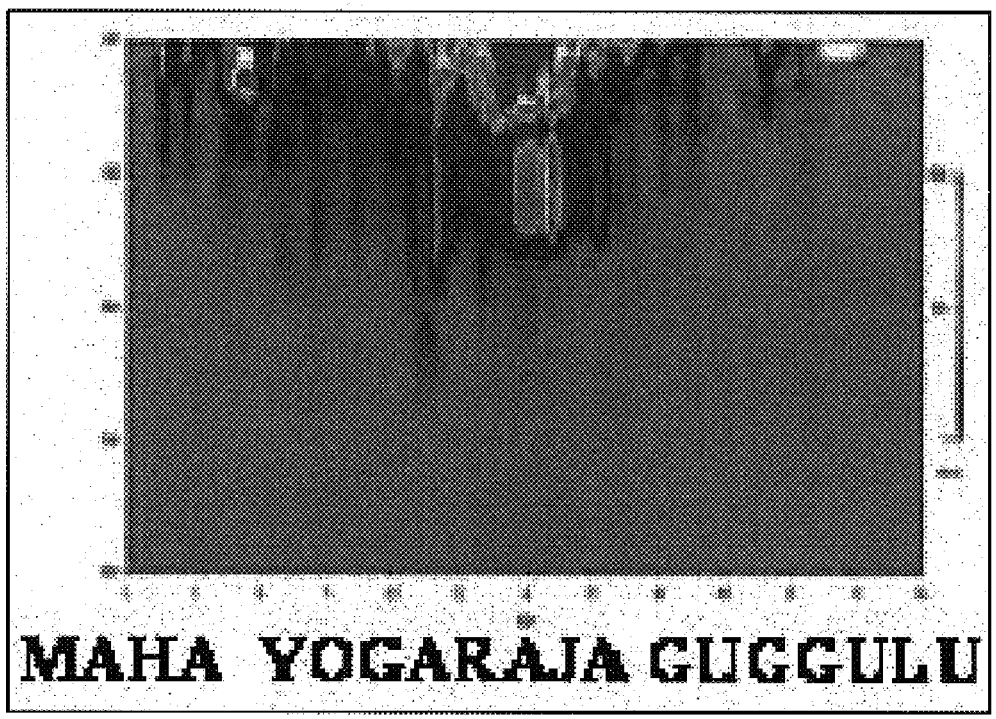
Figure 16E:
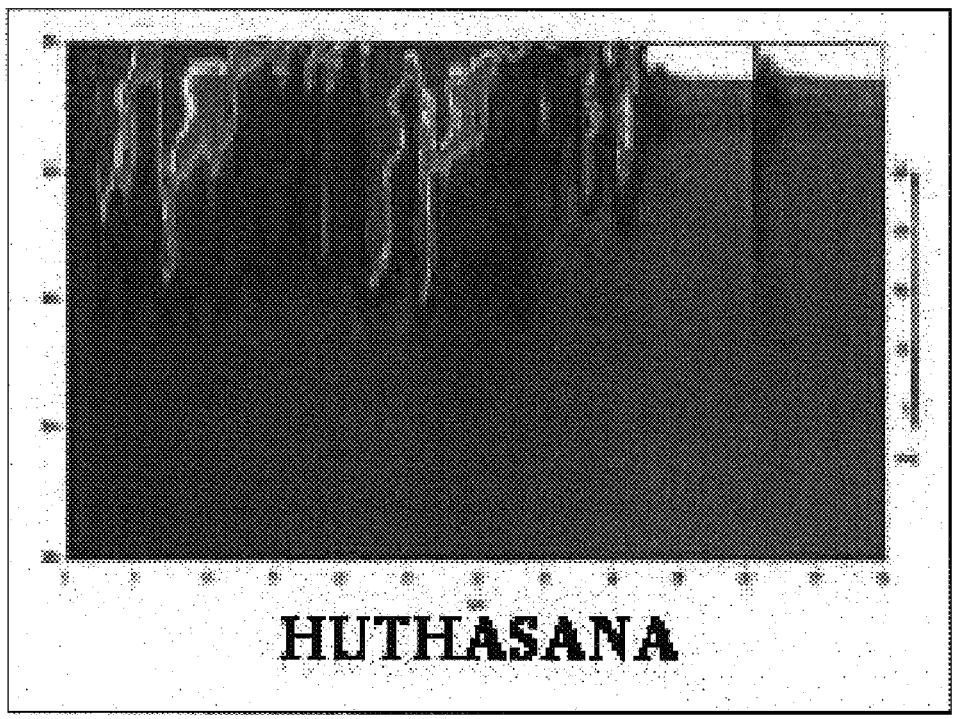
Figure 16F:
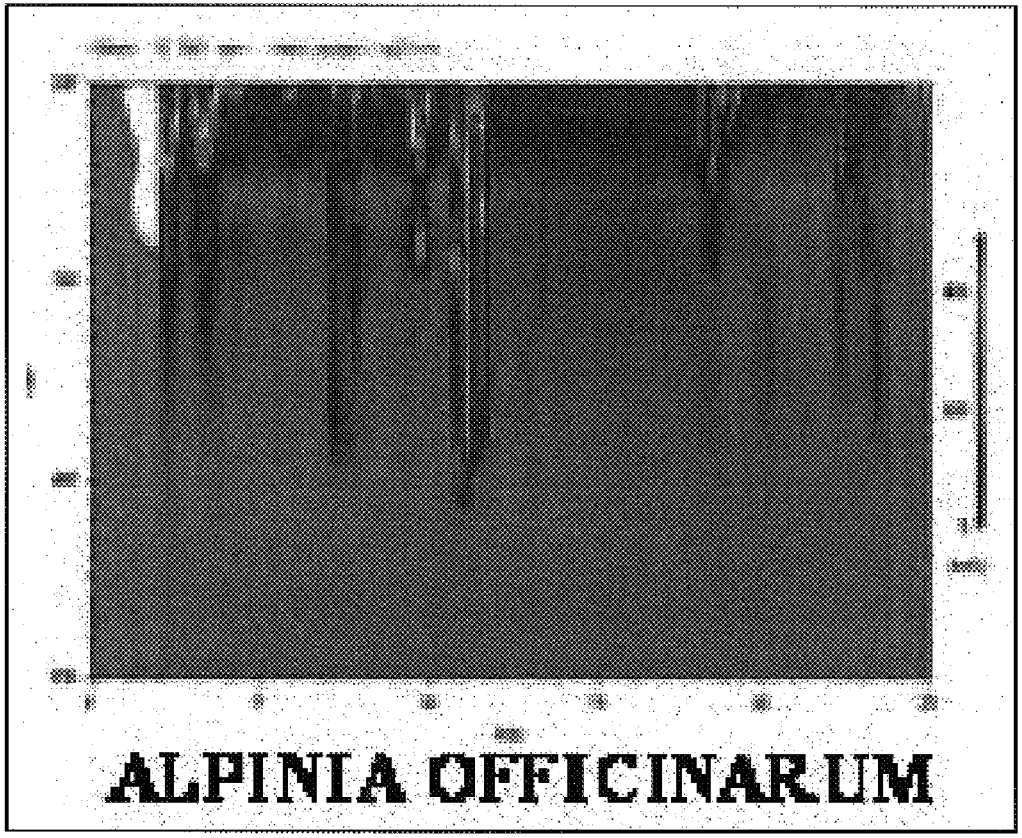
Figure 17A:
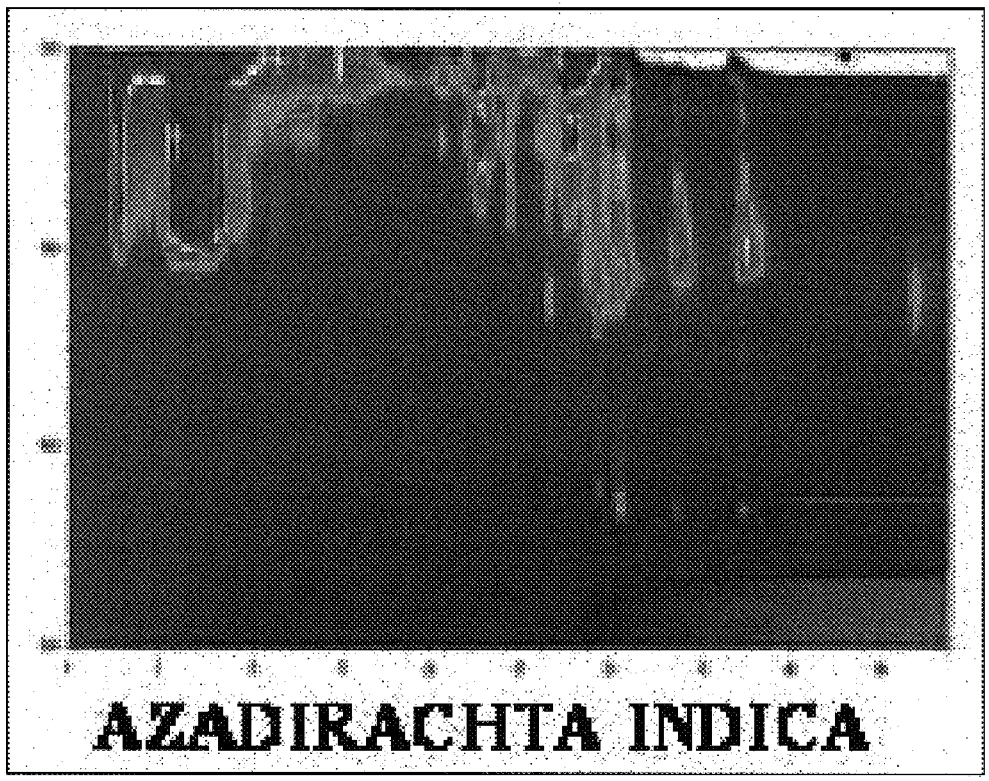
FIG. 17 (A through F) shows the fingerprints of all medicines of PITTA KAPHA HARA in nature. The presence of constituents in zone-1 and zone-2 indicates the efficacy of the medicine.
Figure 17B:
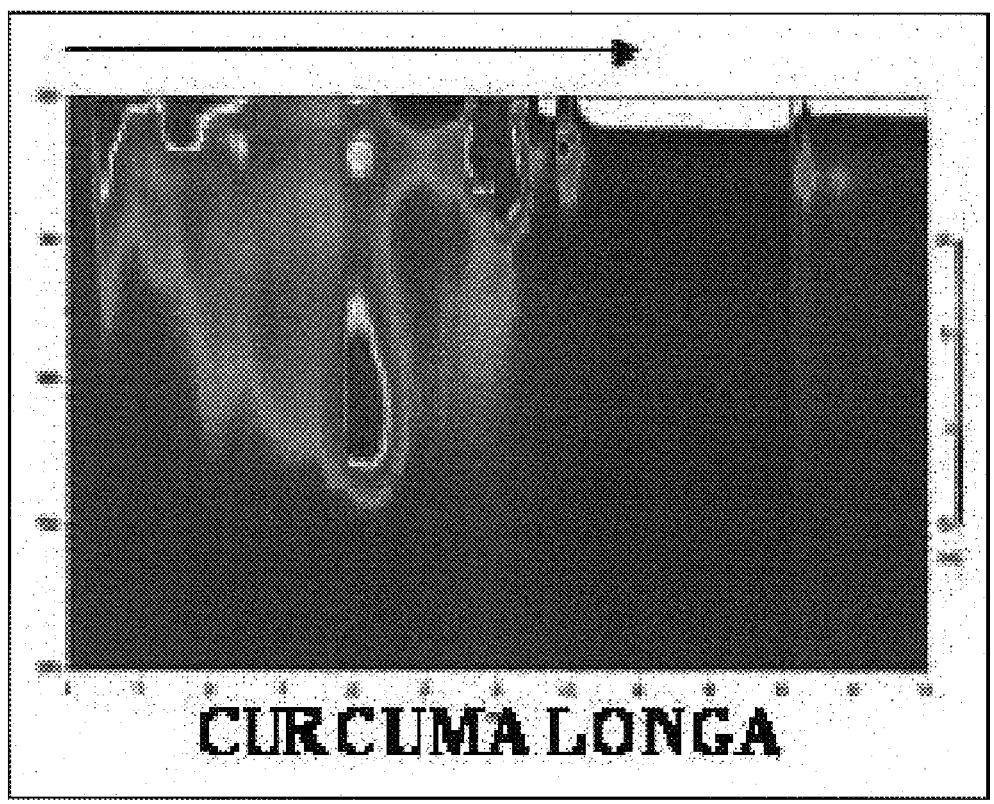
Figure 17C:
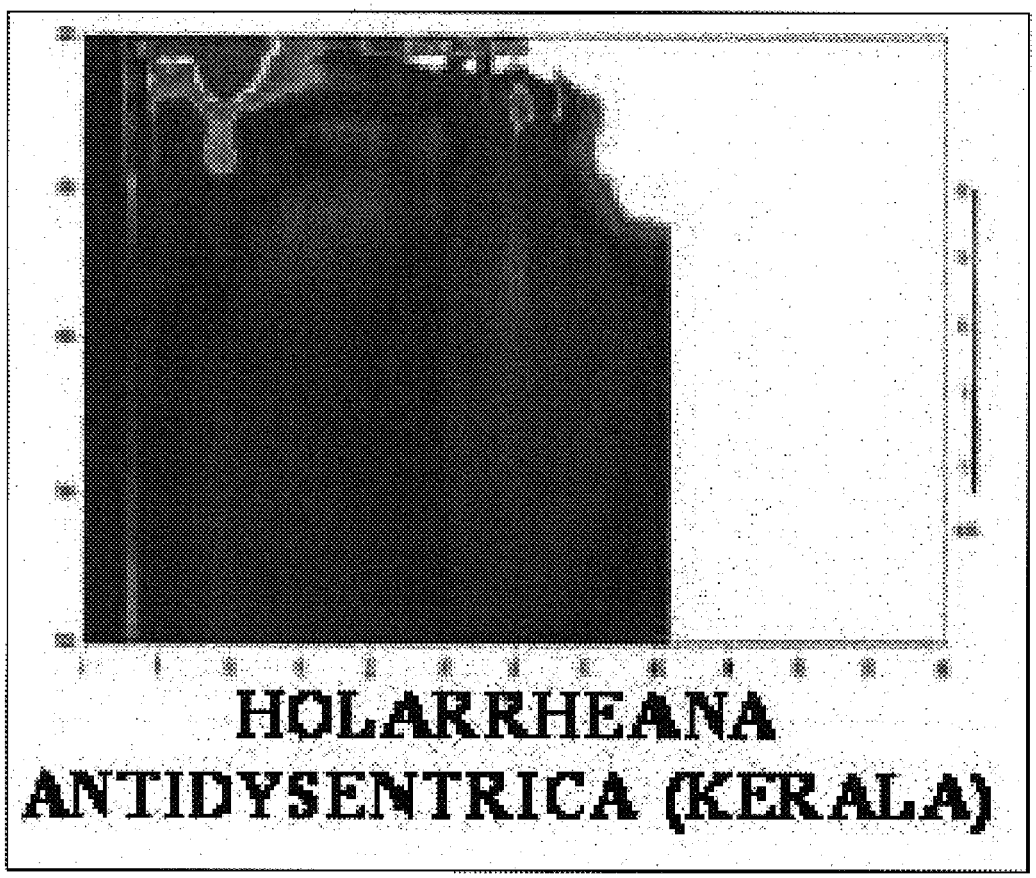
Figure 17D:
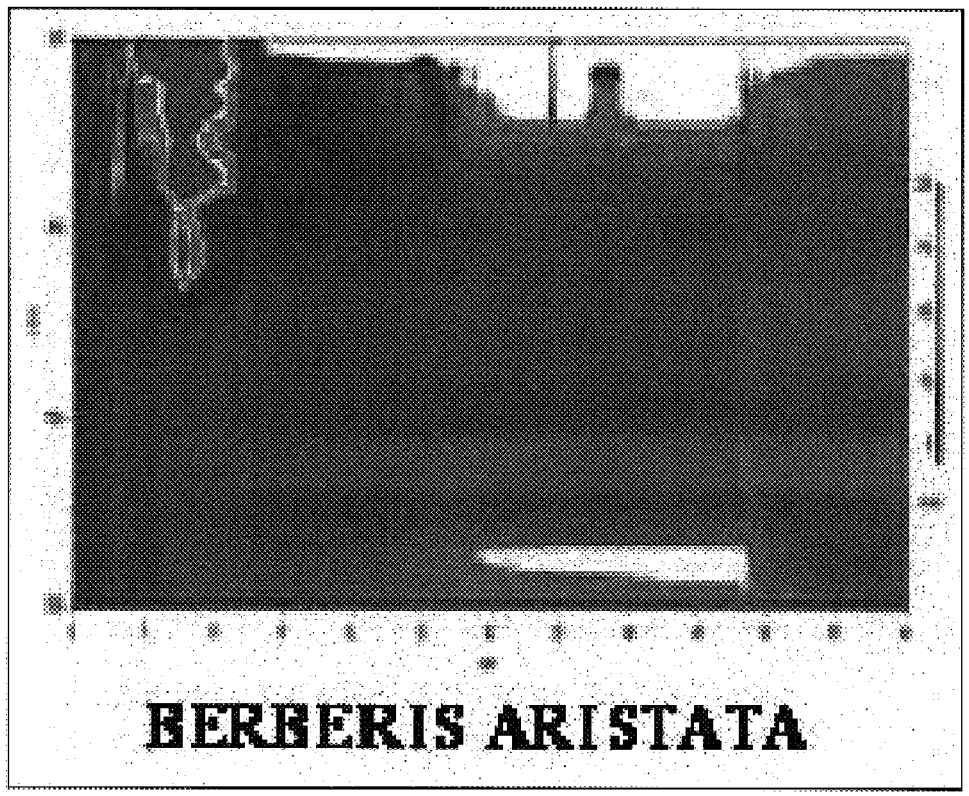
Figure 17E:
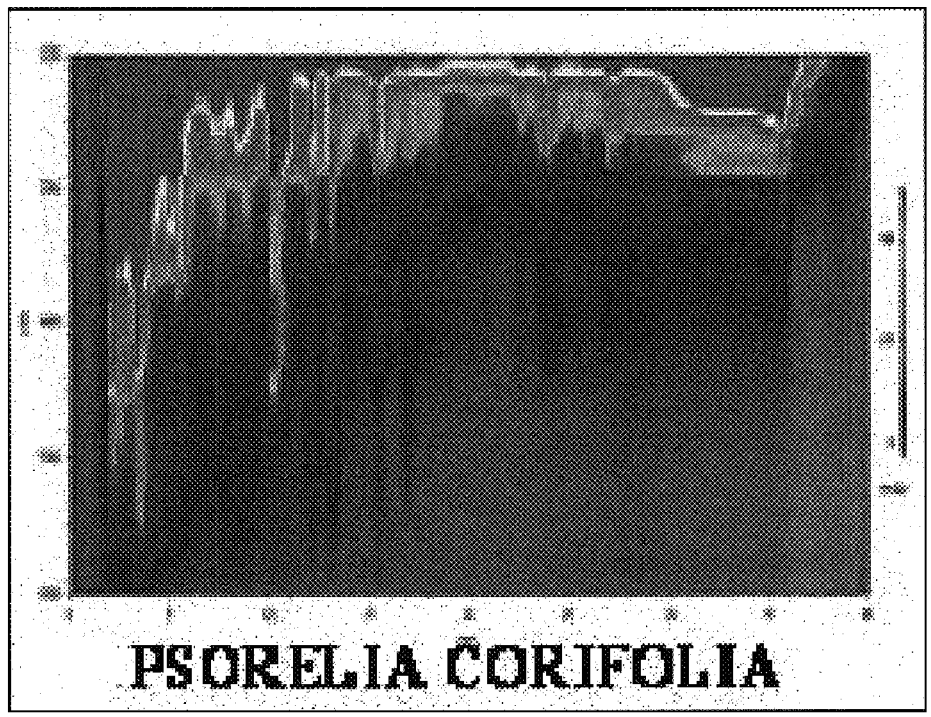
Figure 17F:
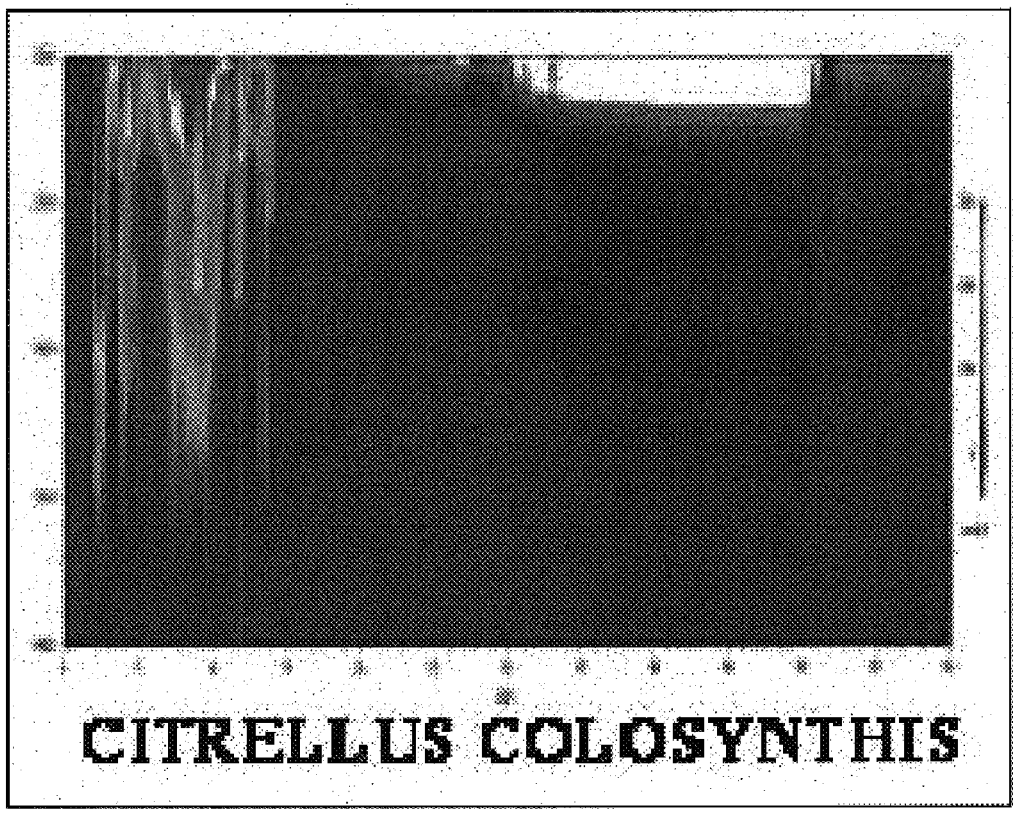
Figure 18A:
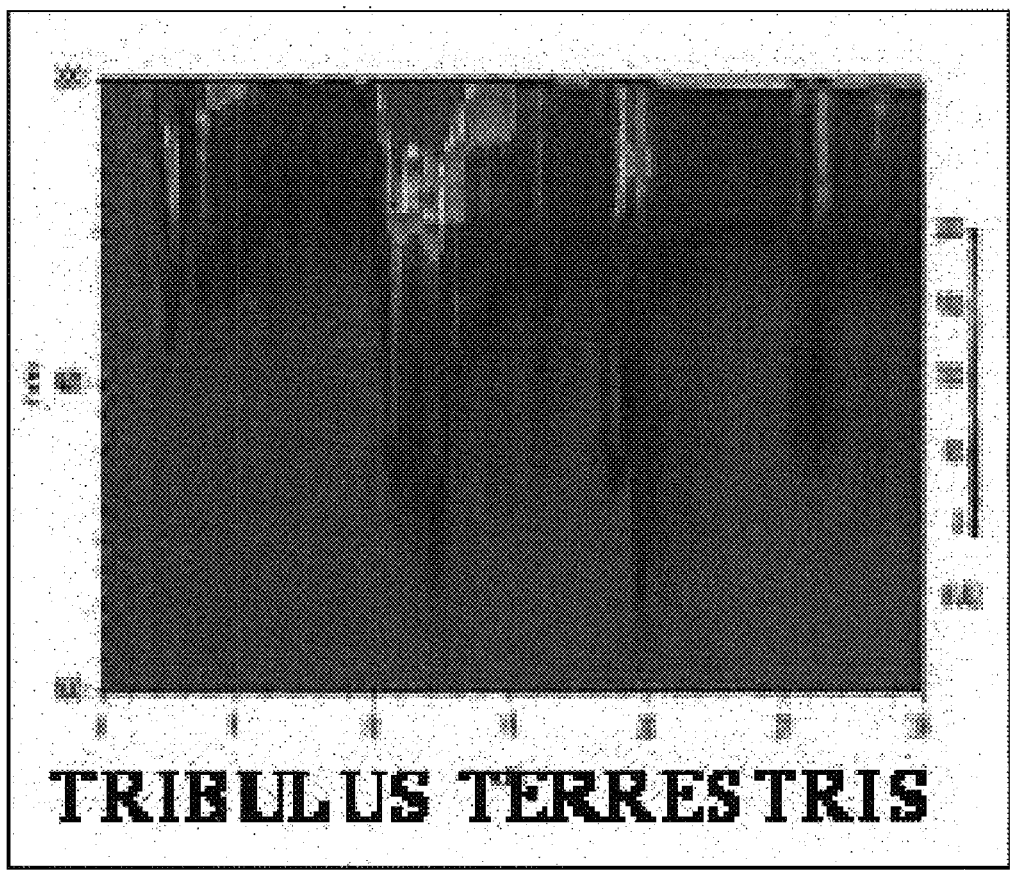
FIG. 18 (A through F) shows the fingerprints of all medicines of KAPHA VATA HARA in nature. The presence of constituents in zone-2 and zone-3 indicates the efficacy of the medicine.
Figure 18B:
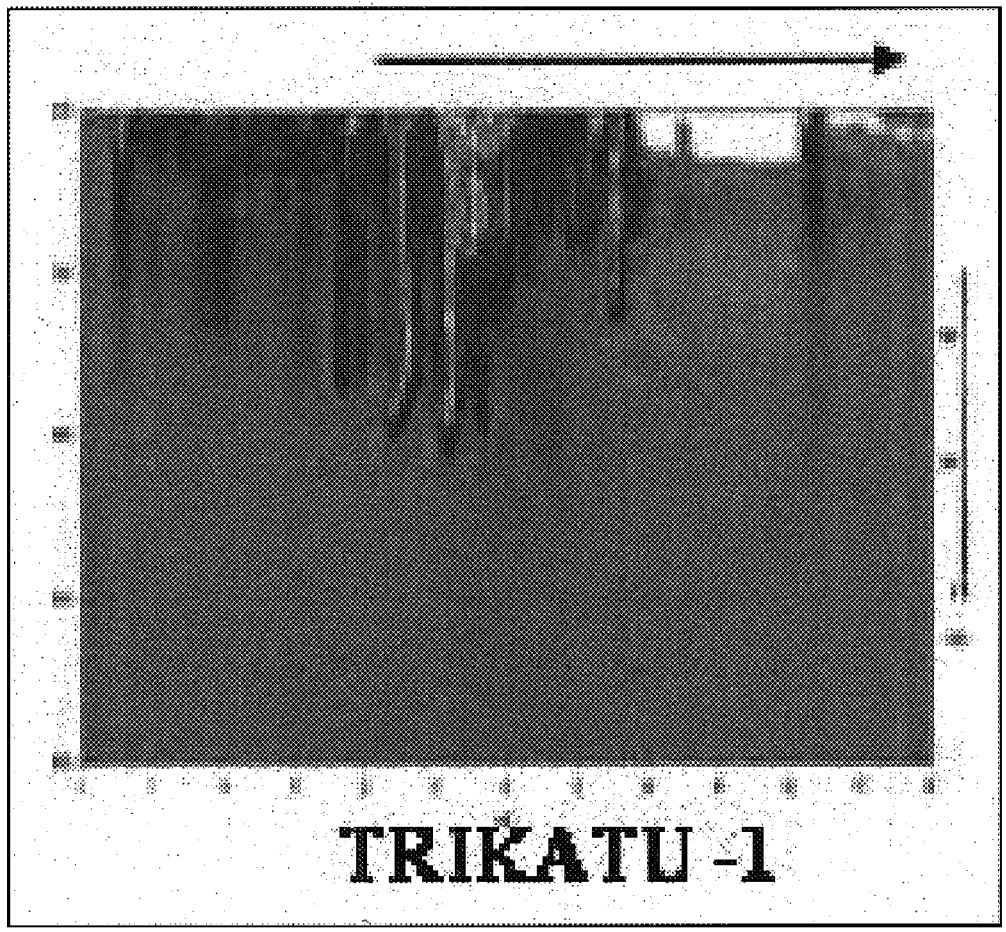
Figure 18C:
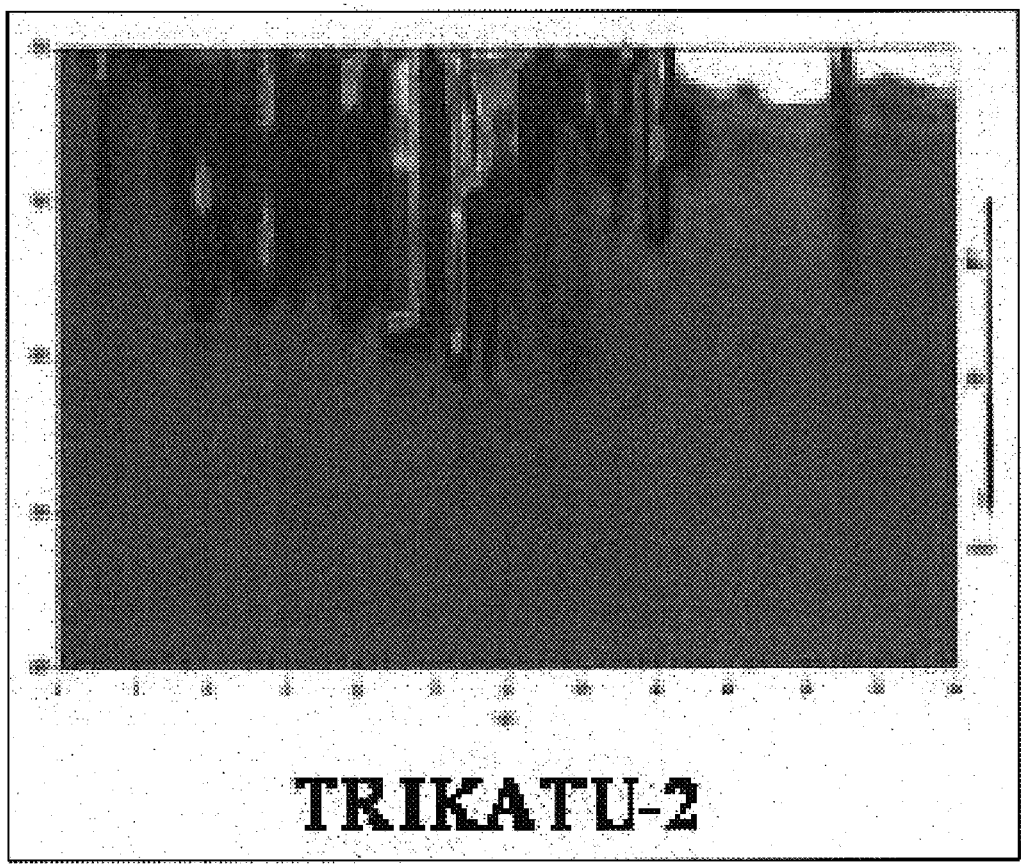
Figure 18D:
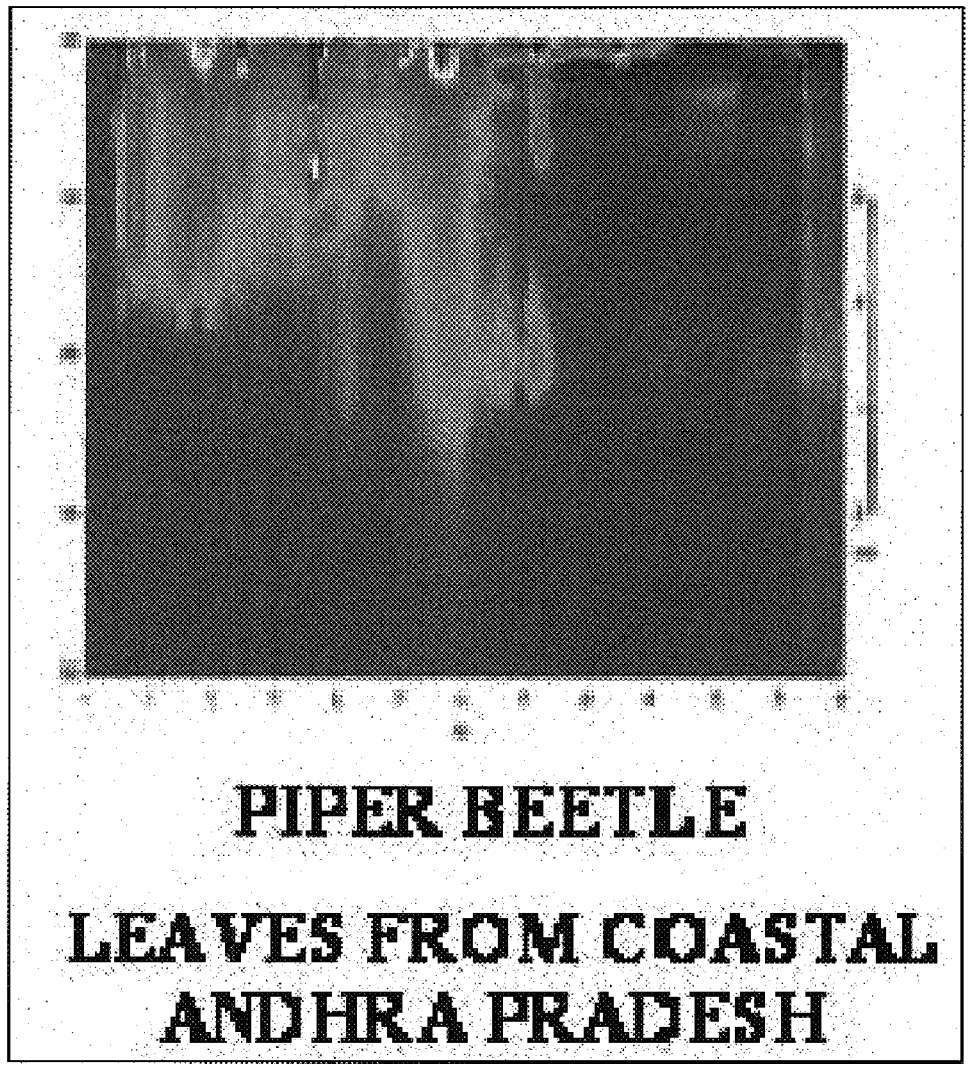
Figure 18E:
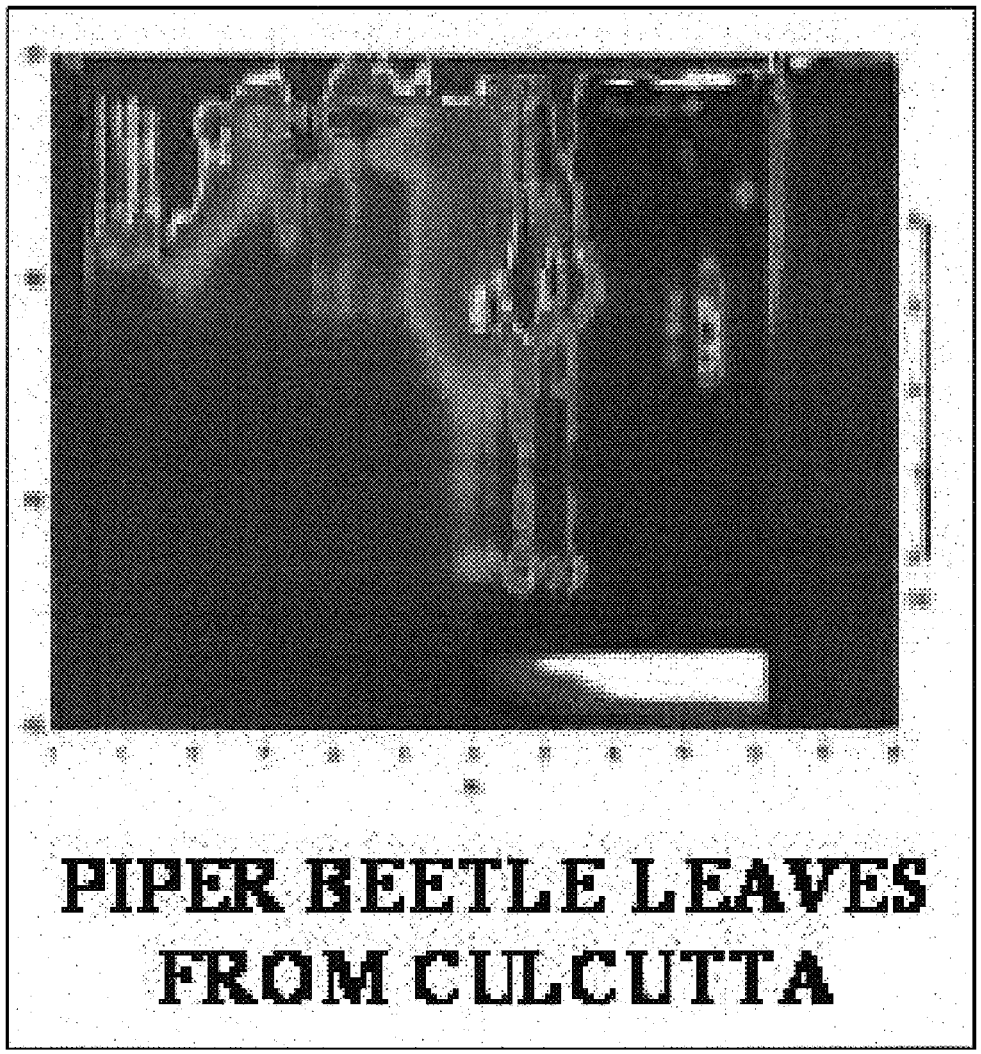
Figure 16F:
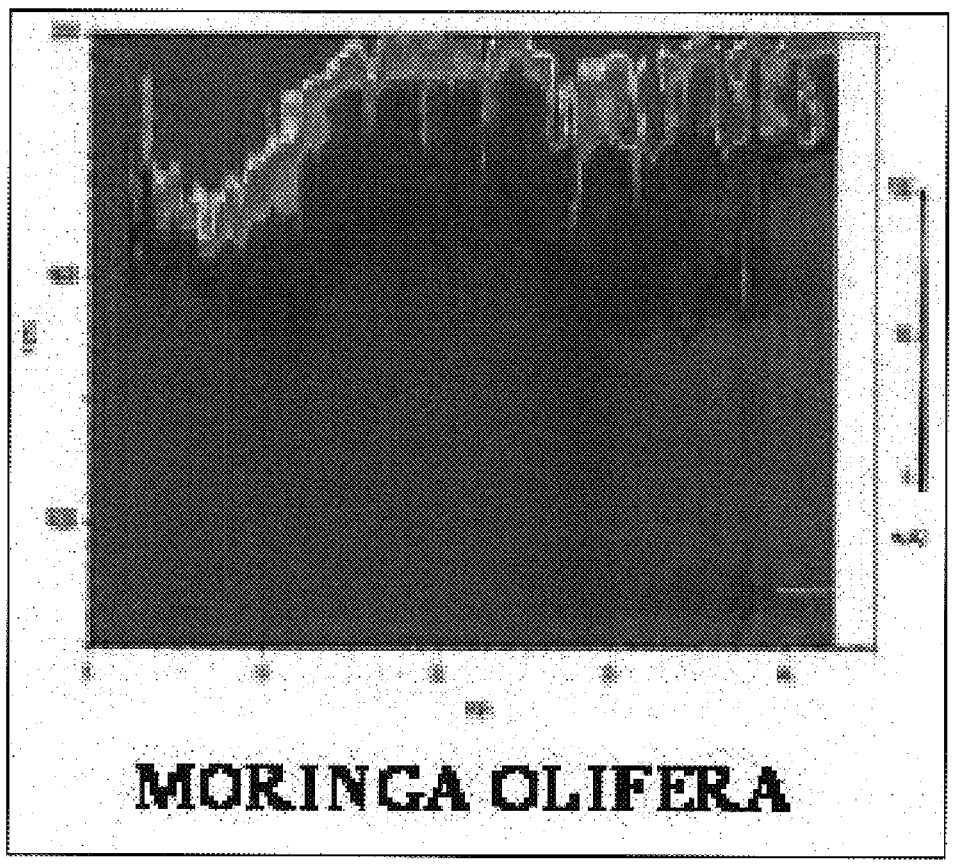
Figure 19A:
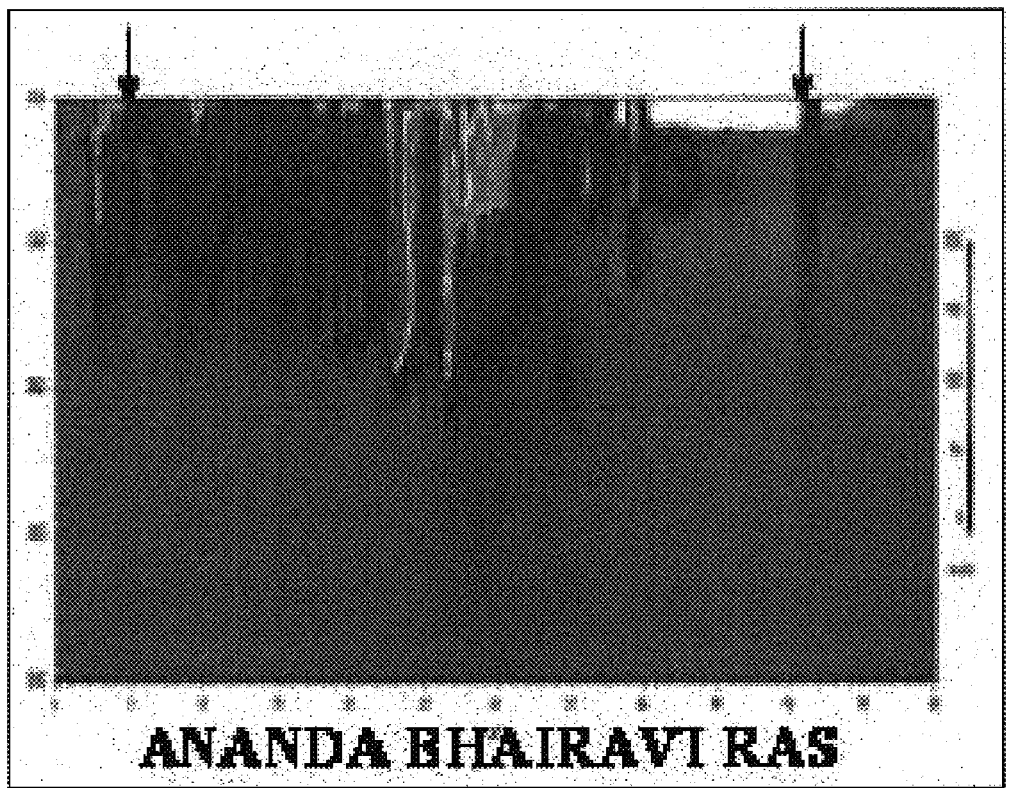
FIG. 19 (A through D) shows the fingerprints of all medicines of PITTA VATA HARA in nature. The presence of constituents in zone-1 and zone-3 indicates the efficacy of the medicine.
Figure 19B:
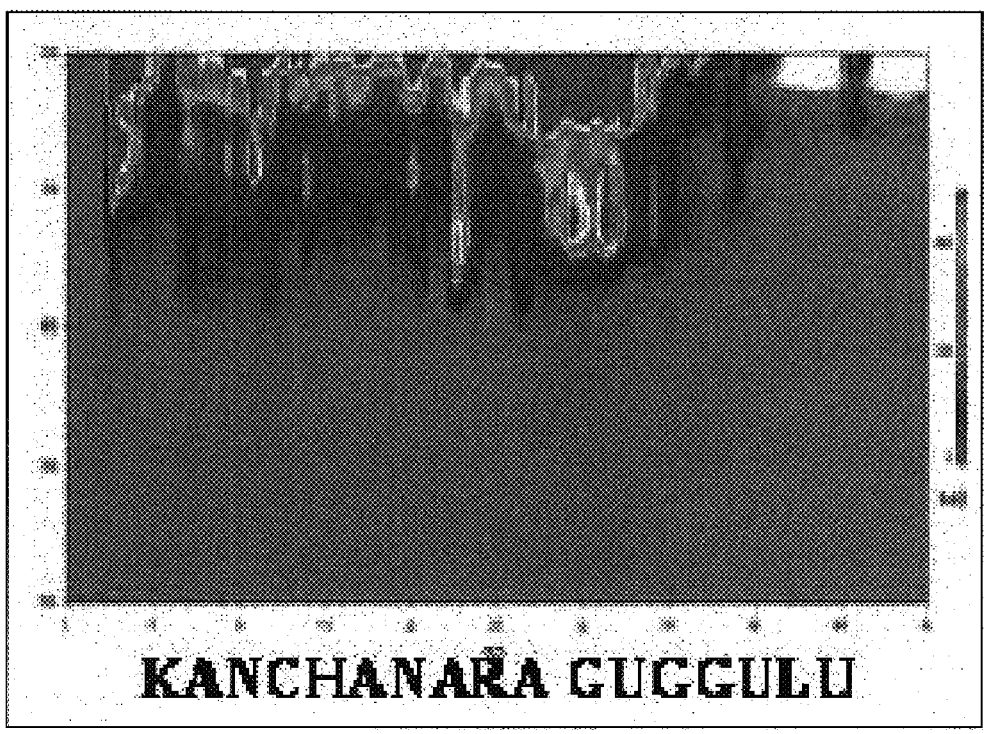
Figure 19C:
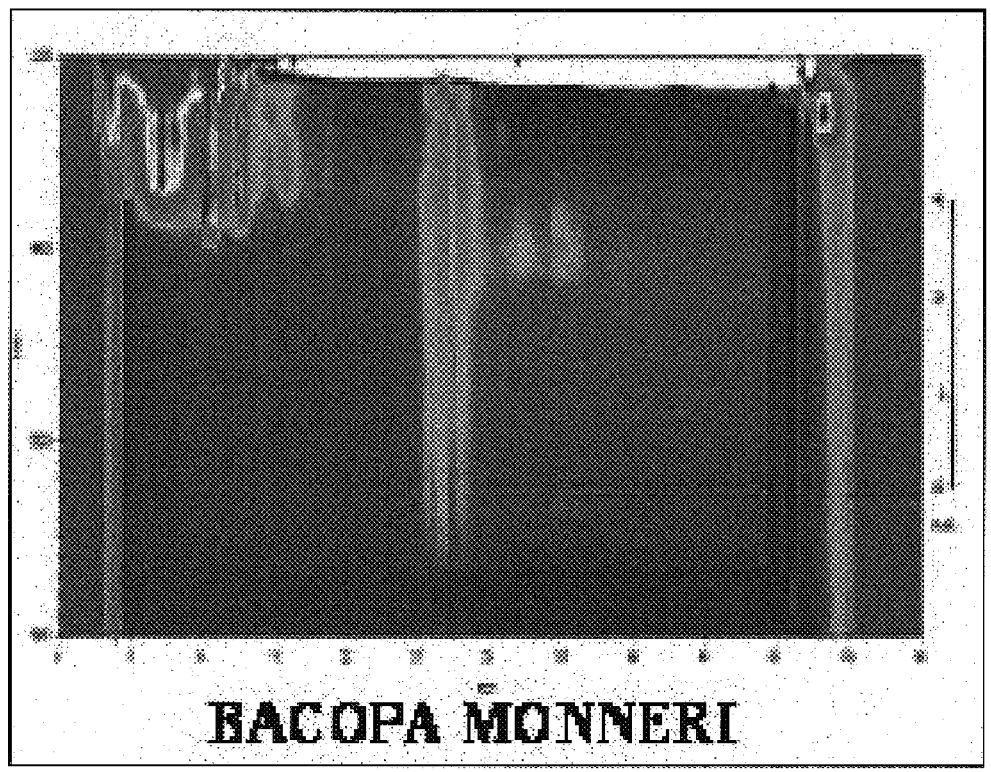
Figure 19D:
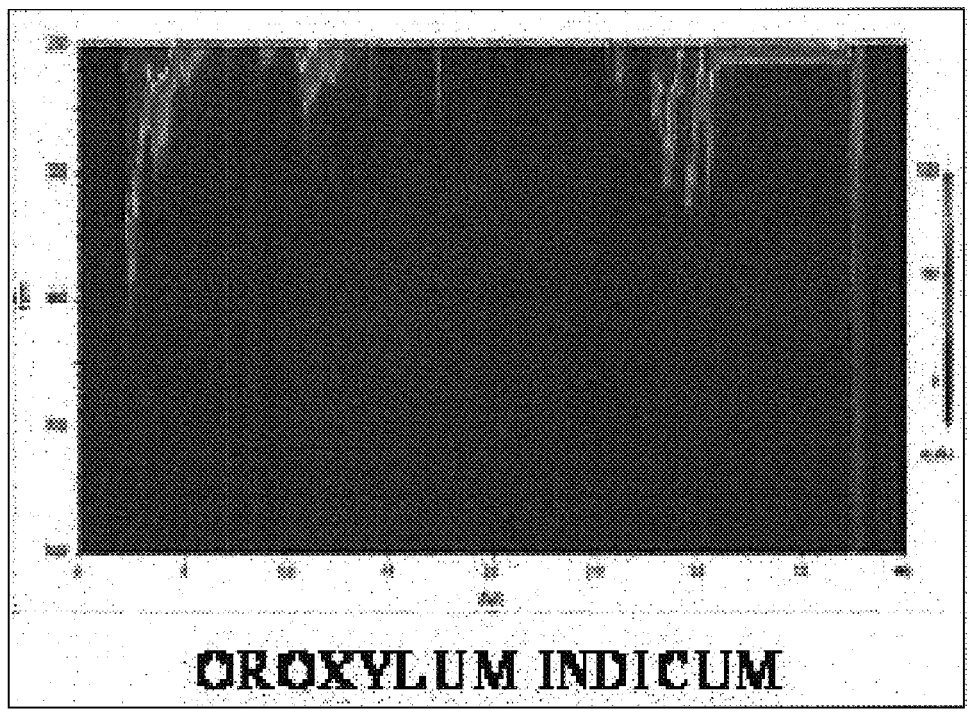
Figure 20A:
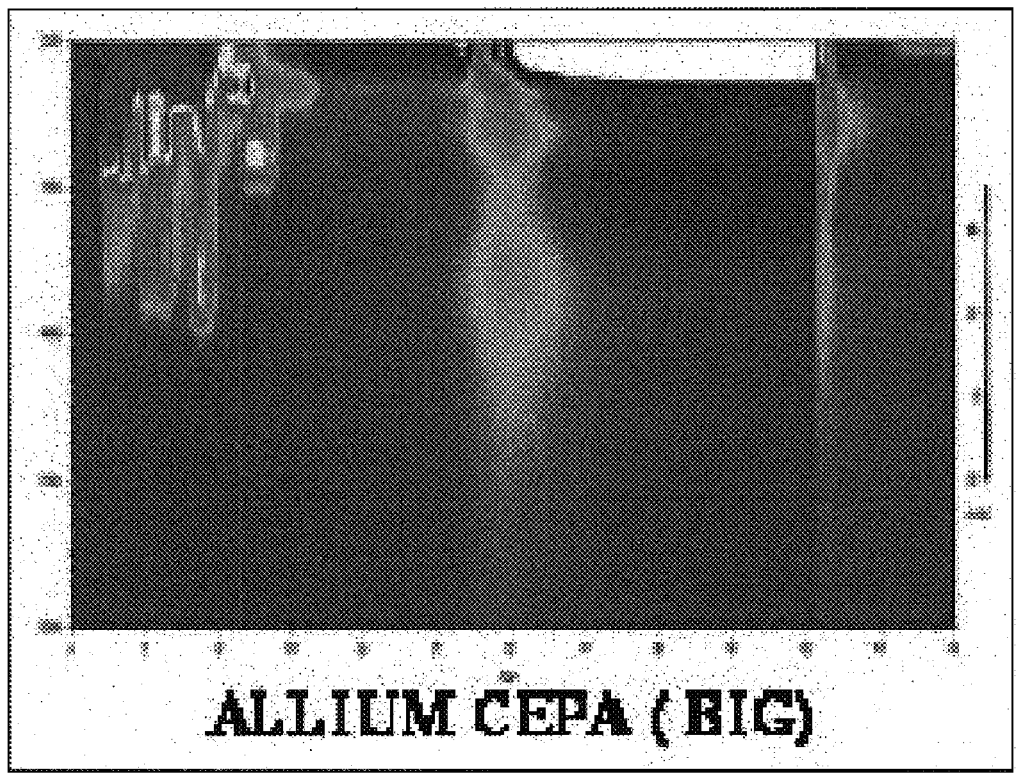
FIG. 20 (A through D) shows the fingerprints of all medicines of TRI DOSHA HARA in nature. The presence of constituents in all three zones indicates the efficacy of the medicine.
Figure 20B:
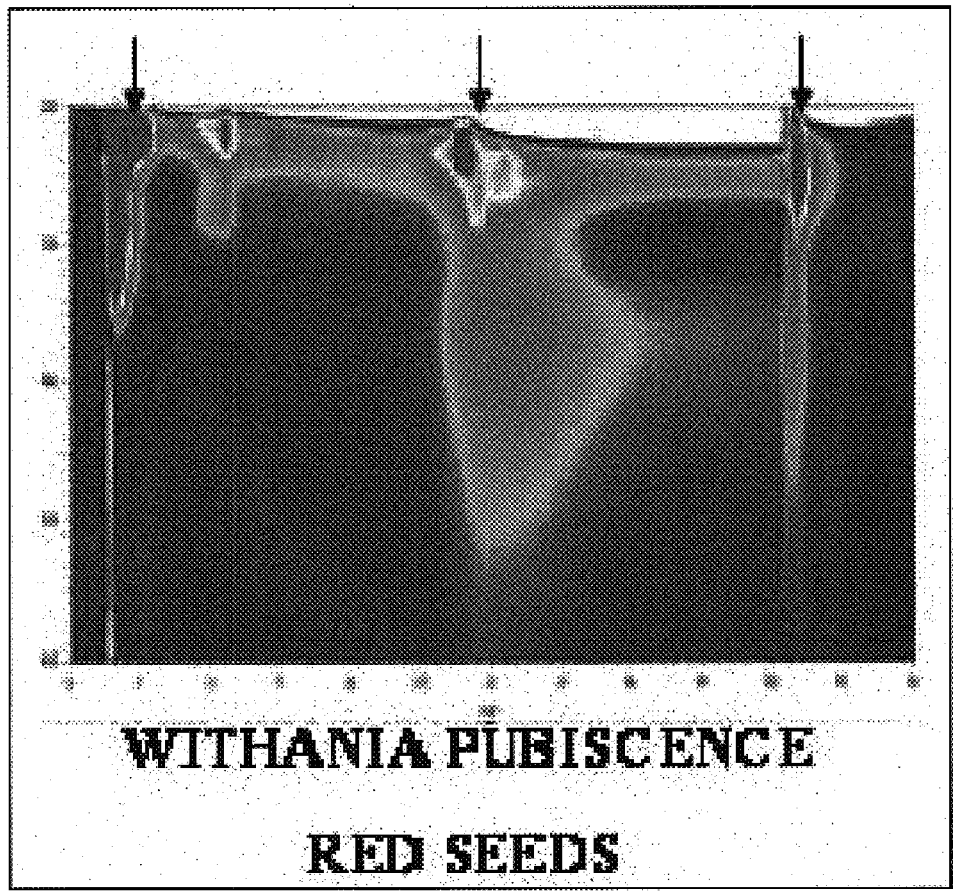
Figure 20C:
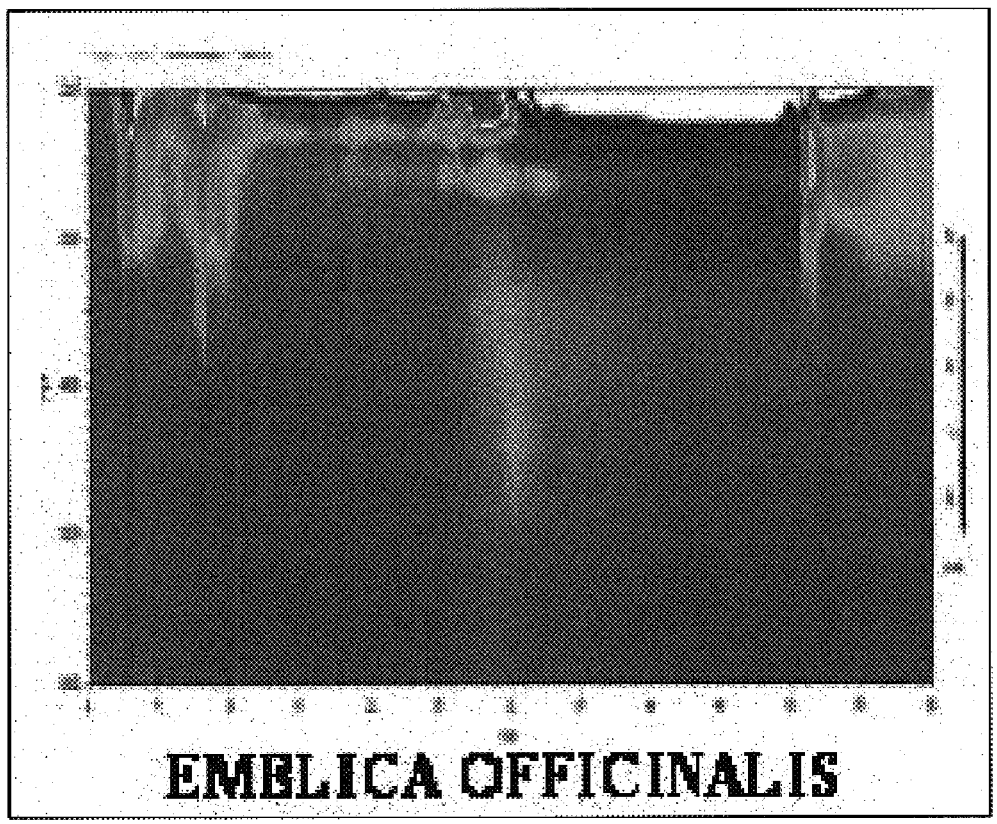
Figure 20D:
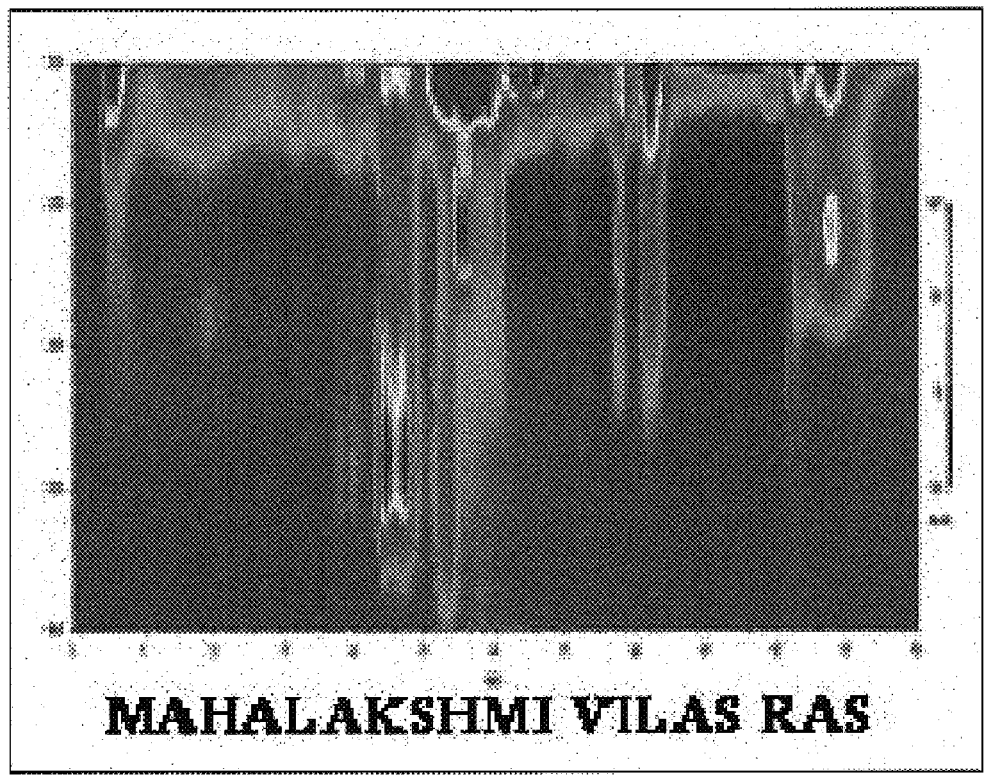
Figure 21A:
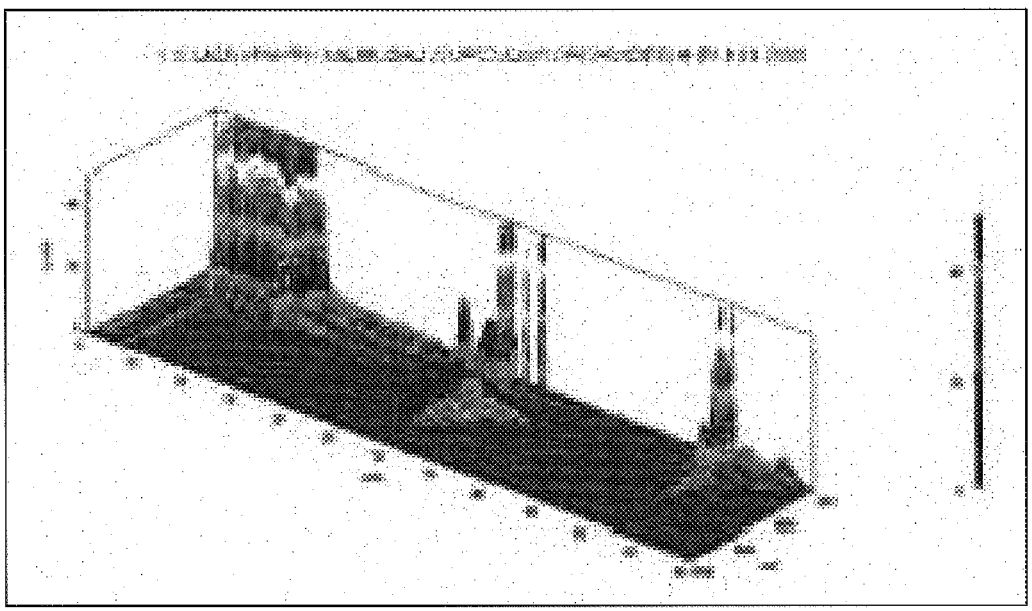
FIG. 21 (A through D) shows the fingerprints of Kali musali and Safed musali that are used as tri-doshahara medicine.
Figure 21B:
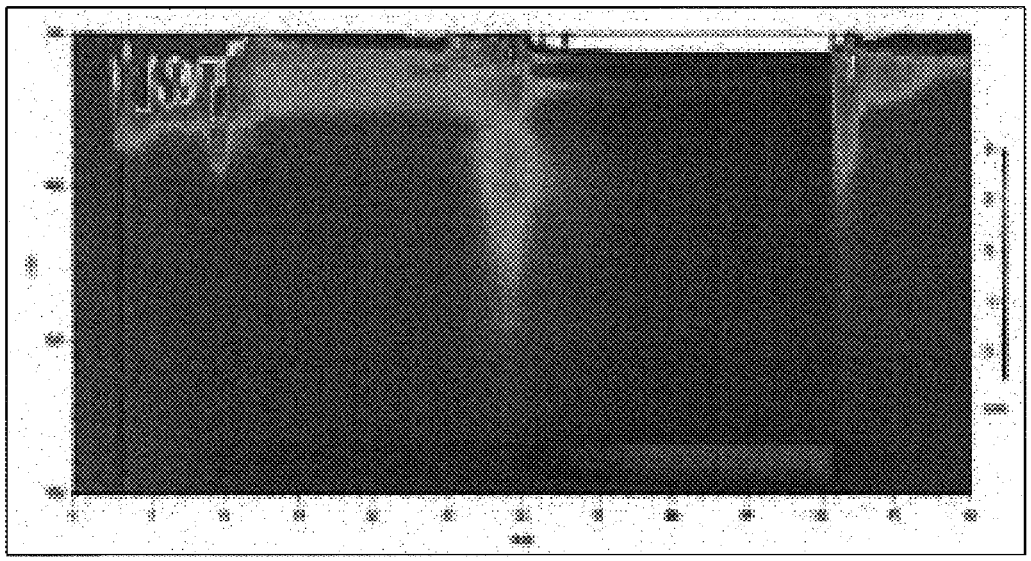
Figure 21C:
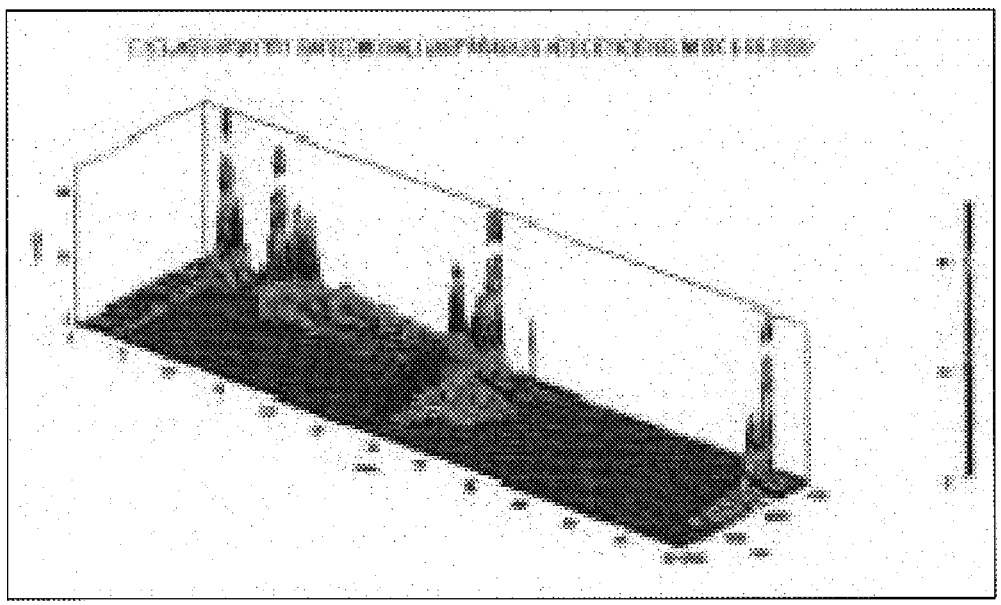
Figure 21B:
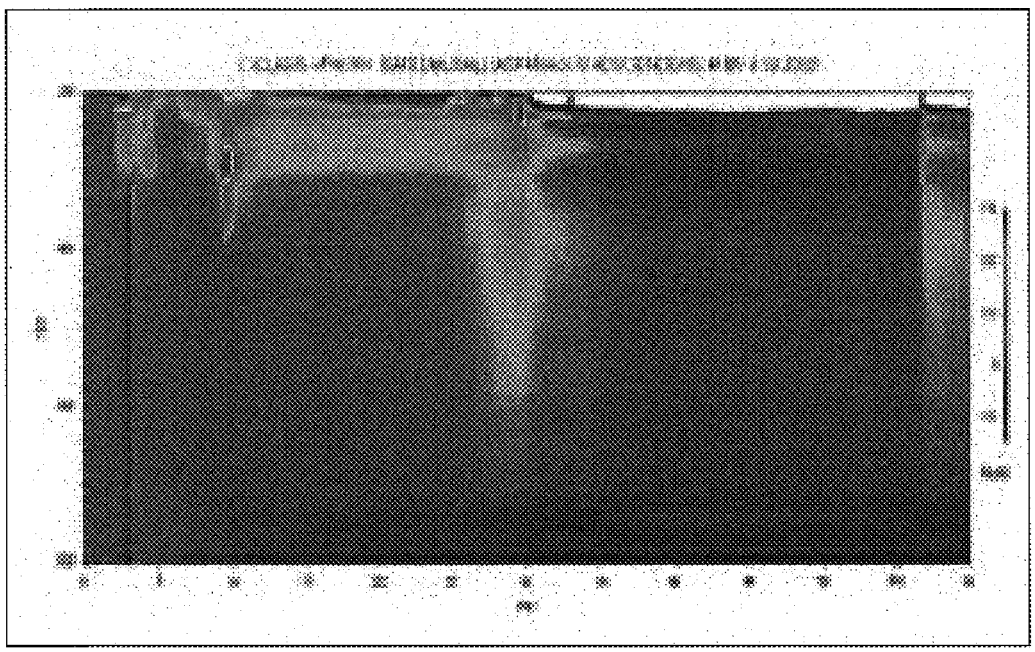

The existing method of TLC fingerprinting FIG. 4 being used as a chromatographic finger print, is showing only an assay of the constituents present in it. It is not providing any chemical property like conjugation or polarity. Another method of fingerprinting by HPLC shows a chromatogram at a single wavelength presented as a "Chromatographic Finger Print" of the medicine. In this, a selected peak is identified chemically, what it is by structure, using various other analytical techniques like NMR, LC-MS and IR for structural elucidation. So, the single chromatogram by it self is not able to say what the efficacy of the medicine is, without the support of other costlier analytical instruments. It will be highly impractical to use such costly techniques for a complex herbal medicine and formulations prepared by formulating various organic and inorganic medicines for a particular therapeutic purpose.

The quality of any formulated medicine will depend on the process with which it was made. This will be different for each pharmacy or pharmacist. What actually needed for the quality control of herbal medicines and formulations is a simple analytical method that can give the number of constituents (qualitative and quantitative) present in a single medicine or formulation, and the therapeutic efficacy of the medicine under study. Hence, any method, which does not provide the above information, is incomplete.

In the method of chemical standardization of the present invention, the constituents were first extracted in to a suitable solvent. The extract was subjected to separation into individual constituents on a High Pressure Liquid Chromatograph under standardized analytical conditions. The 3-D and contour chromatograms given by the instrument were converted in to chromatographic fingerprint images. The images were analyzed using image analysis software specially prepared for this work. The out put data is interpreted for the said standardization. Detailed description of the method is given in experimental description of the method.

Method of Therapeutic Standardization:

The traditional therapeutic standardization is highly individualistic by ability and perception of the doctor. A general availability of such method will be practically difficult. But the existing scientific scenario emphasizes that any method or mechanism needs to be standardized, and reproducible. Hence, in the present method of chemical and therapeutic standardization an instrumental method is proposed which brings down the human factor. This is made possible by an instrumental analytical technique, which explains about the chemical and therapeutic efficacy of the medicines under study in a simple way. In a most scientific and organized society of modern science, the knowledge of assessing the therapeutic efficacy of the medicines should be explained with rational justification rather than individual skills and abilities, as they will differ from individual to individual and are non-reproducible. The method of the invention envisages the same without deviating from the traditional concepts.

As explained above if one can assess the therapeutic efficacy of the medicine by the physico-chemical properties (Polarity and conjugation), the activity of the medicines is understood thus achieving the therapeutic standardization. In the present method, the conjugative and polarity properties are taken in to consideration to assess the therapeutic efficacy of a medicine.

In the ancient literature a clear classification of soils and plants were given based on their physico-chemical nature and therapeutic efficacy. The selection of medicines for a particular disease was done based on the guidelines like color, texture, odor and physical appearance. Table 8 of the effect of different colors on different body parts shows how color was used for this purpose. The soil types and the diversity of the drug action were also mentioned while selecting a medicine. The effect of climate and its effect in the efficacy on the drug plants were also clearly mentioned. Because the chemical constituents present in the plant depends on these geological and ecological variable factors, guide lines were laid down for the place of collection, time (seasonal and daily) of collection, part of plant for collection and age of plant for collection, required for a specific therapeutic action.

Based on the generalia of the plants used for a common type of diseases the plants were classified into 37 groups (Wealth of Susrutha, K.H.Krishnamurthy, Indian Institute of Ayurveda, Coimbatore, India-originally from Susruta Samhita sutrasthana 38). Thus, these plants should contain the chemical constituents having similar therapeutic efficacy on the reported disease.

When the fingerprints of the different classes were studied, some common features are found about the therapeutic efficacies of the medicines. The same efficacy was reported in the traditional literature also. In other words, i.e. the experimental and reported results are equal. Hence, studying different medicines, having different therapeutic efficacy validated the method.

The FIG. 13 shows all medicines, which are yellow in color. In the ancient literature of Ayurveda all these medicines were classified as Haridra class, all the medicines being yellow in color like Haridra (Turmeric). When the fingerprints are studied, it is found that all these medicines are reported to be used as Kapha Hara, vitiation of disorders related to mucogeneous constituents of the body. Hence, it is understood that the color of the medicines has a direct relation with their therapeutic efficacy. Rationally it is also true that the color and the efficacy of the medicines are due to chemical constituents and their physico-chemical properties.

The fingerprints of single medicines like *Rubia cordifolia, Saraca Indica, Picrorrhiza Kurro, Phyllanthus Niruri* and Formulations like *Arogya Vardhini* and *Avipattakara Churna* are presented in FIG. 14. The molecules eluted in Zone 1 indicates the presence of Polar constituents based on the elution pattern due the set analytical conditions. A general tendency of this elution pattern for the medicines reported to be Pitta Hara, confirms that high polar constituents act mainly as Pitta Hara.

The fingerprints of single medicines like *Zinziber officinalis* (Processed), *innula racimosa, Sausserea Lappa, Ocimum Sanctum, Glycerzia glabra* and Shilajit are reported to be Kapha Hara. The molecules eluted in Zone 2 indicate the presence of Medium Polar constituents. A general tendency of this elution pattern for the medicines reported to be Kapha Hara confirms that medium polar constituents act mainly as Kapha Hara as shown in FIG. 15.

The fingerprints of single medicines like *Alpinia offinarum, Ricinus communis,* and Formulations like *Suvarna yogaraja Guggulu, Brihatvata chintamani* with *swarnamakshkam, Huthasana* and *Mahayogaraja Guggulu* are presented in this Figure. The molecules eluted in Zone 3 indicate the presence of very low or non-polar constituents, mostly oily in nature, based on the elution pattern due the set analytical conditions. It is observed that any medicine used for this disorder contain or mixed with oils. Along with oily type of constituents, the herbo mineral organo metallic molecules eluting in this zone are also found Vata Hara. A general tendency of this elution pattern for the medicines reported to be Vata Hara, confirms that low or non-polar constituents act mainly as Vata Hara as shown in FIG. 16.

The fingerprints of single medicines like *Azadiracta indica, Curcuma longa, Hollarrheana Antidyssentrica, Berberis aristata, Psoralia Cordifolia* and *Citrullus Colosynthis* are presented in this Figure. The molecules eluted in Zone 1 and 2 indicate the presence of high polar and medium polar constituents. Thus, these medicines having the medium polar constituents are found to be Pitta-Kapha Hara. This confirms that the efficacies of the medicines are under stood by the polarity of the constituents present in it as shown in FIG. 17.

The finger prints of the single medicines like *Tribulus Terrestrius, Moringa Olifera, Piper Beetle* and formulations like Trikatu indicate the presence of constituents in the Zone 2 and Zone 3 indicating the efficacy as Kapha Vata Hara in nature, FIG. 18 explain the same.

The fingerprints of the single medicines like *Bacopa monneri, Oroxylum Indicum* and formulations like *Kanchanara Guggulu* indicate the presence of constituents in the Zone 1 and Zone 3 indicating the efficacy as Pitta Vata Hara in nature. In a formulation called *Anadabhairavi*, even though the efficacy reported is Pitta Vata Hara it is found Kapha Vata Hara by finger printing. This indicates the artificial preparation of the medicine was not successful to prepare a medicine of the required efficacy. Hence, this method is useful in the process standardization of the preparation of complicated formulations mentioned above. FIG. 19 indicate the same.

The finger prints of the single medicines like *Allium Cepa, Withinia Pubiscence* (Red Seeds), *Embalika Officinalis* and formulation like *Mahalakshmi vilas ras* indicate the presence of constituents in all the three Zones of 1,2 and 3 indicating the presence of molecules of the entire range of polarity. This indicates that they will be of Tri Dosha Hara by efficacy. In the finger print of *Mahalakshmi vilas ras* the presence of two similar type of molecules can be seen like isomeric in nature. The Prabhava effect is understood in these type of medicines when such type of isomeric (Geometrical and Chiral) constituents are present. FIG. 20 shows the fingerprints of all medicines of Tri Dosha Hara.

The fingerprints of *Kalimusali* (*Curculigo Orchioidis*) and *Safedmusali* (*Asparagus Adescendens*) indicate how two plants of different family's were classified under same therapeutic group. The fingerprints show similar constituents in all the three zones with little difference in assay indicating the tri-doshahara property, as indicated in FIG. 21.

With reference to FIG. 22, the fingerprints of a single medicine of two different sources like *Citrullus Colosynthis* used in both Ayurveda and Homoeo are given. The fingerprints contain constituents of three polarities, but mostly high polar molecules are greater in number. On careful observation of the fingerprints, it is observed that the presence and absence of molecules at 12 minutes is the only difference between both the images. The taste of the first medicine was very bitter (the medicine identified as being good by efficacy) when compared to the second one (the medicine identified as being poor by efficacy). Thus using the taste as a measure of the efficacy of the medicines is also proposed, this was mostly used in the ancient literature, as shown in FIG. 22.

The fingerprints of *Hollarrena Antidysentrica*, a medicine collected from two different parts of the country has shown much difference in their chemical profile. This indicates the influence of geological, ecological, genotype and phenotypic and other variable factors on the chemical constituents of the herbal medicines; this is illustrated by FIG. 23.

A vast difference was seen in two samples of beetle leaves one from Andhra Pradesh and another from Calcutta of India FIG. 24. This confirms the role of ecological, genotypic and phenotypic variations in the chemical constituents of plant parts.

In the FIG. 25 the Eco-regions, precipitation, Temperature and Climate of India were shown to understand the role of seasons on the ecology of the flora and fauna of it. The variations in the seasons will have an impact on the chemical constituents of the herbal plants and thereby medicines produced from them. This applies to the entire world whenever an herbal plant is collected from different parts of the world.

Referring to FIG. 26, the fingerprints of two formulations used as cosmetics like Herbal head Bath powders are given. As illustrated, the fingerprint of the pure herbal material is totally different from the adulterated one. The artificial detergents and foaming agents eluted at 25 to 40 minutes are clearly seen in the adulterated sample, these components being highly basic and soapy in nature. This supports that the method of the invention is useful for the regulatory authorities to monitor various commercial herbal products and thus check the pilferage of traditional medicines with adulterations and substitutions, as illustrated in FIG. 26.

The fingerprints of a formulation namely Trikatu of two different brands shows difference in its assay. This may be due to usage of single medicine(s) were used to prepare the formulations from different sources. The present method shows the extent they are different qualitatively and quantitatively, facilitating to prepare standardized medicines and extracts of herbal medicines as shown in FIG. 27.

The fingerprints of a single medicine of three different brands of the same food material like turmeric is given in FIG. 28. In the finger print of the natural turmeric it is observed that the yellow curcumin molecules eluted at 20 minutes. The same molecules are seen in all the brands commonly. The difference in the profile is the commercial samples are because they were prepared processed (Boiled) turmeric rhizomes and the natural is from unprocessed (Un-boiled) rhizomes.

FIGS. 29 to 92 gives the fingerprints developed for various medicines and the image parameters (Elevation and rotation) used for the 3-D and Contour chromatograms of all the medicines given in table 13. In table no 14, the medicines analyzed were classified on the basis of therapeutic efficacy. The analysis of fingerprints of the respective medicines using the proposed software will support the claim of utility of the method of the invention for the therapeutic standardization.

This confirms that this method is useful in many purposes of dealing the traditional medicines. It is useful for modern medicines also to understand their therapeutic efficacy in traditional terms.

Method of Bar Coding, Enterprise Resource Planning (ERP) and Customer Relationship Management Application (CRM) Application In the present method the software analyzes the image and can display the coordinates X retention time, Y wavelength, R number of red pixels, G number of green pixels and B number of blue pixels by the present computer based (Microchip, Dongle switch, hardware and software locked) software for a contour chromatogram, for a particular peak which is specific to the product. When this data is transferred/feed to a resident in built re-salable bar-coding software, automatically an optional pixel value of a peak in the image, it generates the barcode having attached the 'display window' with all details of the product under study.

The method of the invention facilitates to barcode any number of constituents present in a chromatographic finger print of a herbal medicine, using the X retention time, Y wavelength, R number of red pixels, G number of green pixels and B number of blue pixels as the coordinates provided by the present computer based (Microchip, Dongle switch, hardware and software locked) software and the values of each of the constituents provided by the present software. These factors will be representing the chemical and therapeutic efficacies of the constituents. Hence instead of a mere catalogue-number presently used for the bar coding, a novel method of bar coding is proposed where in, the coordinate values of the constituent will be displayed along with other details. Thus, the barcode and the coordinates-will speak about the chemical and therapeutic properties of the product.

It becomes a tool for the regulatory authorities like Drug Controller, Public analysts, Food adulteration enforcement authorities, Forensic and Customs and Central excise departments for the regulation of the herbal Products. The fingerprint of the medicines should be printed on the label and should be tallied when it is checked. This also helps to monitor the various other brands of a same medicine for an industry to monitor. FIGS. 93–94 shows how the software gives the coordinates for a selected peak of the image. These values will be given for a barcode to be generated. FIGS. 95,96 are the barcodes thus generated. FIGS. 97,98 show how a display window will be for an herbal medicine with all label details. The barcode will be able to show when the display windows when they are attached to the barcodes of the respective products. When a large database is prepared for the products and made available in the network, any ERP and CRM application can use for any required purpose by network. FIG. 99 shows how the network woks in an ERP and CRM applications networked.

Various Steps Involved in the Present Invention

In the present method of analysis a Validated High Pressure Liquid Chromatograph equipped with a Binary Gradient system of pumps, a Photo Diode Array Detector (PDA), and a Software based data processor for presentation of the chromatograms was used. After the complete elution of all ingredients, the 3D and contour chromatograms (having the information of the UV—Visible Spectra, absorbance and retention times of all the constituents present in a single medicine or formulation) were converted into an image and proposed as a finger print. This enjoys the merit of not requiring any internal or external standard sample for an authentic qualitative and quantitative analysis of all the ingredients present in a medicine, unlike in the present method of analysis of medicines.

Experimental Description of the Method:

The proposed method is described in 4 steps with reference to the accompanying drawings, flow charts and examples, which are provided to illustrate some of the embodiments of the invention, and the same should not be construed as limitations on the inventive concept embodied herein.

The entire method is described in the steps mentioned below:

Step 1: Selection of medicines and extraction of the constituents

Step 2: Separation of the constituents into individual constituents and generating and converting the 3-D and Contour Chromatograms in to finger prints.

Step 3: Analysis of the fingerprints using the software developed.

Step 4: Interpretation of data

Description of the Present Method of Analysis

Step 1: Sample Preparation

Constituents are extracted from the medicines using ethyl alcohol, selected based on the chemical nature (polarity) of the sample. When the pH of the aqueous alcohol extract is varied, the extraction of constituents also has varied. The basic pH has extracted more number of constituents than acidic pH. Suitable pH was selected for extraction of different medicines and the same was maintained using buffers. The role of acidity and alkalinity was taken into consideration while selecting the pH for extraction.

Step 2

Experimental Work Done on the Instrument:

The extract was subjected to separation analysis, using High-Pressure Liquid Chromatographic (HPLC) instrument. In the present method of analysis, a Validated High Pressure Liquid Chromatograph equipped with a Binary Gradient system of pumps, a Photo Diode Array Detector (PDA), and a Software based data processor, for the preparation of the chromatograms were used. A known amount of the sample (say 20 ul) of extract is injected into rheodyne injector (fitted with 20 ul loop). Elution of the sample was performed with suitable time programmed gradient system of mobile phase at a fixed flow (1 ml/min). Care is taken that no part of the sample is left in the column un-eluted. The following analytical conditions set for the analysis.

a. A reverse phase column was used along with a time programmed gradient elution of an aqueous phosphate buffer (In the pH range of 5.5–7.5) and a non-aqueous solvent (acetonitrile or methanol) is used as eluent based on the chemical nature of the sample under analysis.

b. A wave length range of 200 to 800 nm was used for the PDA detector and the run time is fixed based on the time program.

c. The time program, which changes the concentration of non-aqueous solvent like Acetonitrile 0–100% of organic solvent, is used in the instrumental parameters existing in the instrument.

The instrument was triggered for the analysis after injecting the sample into the injector. The run was stopped whenever the analysis is completed or the instrument will stop the run automatically after the entire time program is completed.

In the three types of display of data, the chromatograms, one window displays chromatogram at a selected wavelength, in another it displays the contour chromatogram which displayed the retention time (run time) of the analysis on X-axis and the wavelength range on Y-axis. In another window, it displayed the 3-D chromatogram of the sample where in it displayed the retention time (run time) of the analysis on X-axis, the concentration range on Y-axis and the wavelength range on Z-axis. The 3-D and contour chromatogram thus developed by the system was converted into an image.

The images thus generated were analyzed by the proposed software, which provides a novel chromatogram and the qualitative and quantitative analytical data of the in-gradients present in the medicines. The pixel values represented by different colors from Violet, Indigo, Blue, Green, Yellow, Orange and Red attributed as a measure of the concentration (quantitative) of the constituents proportional to the color. Extracting the individual colors mentioned above and shows in separate widows for each color. This is the basis of chemical standardization. Some chromatograms thus generated are shown in FIGS. 100–102.

The chromatogram thus provided by the software gives the information of conjugative (shown by the UV-VIS absorbance) and polarity properties of the individual constituents together. The image is divided into three zones representing, Zone 1 (High polar zone), Zone 2 (medium polar zone) and Zone 3 (low or non polar zone) scaled by retention times based on the elution pattern, depending on the column used and the mobile phase. Reversing the analytical conditions can reverse the elution pattern.

The 3-D chromatograms of the medicine are analyzed using all its three dimensional properties of the said image. If the 3-D chromatogram is considered as a cap with a hood the matching of the entire cap 3 dimensionally, with another sample of different qualitative and quantitative properties, the extent it matched will be presented as an analytical report qualitatively and quantitatively. Here the hood of the cap is compared to the peak of the molecule at a particular wavelength. A sample with more number looks like a cap with many hoods. Thus the matching of the three dimensional coordinates provides a foolproof method of comparison and analysis. The coordinate it matched gives qualitative and the extent it matched gives the quantitative data of the sample understudy. This is made possible by special software prepared for this purpose. This becomes an ultimate method of quality control.

The interaction of the polarity of the molecules being separated, the polarity of the stationary phase used and the polarity of the mobile phase used for the elution of the sample controls the elution pattern of the molecules. The resultant inter action of all the three and other related parameters like temperature etc., decides the elution pattern and order of elution of the constituents based on their polarity. Thus, in a medicine all the polar molecules will elute in first 'Zone 1' (Polar zone of the image), all the medium polar molecules will elute in 'Zone 2' (Medium polar zone of the image) and all the low polar or non polar molecules will elute in 'Zone 3' (Non polar zone of the image). When the molecules eluted in these three zones of many fingerprints, many generalizations were made regarding the chemical and therapeutic efficacy of the medicines. This is another basis of therapeutic standardization. The zones are shown marked in the FIGS. 103–105.

Thus, the chromatogram gives the information, how it is going to act chemically and so therapeutically. When the individual constituents present in each zone and represented graphically or by any means of data presentation, the total constituents of the respective zone gives the percentage it is going to act on the particular dosha. Thus, the data explains how it (medicine) is going to act therapeutically on the vitiation of each dosha collectively based on the qualitative and quantitative properties of the constituents present in the medicine. For example if the medicines has 30% constituents in high polar zone (the pixel quantities of various colors like green, yellow, orange and red of a specific zone as quantities) 70% in medium polar zone it can be represented as a medicine acts 30% on pitta and 70% on kapha, as the colors represent different concentrations in the fingerprints. Hence a medicine can be assessed as of Pitta-Kapha Hara (30–70%). Thus, the vitiation of doshas is quantified. This helps the doctor to under stand the efficacy of the medicines and decide his dosage. Some example Pie diagrams are given in the FIGS. 106–108.

3-D and contour Spectra of the reported herbal medicines were developed using the reported analytical conditions. The thumb nail view of the medicines shows how the finger prints can be handled by a software as it is done in the software used in handling the human fingerprints. All the features like searching the similar and compare the similar fingerprints etc., can be done by inserting the necessary software features. In FIGS. 109–114 the thumbnails of the fingerprints for various medicines are given. The lists of medicines shown as fingerprints were shown in table 15.

Step 3

Analysis of the Image Using Image Analysis Software:

After the complete elution of all ingredients, the 3D and contour chromatograms were converted into images and proposed as fingerprints. This enjoys the merit of not requiring any internal or external standard sample for an authentic qualitative and quantitative analysis of all the ingredients present in a herbal medicine, unlike in the analysis of a synthetic medicines.

After developing the image of the 3-D and contour chromatograms of the medicine under study, (Hence forth called as Chromatographic finger print) it is analyzed by the soft ware proposed for the analysis of various colors representing the Qualitative and Quantitative properties of the constituents present in it.

Scientifically, an image cannot become an analytical data, hence a computer based image analysis software (software and hard ware protected) has been developed to analyze the image and give proportional concentrations of the ingredients of the medicine under study. Based on the colors of the constituents present in various retention times and pixel values of the image.

Now the images of the fingerprints were given to Image Analysis software as said above. The analysis of various colors was done by which the constituents will be represented as peaks of the chromatogram and thus providing a novel presentation of chromatogram in the form of a colored bar chart. It shows the number of compounds and their conjugative properties UV-VIS absorptive property of all of the constituents eluted. The detailed description of the process involved in the analysis of the image is discussed in the technical features of the software.

The bar chart type of chromatogram thus developed gives a chromatogram having a scale of Retention time (0–60) on the X-axis and wavelength in the range of 200–800 nm, on the Y-axis. It gives the number of pixels occupied by each of the colors of each in-gradient in the image, facilitating the qualitative and quantitative analysis of the individual constituents present in it. Thus, the chromatogram generated is presenting the number of constituents present in a medicine and their UV absorption range with quantity of pixels proportional to the concentration of the molecules.

When the image is divided into, three zones based on the elution pattern of the molecules and the changing polarity of the mobile phase. The Zone 1 is polar zone as the column used is a reverse phase column, the Zone 2 is medium polar zone where in the medium polar molecules are eluted and finally the Zone3 is low or non polar zone as the non polar and very low polar molecules will elute in this zone. Thus, the molecules eluted in zone 1 will be polar, the molecules eluted in the zone 2 will be of medium polar in nature and the molecules eluted in the zone 3 will be of very low or non polar in nature. Hence, the three zones of the images will give the polarity of all the constituents eluted.

Based on the polarity of the molecules eluted, the medicines are classified according to traditional system of therapeutic efficacy where in the polar compounds are found to be Pitta Hara, the medium polar compounds are Kapha Hara and the low or non polar compounds are Vata Hara. This is the basis of therapeutic standardization of the medicines. The polarity of the constituents is compared to a continuous spectrum of radiation, where in the dosha is classified as acute to chronic of each dosha. The starting of the zone will be acute and the end of the zone will represent the chronic. Thus, the compounds present in the said zone will act on the said intensity of the disease.

Table 16 shows division of the fingerprint in to different therapeutic zone based on the color of absorption and polarity. The scale on X-axis shows the scale of polarity of the molecules based on the polarity of the mobile phase and Y-axis shows the range of wavelength (200–800 nm) absorbed. Based on the reported therapeutic efficacy in the literature based on the physico-chemical properties (Color and Chemical properties) and the experimental the therapeutic efficacy of various medicines was standardized. Some deviations were found which could be due to the effect of variable environmental factors influencing the chemical constituents of the medicines.

Thus, the method will help to know the therapeutic efficacy of the medicines under study. Hence, the proposed method will become a novel visual proof for the understanding the therapeutic efficacy of the medicine reported or new, single or formulated.

The analysis of the images was done using software developed for this purpose. The details of the software is given in the release notes and FIG. 115

Step 4:

Interpretation of the Data

The fingerprints generated are analyzed for their chemical and therapeutic properties. The basic features in a fingerprint are found to be 1) the zone of the polarity in which the constituents have eluted; and
2) the conjugative properties of the individual constituents present.

The polarity of the column is fixed. It is a normal phase or a reversed phase stationary phase. In the normal phase column, stationary phase will be polar and in a reverse phase column, the stationary phase will be non-polar. The extent of polarity of the stationary phase varies from brand to brand even in same type of reverse phase or normal phase column. The polarity of the stationary phase will be controlled using the polarity of the mobile phase, additives like buffers and pH. When the polarity of the mobile phase is varied constantly in the increased or decreased order, on a reverse phase column, the constituents present in the sample will elute in the same order, i.e., the high polar constituents will be eluted by the high polar mobile phase, the medium phase mobile phase will elute the medium polar constituents and the non-polar constituents will be eluted by the non polar or low polar mobile phase. The most preferred pattern is to change the polarity of the mobile phase either increased or decreased order of polarity such that no constituent of any polarity will be left un-eluted from the column thus achieving total elution. Thus by controlling the polarity of the stationary phase, polarity of the mobile phase will be managed to bring a required effect on the polarity of the constituents to achieve separation of required order of elution.

The order and properties of polarity and elution in the case of normal phase columns are applicable as in the case of reverse phase column but reverse to the reverse phase column. The non-polar constituents will elute first, followed by polar constituents, based on the order of polarity of the mobile phase used for elution.

Thus in the present elution also the elution of the constituents is controlled and driven in the required pattern by controlling the polarity of the mobile phase and the order of changing it in an orderly way.

Mostly the elution of the samples were done from high polarity mobile phase to low polarity mobile phase. Thus in the finger prints the constituents present in the first zone (Zone-1) will be of high polar in nature. The same pattern applies to the other zones, the medium polar constituents eluted in the medium polar zone (Zone-2) and the low or non-polar constituents eluted in the non-polar zone (Zone-3). This pattern reverse' when a normal phase column is used due to its elution property as described above.

Most of the high polar molecules will be highly reactive chemically, thus biologically. When they enter the first part of the digestive system mouth, they will immediately start acting on the biological system and the enzymes present there. Then the constituents will enter the stomach and intestine where they will under go different changes (Post assimilation effects, Vipaka in Ayurveda) due to the digestive juices and their enzymes present in the part. In the process of absorption the moment the molecules of high activity (high polar) will immediately start interacting with the biological system and show their therapeutic properties. This can be compared that in Ayurveda, the intestinal part of the human body is classified as Pitta zone, where the high polar molecules are playing a major role. The heat causing mechanism will play an important role in the diseases and biological mechanisms related to. It indirectly indicates the molecules of high reactive, the high polar molecules.

After the absorption, the blood with all the absorbed constituents will carry them to heart and the parts related to it. Then the blood will be sent to different parts of the body. In Ayurveda, the upper portion of the human body is defined as the Kapha zone, where the cold mechanism will be playing an important role. Thus, the molecules of medium polar molecules will play an important role in the mechanisms related to this zone.

The low polar and non-polar constituents will be able to enter to the human body only through blood transfer, Thus the body organs where the mechanism of availability of the chemical constituents is only by blood will be coming in the last category of the polarity. The non-polar oils, fats and other such molecules and mechanisms in the human body are classified as Vata disorders and all such disorders are cure using the same type of materials.

The low and non-polar constituents will be eluting in the last zone of the fingerprint. Thus, this zone (ZONE-3) is considered as Vata zone. Thus the basic humors of the molecules are able to be identified as per their polarity which facilitates to know on what disorder (dosha) it is going to act upon. Thus, the present method is useful for the therapeutic standardization of the medicines.

The image was divided in to three zones on X and Y-axis. The conjugative property (Absorption of a particular wavelength of radiation) is taken on Y-axis and polarity is taken on the X-axis as the elution of the constituents is controlled using the polarity of the mobile phase composition. Now as reported in literature the Y axis is scaled as per, the therapeutic efficacy based on wavelength (color). The entire image is divided in to six chambers where in the chemical constituents have a specific conjugative and polarity property. This in turn is proportional to the therapeutic efficacy of the constituents in the chamber. Thus, when a medicine is fingerprinted, based on the color represented for the absorption of a specific wavelength and having a specific polarity, the total colors in that zone is calculated and interpreted for the therapeutic efficacy of the constituents present in it. Thus, the holistic therapeutic standardization and chemical standardization is achieved using this method. A schematic representation is given in table 15, showing the relation of conjugation and polarity to therapeutic efficacy of the different constituents present in a medicine.

When the 3-D chromatograms of the medicine will be analyzed using all its 3 dimensional properties of the said image: If the 3-D chromatogram is considered as a cap with a hood the matching of the entire cap 3 dimensionally, with another sample of different qualitative and quantitative properties, the extent it matched will be presented as an analytical report qualitatively and quantitatively. Here the hood of the Cap is compared to the peak of the molecule at a particular wavelength. A sample with more number will like a cap with many hoods. Thus the matching of the three dimensional coordinates will provide a foolproof method of comparison and analysis. The coordinate it matched will give qualitative and the extent it matched will give the quantitative data of the sample understudy. This is made possible by special software prepared for this purpose. This becomes an ultimate method of quality control.

But any method without quantification will be of no use. Hence, the total colors of the constituents in the image of a particular zone are considered as a representation of the amount of the polar constituents present in the medicine. Thus the total constituents present in the Zone-1 Pitta zone, Zone-2 Kapha zone, Zone-3 Vata zone are present in the form of a Pie diagram which represents the ratio of the efficacy of the medicine on each of the disorder. Thus, medicines having constituents in the order of 50:20:30 will be medicines of Tridoshahara of the order of 50%: 20%: 30%. This was done using the software developed. Thus, the therapeutic efficacy is standardized quantitatively. The increase or decrease of any one or two of the other doshas can be done by formulating medicine by adding other medicines and prepare a suitable formulation needed to cure a specific individual.

The chemical standardization was done using the software by quantifying the individual constituents based on the colors denoting the concentrations of the in-gradients. The range of the wavelength that a molecule absorbed denotes the conjugative properties.

As described in the traditional standardization methods the colors of the medicines were standardized based on their colors and their therapeutic efficacy. It applies even in the case of any molecules. The Table 8 of colors and their efficacy will explain how colors were used to standardize the efficacy of the medicines. The colors of the molecules can be understood by their absorptive properties of the radiation of the Uv-Vis range of radiation. In the Table 10 of colors and the relation with wavelengths, the colors of the medicines and their characteristic wavelengths are given. Based on the structure, functional groups, conjugation, and the extent of unsaturation will influence the wavelength of absorption (absorbance maxima) of the molecule. The more the molecule is conjugated the longer the wavelength of absorption will be. Hence, the UV-VIS absorbance of any molecule is widely used in the qualitative and quantitative properties of the constituents.

The colors and the therapeutic efficacious of various medicines were given in the ancient literature. The colors of the molecules are due to a specific chemical nature of the molecule. The colors of the flames were used for the quality control of metals and related products, which involves the basic spectrophotometric principles. Thus, study and understanding of the interaction of the electromagnetic radiation will be useful to study the chemical nature and thus the therapeutic efficacy of the medicines. The same principle has been used in the present spectrophotometric method of fingerprinting and standardization. In other terms an existing concept has been presented in the form of a novel analytical method, removing the error of human factor. All the medicines for which fingerprints developed were given in table of therapeutic efficacy of the medicines were given in table 14. The technical details of the software are given in the release notes of the software.

Release Notes for the Software Proposed

I) System Requirements (Minimum)
a. Processor: Pentium II or higher
b. OS: Windows 95, Widows 98, Win NT 4.0 and Linux
c. RAM: 64 MB or higher
d. Monitor: 14" Color Monitor (1024×768) or higher
e. Software: Java Development Kit (JDK 1.2.x)

II) The Operational Mechanism of the Software:
The various operational mechanisms are described below: operational sequences with various functionality are shown in FIG. 115.

Title of the Software: RAINBOW (An Image Analysis Software for Chromatographic Fingerprints)

This software is developed for the chromatographic fingerprints and microscopic images.
1. It is GUI (Graphical User Interface) based software.
2. The software is designed to analyze any kind of image particularly for the analysis of chromatographic fingerprints.
3. The reports are given in form of graphs.
4. Life Cycle a. In put: Image b. Processing:

Analysis involves

Extracting Colors (Standard 7 colors and some of their different shades)

Resizing, Deviding in to 3 zones at 20 minutes interval

Graphing (Bar and Pie graphs)

Bar-coding

Standards Followed for extracting the colors:
The software extracts eight colors viz. Red, Green, Blue, Yellow, Cyan, Magenta and Orange.

Any color is not absolute. It is mixture of the following shades of the colors present before and after it, they vary between a range of values. The range for the colors used to identify as the colors given above the respective values are taken from the international standard 256-color scale. The values used in the present software are:

| Red | Blue | Green |
|---|---|---|
| | For Red color | |
| 200–255 | 0–64 | 0–64 and |
| 192–200 | 0–64 | 0–32 |
| | For Green color | |
| 0–64 | 0–48 | 200–255 |
| 0–65 | 0–64 | 65–191 |
| | For Blue Color | |
| 0–96 | 200–255 | 0–191 |

Similarly, other colors were taken as standards for the extraction of colors. (These standards are exclusive for the present software requirements and are modifiable if required)

While image is analyzed, the software reads the image pixel by pixel and reads and extracts the color according to the color standards designated, stores and transfers them for further display as bar graphs.

c. Output:

Reporting
1. By Graphs
2. By saving data like images, graphs, deviding the image display into three zones
3. By displaying the 'X' (Retention time or Pixel value of the image), Y (Wave length or absorbance of the images of contour and 3-D chromatograms respectively), R (Red color), G (Green color) and B (Blue color) coordinates.
4. By transferring these values to an in-built bar-coding software to generate a bar code.

d. User Interaction: User is allowed to interact with the product in various ways.
1. Inputing the desired image (one or more)
2. Resizing the image to desired size and analyzing it.
3. Saving the image, resized image, and graphs to it.
4. Printing the image, resized image, and graphs to it.

III) Technical Features of the Software
1. It is software entitled 'Rainbow'
2. A software with a facility of opening chromatographic fingerprint images in different Formats (extensions) like .BMP, JPEG, TIF, GIF from the file folders and analyze it for different colors present in the image with single pixel sensitivity.
3. A software with a facility of display of the pixel information in the form of 1. a graph having a scale of X (0-(min. time scale) and Y (200–800 nm) coordinates and 2. a Pie diagram with individual values of each peak (Automatic and Manual) in two separate columns beside the graph.
4. Software with a facility of printing all the data generated after analysis using PRINT Icon.
5. A software with a facility of changing the page setup for printing using PAGE SETUP Icon
6. A software with a facility of selecting a part of the image and analyze using RESIZE Icon.
7. A software with a facility of opening any number of image analysis windows for different images, and display of status in WINDOW icon.
8. A software with a facility of dividing the image in to three Zones at 20 min interval, using ZONE icon.
9. A software with a facility of inverting the selected image using INVERT icon.
10. A software with a facility of switching over to Notepad, Word pad and MS Word, using EDITOR icon.
11. A software with a facility of operational information about various features of the Software using, the HELP icon.
12. Software with a facility of saving the data generated using SAVE AS icon as. JEPG file format.

IV) Installation Instructions for the Software:

a. Installation Procedure of Java 1.2.x Soft Ware Platform on which the Present Software Works.
Explore the Java CD-ROM
Double click on the jdk1.2.0/jdk1.2.1/jdk1.2.2 setup icon
The setup will extract the files and conforms from the user whether to load the software in the system.
On click, 'yes' it asks for the directory into which it should install the files.
By default, c:\jdk1.2 directory will be shown.
If you want to install in "d" drive, change the directory and Install the software.
Once the installation is completed go to c: and open the file named 'autoexec.bat'.
Give the following path in the autoexec.bat file.
Open auto exe. Bat and write as follows
Set path=d:\jdk1.2\bin: % path %
Setup class path=d:\jdk1.2\lib\classes.jar; % classpath %
Reboot and use b. Installation of Image Analyzer Software Proposed
1. Copy the folder of the image analyzer software from the CD on to the system in the desired directory.
2. Explore the batch file form the software folder into which image analyzer software was copied.
3. Right click on it and click on 'send to desktop as short cut'
4. A 'MS dos' iconic short cut appears on the desktop. Right click the icon and go to properties, select program tab and check on the 'close on exit check box', convert window status 'To minimized'.
5. Apply and close.
6. Now the image analyzer software is ready for use. Double click on the image analyzer Icon and it starts working.
7. In the opening window, a box with 'CSIR' will open where in the pass word 'dvk' should be typed.
8. Click the arrow mark (hand) on the right down corner of the opening image to open the Software.
9. Open the directory of the images of contour images without scale and select the image to be analyzed. The image will be shown on the image window.
10. Click on the RED analytical window marked with red boarder. A PIE diagram will be displayed along with a chromatogram with retention time on X-axis and nanometers on the Y-axis.
11. For constituents of lesser concentration click on the Green, Yellow and Orange colors. The Other colors are mostly the base line or less than that hence can be ignored.
12. The details of using the other features of the software are given in the help menu of the software including the various features and applications of the software.

V. Known Bugs:
Not found

VI. Abbreviations Used:
a. JDK: Java Development Kit
b. Con: Contour Chromatogram
c. 3-D: 3-Dimensional Chromatogram
d. WOS: Without Scale
e. X: Represents the Retention Time of the chromatogram
f. Y: Represents the absorbance in the 3-D chromatogram and wave length range in contour chromatogram
g. R: Intensity of red color at a particular pixel position
h. G: Intensity of green color at a particular pixel position
i. B: Intensity of blue color at a particular pixel position VII. Meaning of the Various Icons and Functions
a. PRINT icon will facilitate in printing all the data generated after analysis.
b. PAGE SETUP icon will facilitate in changing the page setup for printing.
c. RESIZE icon will facilitate the selection of a part of the image and analyze the selected part of the image.
d. WINDOW icon will facilitate in opening any number of image analysis windows for different images, and display of status in
e. ZONE icon will facilitate in dividing the image in to three Zones at 20-min interval.

f. INVERT icon will facilitate in inverting the selected image.

g. EDITOR icon will facilitate in switching over to Notepad, Word pad and MS Word.

h. HELP icon will facilitate in the operational information about various features of the Software usage.

i. SAVE AS icon will facilitate in saving the data generated in a *. JPEG file format.

VIII. Constraints:

a) The present software works only for contour chromatograms without scale.

b) The scale on X axis is in 1-(of "minutes" representing retention time of the contour chromatogram c) The scale on Y-axis is 200–800 nm representing the range of wavelength under which the analysis is conducted.

d) The Image developed has to be resized using imaging software to match the run time and wavelength range on X and Y-axis.

e) The images after analysis will be saved only in JPEG format without scale.

f) The clip images should be stored with an extension of the co-ordinates i.e. X1 and Y2.

Main Advantages of the Present Invention are:

1. The contour chromatogram of the medicine becomes a Fingerprint of it. Because it contains the UV-Vis spectrum band with concentration of the ingredients along with the polarity of the molecule. The fingerprints developed for a same medicine extracted under different pH value helps to understand the drug release in the intestine system at different pH values thus facilitating the pharmacodynamics of the medicines under study.

2. The spectral bands of all the constituents are given in a single picture assessing the medicine about its therapeutic properties and nature, very easy.

3. The 3-D Chromatogram becomes a photo of all the UV-spectra of all wavelengths of each constituent in a single picture indicating the chemical (conjugative and polarity) property of the molecule eluted.

4. A database of the fingerprints of various herbal medicines available in the country useful for Quality control, Forensic and customs departments to control the use and misuse of the herbal medicines at the public interest.

5. The database also gives information about the medicinal value of the various medicinal plants of the country (therapeutically classified) in the country and the role of the ecological factors on the chemical constituents of the same plant available in various tropical Zones of the country. This facilitates to select a plant for collection of the herbal medicines suitable to be used for the therapeutic usage for a medicinal professional or an herbal trader.

6. Analysis of the fingerprints using this software gives role of ecological factors on various herbal medicines available in the country and it is useful for Quality Control, Forensic and Customs Departments to control use and misuse of the herbal medicines at the national interest 7. The analysis of the fingerprints is useful to understand the therapeutic efficacy of the medicines using the physico-chemical properties of the medicines as reported in the ancient literature.

8. The analysis also gives information about the medicinal value of the various medicinal plants in the country and the role of the ecological factors on the chemical ingredients of the same medicine available in various parts of the country.

9. The therapeutic and ethano-botanical classification of the fingerprints helps to bring some generalizations useful for the doctors and researchers for a complete understanding of the traditional medicines by analyzing the fingerprints.

10. By bar coding the image properties the medicines/plant extracts/plants are saved from piracy as the facility to create a barcode using the properties of the image through note pad facility.

11. The barcodes are utilized in all commercial transactions of modem ERP and CRM applications.

Application Utilities of the Present Invention

International

It is useful for any country for fingerprinting and patenting the traditional medicines of that country. Because the finger print of a single medicinal plant is not similar to a finger print of the same plant in another place or country due to the variations in its chemical profile. The variations in chemical profile is due to the influence of Ecological factors like the tropical region variations, soil, water quality and the genotypic and phenotypic variations factors on the chemistry of the plant.

This method helps the country to fulfill one of the regulations made by WHO, for the member countries to standardize methods for the utility and quality control of herbal medicines and their regulation.

National

This is useful as a tool to prevent international piracy of traditional medicines by Passing a Law that the "The Medicinal plants for which the finger prints are developed are national property". If a medicine is applied for any type of patent, in any place of the world and if the finger print, tallies with the finger print of the medicine available in the challenging country, the patent could be objected.

Strategic

Bar coding the fingerprints of the medicines helps in the authentic regulation and protection of the medicinal plants.

By converting the barcode of the fingerprint of a medicinal plant into a machine-readable language, commercial and regulatory work becomes easy.

Fingerprints of the medicines helps the Food and Drug controllers, Customs and Central Excise departments to regulate, check the use, misuse and pilferage of the herbal medicines inside the country and while allowing importing of such medicines.

Industrial

A fingerprint developed for a medicine or a formulation helps the industry to protect their process technology by comparing the fingerprint of the same medicine of other brands. Thus, it helps to implement the patent law more efficiently.

The fingerprint helps to monitor how the medicines are changing its medicinal properties by the addition of another medicine at different stages of process of preparing a formulation.

Industry can use the database of fingerprints developed for all the native plants available in the country, for their selection of the place of collection of a medicine. It helps the industry, which part of the country, and in which season is suitable for the collection of herbal medicines, as the ecological factor changes the therapeutic efficacy of the medicines.

Scientific

This method helps the researchers to understand the traditional formulations prepared. It also helps to monitor a new formulation under preparation.

It helps to know how new molecules are formed when a complicated traditional formulation is prepared.

The fingerprints developed for a same medicine extracted under different pH value helps to understand the drug release in the intestine system at different pH values of an individual.

The contour chromatogram of the medicine becomes a Fingerprint of it. Because it contains the UV-Vis spectrum band with concentration of the ingredients along with the polarity of the molecule.

The spectral bands of all the constituents are given in a single picture, assess the medicine about its therapeutic properties and nature, very easily.

The 3-D Chromatogram becomes a photo of all the UV-spectra of all wavelengths of each constituent in a single picture indicating the chemical (conjugative and polarity) property of the molecule eluted.

The database also gives information about the medicinal value of the various medicinal plants of the country (therapeutically classified) in the country and the role of the ecological factors on the chemical constituents of the same plant available in various tropical Zones of the country. This facilitates to select a plant for collection of the herbal medicines suitable to be used for the therapeutic usage for a medical professional or an herbal trader.

The therapeutic and ethano-botanical classification of the fingerprints helps to bring some generalizations useful for the doctors and researchers for complete understanding of the traditional medicines by analyzing the fingerprints.

The present method facilitates to prepare chromatographic finger printing of herbal medicines and formulations, which is useful for many quality control and regulation purposes.

The present method facilitates chemical standardization, (qualitative and quantitative) of the said medicines by providing the conjugative and polarity properties of the individual molecules present in the medicines or any organic or organo-metallic compound which has UV-VIS absorptive property. This kind of analysis is of much use in the chromatographic analysis of Herbal medicines of Single and Formulations, where the use of external or internal standards are practically not possible.

The invention facilitates to study, understand and monitor the therapeutic efficacy of the said medicine under study. It helps to understand the therapeutic actions and properties of traditional medicines reported in the ancient literature and confirm the same in the form of a reproducible analytical data. Thus, it provides therapeutic standardization of the medicines under study. It shows the polarity zones like Polar, Medium polar and Non polar molecules present in the sample, thus facilitating to understand the efficacy of the medicine as a whole.

This method facilitates to re-standardize the reported medicines to the present therapeutic needs. It helps to monitor and study formation of new organic and organo-metallic molecules, which has UV-VIS absorptive property, in the process of preparing a reported or a new formulation. This also helps to standardize the process technology of preparing a reported or new formulation by monitoring the constituents and their changing chemical and therapeutic properties.

It facilitates to generate a barcode by an in built bar coding software, wherein the X retention time, Y wavelength, R number of red pixels, G number of green pixels and B number of blue pixels are the coordinates given by the present software. Some examples of the barcode for chromatograms are given. The invention also facilitates bar coding one or more of the constituents present in the fingerprint thus facilitating the commercial transactions easy by ENTERPRISE RESOURCE PLANNING (ERP) and CUSTOMER RELATIONSHIP MANAGEMENT (CRM) applications. A database thus prepared helps the regulatory authorities to monitor the movement of the said medicines inside or from outside the country, from production to the consumer. The database of the barcodes thus prepared, becomes the resource for the ERP vending machines or of any of such kind. The machine will display all details of the medicines like company, its chemical fingerprint, and the therapeutic efficacy of the medicines the said medicine. This makes the identification of the medicines more authentic than the present.

A data base of the fingerprints thus generated using this method helps to bring many generalizations of the therapeutic efficacy of a particular therapeutic class of plants. Thus, one can under stand why a particular plant is added in that class. This is explained in the Table 14 enclosed.

The fingerprints printed on the label of the medicine helps the doctors to understand the therapeutic efficacy of the medicine just before use and confirm the quality control of the medicines for every batch.

The Image analysis of Chromatographic Finger Print Images (Contour Chromatograms) of various Medicines of any philosophies (Single and Formulations) developed, are useful for many purposes as described in various steps of this application.

Social

This is useful to know for a consumer, the therapeutic efficacy of medicines single or formulated claimed on the label and confirms to contain the same.

This helps the consumer-act to monitor the quality control of herbal medicines sold in the market and protect the interests of the consumer.

Adulteration

The Image analysis of Chromatographic Finger Print Images (Contour Chromatograms) of various Medicines of any philosophies (Single and Formulations) developed is useful for detection of any adulteration of the medicines.

TABLE 1

Table of Different Philosophies And Various Terminology Used in Medicine

| SI No | PHILOSOPHY | TRI DOSHA(Hara) | PANCHA BHUTA | PROPERTIES | SAPTA DHATU | TRI MALAS |
|---|---|---|---|---|---|---|
| 1 | Ayurveda (Shown eloborately in separate table) Binary: Prakriti-Purusha | Vata, Pitta, Kapha. | 1. Prithivi 2. Ap 3. Teja 4. Vayu 5. Akasha | 1. Rasa- Taste - 6 2. Guna- Property-Basically 20 3. Veerya -Potency-2 4. Vipaka- Metabolite-3 5. Prabhava- Specific properties- Innumerable 6. karma-Action | 1. Rasa 2. Rakta 3. Mamsa 4. Medas 5. Asthi 6. Majja 7. Shukra | 1. Purisha 2. Mutra 3. Sweda |
| 2 | Siddha Binary Prakriti-Purusha | Pitta,, Kapha, Vata | 1. Mann(Prithvi) 2. Neer(Ap) 3. Thee(Agni) 4. Vayu(Vayu) 5. Akasa(Akasha) | 1. Rasam 2. Gunam 3. Veeryam 4. Vipakam | 1. Rattam(Blood) 2. Sadhai(Muscle) 3. Kozhuppu(Medas) 4. Elumbu(Bone) 5. Vindhu, Karu(Sperm,Ovum) | 1. Malam 2. Mutram 3. Vervai |
| 3 | Chinese Binary: Yin-Yang | 1. Yang 2. Yin | 1. Wood 2. Fire 3. Earth 4. Metal 5. Water | 1. Sour 2. Bitter 3. Sweet 4. Shark 5. Salty | 1. Sinuses 2. Blood Vessels 3. Muscles 4. hair 5. Bones | Information not available * |
| 4 | Tibetan | Nes Pas 1. Mkhris(Pitta) 2. Bad-Kan(Kapha) 3. Rlun(Vata,Vayu) | 1. Sa(Prithvi) 2. Chu(Ala) 3. Me(Agni) 4. Rluin(Vayu) | Information not available* | Lus Zuns Bdun 1. Dans Ma(Rasa) 2. Khrg(Rakta) 3. Sa(Mamsa) 4. Tsil(Medas) 5. Rvs(Asthi) 6. Rkan(Majja) 7. Khu Ba(Shukra) | Dri Ma 1. Bsan 2. Gcin 3. Rnul |
| 5 | Unani Binary: Normal-Abnormal | Akhalat 1. Damvi(Blood) 2. Balgam(Phlegm) 3. Safravi(Bile) 4. Saudai(Vata) | Arkan 1. Aag(Fire) 2. Hawa(Air) 3. Pani(Warter) 4. Earth(Mitti) | 1. Garm(Hot) 2. Khush(Dry) 3. Sard(Cold) 4. Motadil(Neutral) | 1 Primary: Blood, Phlegm, Bile, Saudai Secondary: 1. Mahsoora(Intravascular) 2. Talliya(Pericellular) 3. Qureeba(Intercellular) 4. Munviya(Cellular) Body organs Simple, Compound | 1. Bole 2. Baraj 3. Paseena |
| 6 | Greek Contrary medicine | 1. Yellow Bile 2. Black Bile 3. Phlegm 4. Blood | 1. Water 2. Earth 3. Fire 4. Air | 1. Hot 2. Dry 3. Wet 4. Cold | 1. Unctuous 2. Rough 3. Hot 4. Cold | |

TABLE 2

Relation Of Humors, Properties, And Different Parts Of The Human Body - An Ayurvedic Approach Approach

| SI No | TRI DOSHA (Hara) | TRI MALAS | PANCHA BHUTA (PHYSICAL PROPERTIES) | SAPTA DHATUS | CHEMICAL PROPERTIES | MAHABHUTA RELATIONS WITH DHATUS | EFFECT ON DOSHAS (DECREASING THE DOSHA) DUE TO DHATUS | RELATION ON GUNA | RELATION ON VIPAKA (POST ASSIMILATIVE EFFECT) |
|---|---|---|---|---|---|---|---|---|---|
| | 1. Vata, 2. Pitta, 3. Kapha. | 1. Purisha 2. Mutra 3. Sweda | 1. Prithivi 2. Ap 3. Teja 4. Vayu 5. Akasha | 1. Rasa 2. Rakta 3. Mamsa 4. Medas 5. Asthi 6. Majja 7. Shukra | 1. Rasa (Shadruchi's) a. Madhura b. Amla c. Lavana d. Katu e. Tikta f. Kashaya 2. Guna-: Broadly classified into 3 groups 1. Vaisheshik 2. Samanya 3. Atma Mostly used are: Guru(Heavy) Laghu(Light) Sheeta(Cold) Ushna(Hot) | a. Prothivi + Ap b. Agni + Prithive c. Jala + Agni d. Aksha + Vayu Eagni + Vayu f. Prithive + Vayu | a. Pitta Vata Hara b. Vata Hara c. Vata Hara d. Kapha Hara e. Kapha Pitta Hara f. Kapha Pitta Hara | a. Guru,Sheeta, Snigdha b. Ushna, Laghu,Snigdha c. Ushna, Laghu,Snigdha d. Ushna, Laghu,Ruksha e. Sheeta, Laghu,Ruksha f. Sheeta,Guru, Ruksha | a. Madhura b. Amla c. Madhura d. Katu e. Katu f. Katu |

TABLE 2-continued

Relation Of Humors, Properties, And Different Parts Of The Human Body - An Ayurvedic Approach Approach

| SI No | TRI DOSHA (Hara) | TRI MALAS | PANCHA BHUTA (PHYSICAL PROPERTIES) | SAPTA DHATUS | CHEMICAL PROPERTIES | MAHABHUTA RELATIONS WITH DHATUS | EFFECT ON DOSHAS (DECREASING THE DOSHA) DUE TO DHATUS | RELATION ON GUNA | RELATION ON VIPAKA (POST ASSIMILATIVE EFFECT) |
|---|---|---|---|---|---|---|---|---|---|
| | | | | | Snigdha(Soft, Lubricated, Supple) | | | | |
| | | | | | Rooksha(Dry) | | | | |
| | | | | | Manda(Slow) | | | | |
| | | | | | Teekshna(Sharp) | | | | |
| | | | | | 3. Veerya-2 | | | | |
| | | | | | 4. Vipaka-3 | | | | |
| | | | | | 5. Prabhava-innumerable | | | | |

The properties of the materials and disease were correlated to select a medicine - The therapeutic standardization

TABLE 3

Table Showing Division in terms of the Macrocosm in Chinese medicine

| SI No. | Elements | Seasons | Color | Taste | After influence | Development |
|---|---|---|---|---|---|---|
| 1 | Wood | Spring | Blue | Sour | Wind | Birth |
| 2 | Fire | Summer | Red | Bitter | Heat | Growth |
| 3 | Earth | Late Summer | Yellow | Sweet | Humidity | Puberty |
| 4 | Metal | Autumn | White | Shark | Drought | Maturity |
| 5 | Water | Winter | Black | Salty | Cold | Senility |

Basis of color for therapeutic standardization

TABLE 4

Table Showing Division In Terms Of the Microcosm in Chinese Medicine

| SL No. | Elements | Sense organs | Fus | Tsangs | Emotional | Structural eluents |
|---|---|---|---|---|---|---|
| 1 | Wood | Eye | Bile | Liver | Anger | Sinuses |
| 2 | Fire | Tongue | Small intestine | Heart | Joy | Blood Vessels |
| 3 | Earth | Mouth | Stomach | Spleen | Anxity | Muscle |
| 4 | Metal | Nose | Large intestine | Lung | Sadness | Hair |
| 5 | Water | Ear | Bladder | Kidney | Fear | Bones |

TABLE 5

Table Showing the Relation of Five Natural Elements and Their Relation, in Chinese Medicine

| | Element | | | Element | Yin & Yang |
|---|---|---|---|---|---|
| 1st Heaven engendered | Water | 2nd | Energy engendered | Fire corresponds to the | Heart & Small intestine |
| 3rd Heaven engendered | Wood | 4th | Energy engendered | Metal corresponds to the | Lung & Large intestine |
| 5th Heaven engendered | Earth | 6th | Energy completed | Water corresponds to the | Kidney & Bladder |
| 7th Heaven completed | Fire | 8th | Energy completed | Wood corresponds to the | Liver & Gall bladder |
| 9th Heaven completed | Metal | 10th | Energy completed | Earth corresponds to the | Spleen & Stomach |

TABLE 6

Table Showing the Meaning of Yin and Yang Used In Chinese Medicine

| Yin (The shady side of the hill) | Yang (The sunny side of the hill) |
|---|---|
| Light | Dark |
| Night | Day |
| Damp | Dry |
| Cold | Hot |
| Water | Fire |
| Evil | Good |
| Ugly | Beautiful |
| Vice | Virtue |
| Poverty | Healthy |
| Sadness | Joy |
| Confusion | Order |
| Punishment | Reward |
| Disease | Health |
| Positive | Negative |
| Female | Male |
| Bad | Good |
| Wife | Husband |

TABLE 7

Table Showing The Basis Of Color For The Therapeutic Standardization Of Medicines

| | White Color Medicines | Yellow Color Medicines | Red Color Medicines | Black Color Medicines |
|---|---|---|---|---|
| Color Name in Sancrit | Shukla Varga | Peeta Varga | Rakta varga | Krishna Varga |
| Sloka | [Sanskrit sloka] | [Sanskrit sloka] | [Sanskrit sloka] | [Sanskrit sloka] |
| Name of the medicines/ materials | Sudha Chuna (Lime) Kachhapa Prista (Shell of tortoise) Shankha (Conch) Shukti (Shell of Pearl) Varatika (Small shells) Brushtashma (Incinerated Stone) Sarkara (Sugar candy) *Rajanighantu by Vaidya Narahari | Kusumba Pushpa Kimshuka (*Butea monosperma*) Haridra (*Curcuma longa*) Patanga (*Caesalpinia sappan*) Madayantika (*Lasonia Inermis*) *Rasamava | Dadima (*Punica granatum*) Palasha (*Butea monosperma*) Laksha (*Laccifera lacca*) Bandhuka Haridra (*Curcuma longa*) Kusumba Pushpa Manjista (*Rubia cordifolia*) *Rajanighantu | Kadali (*Musa paradisiaca*) Karavellika (*Momordia charantia*) Triphala (Three myribalans) Neelika (*Indigofera Tinctoria*) Nala (*Cymbophogan* species) Panka (*Lotus*) Kaseesa ($Fe_2S_3$) Balamra (Unripen Mango) *Rasendra Chudamani |

The names of the medicines were given as sloka

TABLE 8

The Effect Of Different Colors On Different Diseases

| Cool effect | | | Neutral | Creat heat | | |
|---|---|---|---|---|---|---|
| Violet | Indigo | Blue | Green | Yellow | Orange | Red |
| 1. Bones & Bone marrow, 2. Tumour, 3. Baldness, 4. Cataract, 5. Blindness | 1. E-N-T problems 2. Facial paralysis 3. Diseases of the lungs, 4. Asthma, 5. T.B. 6. Less digestive power, 7. Problems of nervous systems, 8. Convulsion, 9. Lunacy | 1. Whooping cough, 2. Throat problems, 3. Fever, 4. Typhoid, 5. Small-pox, 6. Measles, 7. Ulcers in mouth 8. Cholera 9. Swelling in the brain 10. Problems of nerves 11. Insomnia, 12. Mental depression 13. Problems of semen discharge | 1. Heart problems 2. Low and high B.P. 3. Skin problems 4. Cancer 5. Influenza 6. Syphilis 7. pain in the eyes etc., | 1. All disorders of digestion 2. Spleen, liver problems 3. Diabetis 4. Leprosy etc., | 1. Long term Asthma 2. bronchitis 3. Swelling in trachea 4. Gout 5. Swelling 6. Kidney 7. Mental nervousness 8. Epilepsy etc., | 1. Anaemia 2. Disability 3. Sluggishness 4. Cold 5. Paralysis 6. White spots 7. Arthrites 8. T.B etc., |

TABLE 8-continued

The Effect Of Different Colors On Different Diseases

| Cool effect | | | Neutral | | Creat heat | |
| --- | --- | --- | --- | --- | --- | --- |
| Violet | Indigo | Blue | Green | Yellow | Orange | Red |
| | | 14. Burns, Bleeding from nose etc., | | | | |

The role of colors and their influence on different body parts, The basis of color is used for selecting a medicine. For eg. A plant with Indigo flowers will cure ENT problems

TABLE 9

Properties of the SIX Tastes (Rasas in Ayurveda) and their properties and efficacy

| | Predominent | | Examples | |
| --- | --- | --- | --- | --- |
| Taste | element | Effects on Dosha | Dietary Item | Drug |
| Sweet (Madhur) | Earth + Water | Kapha ↑ Vata and Pitta ↓ | Sugar, Banana, Jack fruit, Raisins, Milk, Coconuts, Jaggary | *Glycerrhiza Glabra, Asparagus Racemoses,* Gold |
| Sour (Amla) | Earth + Fire | Pitta and Kapha ↑ Vata ↓ | Tamarind, Buttermilk, Curds, Raw mango | *Embalika officinalis* |
| Salty (Lavana) | Water + Fire | Pitta and Kapha ↑ Vata ↓ | Salt | Rock salt |
| Pungent (Katu) | Air + Fire | Pitta and Vata ↑ Kapha ↓ | Asoefetida, Pepper, Chilli, Dry processed Zinger | *Piper longum* |
| Bitter (Tikta) | Space + Wind | Vata ↑ Pitta and Kapha ↓ | Bitter gourd | *Azadiracta indica, Swertia chiraita, Tinospora Cordifolia* |
| Astringent (Kashaya) | Wind + Earth | Vata ↑ Pitta and Kapha ↓ | Honey | *Terminalia chebula, Treminalia Bellerica,* Pearls, Corals |

This table shows how tastes and medicines are related to vitiation of diseases.

TABLE 10

Table of Colors and The Relation with Wavelengths.

| Wavelength Nm | Color (Absorbed from white light) | Color observed (Transmitted) or Complementary Hue* |
| --- | --- | --- |
| <380 | Ultraviolet | Yellowish green |
| 380–435 | Violet | Yellow |
| 435–480 | Blue | Orange |
| 480–490 | Greenish blue | Red |
| 490–560 | Bluish green | Purple |
| 500–560 | Green | Violet |
| 560–580 | Yellowish green | Blue |
| 580–595 | Yellow | Greenish blue |
| 595–650 | Orange | Bluish green |
| 650–780 | Red | |
| >780 | Near-Infra red | |

*The constituents having these colors will absorb at the respective wavelengths given The materials or medicines will show colors based on the absorption of a particular color from the range of colors in the white light falling on them. They will express the resultant color after absorption.

TABLE 12

Comparison table of existing techniques

| Sl No | Reported Technique | Method | Merits | Demerits |
| --- | --- | --- | --- | --- |
| 1. | TLC Open Chromatography | Fingure Printing | 1. Simple, 2. Less time consuming, 3. Less operational Costs | 1. Inferior compared to Closed chromatography 2. Incomplete Separations leading to ambiguous separations 3. Unreliable fingure printing due to influence of variations in analytical conditions 4. Needs the support of other costlier analytical instruments like LC-MS, NMR and IR with out which the data is incomplete. |

TABLE 12-continued

Comparison table of existing techniques

| Sl No | Reported Technique | Method | Merits | Demerits |
|---|---|---|---|---|
| 2. | HPTLC Open Chromatography | Fingure Printing | 1. Simple 2. Less time consuming 3. Less operational Costs | 1. Inferior compared to Closed chromatography. 2. Incomplete Separations leading to ambiguous separations. 3. Unreliable fingure printing due to influence of variations in analytical conditions. 4. Needs the support of other costilier analytical instruments like LC-MS, NMR and IR with out which the data is incomplete. 5. High instrumental cost. |
| 3. | HPLC Closed Chromatography (Superior than open chromatography) | 1. Chromatogram at a specified wave length | 1. Better separations 2. facility to change the polarity of the mobile phase to elute all molecules of entire range of polarity. | 1. Needs the support of other costilier analytical instruments like LC-MS, NMR and IR with out which the data is incomplete. 2. High instrumental cost 3. High operational cost |
| 4. | PROPOSED METHOD HPLC Closed Chromatography (Superior than open chromatography) | 1. Chromatogram indicates the entire range of wave length. 2. Utilisation of CONTOUR CHROMATO-GRAMS for the analysis of the organic and Organo-metallic molecules 3. Utilisation of 3-D CHROMATO-GRAMS for the analysis of the organic and Organo-metallic molecules | 1. Better separations 2. facility to change the polarity of the mobile phase to elute all molecules of entire range of polarity. 3. Facility to measure the absorbance of the molecules at various wave lengths of the entire range of 200–800 nm. This will not leave any molecule UNSEEN or UNIDENTIFIED. 4. Facilitates to prepare the "Chromatographic Finger Prints" of the native medicinal plants of a country as suggested by WHO. 5. Facilitates to understand the therapeutic efficacy of the medicines by studying the conjugative and polarity properties of the constituents separated by this method. 6. Facilitates to understand the therapeutic efficacy of a particular therapeutic class of plant (just like the method used in the identification of the personality of a culprit, as used in the FINGER PRINT SOFT-WARE used by the Forensic departments. | 1. High instrumental cost (almost equal or less than a HPTLC instrument) 2. High operational cost OPERATIONAL LIMITATIONS OF THE PRESENT COMPUTER BASED METHOD 1. This computer based method works only for contour chromatograms with out scale. 2. The Image developed has to be resized using imaging software to match the run time and wavelength range on X and Y-axis. 3. The images after analysis will be saved only in JPEG format with out scale which occupies less memory of the system. 4. The clip images should be stored with an extension of the co-ordinates ie., X1 and Y2. How ever they can be eliminated by the addition of more software features |

TABLE 13

PARAMETERS USED FOR FINGER PRINTING OF MEDICINES

| | | | | 3-D PARAMETERS* | |
| --- | --- | --- | --- | --- | --- |
| FIG NO. | BOTANICAL NAME OF THE PLANT | VERNACULAR NAME | PART USED | ELEVATION DEGREES | ROTATION DEGREES |
| 29 | ABEL MOSCHUS MOSCHATUS MEDICUM | KASTURI BENDA | WHOLE PLANT | 20 | 15 |
| 30 | ACACIA SUMA | SWETHAKHADIRA | BARK | 15 | 65 |
| 31 | ACALYPHA INDICA | KUPPINTA | LEAF LETS | 10 | 60 |
| 32 | ADHATODA VASAKA | VASA | LEAVES | 25 | 45 |
| 33 | ADIANTUM CAUDATUM | MAYURASHIKHI | LEAVES | 20 | 40 |
| 34 | AILANTHUS EXCELSA | ARALU | STEM BARK | 10 | 65 |
| 35 | ACORUS CALAMUS | VACHA | RHIZOME | 10 | 130 |
| 36 | ALLIUM PORUM | MAHALASUNA | LASSAN, BIG SINGLE CLOVES | 20 | 130 |
| 37 | ALLIUM SATIVAM | LASUNA | LASSAN, SMALL CLOVES | 20 | 130 |

TABLE 13-continued

PARAMETERS USED FOR FINGER PRINTING OF MEDICINES

|  |  |  |  | 3-D PARAMETERS* | |
|---|---|---|---|---|---|
| FIG NO. | BOTANICAL NAME OF THE PLANT | VERNACULAR NAME | PART USED | ELEVATION DEGREES | ROTATION DEGREES |
| 38 | ALPINIA GALANGA | GREATER GALANGA | RHIZOME | 20 | 75 |
| 39 | ALPINIA OFFICINARUM | LESSER GALANGA | RHIZOME | 15 | 75 |
| 40 | ALPINIA SPECIOSA | LIGHTER GALANGA | RHIZOME | 10 | 60 |
| 41 | ARECA CATECHU | BEETLE NUT | UN PROCESSED FRUIT NUT | 15 | 40 |
| 42 | ARECA CATECHU | BEETLE NUT | MILK PROCESSED NUTS | 15 | 40 |
| 43 | ARECA KATEEH | RAKTHA KHADIRA | STEM BARK | 15 | 65 |
| 44 | ARNICA | ARNICA | MOTHER TINCTURE OF WHOLE PLANT | 10 | 55 |
| 45 | BACOPA MONNERI | BRAHMI | WHOLE HERB | 15 | 45 |
| 46 | BERBERIS ARISTATA | DARUHARIDRA | STEM AND BARK | 15 | 170 |
| 47 | BORRHIEVIA DIFFUSA | PUNARNAVA | WHOLE PLANT | 15 | 55 |
| 48 | CAPSCICUM ANNUM L | MIRCH | BIG, RIPED FRUIT | 10 | 70 |
| 49 | CAPSCICUM ANNUM L | MIRCH | BIG UNRIPED FRUIT | 10 | 70 |
| 50 | CAPSCICUM ANNUM L | MIRCH | SMALL, UNRIPED, FRUIT | 10 | 70 |
| 51 | COSCINIUM FENESTRATIUM | LATA DARVI | STEM BARK | 15 | 125 |
| 52 | COCCINIDIUM GRANDIS | DONDA | ROOT AND LEAF | 25 | 30 |
| 53 | DACTLYLACTINIUM AEGYPTIUM(ERECT) | GRASS | LEAF | 25 | 40 |
| 54 | DACTLYLACTINIUM AEGYPTIUM(PROSTRATE) | GRASS | LEAF | 25 | 40 |
| 55 | DIRISTACHIS CINERARIA | TUMMA | LEAF AND BARK | 20 | 15 |
| 56 | EMBLICA OFFICINALIS | AMALAKI | FRUIT EPICARP | 5 | 50 |
| 57 | FACE PACK | BRAND 1 | FORMULATION | 20 | 25 |
| 58 | FACE PACK | BRAND 2 | FORMULATION | 20 | 25 |
| 59 | GLYCERRHZIA GLABRA | YASHTI MADHU | ROOT BARK | 15 | 130 |
| 60 | GLYCERRHZIA GLABRA | YASHTI MADHU | POWDER OF WHOLE PLANT | 15 | 130 |
| 61 | GYMNEMA SYLVESTRAE | PODAPATRI | WHOLE PLANT | 25 | 15 |
| 62 | HOLLERONA ANTIDYSENTRICA | KUTAJA | STEM BARK | 10 | 60 |
| 63 | INNULA RECEMOSA | PUSHKARAMULA | ROOT | 5 | 45 |
| 64 | MICHELLIA CHAMPAKA | MANU SAMPENGA | FLOWER | 20 | 40 |
| 65 | MORINGA OLIFERA | MUNAGA | LEAF | 25 | 40 |
| 66 | MYRICA CEREFERA | BAY BERRY | MOMEOPATHIC MOTHER TINCTURE | 20 | 35 |
| 67 | NAHI AXILLAE | NAHI | WHOLE PLANT | 10 | 130 |
| 68 | OROXYLUM INDICUM | SYONAKA | STEM BARK | 10 | 170 |
| 69 | OCIMUM SANCTUM | RAMA TULASI | LEAF | 15 | 130 |
| 70 | PLUCHEA LANCEOLATA | PATRA RASNA | LEAF | 10 | 65 |
| 71 | PICRORRHIZA KURROH | KATUKI ROHINI | STEM BARK | 15 | 125 |
| 72 | PIPER BEETLE | BEETLE | LEAF | 25 | 160 |
| 73 | PSORALIA CORILIFOLIA | BAKUCHI | SEEDS | 25 | 60 |
| 74 | RAPHANUS SATIVUS | MULLANGI, WHITE | LEAF | 15 | 25 |
| 75 | RICINUS CUMMUNIS | ERANDA MULA | ROOT | 10 | 135 |
| 76 | RUBIA CORDIFOLIA | MANJISTA | STEM AND ROOT | 10 | 40 |
| 77 | SAUSSREA LAPPA | KUSHTA | ROOT | 5 | 80 |
| 78 | SPHERANTHUS INDICUS | MUNDI | WHOLE HERB | 15 | 70 |
| 79 | SYMPLOCUS RACEMOSUS | LODHRA | STEM BARK | 15 | 65 |
| 80 | TERMINALIA CHEBULA | HARITAKI | FRUIT | 10 | 40 |
| 81 | TERMINALIA BELLERICA | VIBHITAKI | FRUIT | 20 | 35 |

TABLE 13-continued

PARAMETERS USED FOR FINGER PRINTING OF MEDICINES

| FIG NO. | BOTANICAL NAME OF THE PLANT | VERNACULAR NAME | PART USED | 3-D PARAMETERS* ELEVATION DEGREES | ROTATION DEGREES |
|---|---|---|---|---|---|
| 82 | *TRIGONELLA FAENUM G.* | MENTHI | WHOLE PLANT | 15 | 160 |
| 83 | *TRIBULUS TERRESTRIAS* | GOSHURA | STEM AND ROOT | 25 | 45 |
| 84 | *TYLOPHORA ASTHMATICA* | | LEAVES | 10 | 65 |
| 85 | *VIBURNUM* | MOTHER TINCTURE | MOTHER TINCTURE OF HOMOEO MEDICINE | 20 | 15 |
| 86 | *WITHINIA SOMNIFERA* | ASWAGANDHA | ROOT | 5 | 50 |
| 87 | *ZINZIBER OFFICINALIS* | SHUNTI | PROCESSED ZINGER, RHIZOME | 15 | 130 |
| 88 | *AVIPATTAKARA CHURNA* | AYURVEDA FORMULATION | POWDER | 25 | 60 |
| 89 | KAMADUGA | SIDDHA FORMULATION | POWDER | 10 | 25 |
| 90 | KUMARAYASAVA | AYURVEDIC MEDDICINE BY FERMENTATION PROCESS | LIQUID | 10 | 35 |
| 91 | *MAHALAKSHMI VILAS RAS* | SIDDHA FORMULATION | POWDER | 20 | 35 |
| 92 | *SUVARNA YOGARAJA GUGGULU* | SIDDHA FORMULATION | POWDER | 10 | 40 |

ALL THE OTHER PARAMETERS OF RANGE OF WAVE LENGTH, ABSORBANCE SCALE AND RETENTION TIMES ARE SHOWN IN INDIVIDUAL FIGURE.

TABLE 14

MEDICINES USED FOR FINGER PRINTING

| BOTANICAL NAME OF THE PLANT | VERNACULAR NAME | EFFICACY* | DOSHA HARA (Disorder on which PACIFIES) PITTA | KAPHA | VATA | PART USED |
|---|---|---|---|---|---|---|
| | | PITTA HARA | | | | |
| *AVIPATTAKARA CHURNA* | AYURVEDA FORMULATION | Laxative, Peptic ulcer, Piles | ↓ | | | POWDER |
| *ACALIPHA INDICA* | HARITA MANJARI | Hepatoprotectitive, Skin diseases, Gyneac disorders | ↓ | | | LEAF |
| ANANDABHAIRAVI | HERBOMINERAL | Pitta jwara | | | | FORMULATION |
| *AROGYA VARDHINI* | HERBOMINERAL | Liver disorders, Skin disorders | ↓ | | | FORMULATION |
| BHUMYAMALAKI | PHYLLANTHUS URINARIA | Jaundice | ↓ | | | WHOLE HERB |
| KAMADUGA | FORMULATION | Peptic ulcer | ↓ | | | FORMULATION |
| KUMARAYASAVA | FERMENTATION PROCESS | Gyenic disorders, Jaundice | ↓ | | | LIQUID |
| *SARACA INDICA* | ASHOKA | Gyeneac disorders | ↓ | | | STEM BARK |
| SURYAVARTI | HERBOMINERAL | Head ache | ↓ | | | FORMULATION |
| | | KAPHA HARA | | | | |
| *AILANTHUS EXCELSA* | ARALU | Digestive disorders | | ↓ | | |
| *ASPARAGUS ADESCENDENTUM* | SAFED MUSALI | Aphrodisiac, impotency | | ↓ | | ROOT |
| *ADHATODA VASICA* | VASA | Respiratory disorders | | ↓ | | ROOT |
| *ADIANTUM CAUDATUM* | MAYURASHIKHI | Piles Cough Diarrhoea | | ↓ | | WHOLE HERB |

TABLE 14-continued

MEDICINES USED FOR FINGER PRINTING

| BOTANICAL NAME OF THE PLANT | VERNACULAR NAME | EFFICACY* | DOSHA HARA (Disorder on which PACIFIES) | | | PART USED |
|---|---|---|---|---|---|---|
| | | | PITTA | KAPHA | VATA | |
| ALLIUM SATIVAM | LASUNA | Swasa | | ↓ | | SMALL CLOVES |
| ALLIUM PORUM | MAHALASUNA | Swasa | | ↓ | | BIG SINGLE CLOVE |
| ACACIA SUMA | SWETHA KHADIRA | Diabetis | | ↓ | | STEM BARK |
| CAPSCICUM ANNUM L | KATUVEERA | Digestive disorders | | ↓ | | BIG UNRIPED, FRUIT |
| COCCINIDIUM GRANDIS | BIMBI | Emitic | | ↓ | | |
| CHOPACHINYADI CHURNAM | HERBAL FORMULATION | Venerial, Skin diseases | | ↓ | | POWDER |
| GLYCERRHZIA GLABRA | YASHTI MADHU | Panduroga, Rasayana | | ↓ | | ROOT, BARK |
| HIBISCUS ABEL MOSCHUS | LATA KASTURI | Slheshma roga, Prameha, urinary blader & kidney disorders | | ↓ | | WHOLE PLANT WITH FLOWERS AND SEEDS |
| INNULA RECEMOSA | PUSHKARAMULA | Kasa, swasa, jaundice, diabetis | | ↓ | | ROOT |
| KRIMIKUTARA RAS | HERBO-MINERAL | Worm infestation | | ↓ | | FORMULATION |
| OCIMUM SANCTUM | RAMA TULASI | Cough, Fever | | ↓ | | LEAF |
| RAPHANUS SATIVUS | MULKA, WHITE | Diabetics, cough, g. i. tract disorders, neutraceuticals | | ↓ | | LEAF |
| SAUSSREA LAPPA | KUSHTA | Respiratory disorders | | ↓ | | ROOT |
| SHILAJIT(H) | HERBOMINERAL | Diabetis, Renal stones | | ↓ | | BITUMINOUS |
| SHILAJIT(G) | HERBOMINERAL | Diabetis, Renal stones | | ↓ | | BITUMINOUS |
| TYLOPHORA ASTHAMATICA | AJADWESHI | Asthama | | | | LEAF |
| VATA HARA | | | | | | |
| ALPINIA GALANGA | GREATER GALANGA, | Rheumatic disorders | | | ↓ | RHIZOME |
| ALPINIA OFFICINARUM | LESSER GALANGA | Rheumatic disorders | | | ↓ | RHIZOME |
| ALPINIA SPECIOSA | LIGHTER GALANGA | Rheumatic disorders | | | ↓ | RHIZOME |
| BRIHATVATACHINTA MANI + SWARNAMAKSHKAM | HERBO-MINERAL | Arthritis | | | ↓ | FORMULATION |
| BORRHIEVIA DIFFUSA | PUNARNAVA | Odema, Urinary tract, diuretic disorders | | | ↓ | WHOLE PLANT |
| HUTHASANA | HERBO-MINERAL | All types of fevers | | | ↓ | FORMULATION |
| MAHAYOGARAJA GUGGULU | HERBAL | Arthrites | | | ↓ | FORMULATION |
| PLUCHEA LANCEOLATA | PATRA RASNA | Rheumatic disorders | | | ↓ | LEAF |
| RICINUS COMMUNIS | ERANDA MULA | Constipation, Rheumatoid disorders | | | ↓ | ROOT |
| SUVARNA YOGARAJA GUGGULU | SIDDHA FORMULATION | Rheumatic diseases | | | ↓ | POWDER |
| SHITAMSU RAS | HERBO-MINERAL | Jwara | | | ↓ | FORMULATION |
| SUVARNA YOGARAJA GUGGULU | HERBAL FORMULATION | Arthrites | | | ↓ | FORMULATION |
| VATA GAJANKUSA RAS | HERBO-MINERAL | Sciatica | | | ↓ | FORMULATION |
| PITTA KAPHA HARA | | | | | | |
| ACACIA CATECHU | RAKTHA KHADIRA | Skin diseases diabetis | ↓ | ↓ | | STEM BARK, EXUDATE |
| AILANTHUS EXCELSA | ARALU | Digestive disorders | ↓ | ↓ | | BARK |
| ARECA CATECHU | KRAMUKA | Diabetis, Skin disorders | ↓ | ↓ | | MILK PROCESSED NUT |
| AZARIDICTA INDICA | NIMBA | Skin diseases, Infective conditions | ↓ | ↓ | | TENDER LEAVES |
| BERBERIS ARISTATA | DARUHARIDRA | Obesity Skin disorders | ↓ | ↓ | | ROOT BARK |

TABLE 14-continued

MEDICINES USED FOR FINGER PRINTING

| BOTANICAL NAME OF THE PLANT | VERNACULAR NAME | EFFICACY* | DOSHA HARA (Disorder on which PACIFIES) | | | PART USED |
|---|---|---|---|---|---|---|
| | | | PITTA | KAPHA | VATA | |
| *CITRULLUS COLOSYNTHIS* | INDRAVARUNI | Purgative, juandice, aborttificient | ↓ | ↓ | | HOMOEO MOTHER TINCTURE |
| *CURCUMA LONGA* | TURMERIC | Worm infestation, dysentry, diarrhoea, skin disorders, wounds | ↓ | ↓ | | COMMERCIAL POWDER-1 |
| *CURCUMA LONGA* | TURMERIC | Worm infestation, dysentry, diarrhoea, skin disorders, wounds | ↓ | ↓ | | COMMERCIAL POWDER-2 |
| *CURCUMA LONGA* | TURMERIC | Worm infestation dysentry, diarrhoea, skin disorders Wounds | ↓ | ↓ | | COMMERCIAL POWDER-3 |
| *COSCINIUM FENESTRATIUM* | LATA DARVI | Diabetis Obesity, Skin disorders | ↓ | ↓ | | STEM |
| *CURCUMA LONGA* | HARIDRA | Skin, Allegic, Diabetic | ↓ | ↓ | | RAW RHIZOME |
| *DACTYLACTINIUM AEGIPTIUM* (PROSTRATE AND ERECT) | GRASS | Diuretic, improves complexion | ↓ | ↓ | | WHOLE PLANT LEAVES |
| *EUGENIA JAMBOLONA SIZYGIUM CUMINI* | JAMBU | Vomiting, diabetic, Dysentry | ↓ | ↓ | | FRUIT |
| *HOLLERNA ANTIDYSENTRICA* | KUTAJA | Diarrhoea, Haemorroids | ↓ | ↓ | | STEM BARK FROM ANDHRA PREADESH |
| *HOLLERNA ANTIDYSENTRICA* | KUTAJA | Diarrhoea, All gi tract disorders | ↓ | ↓ | | STEM BARK FROM KERALA |
| *RUBIA CORDIFOLIA* | MANJISTA | Skin disorders Leukemia Blood purifier | ↓ | ↓ | | STEM, ROOT |
| *PSORALIACORYLIF OLIA* | BAKUCHI | Leucoderma, Skin diseases | ↓ | ↓ | | SEEDS, SEED OIL |
| *PICRORRHIZA KURROA* | KATUKA ROHINI | Laxative Liver disorders | ↓ | ↓ | | ROOT |
| *TRIGONELLA FENUM G.* | METHIKA | Diabetis, colic | ↓ | ↓ | | WHOLE HERB |
| *SYMPLOCOS RACEMOSA* | LODHRA | Bleeding disorders, diarrhoea, dysentry | ↓ | ↓ | | BARK |
| *SPERANTHUS INDICUS* | MUNDI | Krimihara, Migrain, vrishya, lymphatic disorders | ↓ | ↓ | | WHOLE HERB |
| KAPHA VATA HARA | | | | | | |
| *ACORUS CALAMUS* | VACHA | Medhya Speech disorders | | ↓ | ↓ | RHIZOME |
| ALOEVERA | KUMARI | Gyneac disorders, hepatomegaly, spleen o megaly, burns, uterine disorders | | ↓ | ↓ | LEAF, LEAF JUICE |
| AGNITUNDINA | HERBAL FORMULATION | Indigestion, Skin disorders | ↑ | | | FORMULATION |
| *MICHELIA CHAMPAKA* | CHAMPAKA | Cosmetic, Skin diseases | | ↓ | ↓ | FLOWER |
| *MORINGA OLEIFERA* | SIGRU | Abcess, oedema | | ↓ | ↓ | LEAF |
| PIPER BEETLE | NAGA VALLI | Kasa, swasa Digestive disorders | ↑ | ↓ | | LEAVES FROM COASTAL ANDHRA PRADESH |
| PIPER BEETLE | NAGA VALLI | Kasa, swasa Digestive disorders | ↑ | ↓ | | LEAVES CULCATTA |
| *TRIKATU CHURNA*-1 | HERBAL FORMULATION | Indigestion | | ↓ | ↓ | FORMULATION |
| *TRIKATU CHURNA* SP - 2 | HERBAL FORMULATION | Indigestion | | ↓ | ↓ | FORMULATION |
| *TRIKATU CHURNA* GH - 3 | HERBAL FORMULATION | Indigestion | | ↓ | ↓ | FORMULATION |

TABLE 14-continued

MEDICINES USED FOR FINGER PRINTING

| BOTANICAL NAME OF THE PLANT | VERNACULAR NAME | EFFICACY* | DOSHA HARA (Disorder on which PACIFIES) | | | PART USED |
|---|---|---|---|---|---|---|
| | | | PITTA | KAPHA | VATA | |
| *TRIBULUS TERRESTRIAS* | GOKSHURA | Urinary disorders, Oedema | | ↓ | ↓ | STEM AND ROOT |
| *TYLOPHORA ASTHMATICA* | AJADWESHI | Diabetis, asthama | | ↓ | ↓ | LEAVES |
| PITTA VATA HARA | | | | | | |
| *ACACIA SUMA* | SWETHA KHADIRA | Prameha | ↓ | | ↓ | STEM BARK |
| ANANDABHAIRAVI | HERBO-MINERAL | | ↓ | | ↓ | FORMULATION |
| *BACOPA MONNERI* | BRAHMI | Medhya, skin disorders | | ↑ | | WHOLE HERB |
| *DICROSTACHYS CINERA* | VEERATARU, TUMMA | Hridya, Obescity | ↓ | | ↓ | LEAF AND BARK |
| *ENICOSTEMMA AXILLAE* | NAHI | Malaria | ↓ | | ↓ | WHOLE HERB |
| *KANCHANARA GUGGULU* | HERBAL FORMULATION | Inflammatory conditions | ↓ | | ↓ | FORMULATION |
| *OROXYLUM INDICUM* | SYONAKA | Odema Digestive disorders | ↓ | | ↓ | STEM BARK |
| TRI DOSHA HARA | | | | | | |
| *ASPARAGUS ABSCENDENSES* | SWETHA MUSALI | Aphrodisiac | ↓ | ↓ | ↓ | ROOT |
| *CAPSCICUM ANNUM L* | MIRCH, KATIVEERA | G.I tract disorders | ↓ | ↓ | ↓ | BIG, RIPED FRUIT |
| *CURCULIGO ORCHIOIDES* | KALI MUSALI | Aphrodisiac | ↓ | ↓ | ↓ | ROOT |
| *EMBLICA OFFICINALIS* | AMALAKI | Hyridya, Rasaya, na Neutraceutical | ↓ | ↓ | ↓ | FRUIT EPICARP |
| *KARPURADI RAS* | HAEMORRHOIDS | Diarrhoea | ↓ | ↓ | ↓ | FORMULATION |
| *MAHALAKSHMI VILAS RAS* | HERBO-MINERAL | All types of fevers | ↓ | ↓ | ↓ | FORMULATION |
| ONOIN BIG | PALANDU | Haemorrhoids | ↓ | ↓ | ↓ | BULB |
| ONION SMALL | PALANDU | Haemorrhoids | ↓ | ↓ | ↓ | BULB |
| *TERMINALIA CHEBULA* | HARITAKI | Laxative Rasayana | ↓ | ↓ | ↓ | FRUIT |
| *TERMINALIA BELLERICA* | VIBHITAKI | Kasa, swasa, Skin diseases, urinary calliculus | ↓ | ↓ | ↓ | FRUIT |
| *WITHINIA PUB.* | ASWAGANDHA RED SEEDS PLANT ROOT | General debility, rejuvenation | ↓ | ↓ | ↓ | ROOT |
| ADULTERATIONS | | | | | | |
| FACE PACK(G) | | Good by efficacy | | | | FORMULATION |
| FACE PACK(B) | | Absence of some important constituents like kushta(*sausserea lappa*) and manjista (*rubia cordifolia*), making the formulation less effective | | | | FORMULATION |
| HERBAL HEAD BATH POWDER(G) | | No foaming agents found | | | | FORMULATION |
| HERBAL HEAD BATH POWDER(B) | | Adulterated with foaming agents | | | | FORMULATION |
| HOMOEO MEDICINES | | | | | | |
| ARNICA | | Pain reliever, after effects of injury | | | | HOMOEO MOTHER TINCTURE |
| *MYRICA CEREFERA* | BAY BERRY | Hepatoprotective | | | | HOMOEO MOTHER TINCTURE BRAND-1 |
| *MYRICA CEREFERA* | BAY BERRY | Hepatoprotective | | | | HOMOEO MOTHER TINCTURE BRAND-2 |
| *VIBURNUM* | MOTHER TINCTURE | Gynaecological disorders | | | | HOMOEO MEDICINE |

TABLE 14-continued

MEDICINES USED FOR FINGER PRINTING

| BOTANICAL NAME OF THE PLANT | VERNACULAR NAME | EFFICACY* | DOSHA HARA (Disorder on which PACIFIES) | | | PART USED |
|---|---|---|---|---|---|---|
| | | | PITTA | KAPHA | VATA | |
| ISOLATED COMPOUNDS | | | | | | |
| *VITEX NEGUNDO* | SINGLE COMPOUND | Hepatoprotective | | | | A FLAVONOID 7-HYDROXY QUERCETIN |
| AZAMALYCIN A DIABETIC HERBAL MEDICINE | SINGLE COMPOUND | Prameha | | | | SINGLE ISOLATED COMPOUND ADULTERATED WITH A DIURETIC ALLOPATHIC AMIDE CONSTITUENT |
| *BERBERIS ARISTATA* | SINGLE ISOLATED STANDARD COMPOUND | | | | | BERBARIN STD (FLUKA) |

↓: INDICATES DECREASE OF DISORDER
↑: INDICATES INCREASE OF DISORDER
*The therapeutic efficacys reported are as per the information available with the author, many more may be reported elsewhere.

TABLE 15

Names of the medicines shown as thumbnails of fingerprints

| NAME OF THE SAMPLE | PART USED |
|---|---|
| Allopathic medicines | FIG. 109 |
| Vitamin-B complex | Commercial brand |
| Analgin | Commercial brand |
| Atenolol | Commercial brand |
| Bromoflexin | Commercial brand |
| Citerizine | Commercial brand |
| Furazolidine | Commercial brand |
| Ibuprofen-Paracetamol | Commercial brand |
| Paracetamol | Commercial brand |
| Herbal Cosmetic samples | FIG. 110 |
| Face pack (Poor by efficacy) | Commercial brand |
| Face pack (Good by efficacy) | Commercial brand |
| Head bath powder (Poor by efficacy) | Commercial brand |
| Head bath powder (Good by efficacy) | Commercial brand |
| Herbal Formulations | FIG. 111 |
| Agnitundina | Commercial brand |
| Anandabhairavi | Commercial brand |
| Arogyavardhani | Commercial brand |
| Brihatvatachintamani + Swarnamakshakam | Commercial brand |
| Chopachinyadi Churnam | Commercial brand |
| Commercial Turmeric Brand 1 | Commercial brand |
| Commercial Turmeric Brand 2 | Commercial brand |
| Commercial Turmeric Brand 3 | Commercial brand |
| Huthasana | Commercial brand |
| Homoeo medicines | FIG. 112 |
| Arnica | Mother Tincture |
| Calendula | Mother Tincture |
| Colosynthis | Mother Tincture |
| Isolated compounds | FIG. 113 |
| 7-Hydroxy Quercetin | Isolated from *Vitex negundo* |
| A flavonoid | Isolated from *Vitex negundo* |
| Azamalycin | Standard |
| Dexamethasone | Standard |
| Single medicines | FIG. 114 |
| Alovera | Leaf |
| *Acalypha Indica* | Leaf |
| *Embalika officinalis* | Fruit |
| Aralu | Bark |
| *Areca Catachu* | Seeds |
| Aswagandha Red fruits | Roots |
| Aswagandha White fruits | Roots |
| Beetle leaf Andhra pradesh | Leaf |
| Beetle leaf Culcutta | Leaf |
| Coscinium | Stem Bark |
| *Dactlylactenium aegyptium* (Erect) | Leaves |
| *Dacylactinium aegyptium* (Prostrate) | Leaves |
| Daruharidra | Stam Bark |
| Haridra | Raw Rhizome |
| Kalajamun | Fruit |
| Onion | Bulb |
| Kutaja | Stem Bark |
| Raktakhadira | Heart wood |
| Shilajit | Processed Bituminous Source 1 |
| Shilajit | Processed Bituminous Source 2 |
| Brahmi | Leaf |

TABLE 16

The Division of the Fingerprint in to Therapeutic Zone based on the conjugation and polarity

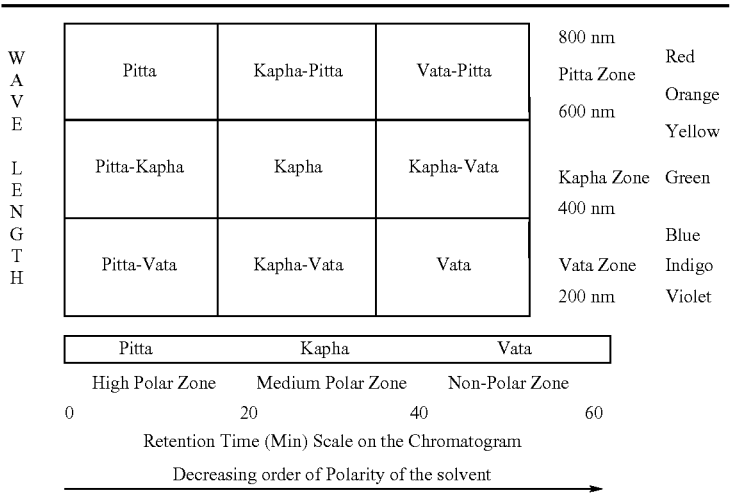

Based on the color reported, the entire image is divided in to 3 Zones on X-axis and 3 Zones on Y-axis. X axis shows the POLARITY SCALE due to the mobile phase composition. Y-axis shows CONJUGATION due to UV-VIS absorbance. When the molecule is more conjugated it absorbs at higher wavelengths (800 nm). Thus constituents present in the respective zones will act as shown in the figure in the respective therapeutic zones will be providing respective therapeutic efficacy. Quantification of these constituents was done using the UV-VIS absorptive property which is directly proportional to the quantity of the constituent.

The invention claimed is:

1. A method for detection and identification of constituents of extracts from plants or animals, natural or synthetic sources possessing medicinal value, using chromatographic finger printing techniques, the method comprising the steps of:

i. extracting organic or organo-metallic compounds from plants or animal, natural or synthetic sources using a solvent;
   ii. subjecting the extract obtained in step I, to separating based on pH and polarity, using High Pressure Liquid Chromatography (HPLC) ultraviolet-visible (UV-Vis) 3-D chromatography technique;
   iii. generating contour and 3-D chromatograms of the constituents eluted in step ii, based on the pH and polarity;
   iv. converting the 3-D and contour chromatogram obtained into a colored image, analyzing the colored image for its individual colors using the co-ordinates denoting all its 3-dimension properties of said image;
   v. denoting the concentrations of the various constituents eluted with time;
   vi. generating a chromatogram based on color analyzed, having peaks at various retention times along with conjugative properties of the constituents;
   vii. identifying the compounds in the said ingredients by the UV-Vis electromagnetic radiation absorptive properties of the various constituents in the image, thus creating a chromatographic fingerprint of the extract;
   viii. identifying, determining and classifying the compounds eluted as polar, medium polar and less or non-polar based on the polarity and conjugative properties;
   ix. generating a barcode for a selected peak using X-axis as Retention Time, the Y-axis as Wavelength, R as the number of Red Pixels, G as the number of Green Pixels and B as the number of Blue Pixels; and
   x. generating a database of fingerprints and barcodes and identifying the respective compounds of the extract.

2. A method as claimed in claim 1 wherein, the solvents with different polarities are selected based on the hydrophilic and hydrophobic nature of the sample under study, and ethyl alcohol is used as a solvent for preparation and for standardization of medicinal extracts.

3. A method as claimed in claim 1 wherein, the fingerprints are developed for the same medicine extracted under different pH ranges.

4. A method as claimed in claim 1 wherein, the HPLC UV-Vis 3-D chromatography technique is used by employing any commercially available HPLC apparatus with the Photo Diode Array detector, preferably with a gradient or ternary system of pumps.

5. The method as claimed in claim 1, wherein the method steps are standardized by implying extraction with ethyl alcohol, maintaining a run time of 0–60 minutes, eluting with a mobile phase of acetonitrile along with a phosphate buffer having a pH in the range of 5.5–7.5, and an UV-Vis detector has the electromagnetic radiation range of 200–800 nm for fingerprinting, chemical and therapeutic standardization.

6. A method as claimed in claim 1, wherein the separation of step ii is based on polarity and is performed with a solvent of known pH.

7. A method as claimed in claim 1, wherein converting the contour chromatograms into a colored image consists of identifying the conjugative and polarity properties of the constituents of the medicinal extract under study by imaging and extraction of colors of the image and presenting as data chromatograms.

8. A method as claimed in claim 1, further comprising assessing a therapeutic efficacy of a single or formulated medicinal extract using the quality of the constituents present in a particular polarity and UV-Vis absorptive zone out of different therapeutic zones of the chromatographic fingerprint.

9. A method as claimed in claim 1, wherein in step ix, the barcode for the selected peak or peaks or image is generated by a software.

10. A method as claimed in claim 1, further including the step of using chemical analysis of the constituents present in the extract under study and their conjugative and polarity properties to determine therapeutic efficacy.

11. A method as claimed in claim 1, wherein said analysis of the colored image in step iv provides a quick identification of the actual profile of the compounds present in the medicine under use along with the therapeutic efficacy of the constituents.

12. A method as claimed in claim 1, wherein said step of analyzing the colored image of step iv utilizes a photo diode array detector (PDA) of said high pressure liquid chromatography of step ii to provide a chromatographic finger printing of herbal medicines and formulations.

13. The method as claimed in claim 12 wherein said chromatographic finger printing delineates the data of the spectral properties of the constituents arranged in a specific order of polarity present in the material having medicinal value for chemical and therapeutic standardization.

14. A method as claimed in claim 1, wherein in step vii, said chromatographic fingerprint of the extract defines the blue print of the constituents present in an herbal medicine or formulation for an assay and for quick identification of the medicine under study.

15. A method as claimed in claim 14 wherein step ix further includes preparing a database of fingerprints together with correlations with the therapeutic efficacy which can be used to form generalizations of the therapeutic efficacy of a particular group of plants, classified as a group for a particular disease or therapeutic classification.

16. A method as claimed in claim 1, wherein the natural or synthetic sources are adulterated, substituted, contradictable and commercial food and drug samples.

* * * * *